US010087254B2

(12) United States Patent
Hofer et al.

(10) Patent No.: US 10,087,254 B2

(45) Date of Patent: Oct. 2, 2018

(54) ASPGR ANTIBODIES AND USES THEREOF

(71) Applicant: ROCHE GLYCART AG, Schlieren (CH)

(72) Inventors: Thomas Hofer, Zurich (CH); Changhua Ji, Livingston, NJ (US); Ekkehard Moessner, Kreuzlingen (CH); Pablo Umana, Wollerau (CH)

(73) Assignee: ROCHE GLYCART AG, Schlieren (CH)

( * ) Notice: Subject to any disclaimer, the term of this patent is extended or adjusted under 35 U.S.C. 154(b) by 0 days.

(21) Appl. No.: 15/711,495

(22) Filed: Sep. 21, 2017

(65) Prior Publication Data

US 2018/0118833 A1 May 3, 2018

Related U.S. Application Data

(62) Division of application No. 14/419,824, filed as application No. PCT/EP2013/066432 on Aug. 6, 2013, now Pat. No. 9,771,427.

(60) Provisional application No. 61/681,239, filed on Aug. 9, 2012.

(51) Int. Cl.

*C07K 16/28* (2006.01)
*A61K 39/00* (2006.01)
*C07K 14/56* (2006.01)

(52) U.S. Cl.

CPC .......... *C07K 16/2851* (2013.01); *C07K 14/56* (2013.01); *A61K 2039/505* (2013.01); *C07K 2317/33* (2013.01); *C07K 2317/52* (2013.01); *C07K 2317/526* (2013.01); *C07K 2317/56* (2013.01); *C07K 2317/71* (2013.01); *C07K 2317/92* (2013.01); *C07K 2319/00* (2013.01); *C07K 2319/01* (2013.01)

(58) Field of Classification Search

CPC ............ C07K 16/2851; C07K 2317/56; A61K 2039/505

See application file for complete search history.

(56) References Cited

FOREIGN PATENT DOCUMENTS

WO 2011086143 A2 7/2011

OTHER PUBLICATIONS

Limin, Cao et al., "Characterization of a Single-Chain Variable Fragment (SCFV) Antibody Directed Against the Human Asialoglycoprotein Receptor", Biotechnology and Applied Biochemistry, Academic Press, US, vol. 44, mp/ 2, May 1, 2006 (May 1, 2006), pp. 65-72, XP002643344, ISSN: 0885-4513, DOI: 10.1042/BA20050081 (retrieved on Dec. 23, 2010) p. 65, 71.

Xiaorong Zhao et al., "Construction and Characterization of an Anti-Asialoglycoprotein Receptor Single-Chain Variable-Fragment-Targeted Melittin", Biotechnology and Applied Biochemistry, vol. 58, No. 6, Nov. 1, 2011 (Nov. 1, 2011), pp. 405-411, XP055084712, ISSN: 0885-4513, DOI: 10.1002/bab.57 pp. 407-708.

Alla Trahtenherts et al., "An Internalizing Antibody Specific for the Human Asialoglycoprotein Receptor", Hybridoma, vol. 28, No. 4, Aug. 1, 2009 (Aug. 1, 2009), pp. 225-233, XP055084704, ISSN: 1554-0014, DOI: 10.1089/hyb.2009.0019, figure 2.

Jung-Hyun Park et al., "Detection of Surface Asialoglycoprotein Receptor Expression in Hepatic and Extra-Hepatic Cells Using a Novel Monoclonal Antibody", Biotechnology Letters, Springer Netherlands, Dordrecht, vol. 28, No. 14, Jun. 24, 2006 (Jun. 24, 2006), pp. 1061-1069, XP019391551, ISSN: 1573-6776, DOI: 10.1007/S10529-006-9191-7.

Cao, L., et al., "Biotechnology and Applied Biochemistry", vol. 44(2), pp. 65-72 (2006).

Zhao, X., et al., "Biotechnology and Applied Biochemistry", vol. 58(6), pp. 405-411 (2011).

Trahtenherts, A., et al., Hybridoma, vol. 28(4), pp. 225-233 (2009).

Park, J.-H., et al., Biotechnology Letters, vol. 28(14), pp. 1061-1069 (2006).

*Primary Examiner* — Ruixiang Li

(74) *Attorney, Agent, or Firm* — Mintz, Levin, Cohn, Ferris, Glovsky and Popeo, P.C.

(57) ABSTRACT

The present invention generally relates to antibodies specific for asialoglycoprotein receptor (ASGPR) and their use for selectively delivering effector moieties that influence cellular activity. In addition, the present invention relates to polynucleotides encoding such antibodies, and vectors and host cells comprising such polynucleotides. The invention further relates to methods for producing the antibodies of the invention, and to methods of using them in the treatment of disease.

5 Claims, 31 Drawing Sheets

Specification includes a Sequence Listing.

Figure 8

| | | 89 | 90 | 91 | 92 | 93 | 94 | 95 | 95a | 95b | 95c | 95d | 96 | 97 | 98 | 99 | | | | |
|---|---|---|---|---|---|---|---|---|---|---|---|---|---|---|---|---|---|---|---|---|
| (A) | C | N | S | R | D | I | C | C | N | R | S | V | R | N | F | G | G | G | T | K |
| (B) | C | N | S | R | D | I | S | S | N | R | A | V | R | N | F | G | G | G | T | K |
| (C) | | | | x | x | x | x | x | x | x | x | x | x | | | | | | | |

Normalized expression
-4 -2 0 2 4
Liver
Blood
Iso-IFN
51A12
Iso-IFN
51A12
ug/kg
1
10
1
10
1
10
1
10
IFIH1
DTX3L
IFITM2
PARP12
HERC6
OAS2
ISG15
MX1
PNPT1
TDRD7
NCOA7
SP100
STAT1
IFI44
IFITM1
ADAR
IFI6
PARP14
XAF1
IRF7
FTSJD2
TREX1
SAMD4A
IFI35
ZNFX1
EPSTI1
PLSCR1
IFIT2
RSAD2
CMPK2
HERC5
OASL
IFIT3
PARP9
PPM1K
NT5C3
RAB8A
Days
Hours

| Sample name | Pictogram | Loss (%) compared to Roferon |
|---|---|---|
| ASGPR 51A12 kih IFNa |  | -94.3 |
| monovalent ASGPR 51A12 kih IFNa |  | -94.9 |
| monovalent ASGPR 52C4 kih IFNa |  | -94.8 |

```
                         SEQUENCE LISTING

<160> NUMBER OF SEQ ID NOS: 151

<210> SEQ ID NO 1
<211> LENGTH: 330
<212> TYPE: DNA
<213> ORGANISM: Artificial Sequence
<220> FEATURE:
<223> OTHER INFORMATION: 51A12 VL-Synthetic oligonucleotide

<400> SEQUENCE: 1

tcgtctgagc tgactcagga ccctgctgtg tctgtggcct tgggacagac agtcaggatc      60

acatgccaag gagacagcct cagaagttat tatgcaagct ggtaccagca gaagccagga     120

caggcccctg tacttgtcat ctatggtaaa aacaaccggc cctcagggat cccagaccga     180

ttctctgcct ccagctcagg aaacacagct tccttgacca tcactggggc tcaggcggaa     240

gatgaggctg actattactg taactcccgt gatatttgtt gtaatcgatc tgtgcgtaat     300

ttcggcggag ggaccaagct gaccgtccta                                      330


<210> SEQ ID NO 2
<211> LENGTH: 110
<212> TYPE: PRT
<213> ORGANISM: Artificial Sequence
<220> FEATURE:
<223> OTHER INFORMATION: 51A12 VL-Synthetic peptide

<400> SEQUENCE: 2

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Ala Ser
    50                  55                  60
```

```
Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ile Cys Cys Asn Arg
                85                  90                  95

Ser Val Arg Asn Phe Gly Gly Gly Thr Lys Leu Thr Val Leu
            100                 105                 110


<210> SEQ ID NO 3
<211> LENGTH: 354
<212> TYPE: DNA
<213> ORGANISM: Artificial Sequence
<220> FEATURE:
<223> OTHER INFORMATION: 51A12 VH-Synthetic oligonucleotide

<400> SEQUENCE: 3

gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaaccgtac    300

ctgggttaca ctattgacta ctggggccaa ggaaccctgg tcaccgtctc gagt          354


<210> SEQ ID NO 4
<211> LENGTH: 118
<212> TYPE: PRT
<213> ORGANISM: Artificial Sequence
<220> FEATURE:
<223> OTHER INFORMATION: 51A12 VH-Synthetic peptide

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Tyr Leu Gly Tyr Thr Ile Asp Tyr Trp Gly Gln Gly Thr
            100                 105                 110

Leu Val Thr Val Ser Ser
        115


<210> SEQ ID NO 5
<211> LENGTH: 324
<212> TYPE: DNA
<213> ORGANISM: Artificial Sequence
<220> FEATURE:
<223> OTHER INFORMATION: 52C4 VL-Synthetic oligonucleotide

<400> SEQUENCE: 5

tcgtctgagc tgactcagga ccctgctgtg tctgtggcct tgggacagac agtcaggatc     60

acatgccaag gagacagcct cagaagttat tatgcaagct ggtaccagca gaagccagga    120
```

-continued

```
caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactccggt gctagtagcg gtaatcagtt ggtattcggc    300

ggagggacca agctgaccgt ccta                                           324


<210> SEQ ID NO 6
<211> LENGTH: 108
<212> TYPE: PRT
<213> ORGANISM: Artificial Sequence
<220> FEATURE:
<223> OTHER INFORMATION: 52C4 VL-Synthetic peptide

<400> SEQUENCE: 6

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Gly Ala Ser Ser Gly Asn Gln
                85                  90                  95

Leu Val Phe Gly Gly Gly Thr Lys Leu Thr Val Leu
            100                 105


<210> SEQ ID NO 7
<211> LENGTH: 360
<212> TYPE: DNA
<213> ORGANISM: Artificial Sequence
<220> FEATURE:
<223> OTHER INFORMATION: 52C4 VH-Synthetic oligonucleotide

<400> SEQUENCE: 7

gaggtgcaat tgttggagtc tggggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agtcgaggac acggccgtat attactgtgc gaaaccggct    300

ggttactctt acggttactt cgactactgg ggccaaggaa ccctggtcac cgtctcgagt    360


<210> SEQ ID NO 8
<211> LENGTH: 120
<212> TYPE: PRT
<213> ORGANISM: Artificial Sequence
<220> FEATURE:
<223> OTHER INFORMATION: 52C4 VH-Synthetic peptide

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Pro Ala Gly Tyr Ser Tyr Gly Tyr Phe Asp Tyr Trp Gly Gln
            100                 105                 110

Gly Thr Leu Val Thr Val Ser Ser
        115                 120


<210> SEQ ID NO 9
<211> LENGTH: 324
<212> TYPE: DNA
<213> ORGANISM: Artificial Sequence
<220> FEATURE:
<223> OTHER INFORMATION: 5A4 VL-Synthetic oligonucleotide

<400> SEQUENCE: 9

tcgtctgagc tgactcagga ccctgctgtg tctgtggcct tgggacagac agtcaggatc      60

acatgccaag gagacagcct cagaagttat tatgcaagct ggtaccagca gaagccagga     120

caggcccctg tacttgtcat ctatggtaaa aacaaccggc cctcagggat cccagaccga     180

ttctctggct ccagctcagg aaacacagct tccttgacca tcactggggc tcaggcggaa     240

gatgaggctg actattactg taactcccgt ttgaggagcg ggaagatggt ggtattcggc     300

ggagggacca agctgaccgt ccta                                            324


<210> SEQ ID NO 10
<211> LENGTH: 108
<212> TYPE: PRT
<213> ORGANISM: Artificial Sequence
<220> FEATURE:
<223> OTHER INFORMATION: 5A4 VL-Synthetic peptide

<400> SEQUENCE: 10

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Leu Arg Ser Gly Lys Met
                85                  90                  95

Val Val Phe Gly Gly Gly Thr Lys Leu Thr Val Leu
            100                 105


<210> SEQ ID NO 11
<211> LENGTH: 366
<212> TYPE: DNA
<213> ORGANISM: Artificial Sequence
<220> FEATURE:
<223> OTHER INFORMATION: 5A4 VH-Synthetic oligonucleotide

<400> SEQUENCE: 11
```

-continued

```
cattcggagg tgcaattgtt ggagtctggg ggaggcttgg tacagcctgg ggggtccctg     60

agactctcct gtgcagcctc cggattcacc tttagcagtt atgccatgag ctgggtccgc    120

caggctccag ggaaggggct ggagtgggtc tcagctatta gtggtagtgg tggtagcaca    180

tactacgcag actccgtgaa gggccggttc accatctcca gagacaattc caagaacacg    240

ctgtatctgc agatgaacag cctgagagcc gaggacacgg ccgtatatta ctgtgcgaaa    300

agttggtacc tgccgggtcg tggtttcgac tactggggcc aaggaaccct ggtcaccgtc    360

tcgagt                                                                366


<210> SEQ ID NO 12
<211> LENGTH: 120
<212> TYPE: PRT
<213> ORGANISM: Artificial Sequence
<220> FEATURE:
<223> OTHER INFORMATION: 5A4 VH-Synthetic peptide

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Tyr Leu Pro Gly Arg Gly Phe Asp Tyr Trp Gly Gln
            100                 105                 110

Gly Thr Leu Val Thr Val Ser Ser
        115                 120


<210> SEQ ID NO 13
<211> LENGTH: 327
<212> TYPE: DNA
<213> ORGANISM: Artificial Sequence
<220> FEATURE:
<223> OTHER INFORMATION: 4F3 VL-Synthetic oligonucleotide

<400> SEQUENCE: 13

tcgtctgagc tgactcagga ccctgctgtg tctgtggcct tgggacagac agtcaggatc     60

acatgccaag gagacagcct cagaagttat tatgcaagct ggtaccagca gaagccagga    120

caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactccctg gagaggatcg ggtatctttc ttatgtattc    300

ggcggaggga ccaagctgac cgtccta                                        327


<210> SEQ ID NO 14
<211> LENGTH: 109
<212> TYPE: PRT
<213> ORGANISM: Artificial Sequence
<220> FEATURE:
<223> OTHER INFORMATION: 4F3 VL-Synthetic peptide

<400> SEQUENCE: 14
```

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Leu Glu Arg Ile Gly Tyr Leu
                85                  90                  95

Ser Tyr Val Phe Gly Gly Gly Thr Lys Leu Thr Val Leu
            100                 105


<210> SEQ ID NO 15
<211> LENGTH: 360
<212> TYPE: DNA
<213> ORGANISM: Artificial Sequence
<220> FEATURE:
<223> OTHER INFORMATION: 4F3 VH-Synthetic oligonucleotide

<400> SEQUENCE: 15

gaggtgcaat tgttggagtc tgggggaggc ttggtacagc ctggggggtc cctgagactc      60

tcctgtgcag cctccggatt cacctttagc agttatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcagatga acagcctgag agccgaggac acggccgtat attactgtgc gaaagacttc     300

tcttctcgtc gttggtacct ggaatactgg ggccaaggaa ccctggtcac cgtctcgagt     360


<210> SEQ ID NO 16
<211> LENGTH: 120
<212> TYPE: PRT
<213> ORGANISM: Artificial Sequence
<220> FEATURE:
<223> OTHER INFORMATION: 4F3 VH-Synthetic peptide

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser
        115                 120
```

<210> SEQ ID NO 17
<211> LENGTH: 321
<212> TYPE: DNA
<213> ORGANISM: Artificial Sequence
<220> FEATURE:
<223> OTHER INFORMATION: R5C2 VL-Synthetic oligonucleotide

<400> SEQUENCE: 17
tcgtctgagc tgactcagga ccctgctgtg tctgtggcct tgggacagac agtcaggatc 60
acatgccaag gagacagcct cagaagttat tatgcaagct ggtaccagca gaagccagga 120
caggcccctg tacttgtcat ctatggtaaa aacaaccggc cctcagggat cccagaccga 180
ttctctggct ccagctcagg aaacacagct tccttgacca tcactggggc tcaggcggaa 240
gatgaggctg actattactg taactcccgg gatcgtagag gttattcggt attcggcgga 300
gggaccaagc tgaccgtcct a 321

<210> SEQ ID NO 18
<211> LENGTH: 107
<212> TYPE: PRT
<213> ORGANISM: Artificial Sequence
<220> FEATURE:
<223> OTHER INFORMATION: R5C2 VL-Synthetic peptide

<400> SEQUENCE: 18

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Arg Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Arg Arg Gly Tyr Ser
85 90 95

Val Phe Gly Gly Gly Thr Lys Leu Thr Val Leu
100 105

<210> SEQ ID NO 19
<211> LENGTH: 360
<212> TYPE: DNA
<213> ORGANISM: Artificial Sequence
<220> FEATURE:
<223> OTHER INFORMATION: R5C2 VH-Synthetic oligonucleotide

<400> SEQUENCE: 19
gaggtgcaat tgttggagtc tgggggaggc ttggtacagc ctggggggtc cctgagactc 60
tcctgtgcgg cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaatcttct 300
ttctcttacc tgcgtgcttt cgactactgg ggccaaggaa ccctggtcac cgtctcgagt 360

<210> SEQ ID NO 20
<211> LENGTH: 120
<212> TYPE: PRT
<213> ORGANISM: Artificial Sequence
<220> FEATURE:
<223> OTHER INFORMATION: R5C2 VH-Synthetic peptide

<400> SEQUENCE: 20

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ser Ser Phe Ser Tyr Leu Arg Ala Phe Asp Tyr Trp Gly Gln
100 105 110

Gly Thr Leu Val Thr Val Ser Ser
115 120

<210> SEQ ID NO 21
<211> LENGTH: 321
<212> TYPE: DNA
<213> ORGANISM: Artificial Sequence
<220> FEATURE:
<223> OTHER INFORMATION: R9E10 VL-Synthetic oligonucleotide

<400> SEQUENCE: 21
tcgtctgagc tgactcagga ccctgctgtg tctgtggcct tgggacagac agtcaggatc 60
acatgccaag gagacagcct cagaagttat tatgcaagct ggtaccagca gaagccagga 120
caggcccctg tacttgtcat ctatggtaaa aacaaccggc cctcagggat cccagaccga 180
ttctctggct ccagctcagg aaacacagct tccttgacca tcactggggc tcaggcggaa 240
gatgaggctg actattactg taactcccgg aatgttcgcg gtaagctcgt attcggcgga 300
gggaccaagc tgaccgtcct a 321

<210> SEQ ID NO 22
<211> LENGTH: 107
<212> TYPE: PRT
<213> ORGANISM: Artificial Sequence
<220> FEATURE:
<223> OTHER INFORMATION: R9E10 VL-Synthetic peptide

<400> SEQUENCE: 22

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asn Val Arg Gly Lys Leu
85 90 95

Val Phe Gly Gly Gly Thr Lys Leu Thr Val Leu
100 105

<210> SEQ ID NO 23
<211> LENGTH: 360
<212> TYPE: DNA
<213> ORGANISM: Artificial Sequence
<220> FEATURE:
<223> OTHER INFORMATION: R9E10 VH-Synthetic oligonucleotide

<400> SEQUENCE: 23
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaaaactct 300
tacacttacg gtcgtgctct ggactactgg ggccaaggaa ccctggtcac cgtctcgagt 360

<210> SEQ ID NO 24
<211> LENGTH: 120
<212> TYPE: PRT
<213> ORGANISM: Artificial Sequence
<220> FEATURE:
<223> OTHER INFORMATION: R9E10 VH-Synthetic peptide

<400> SEQUENCE: 24

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asn Ser Tyr Thr Tyr Gly Arg Ala Leu Asp Tyr Trp Gly Gln
100 105 110

Gly Thr Leu Val Thr Val Ser Ser
115 120

<210> SEQ ID NO 25
<211> LENGTH: 324
<212> TYPE: DNA
<213> ORGANISM: Artificial Sequence
<220> FEATURE:
<223> OTHER INFORMATION: R7E12 VL-Synthetic oligonucleotide

<400> SEQUENCE: 25
tcgtctgagc tgactcagga ccctgctgtg tctgtggcct tgggacagac agtcaggatc 60
acatgccaag gagacagcct cagaagttat tatgcaagct ggtaccagca gaagccagga 120
caggcccctg tacttgtcat ctatggtaaa aacaaccggc cctcagggat cccagaccga 180
ttctctggct ccagctcagg aaacacagct tccttgacca tcactggggc tcaggcggaa 240
gatgaggctg actattactg taactcccgt aagagtagct cgaagaatgt tgtgttcggc 300

-continued

```
ggagggacca agctgaccgt ccta                                        324


<210> SEQ ID NO 26
<211> LENGTH: 108
<212> TYPE: PRT
<213> ORGANISM: Artificial Sequence
<220> FEATURE:
<223> OTHER INFORMATION: R7E12 VL-Synthetic peptide

<400> SEQUENCE: 26

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Lys Ser Ser Ser Lys Asn
                85                  90                  95

Val Val Phe Gly Gly Gly Thr Lys Leu Thr Val Leu
            100                 105


<210> SEQ ID NO 27
<211> LENGTH: 360
<212> TYPE: DNA
<213> ORGANISM: Artificial Sequence
<220> FEATURE:
<223> OTHER INFORMATION: R7E12 VH-Synthetic oligonucleotide

<400> SEQUENCE: 27

gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaatcttct    300

ttcactttcg gtcgttactt cgactactgg ggccaaggaa ccctggtcac cgtctcgagt    360


<210> SEQ ID NO 28
<211> LENGTH: 120
<212> TYPE: PRT
<213> ORGANISM: Artificial Sequence
<220> FEATURE:
<223> OTHER INFORMATION: R7E12 VH-Synthetic peptide

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

-continued

```
Leu Gln Met Asn Ser Leu Arg Ala Glu Asp Thr Ala Val Tyr Tyr Cys
                85                  90                  95

Ala Lys Ser Ser Phe Thr Phe Gly Arg Tyr Phe Asp Tyr Trp Gly Gln
            100                 105                 110

Gly Thr Leu Val Thr Val Ser Ser
        115                 120


<210> SEQ ID NO 29
<211> LENGTH: 330
<212> TYPE: DNA
<213> ORGANISM: Artificial Sequence
<220> FEATURE:
<223> OTHER INFORMATION: 51A12 S116A VL-Synthetic oligonucleotide

<400> SEQUENCE: 29

tcgtctgagc tgactcagga ccctgctgtg tctgtggcct tgggacagac agtcaggatc     60

acatgccaag gagacagcct cagaagttat tatgcaagct ggtaccagca gaagccagga    120

caggcccctg tacttgtcat ctatggtaaa aacaaccggc cctcagggat cccagaccga    180

ttctctgcct ccagctcagg aaacacagct tccttgacca tcactggggc tcaggcggaa    240

gatgaggctg actattactg taactcccgt gatatttgtt gtaatcgagc tgtgcgtaat    300

ttcggcggag ggaccaagct gaccgtccta                                     330


<210> SEQ ID NO 30
<211> LENGTH: 110
<212> TYPE: PRT
<213> ORGANISM: Artificial Sequence
<220> FEATURE:
<223> OTHER INFORMATION: 51A12 S116A VL-Synthetic peptide

<400> SEQUENCE: 30

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Ala Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ile Cys Cys Asn Arg
                85                  90                  95

Ala Val Arg Asn Phe Gly Gly Gly Thr Lys Leu Thr Val Leu
            100                 105                 110


<210> SEQ ID NO 31
<211> LENGTH: 330
<212> TYPE: DNA
<213> ORGANISM: Artificial Sequence
<220> FEATURE:
<223> OTHER INFORMATION: 51A12 A82G S116A VL-Synthetic oligonucleotide

<400> SEQUENCE: 31

tcgtctgagc tgactcagga ccctgctgtg tctgtggcct tgggacagac agtcaggatc     60

acatgccaag gagacagcct cagaagttat tatgcaagct ggtaccagca gaagccagga    120

caggcccctg tacttgtcat ctatggtaaa aacaaccggc cctcagggat cccagaccga    180
```

```
ttctctggct ccagctcagg aaacacagct tccttgacca tcactggggc tcaggcggaa    240

gatgaggctg actattactg taactcccgt gatatttgtt gtaatcgagc tgtgcgtaat    300

ttcggcggag ggaccaagct gaccgtccta                                     330
```

```
<210> SEQ ID NO 32
<211> LENGTH: 110
<212> TYPE: PRT
<213> ORGANISM: Artificial Sequence
<220> FEATURE:
<223> OTHER INFORMATION: 51A12 A82G S116A VL-Synthetic peptide

<400> SEQUENCE: 32

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ile Cys Cys Asn Arg
                85                  90                  95

Ala Val Arg Asn Phe Gly Gly Gly Thr Lys Leu Thr Val Leu
            100                 105                 110
```

```
<210> SEQ ID NO 33
<211> LENGTH: 330
<212> TYPE: DNA
<213> ORGANISM: Artificial Sequence
<220> FEATURE:
<223> OTHER INFORMATION: 51A12 A82G C112S C113S S116A VL-Synthetic
      oligonucleotide

<400> SEQUENCE: 33

tcgtctgagc tgactcagga ccctgctgtg tctgtggcct tgggacagac agtcaggatc     60

acatgccaag gagacagcct cagaagttat tatgcaagct ggtaccagca gaagccagga    120

caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactcccgt gatattagta gtaatcgagc tgtgcgtaat    300

ttcggcggag ggaccaagct gaccgtccta                                     330
```

```
<210> SEQ ID NO 34
<211> LENGTH: 110
<212> TYPE: PRT
<213> ORGANISM: Artificial Sequence
<220> FEATURE:
<223> OTHER INFORMATION: 51A12 A82G C112S C113S S116A VL-Synthetic
      peptide

<400> SEQUENCE: 34

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45
```

```
Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ile Ser Ser Asn Arg
                85                  90                  95

Ala Val Arg Asn Phe Gly Gly Gly Thr Lys Leu Thr Val Leu
            100                 105                 110


<210> SEQ ID NO 35
<211> LENGTH: 330
<212> TYPE: DNA
<213> ORGANISM: Artificial Sequence
<220> FEATURE:
<223> OTHER INFORMATION: 51A12_C1 VL-Synthetic oligonucleotide

<400> SEQUENCE: 35

tcgtctgagc tgactcagga ccctgctgtg tctgtggcct tgggacagac agtcaggatc      60

acatgccaag gagacagcct cagaagttat tatgcaagct ggtaccagca gaagccagga     120

caggcccctg tacttgtcat ctatggtaaa aacaaccggc cctcagggat cccagaccga     180

ttctctggct ccagctcagg aaacacagct tccttgacca tcactggggc tcaggcggaa     240

gatgaggctg actattactg taactcccgt tcttacgctt tcaaccgtgt tgttcgtaac     300

ttcggcggag ggaccaagct gaccgtccta                                      330


<210> SEQ ID NO 36
<211> LENGTH: 110
<212> TYPE: PRT
<213> ORGANISM: Artificial Sequence
<220> FEATURE:
<223> OTHER INFORMATION: 51A12_C1 VL-Synthetic peptide

<400> SEQUENCE: 36

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Ser Tyr Ala Phe Asn Arg
                85                  90                  95

Val Val Arg Asn Phe Gly Gly Gly Thr Lys Leu Thr Val Leu
            100                 105                 110


<210> SEQ ID NO 37
<211> LENGTH: 327
<212> TYPE: DNA
<213> ORGANISM: Artificial Sequence
<220> FEATURE:
<223> OTHER INFORMATION: 51A12_C7 VL-Synthetic oligonucleotide

<400> SEQUENCE: 37

tctgagctga ctcaggaccc tgctgtgtct gtggccttgg gacagacagt caggatcaca      60

tgccaaggag acagcctcag aagttattat gcaagctggt accagcagaa gccaggacag     120
```

gcccctgtac ttgtcatcta tggtaaaaac aaccggccct cagggatccc agaccgattc 180
tctggctcca gctcaggaaa cacagcttcc ttgaccatca ctggggctca ggcggaagat 240
gaggctgact attactgtaa ctcccgtgac atccgttaca accgtgttgt tcgtccgttc 300
ggcggaggga ccaagctgac cgtccta 327

<210> SEQ ID NO 38
<211> LENGTH: 110
<212> TYPE: PRT
<213> ORGANISM: Artificial Sequence
<220> FEATURE:
<223> OTHER INFORMATION: 51A12_C7 VL-Synthetic peptide

<400> SEQUENCE: 38

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Ile Arg Tyr Asn Arg
85 90 95

Val Val Arg Pro Phe Gly Gly Gly Thr Lys Leu Thr Val Leu
100 105 110

<210> SEQ ID NO 39
<211> LENGTH: 330
<212> TYPE: DNA
<213> ORGANISM: Artificial Sequence
<220> FEATURE:
<223> OTHER INFORMATION: 51A12_E7 VL-Synthetic oligonucleotide

<400> SEQUENCE: 39
tcgtctgagc tgactcagga ccctgctgtg tctgtggcct tgggacagac agtcaggatc 60
acatgccaag gagacagcct cagaagttat tatgcaagct ggtaccagca gaagccagga 120
caggcccctg tacttgtcat ctatggtaaa aacaaccggc cctcagggat cccagaccga 180
ttctctggct ccagctcagg aaacacagct tccttgacca tcactggggc tcaggcggaa 240
gatgaggctg actattactg taactcccgt gactaccgtt acaaccgtgc tgttcgtccg 300
ttcggcggag ggaccaagct gaccgtccta 330

<210> SEQ ID NO 40
<211> LENGTH: 110
<212> TYPE: PRT
<213> ORGANISM: Artificial Sequence
<220> FEATURE:
<223> OTHER INFORMATION: 51A12_E7 VL-Synthetic peptide

<400> SEQUENCE: 40

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr

```
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Tyr Arg Tyr Asn Arg
                85                  90                  95

Ala Val Arg Pro Phe Gly Gly Gly Thr Lys Leu Thr Val Leu
            100                 105                 110


<210> SEQ ID NO 41
<211> LENGTH: 330
<212> TYPE: DNA
<213> ORGANISM: Artificial Sequence
<220> FEATURE:
<223> OTHER INFORMATION: 51A12_H3 VL-Synthetic oligonucleotide

<400> SEQUENCE: 41

tcgtctgagc tgactcagga ccctgctgtg tctgtggcct tgggacagac agtcaggatc     60

acatgccaag gagacagcct cagaagttat tatgcaagct ggtaccagca gaagccagga    120

caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactcccgt gactacaaat tcaaccgtgt tgttcgtaac    300

ttcggcggag ggaccaagct gaccgtccta                                     330


<210> SEQ ID NO 42
<211> LENGTH: 110
<212> TYPE: PRT
<213> ORGANISM: Artificial Sequence
<220> FEATURE:
<223> OTHER INFORMATION: 51A12_H3 VL-Synthetic peptide

<400> SEQUENCE: 42

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Tyr Lys Phe Asn Arg
                85                  90                  95

Val Val Arg Asn Phe Gly Gly Gly Thr Lys Leu Thr Val Leu
            100                 105                 110


<210> SEQ ID NO 43
<211> LENGTH: 330
<212> TYPE: DNA
<213> ORGANISM: Artificial Sequence
<220> FEATURE:
<223> OTHER INFORMATION: 51A12_A6 VL-Synthetic oligonucleotide

<400> SEQUENCE: 43

tcgtctgagc tgactcagga ccctgctgtg tctgtggcct tgggacagac agtcaggatc     60
```

```
acatgccaag gagacagcct cagaagttat tatgcaagct ggtaccagca gaagccagga    120

caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactcccgt acttactctt acaaccgtgc tgttcgtaac    300

ttcggcggag ggaccaagct gaccgtccta                                      330


<210> SEQ ID NO 44
<211> LENGTH: 110
<212> TYPE: PRT
<213> ORGANISM: Artificial Sequence
<220> FEATURE:
<223> OTHER INFORMATION: 51A12_A6 VL-Synthetic peptide

<400> SEQUENCE: 44

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Thr Tyr Ser Tyr Asn Arg
                85                  90                  95

Ala Val Arg Asn Phe Gly Gly Gly Thr Lys Leu Thr Val Leu
            100                 105                 110


<210> SEQ ID NO 45
<211> LENGTH: 330
<212> TYPE: DNA
<213> ORGANISM: Artificial Sequence
<220> FEATURE:
<223> OTHER INFORMATION: 51A12_D1 VL-Synthetic oligonucleotide

<400> SEQUENCE: 45

tcgtctgagc tgactcagga ccctgctgtg tctgtggcct tgggacagac agtcaggatc     60

acatgccaag gagacagcct cagaagttat tatgcaagct ggtaccagca gaagccagga    120

caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactcccgt acttactctt acaaccgtgc tgttcgtccg    300

ttcggcggag ggaccaagct gaccgtccta                                      330


<210> SEQ ID NO 46
<211> LENGTH: 110
<212> TYPE: PRT
<213> ORGANISM: Artificial Sequence
<220> FEATURE:
<223> OTHER INFORMATION: 51A12_D1 VL-Synthetic peptide

<400> SEQUENCE: 46

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30
```

-continued

```
Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Thr Tyr Ser Tyr Asn Arg
                85                  90                  95

Ala Val Arg Pro Phe Gly Gly Gly Thr Lys Leu Thr Val Leu
            100                 105                 110


<210> SEQ ID NO 47
<211> LENGTH: 330
<212> TYPE: DNA
<213> ORGANISM: Artificial Sequence
<220> FEATURE:
<223> OTHER INFORMATION: 51A12_H6 VL-Synthetic oligonucleotide

<400> SEQUENCE: 47

tcgtctgagc tgactcagga ccctgctgtg tctgtggcct tgggacagac agtcaggatc      60

acatgccaag gagacagcct cagaagttat tatgcaagct ggtaccagca gaagccagga     120

caggcccctg tacttgtcat ctatggtaaa aacaaccggc cctcagggat cccagaccga     180

ttctctggct ccagctcagg aaacacagct tccttgacca tcactggggc tcaggcggaa     240

gatgaggctg actattactg taactcccgc gactacaaat ggaaccgtgt tgttcgtcat     300

ttcggcggag ggaccaagct gaccgtccta                                      330


<210> SEQ ID NO 48
<211> LENGTH: 110
<212> TYPE: PRT
<213> ORGANISM: Artificial Sequence
<220> FEATURE:
<223> OTHER INFORMATION: 51A12_H6 VL-Synthetic peptide

<400> SEQUENCE: 48

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Tyr Lys Trp Asn Arg
                85                  90                  95

Val Val Arg His Phe Gly Gly Gly Thr Lys Leu Thr Val Leu
            100                 105                 110


<210> SEQ ID NO 49
<211> LENGTH: 330
<212> TYPE: DNA
<213> ORGANISM: Artificial Sequence
<220> FEATURE:
<223> OTHER INFORMATION: 51A12 LC-Synthetic oligonucleotide

<400> SEQUENCE: 49

tcgtctgagc tgactcagga ccctgctgtg tctgtggcct tgggacagac agtcaggatc      60
```

acatgccaag gagacagcct cagaagttat tatgcaagct ggtaccagca gaagccagga 120
caggcccctg tacttgtcat ctatggtaaa aacaaccggc cctcagggat cccagaccga 180
ttctctgcct ccagctcagg aaacacagct tccttgacca tcactggggc tcaggcggaa 240
gatgaggctg actattactg taactcccgt gatatttgtt gtaatcgatc tgtgcgtaat 300
ttcggcggag ggaccaagct gaccgtccta 330

<210> SEQ ID NO 50
<211> LENGTH: 216
<212> TYPE: PRT
<213> ORGANISM: Artificial Sequence
<220> FEATURE:
<223> OTHER INFORMATION: 51A12 LC-Synthetic peptide

<400> SEQUENCE: 50

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Asp Arg Phe Ser Ala Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Ile Cys Cys Asn Arg
85 90 95

Ser Val Arg Asn Phe Gly Gly Gly Thr Lys Leu Thr Val Leu Gly Gln
100 105 110

Pro Lys Ala Ala Pro Ser Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Ser Ser Pro Val Lys
145 150 155 160

Ala Gly Val Glu Thr Thr Thr Pro Ser Lys Gln Ser Asn Asn Lys Tyr
165 170 175

Ala Ala Ser Ser Tyr Leu Ser Leu Thr Pro Glu Gln Trp Lys Ser His
180 185 190

Arg Ser Tyr Ser Cys Gln Val Thr His Glu Gly Ser Thr Val Glu Lys
195 200 205

Thr Val Ala Pro Thr Glu Cys Ser
210 215

<210> SEQ ID NO 51
<211> LENGTH: 1881
<212> TYPE: DNA
<213> ORGANISM: Artificial Sequence
<220> FEATURE:
<223> OTHER INFORMATION: 51A12 HC (knob)-Synthetic oligonucleotide

<400> SEQUENCE: 51
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180

-continued

```
gcagactccg tgaagggccg gttcaccatc tccagagaca attccaagaa cacgctgtat     240
ctgcagatga acagcctgag agccgaggac acggccgtat attactgtgc gaaaccgtac     300
ctgggttaca ctattgacta ctggggccaa ggaaccctgg tcaccgtctc gagtgctagc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct tgggcaccca gacctacatc     600
tgcaacgtga atcacaagcc cagcaacacc aaggtggaca agaaagttga gcccaaatct     660
tgtgacaaaa ctcacacatg cccaccgtgc ccagcacctg aagctgcagg gggaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca aagccgcggg aggagcagta caacagcacg     900
taccgtgtgg tcagcgtcct caccgtcctg caccaggact ggctgaatgg caaggagtac     960
aagtgcaagg tctccaacaa agccctcggc gcccccatcg agaaaaccat ctccaaagcc    1020
aaagggcagc cccgagaacc acaggtgtac accctgcccc catgccggga tgagctgacc    1080
aagaaccagg tcagcctgtg gtgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg tggcggcgga ggctccggag gcggaggatc tggcggcgga    1380
ggcagctgtg acctgcctca gacacacagc ctgggcagcc ggcggaccct gatgctgctg    1440
gcccagatgc ggaagatcag cctgttcagc tgcctgaagg accggcacga cttcggcttc    1500
cctcaggaag agttcggcaa ccagttccag aaggccgaga caatccccgt gctgcacgag    1560
atgatccagc agattttcaa cctgttcagc accaaggaca gcagcgccgc ctgggacgag    1620
acactgctgg acaagttcta caccgagctg taccagcagc tgaacgacct ggaagcctgc    1680
gtgatccagg gcgtgggcgt gaccgagaca cccctgatga aggaagatag catcctggcc    1740
gtgcggaagt atttccagcg gatcaccctg tacctgaaag agaagaagta cagcccctgc    1800
gcctgggagg tcgtgcgggc cgagatcatg cggagcttca gcctgagcac caacctgcag    1860
gaaagcctgc ggagcaaaga g                                               1881
```

<210> SEQ ID NO 52
<211> LENGTH: 627
<212> TYPE: PRT
<213> ORGANISM: Artificial Sequence
<220> FEATURE:
<223> OTHER INFORMATION: 51A12 HC (knob)-Synthetic peptide

<400> SEQUENCE: 52

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Tyr Leu Gly Tyr Thr Ile Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Arg Asp Glu Leu Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445

Gly Gly Gly Ser Gly Gly Gly Gly Ser Gly Gly Gly Gly Ser Cys Asp
    450                 455                 460

Leu Pro Gln Thr His Ser Leu Gly Ser Arg Arg Thr Leu Met Leu Leu
465                 470                 475                 480
```

-continued

```
Ala Gln Met Arg Lys Ile Ser Leu Phe Ser Cys Leu Lys Asp Arg His
                485                 490                 495

Asp Phe Gly Phe Pro Gln Glu Glu Phe Gly Asn Gln Phe Gln Lys Ala
            500                 505                 510

Glu Thr Ile Pro Val Leu His Glu Met Ile Gln Gln Ile Phe Asn Leu
        515                 520                 525

Phe Ser Thr Lys Asp Ser Ser Ala Ala Trp Asp Glu Thr Leu Leu Asp
    530                 535                 540

Lys Phe Tyr Thr Glu Leu Tyr Gln Gln Leu Asn Asp Leu Glu Ala Cys
545                 550                 555                 560

Val Ile Gln Gly Val Gly Val Thr Glu Thr Pro Leu Met Lys Glu Asp
                565                 570                 575

Ser Ile Leu Ala Val Arg Lys Tyr Phe Gln Arg Ile Thr Leu Tyr Leu
            580                 585                 590

Lys Glu Lys Lys Tyr Ser Pro Cys Ala Trp Glu Val Val Arg Ala Glu
        595                 600                 605

Ile Met Arg Ser Phe Ser Leu Ser Thr Asn Leu Gln Glu Ser Leu Arg
    610                 615                 620

Ser Lys Glu
625


<210> SEQ ID NO 53
<211> LENGTH: 1344
<212> TYPE: DNA
<213> ORGANISM: Artificial Sequence
<220> FEATURE:
<223> OTHER INFORMATION: 51A12 HC (hole)-Synthetic oligonucleotide

<400> SEQUENCE: 53

gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaaccgtac    300

ctgggttaca ctattgacta ctggggccaa ggaaccctgg tcaccgtctc gagtgctagc    360

accaagggcc cctccgtgtt cccccctggcc cccagcagca agagcaccag cggcggcaca    420

gccgctctgg gctgcctggt caaggactac ttccccgagc ccgtgaccgt gtcctggaac    480

agcggagccc tgacctccgg cgtgcacacc ttccccgccg tgctgcagag ttctggcctg    540

tatagcctga gcagcgtggt caccgtgcct tctagcagcc tgggcaccca gacctacatc    600

tgcaacgtga accacaagcc cagcaacacc aaggtggaca agaaggtgga gcccaagagc    660

tgcgacaaaa ctcacacatg cccaccgtgc ccagcacctg aagctgcagg gggaccgtca    720

gtcttcctct tcccccccaaa acccaaggac accctcatga tctcccggac ccctgaggtc    780

acatgcgtgg tggtggacgt gagccacgaa gaccctgagg tcaagttcaa ctggtacgtg    840

gacggcgtgg aggtgcataa tgccaagaca aagccgcggg aggagcagta caacagcacg    900

taccgtgtgg tcagcgtcct caccgtcctg caccaggact ggctgaatgg caaggagtac    960

aagtgcaagg tctccaacaa agccctcggc gcccccatcg agaaaaccat ctccaaagcc   1020

aaagggcagc cccgagaacc acaggtgtgc accctgcccc catcccggga tgagctgacc   1080

aagaaccagg tcagcctctc gtgcgcagtc aaaggcttct atcccagcga catcgccgtg   1140

gagtgggaga gcaatgggca gccggagaac aactacaaga ccacgcctcc cgtgctggac   1200
```

```
tccgacggct ccttcttcct cgtgagcaag ctcaccgtgg acaagagcag gtggcagcag   1260

gggaacgtct tctcatgctc cgtgatgcat gaggctctgc acaaccacta cacgcagaag   1320

agcctctccc tgtctccggg taaa                                          1344


<210> SEQ ID NO 54
<211> LENGTH: 448
<212> TYPE: PRT
<213> ORGANISM: Artificial Sequence
<220> FEATURE:
<223> OTHER INFORMATION: 51A12 HC (hole)-Synthetic peptide

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Tyr Leu Gly Tyr Thr Ile Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335
```

```
Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 55
<211> LENGTH: 642
<212> TYPE: DNA
<213> ORGANISM: Artificial Sequence
<220> FEATURE:
<223> OTHER INFORMATION: 52C4 LC-Synthetic oligonucleotide

<400> SEQUENCE: 55

tcgtctgagc tgactcagga ccctgctgtg tctgtggcct tgggacagac agtcaggatc      60

acatgccaag gagacagcct cagaagttat tatgcaagct ggtaccagca gaagccagga     120

caggcccctg tacttgtcat ctatggtaaa aacaaccggc cctcagggat cccagaccga     180

ttctctggct ccagctcagg aaacacagct tccttgacca tcactggggc tcaggcggaa     240

gatgaggctg actattactg taactccggt gctagtagcg gtaatcagtt ggtattcggc     300

ggagggacca agctgaccgt cctaggtcaa cccaaggctg cccccagcgt gaccctgttc     360

ccccccagca gcgaggaact gcaggccaac aaggccaccc tggtctgcct gatcagcgac     420

ttctacccag gcgccgtgac cgtggcctgg aaggccgaca gcagccccgt gaaggccggc     480

gtggagacca ccaccccag caagcagagc aacaacaagt acgccgccag cagctacctg      540

agcctgaccc ccgagcagtg gaagagccac aggtcctaca gctgccaggt gacccacgag     600

ggcagcaccg tggagaaaac cgtggccccc accgagtgca gc                        642


<210> SEQ ID NO 56
<211> LENGTH: 214
<212> TYPE: PRT
<213> ORGANISM: Artificial Sequence
<220> FEATURE:
<223> OTHER INFORMATION: 52C4 LC-Synthetic peptide

<400> SEQUENCE: 56

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80
```

-continued

```
Asp Glu Ala Asp Tyr Tyr Cys Asn Ser Gly Ala Ser Ser Gly Asn Gln
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 57
<211> LENGTH: 1887
<212> TYPE: DNA
<213> ORGANISM: Artificial Sequence
<220> FEATURE:
<223> OTHER INFORMATION: 52C4 HC (knob)-Synthetic oligonucleotide

<400> SEQUENCE: 57

gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agtcgaggac acggccgtat attactgtgc gaaaccggct    300

ggttactctt acggttactt cgactactgg ggccaaggaa ccctggtcac cgtctcgagt    360

gctagcacca agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagaa agttgagccc    660

aaatcttgtg acaaaactca cacatgccca ccgtgcccag cacctgaagc tgcagggggga    720

ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgcgggagga gcagtacaac    900

agcacgtacc gtgtggtcag cgtcctcacc gtcctgcacc aggactggct gaatggcaag    960

gagtacaagt gcaaggtctc caacaaagcc ctcggcgccc ccatcgagaa aaccatctcc   1020

aaagccaaag ggcagccccg agaaccacag gtgtacaccc tgcccccatg ccgggatgag   1080

ctgaccaaga accaggtcag cctgtggtgc ctggtcaaag gcttctatcc cagcgacatc   1140

gccgtggagt gggagagcaa tgggcagccg gagaacaact acaagaccac gcctcccgtg   1200

ctggactccg acggctcctt cttcctctac agcaagctca ccgtggacaa gagcaggtgg   1260
```

```
cagcagggga acgtcttctc atgctccgtg atgcatgagg ctctgcacaa ccactacacg   1320

cagaagagcc tctccctgtc tccgggtggc ggcggaggct ccggaggcgg aggatctggc   1380

ggcggaggca gctgtgacct gcctcagaca cacagcctgg gcagccggcg gaccctgatg   1440

ctgctggccc agatgcggaa gatcagcctg ttcagctgcc tgaaggaccg gcacgacttc   1500

ggcttccctc aggaagagtt cggcaaccag ttccagaagg ccgagacaat ccccgtgctg   1560

cacgagatga tccagcagat tttcaacctg ttcagcacca aggacagcag cgccgcctgg   1620

gacgagacac tgctggacaa gttctacacc gagctgtacc agcagctgaa cgacctggaa   1680

gcctgcgtga tccagggcgt gggcgtgacc gagacacccc tgatgaagga agatagcatc   1740

ctggccgtgc ggaagtattt ccagcggatc accctgtacc tgaaagagaa gaagtacagc   1800

ccctgcgcct gggaggtcgt gcgggccgag atcatgcgga gcttcagcct gagcaccaac   1860

ctgcaggaaa gcctgcggag caaagag                                       1887
```

<210> SEQ ID NO 58
<211> LENGTH: 629
<212> TYPE: PRT
<213> ORGANISM: Artificial Sequence
<220> FEATURE:
<223> OTHER INFORMATION: 52C4 HC (knob)-Synthetic peptide

<400> SEQUENCE: 58

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Pro Ala Gly Tyr Ser Tyr Gly Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Gly Ser Gly Gly Gly Gly Ser Gly Gly Gly Gly Ser
    450                 455                 460

Cys Asp Leu Pro Gln Thr His Ser Leu Gly Ser Arg Arg Thr Leu Met
465                 470                 475                 480

Leu Leu Ala Gln Met Arg Lys Ile Ser Leu Phe Ser Cys Leu Lys Asp
                485                 490                 495

Arg His Asp Phe Gly Phe Pro Gln Glu Glu Phe Gly Asn Gln Phe Gln
            500                 505                 510

Lys Ala Glu Thr Ile Pro Val Leu His Glu Met Ile Gln Gln Ile Phe
        515                 520                 525

Asn Leu Phe Ser Thr Lys Asp Ser Ser Ala Ala Trp Asp Glu Thr Leu
    530                 535                 540

Leu Asp Lys Phe Tyr Thr Glu Leu Tyr Gln Gln Leu Asn Asp Leu Glu
545                 550                 555                 560

Ala Cys Val Ile Gln Gly Val Gly Val Thr Glu Thr Pro Leu Met Lys
                565                 570                 575

Glu Asp Ser Ile Leu Ala Val Arg Lys Tyr Phe Gln Arg Ile Thr Leu
            580                 585                 590

Tyr Leu Lys Glu Lys Lys Tyr Ser Pro Cys Ala Trp Glu Val Val Arg
        595                 600                 605

Ala Glu Ile Met Arg Ser Phe Ser Leu Ser Thr Asn Leu Gln Glu Ser
    610                 615                 620

Leu Arg Ser Lys Glu
625
```

<210> SEQ ID NO 59
<211> LENGTH: 1350
<212> TYPE: DNA
<213> ORGANISM: Artificial Sequence
<220> FEATURE:

<223> OTHER INFORMATION: 52C4 HC (hole)-Synthetic oligonucleotide

<400> SEQUENCE: 59

```
gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agtcgaggac acggccgtat attactgtgc gaaaccggct    300

ggttactctt acggttactt cgactactgg ggccaaggaa ccctggtcac cgtctcgagt    360

gctagcacca agggcccctc cgtgttcccc ctggccccca gcagcaagag caccagcggc    420

ggcacagccg ctctgggctg cctggtcaag gactacttcc ccgagcccgt gaccgtgtcc    480

tggaacagcg gagccctgac ctccggcgtg cacaccttcc ccgccgtgct gcagagttct    540

ggcctgtata gcctgagcag cgtggtcacc gtgccttcta gcagcctggg cacccagacc    600

tacatctgca acgtgaacca caagcccagc aacaccaagg tggacaagaa ggtggagccc    660

aagagctgcg acaaaactca cacatgccca ccgtgcccag cacctgaagc tgcaggggga    720

ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgcgggagga gcagtacaac    900

agcacgtacc gtgtggtcag cgtcctcacc gtcctgcacc aggactggct gaatggcaag    960

gagtacaagt gcaaggtctc caacaaagcc ctcggcgccc ccatcgagaa aaccatctcc   1020

aaagccaaag ggcagccccg agaaccacag gtgtgcaccc tgcccccatc ccgggatgag   1080

ctgaccaaga accaggtcag cctctcgtgc gcagtcaaag gcttctatcc cagcgacatc   1140

gccgtggagt gggagagcaa tgggcagccg gagaacaact acaagaccac gcctcccgtg   1200

ctggactccg acggctcctt cttcctcgtg agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtaaa                                    1350
```

<210> SEQ ID NO 60
<211> LENGTH: 450
<212> TYPE: PRT
<213> ORGANISM: Artificial Sequence
<220> FEATURE:
<223> OTHER INFORMATION: 52C4 HC (hole)-Synthetic peptide

<400> SEQUENCE: 60

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Pro Ala Gly Tyr Ser Tyr Gly Tyr Phe Asp Tyr Trp Gly Gln
```

```
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 61
<211> LENGTH: 642
<212> TYPE: DNA
<213> ORGANISM: Artificial Sequence
<220> FEATURE:
<223> OTHER INFORMATION: 5A4 LC-Synthetic oligonucleotide

<400> SEQUENCE: 61

tcgtctgagc tgactcagga ccctgctgtg tctgtggcct tgggacagac agtcaggatc     60
```

-continued

```
acatgccaag gagacagcct cagaagttat tatgcaagct ggtaccagca gaagccagga    120

caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactcccgt ttgaggagcg ggaagatggt ggtattcggc    300

ggagggacca agctgaccgt cctaggtcaa cccaaggctg cccccagcgt gaccctgttc    360

ccccccagca gcgaggaact gcaggccaac aaggccaccc tggtctgcct gatcagcgac    420

ttctacccag gcgccgtgac cgtggcctgg aaggccgaca gcagccccgt gaaggccggc    480

gtggagacca ccacccccag caagcagagc aacaacaagt acgccgccag cagctacctg    540

agcctgaccc ccgagcagtg gaagagccac aggtcctaca gctgccaggt gacccacgag    600

ggcagcaccg tggagaaaac cgtggccccc accgagtgca gc                       642
```

<210> SEQ ID NO 62
<211> LENGTH: 214
<212> TYPE: PRT
<213> ORGANISM: Artificial Sequence
<220> FEATURE:
<223> OTHER INFORMATION: 5A4 LC-Synthetic peptide

<400> SEQUENCE: 62

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Leu Arg Ser Gly Lys Met
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 63
<211> LENGTH: 1892
<212> TYPE: DNA
<213> ORGANISM: Artificial Sequence
<220> FEATURE:

<223> OTHER INFORMATION: 5A4 HC (knob)-Synthetic oligonucleotide

<400> SEQUENCE: 63
cattcggagg tgcaattgtt ggagtctggg ggaggcttgg tacagcctgg ggggtccctg 60
agactctcct gtgcagcctc cggattcacc tttagcagtt atgccatgag ctgggtccgc 120
caggctccag ggaaggggct ggagtgggtc tcagctatta gtggtagtgg tggtagcaca 180
tactacgcag actccgtgaa gggccggttc accatctcca gagacaattc caagaacacg 240
ctgtatctgc agatgaacag cctgagagcc gaggacacgg ccgtatatta ctgtgcgaaa 300
agttggtacc tgccgggtcg tggtttcgac tactggggcc aaggaaccct ggtcaccgtc 360
tcgagtgcta gcaccaaggg cccatcggtc ttccccctgg caccctcctc caagagcacc 420
tctgggggca cagcggccct gggctgcctg gtcaaggact acttccccga accggtgacg 480
gtgtcgtgga actcaggcgc cctgaccagc ggcgtgcaca ccttcccggc tgtcctacag 540
tcctcaggac tctactccct cagcagcgtg gtgaccgtgc cctccagcag cttgggcacc 600
cagacctaca tctgcaacgt gaatcacaag cccagcaaca ccaaggtgga caagaaagtt 660
gagcccaaat cttgtgacaa aactcacaca tgcccaccgt gcccagcacc tgaagctgca 720
gggggaccgt cagtcttcct cttcccccca aaacccaagg acaccctcat gatctcccgg 780
acccctgagg tcacatgcgt ggtggtggac gtgagccacg aagaccctga ggtcaagttc 840
aactggtacg tggacggcgt ggaggtgcat aatgccaaga caaagccgcg ggaggagcag 900
tacaacagca cgtaccgtgt ggtcagcgtc ctcaccgtcc tgcaccagga ctggctgaat 960
ggcaaggagt acaagtgcaa ggtctccaac aaagccctcg gcgcccccat cgagaaaacc 1020
atctccaaag ccaaagggca gccccgagaa ccacaggtgt acaccctgcc cccatgccgg 1080
gatgagctga ccaagaacca ggtcagcctg tggtgcctgg tcaaaggctt ctatcccagc 1140
gacatcgccg tggagtggga gagcaatggg cagccggaga acaactacaa gaccacgcct 1200
cccgtgctgg actccgacgg ctccttcttc ctctacagca agctcaccgt ggacaagagc 1260
aggtggagca ggggaacgtc ttctcatgct ccgtgatgca tgaggctctg cacaaccact 1320
acacgcagaa gagcctctcc ctgtctccgg gtggcggcgg aggctccgga ggcggaggat 1380
ctggcggcgg aggcagctgt gacctgcctc agacacacag cctgggcagc cggcggaccc 1440
tgatgctgct ggcccagatg cggaagatca gcctgttcag ctgcctgaag gaccggcacg 1500
acttcggctt ccctcaggaa gagttcggca accagttcca gaaggccgag acaatccccg 1560
tgctgcacga gatgatccag cagattttca acctgttcag caccaaggac agcagcgccg 1620
cctgggacga gacactgctg gacaagttct acaccgagct gtaccagcag ctgaacgacc 1680
tggaagcctg cgtgatccag ggcgtgggcg tgaccgagac acccctgatg aaggaagata 1740
gcatcctggc cgtgcggaag tatttccagc ggatcaccct gtacctgaaa gagaagaagt 1800
acagcccctg cgcctgggag gtcgtgcggg ccgagatcat gcggagcttc agcctgagca 1860
ccaacctgca ggaaagcctg cggagcaaag ag 1892

<210> SEQ ID NO 64
<211> LENGTH: 629
<212> TYPE: PRT
<213> ORGANISM: Artificial Sequence
<220> FEATURE:
<223> OTHER INFORMATION: 5A4 HC (knob)-Synthetic peptide

<400> SEQUENCE: 64

Glu Val Gln Leu Leu Glu Ser Gly Gly Gly Leu Val Gln Pro Gly Gly

-continued

```
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Tyr Leu Pro Gly Arg Gly Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

Glu Ala Leu His Asn His Tyr Thr Gln Lys Ser Leu Ser Leu Ser Pro
435 440 445

Gly Gly Gly Gly Gly Ser Gly Gly Gly Gly Ser Gly Gly Gly Gly Ser
450 455 460

Cys Asp Leu Pro Gln Thr His Ser Leu Gly Ser Arg Arg Thr Leu Met
465 470 475 480

Leu Leu Ala Gln Met Arg Lys Ile Ser Leu Phe Ser Cys Leu Lys Asp
485 490 495

Arg His Asp Phe Gly Phe Pro Gln Glu Glu Phe Gly Asn Gln Phe Gln
500 505 510

Lys Ala Glu Thr Ile Pro Val Leu His Glu Met Ile Gln Gln Ile Phe
515 520 525

Asn Leu Phe Ser Thr Lys Asp Ser Ser Ala Ala Trp Asp Glu Thr Leu
530 535 540

Leu Asp Lys Phe Tyr Thr Glu Leu Tyr Gln Gln Leu Asn Asp Leu Glu
545 550 555 560

Ala Cys Val Ile Gln Gly Val Gly Val Thr Glu Thr Pro Leu Met Lys
565 570 575

Glu Asp Ser Ile Leu Ala Val Arg Lys Tyr Phe Gln Arg Ile Thr Leu
580 585 590

Tyr Leu Lys Glu Lys Lys Tyr Ser Pro Cys Ala Trp Glu Val Val Arg
595 600 605

Ala Glu Ile Met Arg Ser Phe Ser Leu Ser Thr Asn Leu Gln Glu Ser
610 615 620

Leu Arg Ser Lys Glu
625

<210> SEQ ID NO 65
<211> LENGTH: 1350
<212> TYPE: DNA
<213> ORGANISM: Artificial Sequence
<220> FEATURE:
<223> OTHER INFORMATION: 5A4 HC (hole)-Synthetic oligonucleotide

<400> SEQUENCE: 65
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaaagttgg 300
tacctgccgg gtcgtggttt cgactactgg ggccaaggaa ccctggtcac cgtctcgagt 360
gctagcacca agggcccctc cgtgttcccc ctggcccccca gcagcaagag caccagcggc 420
ggcacagccg ctctgggctg cctggtcaag gactacttcc ccgagcccgt gaccgtgtcc 480
tggaacagcg gagccctgac ctccggcgtg cacaccttcc ccgccgtgct gcagagttct 540
ggcctgtata gcctgagcag cgtggtcacc gtgccttcta gcagcctggg cacccagacc 600
tacatctgca acgtgaacca caagcccagc aacaccaagg tggacaagaa ggtggagccc 660
aagagctgcg acaaaactca cacatgccca ccgtgcccag cacctgaagc tgcagggggga 720 ccgtcagtct tcctcttccc cccaaaaccc aaggacaccc tcatgatctc ccggacccct 780
gaggtcacat gcgtggtggt ggacgtgagc cacgaagacc ctgaggtcaa gttcaactgg 840
tacgtggacg gcgtggaggt gcataatgcc aagacaaagc cgcgggagga gcagtacaac 900

-continued

```
agcacgtacc gtgtggtcag cgtcctcacc gtcctgcacc aggactggct gaatggcaag    960

gagtacaagt gcaaggtctc caacaaagcc ctcggcgccc ccatcgagaa aaccatctcc   1020

aaagccaaag ggcagccccg agaaccacag gtgtgcaccc tgcccccatc ccgggatgag   1080

ctgaccaaga accaggtcag cctctcgtgc gcagtcaaag gcttctatcc cagcgacatc   1140

gccgtggagt gggagagcaa tgggcagccg gagaacaact acaagaccac gcctcccgtg   1200

ctggactccg acggctcctt cttcctcgtg agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtaaa                                     1350
```

<210> SEQ ID NO 66
<211> LENGTH: 450
<212> TYPE: PRT
<213> ORGANISM: Artificial Sequence
<220> FEATURE:
<223> OTHER INFORMATION: 5A4 HC (hole)-Synthetic peptide

<400> SEQUENCE: 66

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Trp Tyr Leu Pro Gly Arg Gly Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
```

-continued

```
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 67
<211> LENGTH: 645
<212> TYPE: DNA
<213> ORGANISM: Artificial Sequence
<220> FEATURE:
<223> OTHER INFORMATION: 4F3 LC-Synthetic oligonucleotide

<400> SEQUENCE: 67

tcgtctgagc tgactcagga ccctgctgtg tctgtggcct tgggacagac agtcaggatc     60

acatgccaag gagacagcct cagaagttat tatgcaagct ggtaccagca gaagccagga    120

caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactccctg gagaggatcg ggtatctttc ttatgtattc    300

ggcggaggga ccaagctgac cgtcctaggt caacccaagg ctgcccccag cgtgaccctg    360

ttccccccca gcagcgagga actgcaggcc aacaaggcca ccctggtctg cctgatcagc    420

gacttctacc caggcgccgt gaccgtggcc tggaaggccg acagcagccc cgtgaaggcc    480

ggcgtggaga ccaccacccc cagcaagcag agcaacaaca agtacgccgc cagcagctac    540

ctgagcctga cccccgagca gtggaagagc cacaggtcct acagctgcca ggtgacccac    600

gagggcagca ccgtggagaa aaccgtggcc cccaccgagt gcagc                    645


<210> SEQ ID NO 68
<211> LENGTH: 215
<212> TYPE: PRT
<213> ORGANISM: Artificial Sequence
<220> FEATURE:
<223> OTHER INFORMATION: 4F3 LC-Synthetic peptide

<400> SEQUENCE: 68

Ser Ser Glu Leu Thr Gln Asp Pro Ala Val Ser Val Ala Leu Gly Gln
1               5                   10                  15
```

```
Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Leu Glu Arg Ile Gly Tyr Leu
                85                  90                  95

Ser Tyr Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 69
<211> LENGTH: 1887
<212> TYPE: DNA
<213> ORGANISM: Artificial Sequence
<220> FEATURE:
<223> OTHER INFORMATION: 4F3 HC (knob)-Synthetic oligonucleotide

<400> SEQUENCE: 69

gaggtgcaat tgttggagtc tgggggaggc ttggtacagc ctggggggtc cctgagactc      60

tcctgtgcag cctccggatt cacctttagc agttatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcagatga acagcctgag agccgaggac acggccgtat attactgtgc gaaagacttc     300

tcttctcgtc gttggtacct ggaatactgg ggccaaggaa ccctggtcac cgtctcgagt     360

gctagcacca agggcccatc ggtcttcccc ctggcaccct cctccaagag cacctctggg     420

ggcacagcgg ccctgggctg cctggtcaag gactacttcc ccgaaccggt gacggtgtcg     480

tggaactcag gcgccctgac cagcggcgtg cacaccttcc cggctgtcct acagtcctca     540

ggactctact ccctcagcag cgtggtgacc gtgccctcca gcagcttggg cacccagacc     600

tacatctgca acgtgaatca caagcccagc aacaccaagg tggacaagaa agttgagccc     660

aaatcttgtg acaaaactca cacatgccca ccgtgcccag cacctgaagc tgcaggggga     720

ccgtcagtct tcctcttccc cccaaaaccc aaggacaccc tcatgatctc ccggacccct     780

gaggtcacat gcgtggtggt ggacgtgagc cacgaagacc ctgaggtcaa gttcaactgg     840

tacgtggacg gcgtggaggt gcataatgcc aagacaaagc cgcgggagga gcagtacaac     900
```

-continued agcacgtacc gtgtggtcag cgtcctcacc gtcctgcacc aggactggct gaatggcaag 960
gagtacaagt gcaaggtctc caacaaagcc ctcggcgccc ccatcgagaa aaccatctcc 1020
aaagccaaag ggcagccccg agaaccacag gtgtacaccc tgcccccatg ccgggatgag 1080
ctgaccaaga accaggtcag cctgtggtgc ctggtcaaag gcttctatcc cagcgacatc 1140
gccgtggagt gggagagcaa tgggcagccg gagaacaact acaagaccac gcctcccgtg 1200
ctggactccg acggctcctt cttcctctac agcaagctca ccgtggacaa gagcaggtgg 1260
cagcagggga acgtcttctc atgctccgtg atgcatgagg ctctgcacaa ccactacacg 1320
cagaagagcc tctccctgtc tccgggtggc ggcggaggct ccggaggcgg aggatctggc 1380
ggcggaggca gctgtgacct gcctcagaca cacagcctgg gcagccggcg gaccctgatg 1440
ctgctggccc agatgcggaa gatcagcctg ttcagctgcc tgaaggaccg gcacgacttc 1500
ggcttccctc aggaagagtt cggcaaccag ttccagaagg ccgagacaat ccccgtgctg 1560
cacgagatga tccagcagat tttcaacctg ttcagcacca aggacagcag cgccgcctgg 1620
gacgagacac tgctggacaa gttctacacc gagctgtacc agcagctgaa cgacctggaa 1680
gcctgcgtga tccagggcgt gggcgtgacc gagacacccc tgatgaagga agatagcatc 1740
ctggccgtgc ggaagtattt ccagcggatc accctgtacc tgaaagagaa gaagtacagc 1800
ccctgcgcct gggaggtcgt gcgggccgag atcatgcgga gcttcagcct gagcaccaac 1860
ctgcaggaaa gcctgcggag caaagag 1887

<210> SEQ ID NO 70
<211> LENGTH: 629
<212> TYPE: PRT
<213> ORGANISM: Artificial Sequence
<220> FEATURE:
<223> OTHER INFORMATION: 4F3 HC (knob)-Synthetic peptide

<400> SEQUENCE: 70

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Phe Ser Ser Arg Arg Trp Tyr Leu Glu Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro

-continued

```
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Gly Ser Gly Gly Gly Gly Ser Gly Gly Gly Gly Ser
    450                 455                 460

Cys Asp Leu Pro Gln Thr His Ser Leu Gly Ser Arg Arg Thr Leu Met
465                 470                 475                 480

Leu Leu Ala Gln Met Arg Lys Ile Ser Leu Phe Ser Cys Leu Lys Asp
                485                 490                 495

Arg His Asp Phe Gly Phe Pro Gln Glu Glu Phe Gly Asn Gln Phe Gln
            500                 505                 510

Lys Ala Glu Thr Ile Pro Val Leu His Glu Met Ile Gln Gln Ile Phe
        515                 520                 525

Asn Leu Phe Ser Thr Lys Asp Ser Ser Ala Ala Trp Asp Glu Thr Leu
    530                 535                 540

Leu Asp Lys Phe Tyr Thr Glu Leu Tyr Gln Gln Leu Asn Asp Leu Glu
545                 550                 555                 560

Ala Cys Val Ile Gln Gly Val Gly Val Thr Glu Thr Pro Leu Met Lys
                565                 570                 575

Glu Asp Ser Ile Leu Ala Val Arg Lys Tyr Phe Gln Arg Ile Thr Leu
            580                 585                 590

Tyr Leu Lys Glu Lys Lys Tyr Ser Pro Cys Ala Trp Glu Val Val Arg
        595                 600                 605
```

```
Ala Glu Ile Met Arg Ser Phe Ser Leu Ser Thr Asn Leu Gln Glu Ser
    610                 615                 620

Leu Arg Ser Lys Glu
625
```

<210> SEQ ID NO 71
<211> LENGTH: 1350
<212> TYPE: DNA
<213> ORGANISM: Artificial Sequence
<220> FEATURE:
<223> OTHER INFORMATION: 4F3 HC (hole)-Synthetic oligonucleotide

<400> SEQUENCE: 71

```
gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaagacttc    300

tcttctcgtc gttggtacct ggaatactgg ggccaaggaa ccctggtcac cgtctcgagt    360

gctagcacca agggcccctc cgtgttcccc ctggccccca gcagcaagag caccagcggc    420

ggcacagccg ctctgggctg cctggtcaag gactacttcc ccgagcccgt gaccgtgtcc    480

tggaacagcg gagccctgac ctccggcgtg cacaccttcc ccgccgtgct gcagagttct    540

ggcctgtata gcctgagcag cgtggtcacc gtgccttcta gcagcctggg cacccagacc    600

tacatctgca acgtgaacca caagcccagc aacaccaagg tggacaagaa ggtggagccc    660

aagagctgcg acaaaactca cacatgccca ccgtgcccag cacctgaagc tgcaggggga    720

ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgcgggagga gcagtacaac    900

agcacgtacc gtgtggtcag cgtcctcacc gtcctgcacc aggactggct gaatggcaag    960

gagtacaagt gcaaggtctc caacaaagcc ctcggcgccc ccatcgagaa aaccatctcc   1020

aaagccaaag ggcagccccg agaaccacag gtgtgcaccc tgcccccatc ccgggatgag   1080

ctgaccaaga accaggtcag cctctcgtgc gcagtcaaag gcttctatcc cagcgacatc   1140

gccgtggagt gggagagcaa tgggcagccg gagaacaact acaagaccac gcctcccgtg   1200

ctggactccg acggctcctt cttcctcgtg agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtaaa                                    1350
```

<210> SEQ ID NO 72
<211> LENGTH: 450
<212> TYPE: PRT
<213> ORGANISM: Artificial Sequence
<220> FEATURE:
<223> OTHER INFORMATION: 4F3 HC (hole)-Synthetic peptide

<400> SEQUENCE: 72

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

-continued

```
Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ser Arg Arg Trp Tyr Leu Glu Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
```

450

<210> SEQ ID NO 73
<211> LENGTH: 639
<212> TYPE: DNA
<213> ORGANISM: Artificial Sequence
<220> FEATURE:
<223> OTHER INFORMATION: R5C2 L-Synthetic oligonucleotide

<400> SEQUENCE: 73
tcgtctgagc tgactcagga ccctgctgtg tctgtggcct tgggacagac agtcaggatc 60
acatgccaag gagacagcct cagaagttat tatgcaagct ggtaccagca gaagccagga 120
caggcccctg tacttgtcat ctatggtaaa aacaaccggc cctcagggat cccagaccga 180
ttctctggct ccagctcagg aaacacagct tccttgacca tcactggggc tcaggcggaa 240
gatgaggctg actattactg taactcccgg gatcgtagag gttattcggt attcggcgga 300
gggaccaagc tgaccgtcct aggtcaaccc aaggctgccc ccagcgtgac cctgttcccc 360
cccagcagcg aggaactgca ggccaacaag gccaccctgg tctgcctgat cagcgacttc 420
tacccaggcg ccgtgaccgt ggcctggaag gccgacagca gccccgtgaa ggccggcgtg 480
gagaccacca cccccagcaa gcagagcaac aacaagtacg ccgccagcag ctacctgagc 540
ctgacccccg agcagtggaa gagccacagg tcctacagct gccaggtgac ccacgagggc 600
agcaccgtgg agaaaaccgt ggcccccacc gagtgcagc 639

<210> SEQ ID NO 74
<211> LENGTH: 213
<212> TYPE: PRT
<213> ORGANISM: Artificial Sequence
<220> FEATURE:
<223> OTHER INFORMATION: R5C2 LC-Synthetic peptide

<400> SEQUENCE: 74

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Arg Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

Asp Glu Ala Asp Tyr Tyr Cys Asn Ser Arg Asp Arg Arg Gly Tyr Ser
85 90 95

Val Phe Gly Gly Gly Thr Lys Leu Thr Val Leu Gly Gln Pro Lys Ala
100 105 110

Ala Pro Ser Val Thr Leu Phe Pro Pro Ser Ser Glu Glu Leu Gln Ala
115 120 125

Asn Lys Ala Thr Leu Val Cys Leu Ile Ser Asp Phe Tyr Pro Gly Ala
130 135 140

Val Thr Val Ala Trp Lys Ala Asp Ser Ser Pro Val Lys Ala Gly Val
145 150 155 160

Glu Thr Thr Thr Pro Ser Lys Gln Ser Asn Asn Lys Tyr Ala Ala Ser
165 170 175

Ser Tyr Leu Ser Leu Thr Pro Glu Gln Trp Lys Ser His Arg Ser Tyr
180 185 190

```
Ser Cys Gln Val Thr His Glu Gly Ser Thr Val Glu Lys Thr Val Ala
        195                 200                 205

Pro Thr Glu Cys Ser
    210


<210> SEQ ID NO 75
<211> LENGTH: 1887
<212> TYPE: DNA
<213> ORGANISM: Artificial Sequence
<220> FEATURE:
<223> OTHER INFORMATION: R5C2 HC (knob)-Synthetic oligonucleotide

<400> SEQUENCE: 75

gaggtgcaat tgttggagtc tggggggaggc ttggtacagc ctggggggtc cctgagactc     60

tcctgtgcgg cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaatcttct    300

ttctcttacc tgcgtgcttt cgactactgg ggccaaggaa ccctggtcac cgtctcgagt    360

gctagcacca agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagaa agttgagccc    660

aaatcttgtg acaaaactca cacatgccca ccgtgcccag cacctgaagc tgcaggggga    720

ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgcgggagga gcagtacaac    900

agcacgtacc gtgtggtcag cgtcctcacc gtcctgcacc aggactggct gaatggcaag    960

gagtacaagt gcaaggtctc caacaaagcc ctcggcgccc ccatcgagaa aaccatctcc   1020

aaagccaaag ggcagccccg agaaccacag gtgtacaccc tgccccccatg ccgggatgag   1080

ctgaccaaga accaggtcag cctgtggtgc ctggtcaaag gcttctatcc cagcgacatc   1140

gccgtggagt gggagagcaa tgggcagccg gagaacaact acaagaccac gcctcccgtg   1200

ctggactccg acggctcctt cttcctctac agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtggc ggcggaggct ccggaggcgg aggatctggc   1380

ggcggaggca gctgtgacct gcctcagaca cacagcctgg gcagccggcg gaccctgatg   1440

ctgctggccc agatgcggaa gatcagcctg ttcagctgcc tgaaggaccg gcacgacttc   1500

ggcttccctc aggaagagtt cggcaaccag ttccagaagg ccgagacaat ccccgtgctg   1560

cacgagatga tccagcagat tttcaacctg ttcagcacca aggacagcag cgccgcctgg   1620

gacgagacac tgctggacaa gttctacacc gagctgtacc agcagctgaa cgacctggaa   1680

gcctgcgtga tccagggcgt gggcgtgacc gagacacccc tgatgaagga agatagcatc   1740

ctggccgtgc ggaagtattt ccagcggatc accctgtacc tgaaagagaa gaagtacagc   1800

ccctgcgcct gggaggtcgt gcgggccgag atcatgcgga gcttcagcct gagcaccaac   1860
```

ctgcaggaaa gcctgcggag caaagag 1887

<210> SEQ ID NO 76
<211> LENGTH: 629
<212> TYPE: PRT
<213> ORGANISM: Artificial Sequence
<220> FEATURE:
<223> OTHER INFORMATION: R5C2 HC (knob)-Synthetic peptide

<400> SEQUENCE: 76

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Phe Ser Tyr Leu Arg Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
```

```
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Gly Ser Gly Gly Gly Gly Ser Gly Gly Gly Gly Ser
    450                 455                 460

Cys Asp Leu Pro Gln Thr His Ser Leu Gly Ser Arg Arg Thr Leu Met
465                 470                 475                 480

Leu Leu Ala Gln Met Arg Lys Ile Ser Leu Phe Ser Cys Leu Lys Asp
                485                 490                 495

Arg His Asp Phe Gly Phe Pro Gln Glu Glu Phe Gly Asn Gln Phe Gln
            500                 505                 510

Lys Ala Glu Thr Ile Pro Val Leu His Glu Met Ile Gln Gln Ile Phe
        515                 520                 525

Asn Leu Phe Ser Thr Lys Asp Ser Ser Ala Ala Trp Asp Glu Thr Leu
    530                 535                 540

Leu Asp Lys Phe Tyr Thr Glu Leu Tyr Gln Gln Leu Asn Asp Leu Glu
545                 550                 555                 560

Ala Cys Val Ile Gln Gly Val Gly Val Thr Glu Thr Pro Leu Met Lys
                565                 570                 575

Glu Asp Ser Ile Leu Ala Val Arg Lys Tyr Phe Gln Arg Ile Thr Leu
            580                 585                 590

Tyr Leu Lys Glu Lys Lys Tyr Ser Pro Cys Ala Trp Glu Val Val Arg
        595                 600                 605

Ala Glu Ile Met Arg Ser Phe Ser Leu Ser Thr Asn Leu Gln Glu Ser
    610                 615                 620

Leu Arg Ser Lys Glu
625
```

<210> SEQ ID NO 77
<211> LENGTH: 1350
<212> TYPE: DNA
<213> ORGANISM: Artificial Sequence
<220> FEATURE:
<223> OTHER INFORMATION: R5C2 HC (hole)-Synthetic oligonucleotide

<400> SEQUENCE: 77

```
gaggtgcaat tgttggagtc tggggggaggc ttggtacagc ctggggggtc cctgagactc      60

tcctgtgcgg cctccggatt cacctttagc agttatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcagatga acagcctgag agccgaggac acggccgtat attactgtgc gaaatcttct     300

ttctcttacc tgcgtgcttt cgactactgg ggccaaggaa ccctggtcac cgtctcgagt     360

gctagcacca agggcccctc cgtgttcccc ctggccccca gcagcaagag caccagcggc     420

ggcacagccg ctctgggctg cctggtcaag gactacttcc ccgagcccgt gaccgtgtcc     480
```

-continued

```
tggaacagcg gagccctgac ctccggcgtg cacaccttcc ccgccgtgct gcagagttct    540

ggcctgtata gcctgagcag cgtggtcacc gtgccttcta gcagcctggg cacccagacc    600

tacatctgca acgtgaacca caagcccagc aacaccaagg tggacaagaa ggtggagccc    660

aagagctgcg acaaaactca cacatgccca ccgtgcccag cacctgaagc tgcagggga     720

ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgcgggagga gcagtacaac    900

agcacgtacc gtgtggtcag cgtcctcacc gtcctgcacc aggactggct gaatggcaag    960

gagtacaagt gcaaggtctc caacaaagcc ctcggcgccc ccatcgagaa aaccatctcc   1020

aaagccaaag ggcagccccg agaaccacag gtgtgcaccc tgcccccatc ccgggatgag   1080

ctgaccaaga accaggtcag cctctcgtgc gcagtcaaag gcttctatcc cagcgacatc   1140

gccgtggagt gggagagcaa tgggcagccg gagaacaact acaagaccac gcctcccgtg   1200

ctggactccg acggctcctt cttcctcgtg agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtaaa                                    1350
```

<210> SEQ ID NO 78
<211> LENGTH: 450
<212> TYPE: PRT
<213> ORGANISM: Artificial Sequence
<220> FEATURE:
<223> OTHER INFORMATION: R5C2 HC (hole)-Synthetic peptide

<400> SEQUENCE: 78

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Phe Ser Tyr Leu Arg Ala Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 79
<211> LENGTH: 639
<212> TYPE: DNA
<213> ORGANISM: Artificial Sequence
<220> FEATURE:
<223> OTHER INFORMATION: R9E10 LC-Synthetic oligonucleotide

<400> SEQUENCE: 79

tcgtctgagc tgactcagga ccctgctgtg tctgtggcct tgggacagac agtcaggatc      60

acatgccaag gagacagcct cagaagttat tatgcaagct ggtaccagca gaagccagga     120

caggcccctg tacttgtcat ctatggtaaa aacaaccggc cctcagggat cccagaccga     180

ttctctggct ccagctcagg aaacacagct tccttgacca tcactggggc tcaggcggaa     240

gatgaggctg actattactg taactcccgg aatgttcgcg gtaagctcgt attcggcgga     300

gggaccaagc tgaccgtcct aggtcaaccc aaggctgccc ccagcgtgac cctgttcccc     360

cccagcagcg aggaactgca ggccaacaag gccaccctgg tctgcctgat cagcgacttc     420

tacccaggcg ccgtgaccgt ggcctggaag gccgacagca gccccgtgaa ggccggcgtg     480

gagaccacca cccccagcaa gcagagcaac aacaagtacg ccgccagcag ctacctgagc     540

ctgacccccg agcagtggaa gagccacagg tcctacagct gccaggtgac ccacgagggc     600

agcaccgtgg agaaaaccgt ggcccccacc gagtgcagc                            639
```

<210> SEQ ID NO 80
<211> LENGTH: 213
<212> TYPE: PRT
<213> ORGANISM: Artificial Sequence
<220> FEATURE:
<223> OTHER INFORMATION: R9E10 LC-Synthetic peptide

<400> SEQUENCE: 80

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asn Val Arg Gly Lys Leu
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

<210> SEQ ID NO 81
<211> LENGTH: 1887
<212> TYPE: DNA
<213> ORGANISM: Artificial Sequence
<220> FEATURE:
<223> OTHER INFORMATION: R9E10 HC (knob)-Synthetic oligonucleotide

<400> SEQUENCE: 81

```
gaggtgcaat tgttggagtc tgggggaggc ttggtacagc ctggggggtc cctgagactc      60

tcctgtgcag cctccggatt cacctttagc agttatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcagatga acagcctgag agccgaggac acggccgtat attactgtgc gaaaaactct     300

tacacttacg gtcgtgctct ggactactgg ggccaaggaa ccctggtcac cgtctcgagt     360

gctagcacca agggcccatc ggtcttcccc ctggcaccct cctccaagag cacctctggg     420

ggcacagcgg ccctgggctg cctggtcaag gactacttcc ccgaaccggt gacggtgtcg     480
```

-continued

```
tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagaa agttgagccc    660

aaatcttgtg acaaaactca cacatgccca ccgtgcccag cacctgaagc tgcaggggga    720

ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgcgggagga gcagtacaac    900

agcacgtacc gtgtggtcag cgtcctcacc gtcctgcacc aggactggct gaatggcaag    960

gagtacaagt gcaaggtctc caacaaagcc ctcggcgccc ccatcgagaa aaccatctcc   1020

aaagccaaag ggcagccccg agaaccacag gtgtacaccc tgcccccatg ccgggatgag   1080

ctgaccaaga accaggtcag cctgtggtgc ctggtcaaag gcttctatcc cagcgacatc   1140

gccgtggagt gggagagcaa tgggcagccg gagaacaact acaagaccac gcctcccgtg   1200

ctggactccg acggctcctt cttcctctac agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtggc ggcggaggct ccggaggcgg aggatctggc   1380

ggcggaggca gctgtgacct gcctcagaca cacagcctgg gcagccggcg gaccctgatg   1440

ctgctggccc agatgcggaa gatcagcctg ttcagctgcc tgaaggaccg gcacgacttc   1500

ggcttccctc aggaagagtt cggcaaccag ttccagaagg ccgagacaat ccccgtgctg   1560

cacgagatga tccagcagat tttcaacctg ttcagcacca aggacagcag cgccgcctgg   1620

gacgagacac tgctggacaa gttctacacc gagctgtacc agcagctgaa cgacctggaa   1680

gcctgcgtga tccagggcgt gggcgtgacc gagacacccc tgatgaagga agatagcatc   1740

ctggccgtgc ggaagtattt ccagcggatc accctgtacc tgaaagagaa gaagtacagc   1800

ccctgcgcct gggaggtcgt gcgggccgag atcatgcgga gcttcagcct gagcaccaac   1860

ctgcaggaaa gcctgcggag caaagag                                        1887
```

```
<210> SEQ ID NO 82
<211> LENGTH: 629
<212> TYPE: PRT
<213> ORGANISM: Artificial Sequence
<220> FEATURE:
<223> OTHER INFORMATION: R9E10 HC (knob)-Synthetic peptide

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ser Tyr Thr Tyr Gly Arg Ala Leu Asp Tyr Trp Gly Gln
            100                 105                 110
```

-continued

```
Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Gly Ser Gly Gly Gly Gly Ser Gly Gly Gly Gly Ser
    450                 455                 460

Cys Asp Leu Pro Gln Thr His Ser Leu Gly Ser Arg Arg Thr Leu Met
465                 470                 475                 480

Leu Leu Ala Gln Met Arg Lys Ile Ser Leu Phe Ser Cys Leu Lys Asp
                485                 490                 495

Arg His Asp Phe Gly Phe Pro Gln Glu Glu Phe Gly Asn Gln Phe Gln
            500                 505                 510

Lys Ala Glu Thr Ile Pro Val Leu His Glu Met Ile Gln Gln Ile Phe
        515                 520                 525

Asn Leu Phe Ser Thr Lys Asp Ser Ser Ala Ala Trp Asp Glu Thr Leu
```

```
    530                 535                 540

Leu Asp Lys Phe Tyr Thr Glu Leu Tyr Gln Gln Leu Asn Asp Leu Glu
545                 550                 555                 560

Ala Cys Val Ile Gln Gly Val Gly Val Thr Glu Thr Pro Leu Met Lys
                565                 570                 575

Glu Asp Ser Ile Leu Ala Val Arg Lys Tyr Phe Gln Arg Ile Thr Leu
            580                 585                 590

Tyr Leu Lys Glu Lys Lys Tyr Ser Pro Cys Ala Trp Glu Val Val Arg
        595                 600                 605

Ala Glu Ile Met Arg Ser Phe Ser Leu Ser Thr Asn Leu Gln Glu Ser
    610                 615                 620

Leu Arg Ser Lys Glu
625


<210> SEQ ID NO 83
<211> LENGTH: 1350
<212> TYPE: DNA
<213> ORGANISM: Artificial Sequence
<220> FEATURE:
<223> OTHER INFORMATION: R9E10 HC (hole)-Synthetic oligonucleotide

<400> SEQUENCE: 83

gaggtgcaat tgttggagtc tgggggaggc ttggtacagc ctggggggtc cctgagactc      60

tcctgtgcag cctccggatt cacctttagc agttatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcagatga acagcctgag agccgaggac acggccgtat attactgtgc gaaaaactct     300

tacacttacg gtcgtgctct ggactactgg ggccaaggaa ccctggtcac cgtctcgagt     360

gctagcacca agggcccctc cgtgttcccc ctggccccca gcagcaagag caccagcggc     420

ggcacagccg ctctgggctg cctggtcaag gactacttcc ccgagcccgt gaccgtgtcc     480

tggaacagcg gagccctgac ctccggcgtg cacaccttcc ccgccgtgct gcagagttct     540

ggcctgtata gcctgagcag cgtggtcacc gtgccttcta gcagcctggg cacccagacc     600

tacatctgca acgtgaacca caagcccagc aacaccaagg tggacaagaa ggtggagccc     660

aagagctgcg acaaaactca cacatgccca ccgtgcccag cacctgaagc tgcaggggga     720

ccgtcagtct tcctcttccc cccaaaaccc aaggacaccc tcatgatctc ccggacccct     780

gaggtcacat gcgtggtggt ggacgtgagc cacgaagacc ctgaggtcaa gttcaactgg     840

tacgtggacg gcgtggaggt gcataatgcc aagacaaagc cgcgggagga gcagtacaac     900

agcacgtacc gtgtggtcag cgtcctcacc gtcctgcacc aggactggct gaatggcaag     960

gagtacaagt gcaaggtctc caacaaagcc ctcggcgccc ccatcgagaa aaccatctcc    1020

aaagccaaag ggcagccccg agaaccacag gtgtgcaccc tgcccccatc ccgggatgag    1080

ctgaccaaga accaggtcag cctctcgtgc gcagtcaaag gcttctatcc cagcgacatc    1140

gccgtggagt gggagagcaa tgggcagccg gagaacaact acaagaccac gcctcccgtg    1200

ctggactccg acggctcctt cttcctcgtg agcaagctca ccgtggacaa gagcaggtgg    1260

cagcagggga acgtcttctc atgctccgtg atgcatgagg ctctgcacaa ccactacacg    1320

cagaagagcc tctccctgtc tccgggtaaa                                     1350


<210> SEQ ID NO 84
<211> LENGTH: 450
```

<212> TYPE: PRT
<213> ORGANISM: Artificial Sequence
<220> FEATURE:
<223> OTHER INFORMATION: R9E10 HC (hole)-Synthetic peptide

<400> SEQUENCE: 84

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ser Tyr Thr Tyr Gly Arg Ala Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 85
<211> LENGTH: 642
<212> TYPE: DNA
<213> ORGANISM: Artificial Sequence
<220> FEATURE:
<223> OTHER INFORMATION: R7E12 LC-Synthetic oligonucleotide

<400> SEQUENCE: 85

tcgtctgagc tgactcagga ccctgctgtg tctgtggcct tgggacagac agtcaggatc      60

acatgccaag gagacagcct cagaagttat tatgcaagct ggtaccagca gaagccagga     120

caggcccctg tacttgtcat ctatggtaaa aacaaccggc cctcagggat cccagaccga     180

ttctctggct ccagctcagg aaacacagct tccttgacca tcactggggc tcaggcggaa     240

gatgaggctg actattactg taactcccgt aagagtagct cgaagaatgt tgtgttcggc     300

ggagggacca agctgaccgt cctaggtcaa cccaaggctg cccccagcgt gaccctgttc     360

ccccccagca gcgaggaact gcaggccaac aaggccaccc tggtctgcct gatcagcgac     420

ttctacccag gcgccgtgac cgtggcctgg aaggccgaca gcagccccgt gaaggccggc     480

gtggagacca ccacccccag caagcagagc aacaacaagt acgccgccag cagctacctg     540

agcctgaccc ccgagcagtg gaagagccac aggtcctaca gctgccaggt gacccacgag     600

ggcagcaccg tggagaaaac cgtggccccc accgagtgca gc                        642


<210> SEQ ID NO 86
<211> LENGTH: 214
<212> TYPE: PRT
<213> ORGANISM: Artificial Sequence
<220> FEATURE:
<223> OTHER INFORMATION: R7E12 LC-Synthetic peptide

<400> SEQUENCE: 86

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Lys Ser Ser Ser Lys Asn
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
```

```
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210


<210> SEQ ID NO 87
<211> LENGTH: 1887
<212> TYPE: DNA
<213> ORGANISM: Artificial Sequence
<220> FEATURE:
<223> OTHER INFORMATION: R7E12 HC (knob)-Synthetic oligonucleotide

<400> SEQUENCE: 87

gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaatcttct    300

ttcactttcg gtcgttactt cgactactgg ggccaaggaa ccctggtcac cgtctcgagt    360

gctagcacca agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtg cacaccttcc cggctgtcct acagtcctca    540

ggactctact ccctcagcag cgtggtgacc gtgccctcca gcagcttggg cacccagacc    600

tacatctgca acgtgaatca caagcccagc aacaccaagg tggacaagaa agttgagccc    660

aaatcttgtg acaaaactca cacatgccca ccgtgcccag cacctgaagc tgcaggggga    720

ccgtcagtct tcctcttccc cccaaaaccc aaggacaccc tcatgatctc ccggacccct    780

gaggtcacat gcgtggtggt ggacgtgagc cacgaagacc ctgaggtcaa gttcaactgg    840

tacgtggacg gcgtggaggt gcataatgcc aagacaaagc cgcgggagga gcagtacaac    900

agcacgtacc gtgtggtcag cgtcctcacc gtcctgcacc aggactggct gaatggcaag    960

gagtacaagt gcaaggtctc caacaaagcc ctcggcgccc ccatcgagaa aaccatctcc   1020

aaagccaaag ggcagccccg agaaccacag gtgtacaccc tgcccccatg ccgggatgag   1080

ctgaccaaga accaggtcag cctgtggtgc ctggtcaaag gcttctatcc cagcgacatc   1140

gccgtggagt gggagagcaa tgggcagccg gagaacaact acaagaccac gcctcccgtg   1200

ctggactccg acggctcctt cttcctctac agcaagctca ccgtggacaa gagcaggtgg   1260

cagcagggga acgtcttctc atgctccgtg atgcatgagg ctctgcacaa ccactacacg   1320

cagaagagcc tctccctgtc tccgggtggc ggcggaggct ccggaggcgg aggatctggc   1380

ggcggaggca gctgtgacct gcctcagaca cacagcctgg gcagccggcg gaccctgatg   1440

ctgctggccc agatgcggaa gatcagcctg ttcagctgcc tgaaggaccg gcacgacttc   1500
```

-continued ggcttccctc aggaagagtt cggcaaccag ttccagaagg ccgagacaat ccccgtgctg 1560
cacgagatga tccagcagat tttcaacctg ttcagcacca aggacagcag cgccgcctgg 1620
gacgagacac tgctggacaa gttctacacc gagctgtacc agcagctgaa cgacctggaa 1680
gcctgcgtga tccagggcgt gggcgtgacc gagacacccc tgatgaagga agatagcatc 1740
ctggccgtgc ggaagtattt ccagcggatc accctgtacc tgaaagagaa gaagtacagc 1800
ccctgcgcct gggaggtcgt gcgggccgag atcatgcgga gcttcagcct gagcaccaac 1860
ctgcaggaaa gcctgcggag caaagag 1887

<210> SEQ ID NO 88
<211> LENGTH: 629
<212> TYPE: PRT
<213> ORGANISM: Artificial Sequence
<220> FEATURE:
<223> OTHER INFORMATION: R7E12 HC (knob)-Synthetic peptide

<400> SEQUENCE: 88

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Ser Ser Phe Thr Phe Gly Arg Tyr Phe Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Ala Ala Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

-continued

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Gly Ser Gly Gly Gly Gly Ser Gly Gly Gly Gly Ser
    450                 455                 460

Cys Asp Leu Pro Gln Thr His Ser Leu Gly Ser Arg Arg Thr Leu Met
465                 470                 475                 480

Leu Leu Ala Gln Met Arg Lys Ile Ser Leu Phe Ser Cys Leu Lys Asp
                485                 490                 495

Arg His Asp Phe Gly Phe Pro Gln Glu Glu Phe Gly Asn Gln Phe Gln
            500                 505                 510

Lys Ala Glu Thr Ile Pro Val Leu His Glu Met Ile Gln Gln Ile Phe
        515                 520                 525

Asn Leu Phe Ser Thr Lys Asp Ser Ser Ala Ala Trp Asp Glu Thr Leu
    530                 535                 540

Leu Asp Lys Phe Tyr Thr Glu Leu Tyr Gln Gln Leu Asn Asp Leu Glu
545                 550                 555                 560

Ala Cys Val Ile Gln Gly Val Gly Val Thr Glu Thr Pro Leu Met Lys
                565                 570                 575

Glu Asp Ser Ile Leu Ala Val Arg Lys Tyr Phe Gln Arg Ile Thr Leu
            580                 585                 590

Tyr Leu Lys Glu Lys Lys Tyr Ser Pro Cys Ala Trp Glu Val Val Arg
        595                 600                 605

Ala Glu Ile Met Arg Ser Phe Ser Leu Ser Thr Asn Leu Gln Glu Ser
    610                 615                 620

Leu Arg Ser Lys Glu
625
```

<210> SEQ ID NO 89
<211> LENGTH: 1350
<212> TYPE: DNA
<213> ORGANISM: Artificial Sequence
<220> FEATURE:
<223> OTHER INFORMATION: R7E12 HC (hole)Synthetic oligonucleotide

<400> SEQUENCE: 89

```
gaggtgcaat tgttggagtc tgggggaggc ttggtacagc ctgggggtc cctgagactc      60

tcctgtgcag cctccggatt cacctttagc agttatgcca tgagctgggt ccgccaggct    120
```

```
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaatcttct    300
ttcactttcg gtcgttactt cgactactgg ggccaaggaa ccctggtcac cgtctcgagt    360
gctagcacca agggcccctc cgtgttcccc ctggcccca gcagcaagag caccagcggc    420
ggcacagccg ctctgggctg cctggtcaag gactacttcc ccgagcccgt gaccgtgtcc    480
tggaacagcg gagccctgac ctccggcgtg cacaccttcc ccgccgtgct gcagagttct    540
ggcctgtata gcctgagcag cgtggtcacc gtgccttcta gcagcctggg cacccagacc    600
tacatctgca acgtgaacca caagcccagc aacaccaagg tggacaagaa ggtggagccc    660
aagagctgcg acaaaactca cacatgccca ccgtgcccag cacctgaagc tgcaggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcggcgccc ccatcgagaa aaccatctcc   1020
aaagccaaag ggcagccccg agaaccacag gtgtgcaccc tgcccccatc ccgggatgag   1080
ctgaccaaga accaggtcag cctctcgtgc gcagtcaaag gcttctatcc cagcgacatc   1140
gccgtggagt gggagagcaa tgggcagccg gagaacaact acaagaccac gcctcccgtg   1200
ctggactccg acggctcctt cttcctcgtg agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                    1350
```

<210> SEQ ID NO 90
<211> LENGTH: 450
<212> TYPE: PRT
<213> ORGANISM: Artificial Sequence
<220> FEATURE:
<223> OTHER INFORMATION: R7E12 HC (hole)-Synthetic peptide

<400> SEQUENCE: 90

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Phe Thr Phe Gly Arg Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Cys
            340                 345                 350

Thr Leu Pro Pro Ser Arg Asp Glu Leu Thr Lys Asn Gln Val Ser Leu
        355                 360                 365

Ser Cys Ala Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 91
<211> LENGTH: 648
<212> TYPE: DNA
<213> ORGANISM: Artificial Sequence
<220> FEATURE:
<223> OTHER INFORMATION: 51A12 S116A LC-Synthetic oligonucleotide

<400> SEQUENCE: 91

```
tcgtctgagc tgactcagga ccctgctgtg tctgtggcct tgggacagac agtcaggatc     60

acatgccaag gagacagcct cagaagttat tatgcaagct ggtaccagca gaagccagga    120

caggcccctg tacttgtcat ctatggtaaa aacaaccggc cctcagggat cccagaccga    180

ttctctgcct ccagctcagg aaacacagct tccttgacca tcactggggc tcaggcggaa    240
```

-continued

```
gatgaggctg actattactg taactcccgt gatatttgtt gtaatcgagc tgtgcgtaat    300

ttcggcggag ggaccaagct gaccgtccta ggtcaaccca aggctgcccc cagcgtgacc    360

ctgttccccc ccagcagcga ggaactgcag gccaacaagg ccaccctggt ctgcctgatc    420

agcgacttct acccaggcgc cgtgaccgtg gcctggaagg ccgacagcag ccccgtgaag    480

gccggcgtgg agaccaccac ccccagcaag cagagcaaca acaagtacgc cgccagcagc    540

tacctgagcc tgacccccga gcagtggaag agccacaggt cctacagctg ccaggtgacc    600

cacgagggca gcaccgtgga gaaaaccgtg gccccaccg agtgcagc                648
```

<210> SEQ ID NO 92
<211> LENGTH: 216
<212> TYPE: PRT
<213> ORGANISM: Artificial Sequence
<220> FEATURE:
<223> OTHER INFORMATION: 51A12 S116A LC-Synthetic peptide

<400> SEQUENCE: 92

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Ala Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ile Cys Cys Asn Arg
                85                  90                  95

Ala Val Arg Asn Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 93
<211> LENGTH: 648
<212> TYPE: DNA
<213> ORGANISM: Artificial Sequence
<220> FEATURE:
<223> OTHER INFORMATION: 51A12 A82G S116A LC-Synthetic oligonucleotide

<400> SEQUENCE: 93

```
tcgtctgagc tgactcagga ccctgctgtg tctgtggcct tgggacagac agtcaggatc     60

acatgccaag gagacagcct cagaagttat tatgcaagct ggtaccagca gaagccagga    120
```

```
caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactcccgt gatatttgtt gtaatcgagc tgtgcgtaat    300

ttcggcggag ggaccaagct gaccgtccta ggtcaaccca aggctgcccc cagcgtgacc    360

ctgttccccc ccagcagcga ggaactgcag gccaacaagg ccaccctggt ctgcctgatc    420

agcgacttct acccaggcgc cgtgaccgtg gcctggaagg ccgacagcag ccccgtgaag    480

gccggcgtgg agaccaccac ccccagcaag cagagcaaca acaagtacgc cgccagcagc    540

tacctgagcc tgacccccga gcagtggaag agccacaggt cctacagctg ccaggtgacc    600

cacgagggca gcaccgtgga gaaaaccgtg gccccccaccg agtgcagc              648
```

<210> SEQ ID NO 94
<211> LENGTH: 216
<212> TYPE: PRT
<213> ORGANISM: Artificial Sequence
<220> FEATURE:
<223> OTHER INFORMATION: 51A12 A82G S116A LC-Synthetic peptide

<400> SEQUENCE: 94

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ile Cys Cys Asn Arg
                85                  90                  95

Ala Val Arg Asn Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 95
<211> LENGTH: 649
<212> TYPE: DNA
<213> ORGANISM: Artificial Sequence
<220> FEATURE:
<223> OTHER INFORMATION: 51A12_C1 LC-Synthetic oligonucleotide

<400> SEQUENCE: 95

```
tcgtctgagc tgactcagga ccctgctgtg tctgtggcct tgggacagac agtcaggatc     60
acatgccaag gagacagcct cagaagttat tatgcaagct ggtaccagca gaagccagga    120
caggcccctg tacttgtcat ctatggtaaa aacaaccggc cctcagggat cccagaccga    180
ttctctggct ccagctcagg aaacacagct tccttgacca tcactggggc tcaggcggaa    240
gatgaggctg actattactg taactcccgt tcttacgctt tcaaccgtgt tgttcgtaac    300
ttcggcggag ggaccaagct gaccgtccta ggtcaaccca aggctgcccc cagcgtgacc    360
ctgttccccc ccagcagcga ggaactgcag gccaacaagg ccaccctggt ctgcctgatc    420
agcgacttct acccaggcgc cgtgaccgtg gcctggaagg ccgacagcag ccccgtgaag    480
gccggcgtgg agaccaccac ccccagcaag cagagcaaca acaagtacgc cgccagcagc    540
tacctgagcc tgacccccga gcagtggaag agccacaggt cctacagctg ccaggtgacc    600
cacgagggca gcaccgtgga gaaaaccgtg gcccccaccg agtgcagct               649
```

<210> SEQ ID NO 96
<211> LENGTH: 216
<212> TYPE: PRT
<213> ORGANISM: Artificial Sequence
<220> FEATURE:
<223> OTHER INFORMATION: 51A12_C1 LC-Synthetic peptide

<400> SEQUENCE: 96

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Ser Tyr Ala Phe Asn Arg
                85                  90                  95

Val Val Arg Asn Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 97
<211> LENGTH: 649

<212> TYPE: DNA
<213> ORGANISM: Artificial Sequence
<220> FEATURE:
<223> OTHER INFORMATION: 51A12_C7 LC-Synthetic oligonucleotide

<400> SEQUENCE: 97

```
tcgtctgagc tgactcagga ccctgctgtg tctgtggcct tgggacagac agtcaggatc     60

acatgccaag gagacagcct cagaagttat tatgcaagct ggtaccagca gaagccagga    120

caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactcccgt gacatccgtt acaaccgtgt tgttcgtccg    300

ttcggcggag ggaccaagct gaccgtccta ggtcaaccca aggctgcccc cagcgtgacc    360

ctgttccccc ccagcagcga ggaactgcag gccaacaagg ccaccctggt ctgcctgatc    420

agcgacttct acccaggcgc cgtgaccgtg gcctggaagg ccgacagcag ccccgtgaag    480

gccggcgtgg agaccaccac ccccagcaag cagagcaaca acaagtacgc cgccagcagc    540

tacctgagcc tgacccccga gcagtggaag agccacaggt cctacagctg ccaggtgacc    600

cacgagggca gcaccgtgga gaaaaccgtg gcccccaccg agtgcagct               649
```

<210> SEQ ID NO 98
<211> LENGTH: 216
<212> TYPE: PRT
<213> ORGANISM: Artificial Sequence
<220> FEATURE:
<223> OTHER INFORMATION: 51A12_C7 LC-Synthetic peptide

<400> SEQUENCE: 98

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ile Arg Tyr Asn Arg
                85                  90                  95

Val Val Arg Pro Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
```

```
    210                 215


<210> SEQ ID NO 99
<211> LENGTH: 649
<212> TYPE: DNA
<213> ORGANISM: Artificial Sequence
<220> FEATURE:
<223> OTHER INFORMATION: 51A12_E7 LC-Synthetic oligonucleotide

<400> SEQUENCE: 99

tcgtctgagc tgactcagga ccctgctgtg tctgtggcct tgggacagac agtcaggatc     60

acatgccaag gagacagcct cagaagttat tatgcaagct ggtaccagca gaagccagga    120

caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactcccgt gactaccgtt acaaccgtgc tgttcgtccg    300

ttcggcggag ggaccaagct gaccgtccta ggtcaaccca aggctgcccc cagcgtgacc    360

ctgttccccc ccagcagcga ggaactgcag gccaacaagg ccaccctggt ctgcctgatc    420

agcgacttct acccaggcgc cgtgaccgtg gcctggaagg ccgacagcag ccccgtgaag    480

gccggcgtgg agaccaccac ccccagcaag cagagcaaca acaagtacgc cgccagcagc    540

tacctgagcc tgacccccga gcagtggaag agccacaggt cctacagctg ccaggtgacc    600

cacgagggca gcaccgtgga gaaaaccgtg gcccccaccg agtgcagct                649


<210> SEQ ID NO 100
<211> LENGTH: 216
<212> TYPE: PRT
<213> ORGANISM: Artificial Sequence
<220> FEATURE:
<223> OTHER INFORMATION: 51A12_E7 LC-Synthetic peptide

<400> SEQUENCE: 100

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Tyr Arg Tyr Asn Arg
                85                  90                  95

Ala Val Arg Pro Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190
```

```
Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 101
<211> LENGTH: 649
<212> TYPE: DNA
<213> ORGANISM: Artificial Sequence
<220> FEATURE:
<223> OTHER INFORMATION: 51A12_H3 LC-Synthetic oligonucleotide

<400> SEQUENCE: 101

tcgtctgagc tgactcagga ccctgctgtg tctgtggcct tgggacagac agtcaggatc     60

acatgccaag gagacagcct cagaagttat tatgcaagct ggtaccagca gaagccagga    120

caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactcccgt gactacaaat tcaaccgtgt tgttcgtaac    300

ttcggcggag ggaccaagct gaccgtccta ggtcaaccca aggctgcccc cagcgtgacc    360

ctgttccccc ccagcagcga ggaactgcag gccaacaagg ccaccctggt ctgcctgatc    420

agcgacttct acccaggcgc cgtgaccgtg gcctggaagg ccgacagcag ccccgtgaag    480

gccggcgtgg agaccaccac ccccagcaag cagagcaaca acaagtacgc cgccagcagc    540

tacctgagcc tgacccccga gcagtggaag agccacaggt cctacagctg ccaggtgacc    600

cacgagggca gcaccgtgga gaaaaccgtg gcccccaccg agtgcagct                649


<210> SEQ ID NO 102
<211> LENGTH: 216
<212> TYPE: PRT
<213> ORGANISM: Artificial Sequence
<220> FEATURE:
<223> OTHER INFORMATION: 51A12_H3 LC-Synthetic peptide

<400> SEQUENCE: 102

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Tyr Lys Phe Asn Arg
                85                  90                  95

Val Val Arg Asn Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160
```

```
Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 103
<211> LENGTH: 649
<212> TYPE: DNA
<213> ORGANISM: Artificial Sequence
<220> FEATURE:
<223> OTHER INFORMATION: 51A12_A6 LC-Synthetic oligonucleotide

<400> SEQUENCE: 103

```
tcgtctgagc tgactcagga ccctgctgtg tctgtggcct tgggacagac agtcaggatc     60

acatgccaag gagacagcct cagaagttat tatgcaagct ggtaccagca gaagccagga    120

caggcccctg tacttgtcat ctatggtaaa aacaaccggc cctcagggat cccagaccga    180

ttctctggct ccagctcagg aaacacagct tccttgacca tcactggggc tcaggcggaa    240

gatgaggctg actattactg taactcccgt acttactctt acaaccgtgc tgttcgtaac    300

ttcggcggag ggaccaagct gaccgtccta ggtcaaccca aggctgcccc cagcgtgacc    360

ctgttccccc ccagcagcga ggaactgcag gccaacaagg ccaccctggt ctgcctgatc    420

agcgacttct acccaggcgc cgtgaccgtg gcctggaagg ccgacagcag ccccgtgaag    480

gccggcgtgg agaccaccac ccccagcaag cagagcaaca acaagtacgc cgccagcagc    540

tacctgagcc tgacccccga gcagtggaag agccacaggt cctacagctg ccaggtgacc    600

cacgagggca gcaccgtgga gaaaaccgtg gcccccaccg agtgcagct                649
```

<210> SEQ ID NO 104
<211> LENGTH: 216
<212> TYPE: PRT
<213> ORGANISM: Artificial Sequence
<220> FEATURE:
<223> OTHER INFORMATION: 51A12_A6 LC-Synthetic peptide

<400> SEQUENCE: 104

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Thr Tyr Ser Tyr Asn Arg
                85                  90                  95

Ala Val Arg Asn Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
```

```
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 105
<211> LENGTH: 649
<212> TYPE: DNA
<213> ORGANISM: Artificial Sequence
<220> FEATURE:
<223> OTHER INFORMATION: 51A12_D1 LC-Synthetic oligonucleotide

<400> SEQUENCE: 105

tcgtctgagc tgactcagga ccctgctgtg tctgtggcct tgggacagac agtcaggatc      60

acatgccaag gagacagcct cagaagttat tatgcaagct ggtaccagca gaagccagga     120

caggcccctg tacttgtcat ctatggtaaa aacaaccggc cctcagggat cccagaccga     180

ttctctggct ccagctcagg aaacacagct tccttgacca tcactggggc tcaggcggaa     240

gatgaggctg actattactg taactcccgt acttactctt acaaccgtgc tgttcgtccg     300

ttcggcggag ggaccaagct gaccgtccta ggtcaaccca aggctgcccc cagcgtgacc     360

ctgttccccc ccagcagcga ggaactgcag gccaacaagg ccaccctggt ctgcctgatc     420

agcgacttct acccaggcgc cgtgaccgtg gcctggaagg ccgacagcag ccccgtgaag     480

gccggcgtgg agaccaccac ccccagcaag cagagcaaca acaagtacgc cgccagcagc     540

tacctgagcc tgacccccga gcagtggaag agccacaggt cctacagctg ccaggtgacc     600

cacgagggca gcaccgtgga gaaaaccgtg gcccccaccg agtgcagct                649


<210> SEQ ID NO 106
<211> LENGTH: 216
<212> TYPE: PRT
<213> ORGANISM: Artificial Sequence
<220> FEATURE:
<223> OTHER INFORMATION: 51A12_D1 LC-Synthetic peptide

<400> SEQUENCE: 106

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Thr Tyr Ser Tyr Asn Arg
                85                  90                  95

Ala Val Arg Pro Phe Gly Gly Gly Thr Lys Leu Thr Val Leu Gly Gln
            100                 105                 110
```

Pro Lys Ala Ala Pro Ser Val Thr Leu Phe Pro Pro Ser Ser Glu Glu
115 120 125

Leu Gln Ala Asn Lys Ala Thr Leu Val Cys Leu Ile Ser Asp Phe Tyr
130 135 140

Pro Gly Ala Val Thr Val Ala Trp Lys Ala Asp Ser Ser Pro Val Lys
145 150 155 160

Ala Gly Val Glu Thr Thr Thr Pro Ser Lys Gln Ser Asn Asn Lys Tyr
165 170 175

Ala Ala Ser Ser Tyr Leu Ser Leu Thr Pro Glu Gln Trp Lys Ser His
180 185 190

Arg Ser Tyr Ser Cys Gln Val Thr His Glu Gly Ser Thr Val Glu Lys
195 200 205

Thr Val Ala Pro Thr Glu Cys Ser
210 215

<210> SEQ ID NO 107
<211> LENGTH: 649
<212> TYPE: DNA
<213> ORGANISM: Artificial Sequence
<220> FEATURE:
<223> OTHER INFORMATION: 51A12_H6 LC-Synthetic oligonucleotide

<400> SEQUENCE: 107
tcgtctgagc tgactcagga ccctgctgtg tctgtggcct tgggacagac agtcaggatc 60
acatgccaag gagacagcct cagaagttat tatgcaagct ggtaccagca gaagccagga 120
caggcccctg tacttgtcat ctatggtaaa aacaaccggc cctcagggat cccagaccga 180
ttctctggct ccagctcagg aaacacagct tccttgacca tcactggggc tcaggcggaa 240
gatgaggctg actattactg taactcccgc gactacaaat ggaaccgtgt tgttcgtcat 300
ttcggcggag ggaccaagct gaccgtccta ggtcaaccca aggctgcccc cagcgtgacc 360
ctgttccccc ccagcagcga ggaactgcag gccaacaagg ccaccctggt ctgcctgatc 420
agcgacttct acccaggcgc cgtgaccgtg gcctggaagg ccgacagcag ccccgtgaag 480
gccggcgtgg agaccaccac ccccagcaag cagagcaaca acaagtacgc cgccagcagc 540
tacctgagcc tgacccccga gcagtggaag agccacaggt cctacagctg ccaggtgacc 600
cacgagggca gcaccgtgga gaaaaccgtg gcccccaccg agtgcagct 649

<210> SEQ ID NO 108
<211> LENGTH: 216
<212> TYPE: PRT
<213> ORGANISM: Artificial Sequence
<220> FEATURE:
<223> OTHER INFORMATION: 51A12_H6 LC-Synthetic peptide

<400> SEQUENCE: 108

Ser Ser Glu Leu Thr Gln Asp Pro Ala Val Ser Val Ala Leu Gly Gln
1 5 10 15

Thr Val Arg Ile Thr Cys Gln Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Lys Asn Asn Arg Pro Ser Gly Ile Pro Asp Arg Phe Ser Gly Ser
50 55 60

Ser Ser Gly Asn Thr Ala Ser Leu Thr Ile Thr Gly Ala Gln Ala Glu
65 70 75 80

```
Asp Glu Ala Asp Tyr Tyr Cys Asn Ser Arg Asp Tyr Lys Trp Asn Arg
                85                  90                  95

Val Val Arg His Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 109
<211> LENGTH: 643
<212> TYPE: DNA
<213> ORGANISM: Artificial Sequence
<220> FEATURE:
<223> OTHER INFORMATION: DPL16 LC-Synthetic oligonucleotide

<400> SEQUENCE: 109

tcgtctgagc tgactcagga ccctgctgtg tctgtggcct tgggacagac agtcaggatc      60

acatgccaag gagacagcct cagaagttat tatgcaagct ggtaccagca gaagccagga     120

caggcccctg tacttgtcat ctatggtaaa aacaaccggc cctcagggat cccagaccga     180

ttctctggct ccagctcagg aaacacagct tccttgacca tcactggggc tcaggcggaa     240

gatgaggctg actattactg taactcccgt gatagtagcg gtaatcatgt ggtattcggc     300

ggagggacca agctgaccgt cctaggtcaa cccaaggctg cccccagcgt gaccctgttc     360

ccccccagca gcgaggaact gcaggccaac aaggccaccc tggtctgcct gatcagcgac     420

ttctacccag gcgccgtgac cgtggcctgg aaggccgaca gcagccccgt gaaggccggc     480

gtggagacca ccacccccag caagcagagc aacaacaagt acgccgccag cagctacctg     540

agcctgaccc ccgagcagtg gaagagccac aggtcctaca gctgccaggt gacccacgag     600

ggcagcaccg tggagaaaac cgtggccccc accgagtgca gct                       643


<210> SEQ ID NO 110
<211> LENGTH: 214
<212> TYPE: PRT
<213> ORGANISM: Artificial Sequence
<220> FEATURE:
<223> OTHER INFORMATION: DPL16 LC-Synthetic peptide

<400> SEQUENCE: 110

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
```

```
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 111
<211> LENGTH: 1872
<212> TYPE: DNA
<213> ORGANISM: Artificial Sequence
<220> FEATURE:
<223> OTHER INFORMATION: DP47GS HC (knob)-Synthetic oligonucleotide

<400> SEQUENCE: 111

```
gaggtgcaat tgttggagtc tggggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaaggcagc    300

ggatttgact actggggcca aggaaccctg gtcaccgtct cgagtgctag caccaagggc    360

ccatcggtct tccccctggc accctcctcc aagagcacct ctgggggcac agcggccctg    420

ggctgcctgg tcaaggacta cttccccgaa ccggtgacgg tgtcgtggaa ctcaggcgcc    480

ctgaccagcg gcgtgcacac cttcccggct gtcctacagt cctcaggact ctactccctc    540

agcagcgtgg tgaccgtgcc ctccagcagc ttgggcaccc agacctacat ctgcaacgtg    600

aatcacaagc ccagcaacac caaggtggac aagaaagttg agcccaaatc ttgtgacaaa    660

actcacacat gcccaccgtg cccagcacct gaagctgcag gggaccgtc agtcttcctc     720

ttccccccaa aacccaagga caccctcatg atctcccgga cccctgaggt cacatgcgtg    780

gtggtggacg tgagccacga agaccctgag gtcaagttca actggtacgt ggacggcgtg    840

gaggtgcata atgccaagac aaagccgcgg gaggagcagt acaacagcac gtaccgtgtg    900

gtcagcgtcc tcaccgtcct gcaccaggac tggctgaatg gcaaggagta caagtgcaag    960

gtctccaaca aagccctcgg cgcccccatc gagaaaacca tctccaaagc caaagggcag   1020

ccccgagaac cacaggtgta caccctgccc ccatgccggg atgagctgac caagaaccag   1080

gtcagcctgt ggtgcctggt caaaggcttc tatcccagcg acatcgccgt ggagtgggag   1140
```

-continued

```
agcaatgggc agccggagaa caactacaag accacgcctc ccgtgctgga ctccgacggc   1200

tccttcttcc tctacagcaa gctcaccgtg gacaagagca ggtggcagca ggggaacgtc   1260

ttctcatgct ccgtgatgca tgaggctctg cacaaccact acacgcagaa gagcctctcc   1320

ctgtctccgg gtggcggcgg aggctccgga ggcggaggat ctggcggcgg aggcagctgt   1380

gacctgcctc agacacacag cctgggcagc cggcggaccc tgatgctgct ggcccagatg   1440

cggaagatca gcctgttcag ctgcctgaag gaccggcacg acttcggctt ccctcaggaa   1500

gagttcggca accagttcca gaaggccgag acaatccccg tgctgcacga gatgatccag   1560

cagattttca acctgttcag caccaaggac agcagcgccg cctgggacga gacactgctg   1620

gacaagttct acaccgagct gtaccagcag ctgaacgacc tggaagcctg cgtgatccag   1680

ggcgtgggcg tgaccgagac acccctgatg aaggaagata gcatcctggc cgtgcggaag   1740

tatttccagc ggatcaccct gtacctgaaa gagaagaagt acagcccctg cgcctgggag   1800

gtcgtgcggg ccgagatcat gcggagcttc agcctgagca ccaacctgca ggaaagcctg   1860

cggagcaaag ag                                                       1872
```

<210> SEQ ID NO 112
<211> LENGTH: 624
<212> TYPE: PRT
<213> ORGANISM: Artificial Sequence
<220> FEATURE:
<223> OTHER INFORMATION: DP47GS HC (knob)-Synthetic peptide

<400> SEQUENCE: 112

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220
```

Pro Pro Cys Pro Ala Pro Glu Ala Ala Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser His Glu Asp Pro Glu Val Lys
260 265 270

Phe Asn Trp Tyr Val Asp Gly Val Glu Val His Asn Ala Lys Thr Lys
275 280 285

Pro Arg Glu Glu Gln Tyr Asn Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Ala Leu Gly Ala Pro Ile Glu Lys Thr Ile Ser Lys
325 330 335

Ala Lys Gly Gln Pro Arg Glu Pro Gln Val Tyr Thr Leu Pro Pro Cys
340 345 350

Arg Asp Glu Leu Thr Lys Asn Gln Val Ser Leu Trp Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Gly Gly Gly Gly
435 440 445

Ser Gly Gly Gly Gly Ser Gly Gly Gly Gly Ser Cys Asp Leu Pro Gln
450 455 460

Thr His Ser Leu Gly Ser Arg Arg Thr Leu Met Leu Leu Ala Gln Met
465 470 475 480

Arg Lys Ile Ser Leu Phe Ser Cys Leu Lys Asp Arg His Asp Phe Gly
485 490 495

Phe Pro Gln Glu Glu Phe Gly Asn Gln Phe Gln Lys Ala Glu Thr Ile
500 505 510

Pro Val Leu His Glu Met Ile Gln Gln Ile Phe Asn Leu Phe Ser Thr
515 520 525

Lys Asp Ser Ser Ala Ala Trp Asp Glu Thr Leu Leu Asp Lys Phe Tyr
530 535 540

Thr Glu Leu Tyr Gln Gln Leu Asn Asp Leu Glu Ala Cys Val Ile Gln
545 550 555 560

Gly Val Gly Val Thr Glu Thr Pro Leu Met Lys Glu Asp Ser Ile Leu
565 570 575

Ala Val Arg Lys Tyr Phe Gln Arg Ile Thr Leu Tyr Leu Lys Glu Lys
580 585 590

Lys Tyr Ser Pro Cys Ala Trp Glu Val Val Arg Ala Glu Ile Met Arg
595 600 605

Ser Phe Ser Leu Ser Thr Asn Leu Gln Glu Ser Leu Arg Ser Lys Glu
610 615 620

<210> SEQ ID NO 113
<211> LENGTH: 1335
<212> TYPE: DNA

<213> ORGANISM: Artificial Sequence
<220> FEATURE:
<223> OTHER INFORMATION: DP47GS HC (hole)-Synthetic oligonucleotide

<400> SEQUENCE: 113

```
gaggtgcaat tgttggagtc tgggggaggc ttggtacagc ctggggggtc cctgagactc     60
tcctgtgcag cctccggatt cacctttagc agttatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gaaaggcagc    300
ggatttgact actggggcca aggaaccctg gtcaccgtct cgagtgctag caccaagggc    360
ccctccgtgt tcccccctggc ccccagcagc aagagcacca gcggcggcac agccgctctg    420
ggctgcctgg tcaaggacta cttccccgag cccgtgaccg tgtcctggaa cagcggagcc    480
ctgacctccg gcgtgcacac cttccccgcc gtgctgcaga gttctggcct gtatagcctg    540
agcagcgtgg tcaccgtgcc ttctagcagc ctgggcaccc agacctacat ctgcaacgtg    600
aaccacaagc ccagcaacac caaggtggac aagaaggtgg agcccaagag ctgcgacaaa    660
actcacacat gcccaccgtg cccagcacct gaagctgcag gggggaccgtc agtcttcctc    720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctcgg cgcccccatc gagaaaacca tctccaaagc caaagggcag   1020
ccccgagaac cacaggtgtg caccctgccc ccatcccggg atgagctgac caagaaccag   1080
gtcagcctct cgtgcgcagt caaaggcttc tatcccagcg acatcgccgt ggagtgggag   1140
agcaatgggc agccggagaa caactacaag accacgcctc ccgtgctgga ctccgacggc   1200
tccttcttcc tcgtgagcaa gctcaccgtg gacaagagca ggtggcagca ggggaacgtc   1260
ttctcatgct ccgtgatgca tgaggctctg cacaaccact acacgcagaa gagcctctcc   1320
ctgtctccgg gtaaa                                                      1335
```

<210> SEQ ID NO 114
<211> LENGTH: 445
<212> TYPE: PRT
<213> ORGANISM: Artificial Sequence
<220> FEATURE:
<223> OTHER INFORMATION: DP47GS HC (hole)-Synthetic peptide

<400> SEQUENCE: 114

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Gly Ser Gly Phe Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Gly Ala Pro Ile Glu Lys Thr Ile Ser Lys
                325                 330                 335

Ala Lys Gly Gln Pro Arg Glu Pro Gln Val Cys Thr Leu Pro Pro Ser
            340                 345                 350

Arg Asp Glu Leu Thr Lys Asn Gln Val Ser Leu Ser Cys Ala Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Val Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 115
<211> LENGTH: 681
<212> TYPE: DNA
<213> ORGANISM: Artificial Sequence
<220> FEATURE:
<223> OTHER INFORMATION: Fc (hole)-Synthetic oligonucleotide

<400> SEQUENCE: 115
gacaaaactc acacatgccc accgtgccca gcacctgaag ctgcaggggg accgtcagtc     60

-continued

```
ttcctcttcc ccccaaaacc caaggacacc ctcatgatct cccggacccc tgaggtcaca    120

tgcgtggtgg tggacgtgag ccacgaagac cctgaggtca agttcaactg gtacgtggac    180

ggcgtggagg tgcataatgc caagacaaag ccgcgggagg agcagtacaa cagcacgtac    240

cgtgtggtca gcgtcctcac cgtcctgcac caggactggc tgaatggcaa ggagtacaag    300

tgcaaggtct ccaacaaagc cctcggcgcc cccatcgaga aaaccatctc caaagccaaa    360

gggcagcccc gagaaccaca ggtgtgcacc ctgcccccat cccgggatga gctgaccaag    420

aaccaggtca gcctctcgtg cgcagtcaaa ggcttctatc ccagcgacat cgccgtggag    480

tgggagagca atgggcagcc ggagaacaac tacaagacca cgcctcccgt gctggactcc    540

gacggctcct tcttcctcgt gagcaagctc accgtggaca agagcaggtg gcagcagggg    600

aacgtcttct catgctccgt gatgcatgag gctctgcaca accactacac gcagaagagc    660

ctctccctgt ctccgggtaa a                                              681


<210> SEQ ID NO 116
<211> LENGTH: 227
<212> TYPE: PRT
<213> ORGANISM: Artificial Sequence
<220> FEATURE:
<223> OTHER INFORMATION: Fc (hole)-Synthetic peptide

<400> SEQUENCE: 116

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Gly Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 117
```

<211> LENGTH: 1206
<212> TYPE: DNA
<213> ORGANISM: Artificial Sequence
<220> FEATURE:
<223> OTHER INFORMATION: avi-Fc-huASGPR H1 CRD (hole)-Synthetic oligonucleotide

<400> SEQUENCE: 117
ggcctgaacg atatttttga agcccagaaa atcgaatggc atgaggacaa aactcacaca 60
tgcccaccgt gcccagcacc tgaactcctg gggggaccgt cagtcttcct cttcccccca 120
aaacccaagg acaccctcat gatctcccgg acccctgagg tcacatgcgt ggtggtggac 180
gtgagccacg aagaccctga ggtcaagttc aactggtacg tggacggcgt ggaggtgcat 240
aatgccaaga caaagccgcg ggaggagcag tacaacagca cgtaccgtgt ggtcagcgtc 300
ctcaccgtcc tgcaccagga ctggctgaat ggcaaggagt acaagtgcaa ggtctccaac 360
aaagccctcc cagcccccat cgagaaaacc atctccaaag ccaaagggca gccccgagaa 420
ccacaggtgt gcaccctgcc cccatcccgg gatgagctga ccaagaacca ggtcagcctc 480
tcgtgcgcag tcaaaggctt ctatcccagc gacatcgccg tggagtggga gagcaatggg 540
cagccggaga acaactacaa gaccacgcct cccgtgctgg actccgacgg ctccttcttc 600
ctcgtgagca agctcaccgt ggacaagagc aggtggcagc aggggaacgt cttctcatgc 660
tccgtgatgc atgaggctct gcacaaccac tacacgcaga agagcctctc cctgtctccg 720
ggtggatccg gcggtggtag tccgacacct ccgacacccg ggggtggtag caatggtagc 780
gaacgtacct gttgtccggt taattgggtt gaacatgaac gtagctgcta ttggtttagc 840
cgtagcggta aagcatgggc agatgcagat aattattgtc gtctggaaga tgcacatctg 900
gttgttgtga ccagctggga agaacagaaa tttgttcagc atcatattgg tccggtgaat 960
acctggatgg gtctgcatga tcagaatggt ccgtggaaat gggttgatgg caccgattat 1020
gaaaccggtt ttaaaaattg gcgtccggaa cagccggatg attggtatgg tcatggtctg 1080
ggtggtggtg aagattgtgc acattttacc gatgatggtc gttggaatga tgatgtttgt 1140
cagcgtccgt atcgttgggt ttgtgaaacc gaactggata aagcaagcca ggaaccgccg 1200
ctgctg 1206

<210> SEQ ID NO 118
<211> LENGTH: 402
<212> TYPE: PRT
<213> ORGANISM: Artificial Sequence
<220> FEATURE:
<223> OTHER INFORMATION: avi-Fc-huASGPR H1 CRD (hole)-Synthetic peptide

<400> SEQUENCE: 118

Gly Leu Asn Asp Ile Phe Glu Ala Gln Lys Ile Glu Trp His Glu Asp
1 5 10 15

Lys Thr His Thr Cys Pro Pro Cys Pro Ala Pro Glu Leu Leu Gly Gly
20 25 30

Pro Ser Val Phe Leu Phe Pro Pro Lys Pro Lys Asp Thr Leu Met Ile
35 40 45

Ser Arg Thr Pro Glu Val Thr Cys Val Val Val Asp Val Ser His Glu
50 55 60

Asp Pro Glu Val Lys Phe Asn Trp Tyr Val Asp Gly Val Glu Val His
65 70 75 80

Asn Ala Lys Thr Lys Pro Arg Glu Glu Gln Tyr Asn Ser Thr Tyr Arg
85 90 95

```
Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Cys
    130                 135                 140

Thr Leu Pro Pro Ser Arg Asp Glu Leu Thr Lys Asn Gln Val Ser Leu
145                 150                 155                 160

Ser Cys Ala Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Val Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Gly Ser Gly Gly Gly Ser Pro Thr Pro Pro Thr Pro Gly Gly Gly
                245                 250                 255

Ser Asn Gly Ser Glu Arg Thr Cys Cys Pro Val Asn Trp Val Glu His
            260                 265                 270

Glu Arg Ser Cys Tyr Trp Phe Ser Arg Ser Gly Lys Ala Trp Ala Asp
        275                 280                 285

Ala Asp Asn Tyr Cys Arg Leu Glu Asp Ala His Leu Val Val Val Thr
    290                 295                 300

Ser Trp Glu Glu Gln Lys Phe Val Gln His His Ile Gly Pro Val Asn
305                 310                 315                 320

Thr Trp Met Gly Leu His Asp Gln Asn Gly Pro Trp Lys Trp Val Asp
                325                 330                 335

Gly Thr Asp Tyr Glu Thr Gly Phe Lys Asn Trp Arg Pro Glu Gln Pro
            340                 345                 350

Asp Asp Trp Tyr Gly His Gly Leu Gly Gly Gly Glu Asp Cys Ala His
        355                 360                 365

Phe Thr Asp Asp Gly Arg Trp Asn Asp Asp Val Cys Gln Arg Pro Tyr
    370                 375                 380

Arg Trp Val Cys Glu Thr Glu Leu Asp Lys Ala Ser Gln Glu Pro Pro
385                 390                 395                 400

Leu Leu


<210> SEQ ID NO 119
<211> LENGTH: 1179
<212> TYPE: DNA
<213> ORGANISM: Artificial Sequence
<220> FEATURE:
<223> OTHER INFORMATION: avi-Fc-huCLEC10A CRD (hole)-Synthetic
      oligonucleotide

<400> SEQUENCE: 119

ggcctgaacg atatttttga agcccagaaa atcgaatggc atgaggacaa aactcacaca      60

tgcccaccgt gcccagcacc tgaactcctg gggggaccgt cagtcttcct cttcccccca     120

aaacccaagg acaccctcat gatctcccgg acccctgagg tcacatgcgt ggtggtggac     180

gtgagccacg aagaccctga ggtcaagttc aactggtacg tggacggcgt ggaggtgcat     240

aatgccaaga caaagccgcg ggaggagcag tacaacagca cgtaccgtgt ggtcagcgtc     300
```

-continued

```
ctcaccgtcc tgcaccagga ctggctgaat ggcaaggagt acaagtgcaa ggtctccaac    360

aaagccctcc cagcccccat cgagaaaacc atctccaaag ccaaagggca gccccgagaa    420

ccacaggtgt gcaccctgcc cccatcccgg gatgagctga ccaagaacca ggtcagcctc    480

tcgtgcgcag tcaaaggctt ctatcccagc gacatcgccg tggagtggga gagcaatggg    540

cagccggaga acaactacaa gaccacgcct cccgtgctgg actccgacgg ctccttcttc    600

ctcgtgagca agctcaccgt ggacaagagc aggtggcagc aggggaacgt cttctcatgc    660

tccgtgatgc atgaggctct gcacaaccac tacacgcaga agagcctctc cctgtctccg    720

ggtggatccg gcggtggtag tccgacacct ccgacacccg gggtggtag ctgtccggtt     780

aattgggttg aacatcagga tagctgctat tggtttagcc atagcggtat gagctgggca    840

gaagcagaaa aatattgcca gctgaaaaat gcccatctgg ttgttattaa tagccgtgaa    900

gaacagaatt ttgtgcagaa atatctgggt agcgcatata cctggatggg tctgagcgat    960

ccggaaggtg catggaaatg ggttgatggc accgattatg caaccggttt tcagaattgg   1020

aaaccgggtc agccggatga ttggcagggt catggtctgg gtggtggtga agattgtgca   1080

cattttcatc cggatggtcg ttggaatgat gatgtttgtc agcgtccgta tcattgggtt   1140

tgtgaagcag gtctgggtca gaccagccag gaaagccat                          1179
```

<210> SEQ ID NO 120
<211> LENGTH: 402
<212> TYPE: PRT
<213> ORGANISM: Artificial Sequence
<220> FEATURE:
<223> OTHER INFORMATION: avi-Fc-huCLEC10A CRD (hole)-Synthetic peptide

<400> SEQUENCE: 120

```
Gly Leu Asn Asp Ile Phe Glu Ala Gln Lys Ile Glu Trp His Glu Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Cys
    130                 135                 140

Thr Leu Pro Pro Ser Arg Asp Glu Leu Thr Lys Asn Gln Val Ser Leu
145                 150                 155                 160

Ser Cys Ala Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Val Ser Lys Leu Thr Val Asp
        195                 200                 205
```

```
Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Gly Ser Gly Gly Gly Ser Pro Thr Pro Pro Thr Pro Gly Gly Gly
                245                 250                 255

Ser Asn Gly Ser Glu Arg Thr Cys Cys Pro Val Asn Trp Val Glu His
            260                 265                 270

Glu Arg Ser Cys Tyr Trp Phe Ser Arg Ser Gly Lys Ala Trp Ala Asp
        275                 280                 285

Ala Asp Asn Tyr Cys Arg Leu Glu Asp Ala His Leu Val Val Val Thr
    290                 295                 300

Ser Trp Glu Glu Gln Lys Phe Val Gln His His Ile Gly Pro Val Asn
305                 310                 315                 320

Thr Trp Met Gly Leu His Asp Gln Asn Gly Pro Trp Lys Trp Val Asp
                325                 330                 335

Gly Thr Asp Tyr Glu Thr Gly Phe Lys Asn Trp Arg Pro Glu Gln Pro
            340                 345                 350

Asp Asp Trp Tyr Gly His Gly Leu Gly Gly Gly Glu Asp Cys Ala His
        355                 360                 365

Phe Thr Asp Asp Gly Arg Trp Asn Asp Asp Val Cys Gln Arg Pro Tyr
    370                 375                 380

Arg Trp Val Cys Glu Thr Glu Leu Asp Lys Ala Ser Gln Glu Pro Pro
385                 390                 395                 400

Leu Leu
```

<210> SEQ ID NO 121
<211> LENGTH: 726
<212> TYPE: DNA
<213> ORGANISM: Artificial Sequence
<220> FEATURE:
<223> OTHER INFORMATION: avi-Fc (hole)-Synthetic oligonucleotide

<400> SEQUENCE: 121

```
ggcctgaacg atatttttga agcccagaaa atcgaatggc atgaggacaa aactcacaca     60

tgcccaccgt gcccagcacc tgaactcctg gggggaccgt cagtcttcct cttcccccca    120

aaacccaagg acaccctcat gatctcccgg acccctgagg tcacatgcgt ggtggtggac    180

gtgagccacg aagaccctga ggtcaagttc aactggtacg tggacggcgt ggaggtgcat    240

aatgccaaga caaagccgcg ggaggagcag tacaacagca cgtaccgtgt ggtcagcgtc    300

ctcaccgtcc tgcaccagga ctggctgaat ggcaaggagt acaagtgcaa ggtctccaac    360

aaagccctcc cagcccccat cgagaaaacc atctccaaag ccaaagggca gccccgagaa    420

ccacaggtgt acaccctgcc cccatgccgg gatgagctga ccaagaacca ggtcagcctg    480

tggtgcctgg tcaaaggctt ctatcccagc gacatcgccg tggagtggga gagcaatggg    540

cagccggaga acaactacaa gaccacgcct cccgtgctgg actccgacgg ctccttcttc    600

ctctacagca agctcaccgt ggacaagagc aggtggcagc aggggaacgt cttctcatgc    660

tccgtgatgc atgaggctct gcacaaccac tacacgcaga agagcctctc cctgtctccg    720

ggtaaa                                                                726
```

<210> SEQ ID NO 122
<211> LENGTH: 242
<212> TYPE: PRT

<213> ORGANISM: Artificial Sequence
<220> FEATURE:
<223> OTHER INFORMATION: avi-Fc (hole)-Synthetic peptide

<400> SEQUENCE: 122

Gly Leu Asn Asp Ile Phe Glu Ala Gln Lys Ile Glu Trp His Glu Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Cys Arg Asp Glu Leu Thr Lys Asn Gln Val Ser Leu
145                 150                 155                 160

Trp Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys

<210> SEQ ID NO 123
<211> LENGTH: 1056
<212> TYPE: DNA
<213> ORGANISM: Artificial Sequence
<220> FEATURE:
<223> OTHER INFORMATION: avi-Fc-huASGPR H1 stalk-Synthetic
      oligonucleotide

<400> SEQUENCE: 123
ggcctgaacg atatttttga agcccagaaa atcgaatggc atgaggacaa aactcacaca      60
tgcccaccgt gcccagcacc tgaactcctg gggggaccgt cagtcttcct cttcccccca     120
aaacccaagg acaccctcat gatctcccgg acccctgagg tcacatgcgt ggtggtggac     180
gtgagccacg aagaccctga ggtcaagttc aactggtacg tggacggcgt ggaggtgcat     240
aatgccaaga caaagccgcg ggaggagcag tacaacagca cgtaccgtgt ggtcagcgtc     300
ctcaccgtcc tgcaccagga ctggctgaat ggcaaggagt acaagtgcaa ggtctccaac     360
aaagccctcg gcgcccccat cgagaaaacc atctccaaag ccaaagggca gccccgagaa     420
ccacaggtgt acaccctgcc cccatcccgg gatgagctga ccaagaacca ggtcagcctg     480

-continued

```
acctgcctgg tcaaaggctt ctatcccagc gacatcgccg tggagtggga gagcaatggg    540

cagccggaga acaactacaa gaccacgcct cccgtgctgg actccgacgg ctccttcttc    600

ctctacagca agctcaccgt ggacaagagc aggtggcagc aggggaacgt cttctcatgc    660

tccgtgatgc atgaggctct gcacaaccac tacacgcaga agagcctctc cctgtctccg    720

ggtggcggag gggatctgg aggtggcggc tccggaggcg gaggatctgg cggaggcgga    780

tcccagaata gccagctgca agaggaactg cgtggtctgc gtgaaacctt tagcaatttc    840

accgcaagca ccgaagcaca ggttaaaggt ctgagcaccc agggtggtaa tgttggtcgt    900

aaaatgaaaa gcctggaaag ccagctggaa aaacagcaga aagatctgag cgaagatcat    960

tcatcactgc tgctgcatgt taaacagttt gttagcgatc tgcgtagcct gagctgtcag   1020

atggcagcac tgcagggtaa tggtagcgaa cgtacc                             1056
```

```
<210> SEQ ID NO 124
<211> LENGTH: 352
<212> TYPE: PRT
<213> ORGANISM: Artificial Sequence
<220> FEATURE:
<223> OTHER INFORMATION: avi-Fc-huASGPR H1 stalk-Synthetic peptide

<400> SEQUENCE: 124

Gly Leu Asn Asp Ile Phe Glu Ala Gln Lys Ile Glu Trp His Glu Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Gly Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Gly Gly Gly Gly Ser Gly Gly Gly Gly Ser Gly Gly Gly Gly Ser
                245                 250                 255
```

-continued

```
Gly Gly Gly Gly Ser Gln Asn Ser Gln Leu Gln Glu Glu Leu Arg Gly
            260                 265                 270

Leu Arg Glu Thr Phe Ser Asn Phe Thr Ala Ser Thr Glu Ala Gln Val
        275                 280                 285

Lys Gly Leu Ser Thr Gln Gly Gly Asn Val Gly Arg Lys Met Lys Ser
    290                 295                 300

Leu Glu Ser Gln Leu Glu Lys Gln Gln Lys Asp Leu Ser Glu Asp His
305                 310                 315                 320

Ser Ser Leu Leu Leu His Val Lys Gln Phe Val Ser Asp Leu Arg Ser
                325                 330                 335

Leu Ser Cys Gln Met Ala Ala Leu Gln Gly Asn Gly Ser Glu Arg Thr
            340                 345                 350
```

<210> SEQ ID NO 125
<211> LENGTH: 1056
<212> TYPE: DNA
<213> ORGANISM: Artificial Sequence
<220> FEATURE:
<223> OTHER INFORMATION: avi-Fc-cyASGPR H1 stalk-Synthetic oligonucleotide

<400> SEQUENCE: 125

```
ggcctgaacg atatttttga agcccagaaa atcgaatggc atgaggacaa aactcacaca     60

tgcccaccgt gcccagcacc tgaactcctg gggggaccgt cagtcttcct cttcccccca    120

aaacccaagg acaccctcat gatctcccgg acccctgagg tcacatgcgt ggtggtggac    180

gtgagccacg aagaccctga ggtcaagttc aactggtacg tggacggcgt ggaggtgcat    240

aatgccaaga caaagccgcg ggaggagcag tacaacagca cgtaccgtgt ggtcagcgtc    300

ctcaccgtcc tgcaccagga ctggctgaat ggcaaggagt acaagtgcaa ggtctccaac    360

aaagccctcg gcgcccccat cgagaaaacc atctccaaag ccaaagggca gccccgagaa    420

ccacaggtgt acaccctgcc cccatcccgg gatgagctga ccaagaacca ggtcagcctg    480

acctgcctgg tcaaaggctt ctatcccagc gacatcgccg tggagtggga gagcaatggg    540

cagccggaga acaactacaa gaccacgcct cccgtgctgg actccgacgg ctccttcttc    600

ctctacagca agctcaccgt ggacaagagc aggtggcagc aggggaacgt cttctcatgc    660

tccgtgatgc atgaggctct gcacaaccac tacacgcaga agagcctctc cctgtctccg    720

ggtggcggag gggatctgg aggtggcggc tccggaggcg gaggatctgg cggaggcgga    780

tcccaaaacg cccagctgca gcgggagctg cggggcctga gagagacgct cagcaacttc    840

acagcgagca ccgaggccca ggtcaagggc ttgagcaccc agggaggcaa tgtgggaaga    900

aagatgaagt cgctggagtc ccagctggag aaacagcaga aggacttgag tgaagatcac    960

tccagcctgc tgctccacgt gaagcagttc gtgtctgacc tgcggagcct gagctgtcag   1020

atggcggcgc tccagggcaa tggctcggaa agggcc                             1056
```

<210> SEQ ID NO 126
<211> LENGTH: 352
<212> TYPE: PRT
<213> ORGANISM: Artificial Sequence
<220> FEATURE:
<223> OTHER INFORMATION: avi-Fc-cyASGPR H1 stalk-Synthetic peptide

<400> SEQUENCE: 126

```
Gly Leu Asn Asp Ile Phe Glu Ala Gln Lys Ile Glu Trp His Glu Asp
1               5                   10                  15

Lys Thr His Thr Cys Pro Pro Cys Pro Ala Pro Glu Leu Leu Gly Gly
```

```
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Gly Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Gly Gly Gly Gly Ser Gly Gly Gly Gly Ser Gly Gly Gly Gly Ser
                245                 250                 255

Gly Gly Gly Gly Ser Gln Asn Ala Gln Leu Gln Arg Glu Leu Arg Gly
            260                 265                 270

Leu Arg Glu Thr Leu Ser Asn Phe Thr Ala Ser Thr Glu Ala Gln Val
        275                 280                 285

Lys Gly Leu Ser Thr Gln Gly Gly Asn Val Gly Arg Lys Met Lys Ser
    290                 295                 300

Leu Glu Ser Gln Leu Glu Lys Gln Gln Lys Asp Leu Ser Glu Asp His
305                 310                 315                 320

Ser Ser Leu Leu Leu His Val Lys Gln Phe Val Ser Asp Leu Arg Ser
                325                 330                 335

Leu Ser Cys Gln Met Ala Ala Leu Gln Gly Asn Gly Ser Glu Arg Ala
            340                 345                 350


<210> SEQ ID NO 127
<211> LENGTH: 1023
<212> TYPE: DNA
<213> ORGANISM: Artificial Sequence
<220> FEATURE:
<223> OTHER INFORMATION: avi-Fc-huCLEC10A stalk-Synthetic
      oligonucleotide

<400> SEQUENCE: 127

gacaaaactc acacatgccc accgtgccca gcacctgaac tcctgggggg accgtcagtc      60

ttcctcttcc ccccaaaacc caaggacacc ctcatgatct cccggacccc tgaggtcaca     120

tgcgtggtgg tggacgtgag ccacgaagac cctgaggtca agttcaactg gtacgtggac     180
```

-continued

```
ggcgtggagg tgcataatgc caagacaaag ccgcgggagg agcagtacaa cagcacgtac    240

cgtgtggtca gcgtcctcac cgtcctgcac caggactggc tgaatggcaa ggagtacaag    300

tgcaaggtct ccaacaaagc cctcggcgcc cccatcgaga aaaccatctc caaagccaaa    360

gggcagcccc gagaaccaca ggtgtacacc ctgcccccat cccgggatga gctgaccaag    420

aaccaggtca gcctgacctg cctggtcaaa ggcttctatc ccagcgacat cgccgtggag    480

tgggagagca atgggcagcc ggagaacaac tacaagacca cgcctcccgt gctggactcc    540

gacggctcct tcttcctcta cagcaagctc accgtggaca agagcaggtg gcagcagggg    600

aacgtcttct catgctccgt gatgcatgag gctctgcaca accactacac gcagaagagc    660

ctctccctgt ctccgggtgg cggagggggga tctggaggtg gcggctccgg aggcggagga    720

tctggcggag gcggatccca gaacagcaag ttccagcggg acctggtcac cctgcggacc    780

gacttcagca acttcaccag caacaccgtg gccgagatcc aggccctgac cagccagggc    840

agcagcctgg aagagacaat cgccagcctg aaggccgagg tggaaggctt caagcaggaa    900

cggcaggccg tccacagcga gatgctgctg cgggtgcagc agctggtgca ggacctgaag    960

aaactgacct gccaggtggc caccctgaac aacaacggcg aggaagctag cactgaaggg   1020

acc                                                                 1023


<210> SEQ ID NO 128
<211> LENGTH: 356
<212> TYPE: PRT
<213> ORGANISM: Artificial Sequence
<220> FEATURE:
<223> OTHER INFORMATION: avi-Fc-huCLEC10A stalk-Synthetic peptide

<400> SEQUENCE: 128

Gly Leu Asn Asp Ile Phe Glu Ala Gln Lys Ile Glu Trp His Glu Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Gly Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205
```

```
Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Gly Gly Gly Gly Ser Gly Gly Gly Gly Ser Gly Gly Gly Gly Ser
                245                 250                 255

Gly Gly Gly Gly Ser Gln Asn Ser Lys Phe Gln Arg Asp Leu Val Thr
            260                 265                 270

Leu Arg Thr Asp Phe Ser Asn Phe Thr Ser Asn Thr Val Ala Glu Ile
        275                 280                 285

Gln Ala Leu Thr Ser Gln Gly Ser Ser Leu Glu Glu Thr Ile Ala Ser
    290                 295                 300

Leu Lys Ala Glu Val Glu Gly Phe Lys Gln Glu Arg Gln Ala Val His
305                 310                 315                 320

Ser Glu Met Leu Leu Arg Val Gln Gln Leu Val Gln Asp Leu Lys Lys
                325                 330                 335

Leu Thr Cys Gln Val Ala Thr Leu Asn Asn Asn Gly Glu Glu Ala Ser
            340                 345                 350

Thr Glu Gly Thr
        355


<210> SEQ ID NO 129
<211> LENGTH: 1473
<212> TYPE: DNA
<213> ORGANISM: Artificial Sequence
<220> FEATURE:
<223> OTHER INFORMATION: avi-Fc-huASGPR H1 stalk CRD-Synthetic
      oligonucleotide

<400> SEQUENCE: 129

ggcctgaacg atatttttga agcccagaaa atcgaatggc atgaggacaa aactcacaca      60

tgcccaccgt gcccagcacc tgaactcctg gggggaccgt cagtcttcct cttcccccca     120

aaacccaagg acaccctcat gatctcccgg acccctgagg tcacatgcgt ggtggtggac     180

gtgagccacg aagaccctga ggtcaagttc aactggtacg tggacggcgt ggaggtgcat     240

aatgccaaga caaagccgcg ggaggagcag tacaacagca cgtaccgtgt ggtcagcgtc     300

ctcaccgtcc tgcaccagga ctggctgaat ggcaaggagt acaagtgcaa ggtctccaac     360

aaagccctcg gcgcccccat cgagaaaacc atctccaaag ccaaagggca gccccgagaa     420

ccacaggtgt acaccctgcc cccatcccgg gatgagctga ccaagaacca ggtcagcctg     480

acctgcctgg tcaaaggctt ctatcccagc gacatcgccg tggagtggga gagcaatggg     540

cagccggaga acaactacaa gaccacgcct cccgtgctgg actccgacgg ctccttcttc     600

ctctacagca agctcaccgt ggacaagagc aggtggcagc aggggaacgt cttctcatgc     660

tccgtgatgc atgaggctct gcacaaccac tacacgcaga agagcctctc cctgtctccg     720

ggtggcggag gggatctgg aggtggcggc tccggaggcg gaggatctgg cggaggcgga     780

tcccagaata gccagctgca agaggaactg cgtggtctgc gtgaaacctt tagcaatttc     840

accgcaagca ccgaagcaca ggttaaaggt ctgagcaccc agggtggtaa tgttggtcgt     900

aaaatgaaaa gcctggaaag ccagctggaa aaacagcaga aagatctgag cgaagatcat     960

tcatcactgc tgctgcatgt taaacagttt gttagcgatc tgcgtagcct gagctgtcag    1020

atggcagcac tgcagggtaa tggtagcgaa cgtacctgtt gtccggttaa ttgggttgaa    1080

catgaacgta gctgctattg gtttagccgt agcggtaaag catgggcaga tgcagataat    1140
```

```
tattgtcgtc tggaagatgc acatctggtt gttgtgacca gctgggaaga acagaaattt   1200

gttcagcatc atattggtcc ggtgaatacc tggatgggtc tgcatgatca gaatggtccg   1260

tggaaatggg ttgatggcac cgattatgaa accggtttta aaaattggcg tccggaacag   1320

ccggatgatt ggtatggtca tggtctgggt ggtggtgaag attgtgcaca ttttaccgat   1380

gatggtcgtt ggaatgatga tgtttgtcag cgtccgtatc gttgggtttg tgaaaccgaa   1440

ctggataaag caagccagga accgccgctg ctg                                1473
```

```
<210> SEQ ID NO 130
<211> LENGTH: 491
<212> TYPE: PRT
<213> ORGANISM: Artificial Sequence
<220> FEATURE:
<223> OTHER INFORMATION: avi-Fc-huASGPR H1 stalk CRD-Synthetic peptide

<400> SEQUENCE: 130

Gly Leu Asn Asp Ile Phe Glu Ala Gln Lys Ile Glu Trp His Glu Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Gly Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Gly Gly Gly Gly Ser Gly Gly Gly Gly Ser Gly Gly Gly Gly Ser
                245                 250                 255

Gly Gly Gly Gly Ser Gln Asn Ser Gln Leu Gln Glu Glu Leu Arg Gly
            260                 265                 270

Leu Arg Glu Thr Phe Ser Asn Phe Thr Ala Ser Thr Glu Ala Gln Val
        275                 280                 285

Lys Gly Leu Ser Thr Gln Gly Gly Asn Val Gly Arg Lys Met Lys Ser
    290                 295                 300
```

-continued

```
Leu Glu Ser Gln Leu Glu Lys Gln Gln Lys Asp Leu Ser Glu Asp His
305                 310                 315                 320

Ser Ser Leu Leu Leu His Val Lys Gln Phe Val Ser Asp Leu Arg Ser
                325                 330                 335

Leu Ser Cys Gln Met Ala Ala Leu Gln Gly Asn Gly Ser Glu Arg Thr
            340                 345                 350

Cys Cys Pro Val Asn Trp Val Glu His Glu Arg Ser Cys Tyr Trp Phe
        355                 360                 365

Ser Arg Ser Gly Lys Ala Trp Ala Asp Ala Asp Asn Tyr Cys Arg Leu
    370                 375                 380

Glu Asp Ala His Leu Val Val Val Thr Ser Trp Glu Glu Gln Lys Phe
385                 390                 395                 400

Val Gln His His Ile Gly Pro Val Asn Thr Trp Met Gly Leu His Asp
                405                 410                 415

Gln Asn Gly Pro Trp Lys Trp Val Asp Gly Thr Asp Tyr Glu Thr Gly
            420                 425                 430

Phe Lys Asn Trp Arg Pro Glu Gln Pro Asp Asp Trp Tyr Gly His Gly
        435                 440                 445

Leu Gly Gly Gly Glu Asp Cys Ala His Phe Thr Asp Asp Gly Arg Trp
    450                 455                 460

Asn Asp Asp Val Cys Gln Arg Pro Tyr Arg Trp Val Cys Glu Thr Glu
465                 470                 475                 480

Leu Asp Lys Ala Ser Gln Glu Pro Pro Leu Leu
                485                 490
```

<210> SEQ ID NO 131
<211> LENGTH: 1473
<212> TYPE: DNA
<213> ORGANISM: Artificial Sequence
<220> FEATURE:
<223> OTHER INFORMATION: avi-Fc-cyASGPR H1 stalk CRD-Synthetic
oligonucleotide

<400> SEQUENCE: 131

```
ggcctgaacg atatttttga agcccagaaa atcgaatggc atgaggacaa aactcacaca      60

tgcccaccgt gcccagcacc tgaactcctg gggggaccgt cagtcttcct cttcccccca     120

aaacccaagg acaccctcat gatctcccgg acccctgagg tcacatgcgt ggtggtggac     180

gtgagccacg aagaccctga ggtcaagttc aactggtacg tggacggcgt ggaggtgcat     240

aatgccaaga caaagccgcg ggaggagcag tacaacagca cgtaccgtgt ggtcagcgtc     300

ctcaccgtcc tgcaccagga ctggctgaat ggcaaggagt acaagtgcaa ggtctccaac     360

aaagccctcg gcgcccccat cgagaaaacc atctccaaag ccaaagggca gccccgagaa     420

ccacaggtgt acaccctgcc cccatcccgg gatgagctga ccaagaacca ggtcagcctg     480

acctgcctgg tcaaaggctt ctatcccagc gacatcgccg tggagtggga gagcaatggg     540

cagccggaga acaactacaa gaccacgcct cccgtgctgg actccgacgg ctccttcttc     600

ctctacagca agctcaccgt ggacaagagc aggtggcagc aggggaacgt cttctcatgc     660

tccgtgatgc atgaggctct gcacaaccac tacacgcaga agagcctctc cctgtctccg     720

ggtggcggag ggggatctgg aggtggcggc tccggaggcg gaggatctgg cggaggcgga     780

tcccaaaacg cccagctgca gcgggagctg cggggcctga gagagacgct cagcaacttc     840

acagcgagca ccgaggccca ggtcaagggc ttgagcaccc agggaggcaa tgtgggaaga     900

aagatgaagt cgctggagtc ccagctggag aaacagcaga aggacttgag tgaagatcac     960
```

```
tccagcctgc tgctccacgt gaagcagttc gtgtctgacc tgcggagcct gagctgtcag   1020

atggcggcgc tccagggcaa tggctcggaa agggcctgct gcccagtcaa ctgggtggag   1080

cacgagcgca gctgctactg gttctctcgc tccgggaagg cctgggccga cgccgacaac   1140

tactgccggc tggaggacgc gcacctggtg gtggtcacgt cctgggagga gcagaaattt   1200

gtccagcacc acataggtcc tgtgaacacc tggatgggcc tccacgacca aaacgggccc   1260

tggaagtggg tggacgggac ggactacgag acgggcttca agaactggag accggagcag   1320

ccggacgact ggtacggcca cgggctcggg ggaggggagg actgtgccca cttcaccgac   1380

gacggccgct ggaacgacga cgtctgccag aggccctacc gctgggtctg cgagacagag   1440

ctggacaagg ccagccagga gccacctctc ctt                               1473
```

<210> SEQ ID NO 132
<211> LENGTH: 491
<212> TYPE: PRT
<213> ORGANISM: Artificial Sequence
<220> FEATURE:
<223> OTHER INFORMATION: avi-Fc-cyASGPR H1 stalk CRD-Synthetic peptide

<400> SEQUENCE: 132

```
Gly Leu Asn Asp Ile Phe Glu Ala Gln Lys Ile Glu Trp His Glu Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Gly Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Gly Gly Gly Gly Ser Gly Gly Gly Gly Ser Gly Gly Gly Gly Ser
                245                 250                 255

Gly Gly Gly Gly Ser Gln Asn Ala Gln Leu Gln Arg Glu Leu Arg Gly
            260                 265                 270
```

```
Leu Arg Glu Thr Leu Ser Asn Phe Thr Ala Ser Thr Glu Ala Gln Val
        275                 280                 285

Lys Gly Leu Ser Thr Gln Gly Gly Asn Val Gly Arg Lys Met Lys Ser
    290                 295                 300

Leu Glu Ser Gln Leu Glu Lys Gln Gln Lys Asp Leu Ser Glu Asp His
305                 310                 315                 320

Ser Ser Leu Leu Leu His Val Lys Gln Phe Val Ser Asp Leu Arg Ser
                325                 330                 335

Leu Ser Cys Gln Met Ala Ala Leu Gln Gly Asn Gly Ser Glu Arg Ala
            340                 345                 350

Cys Cys Pro Val Asn Trp Val Glu His Glu Arg Ser Cys Tyr Trp Phe
        355                 360                 365

Ser Arg Ser Gly Lys Ala Trp Ala Asp Ala Asp Asn Tyr Cys Arg Leu
    370                 375                 380

Glu Asp Ala His Leu Val Val Val Thr Ser Trp Glu Glu Gln Lys Phe
385                 390                 395                 400

Val Gln His His Ile Gly Pro Val Asn Thr Trp Met Gly Leu His Asp
                405                 410                 415

Gln Asn Gly Pro Trp Lys Trp Val Asp Gly Thr Asp Tyr Glu Thr Gly
            420                 425                 430

Phe Lys Asn Trp Arg Pro Glu Gln Pro Asp Asp Trp Tyr Gly His Gly
        435                 440                 445

Leu Gly Gly Gly Glu Asp Cys Ala His Phe Thr Asp Asp Gly Arg Trp
    450                 455                 460

Asn Asp Asp Val Cys Gln Arg Pro Tyr Arg Trp Val Cys Glu Thr Glu
465                 470                 475                 480

Leu Asp Lys Ala Ser Gln Glu Pro Pro Leu Leu
                485                 490
```

<210> SEQ ID NO 133
<211> LENGTH: 1434
<212> TYPE: DNA
<213> ORGANISM: Artificial Sequence
<220> FEATURE:
<223> OTHER INFORMATION: avi-Fc-huCLEC10A stalk CRD-Synthetic
      oligonucleotide

<400> SEQUENCE: 133

```
gacaaaactc acacatgccc accgtgccca gcacctgaac tcctgggggg accgtcagtc     60

ttcctcttcc ccccaaaacc caaggacacc ctcatgatct cccggacccc tgaggtcaca    120

tgcgtggtgg tggacgtgag ccacgaagac cctgaggtca agttcaactg gtacgtggac    180

ggcgtggagg tgcataatgc caagacaaag ccgcgggagg agcagtacaa cagcacgtac    240

cgtgtggtca gcgtcctcac cgtcctgcac caggactggc tgaatggcaa ggagtacaag    300

tgcaaggtct ccaacaaagc cctcggcgcc cccatcgaga aaaccatctc caaagccaaa    360

gggcagcccc gagaaccaca ggtgtacacc ctgcccccat cccgggatga gctgaccaag    420

aaccaggtca gcctgacctg cctggtcaaa ggcttctatc ccagcgacat cgccgtggag    480

tgggagagca atgggcagcc ggagaacaac tacaagacca cgcctcccgt gctggactcc    540

gacggctcct tcttcctcta cagcaagctc accgtggaca agagcaggtg gcagcagggg    600

aacgtcttct catgctccgt gatgcatgag gctctgcaca accactacac gcagaagagc    660

ctctccctgt ctccgggtgg cggaggggga tctggaggtg gcggctccgg aggcggagga    720

tctggcggag gcggatccca gaacagcaag ttccagcggg acctggtcac cctgcggacc    780
```

```
gacttcagca acttcaccag caacaccgtg gccgagatcc aggccctgac cagccagggc    840

agcagcctgg aagagacaat cgccagcctg aaggccgagg tggaaggctt caagcaggaa    900

cggcaggccg tccacagcga gatgctgctg cgggtgcagc agctggtgca ggacctgaag    960

aaactgacct gccaggtggc caccctgaac aacaacggcg aggaagctag cactgaaggg   1020

acctgctgtc cggttaattg ggttgaacat caggatagct gctattggtt tagccatagc   1080

ggtatgagct gggcagaagc agaaaaatat tgccagctga aaaatgccca tctggttgtt   1140

attaatagcc gtgaagaaca gaattttgtg cagaaatatc tgggtagcgc atatacctgg   1200

atgggtctga gcgatccgga aggtgcatgg aaatgggttg atggcaccga ttatgcaacc   1260

ggttttcaga attggaaacc gggtcagccg gatgattggc agggtcatgg tctgggtggt   1320

ggtgaagatt gtgcacattt tcatccggat ggtcgttgga atgatgatgt ttgtcagcgt   1380

ccgtatcatt gggtttgtga agcaggtctg ggtcagacca gccaggaaag ccat         1434
```

```
<210> SEQ ID NO 134
<211> LENGTH: 493
<212> TYPE: PRT
<213> ORGANISM: Artificial Sequence
<220> FEATURE:
<223> OTHER INFORMATION: avi-Fc-huCLEC10A stalk CRD-Synthetic peptide

<400> SEQUENCE: 134

Gly Leu Asn Asp Ile Phe Glu Ala Gln Lys Ile Glu Trp His Glu Asp
1               5                   10                  15

Lys Thr His Thr Cys Pro Pro Cys Pro Ala Pro Glu Leu Leu Gly Gly
            20                  25                  30

Pro Ser Val Phe Leu Phe Pro Pro Lys Pro Lys Asp Thr Leu Met Ile
        35                  40                  45

Ser Arg Thr Pro Glu Val Thr Cys Val Val Val Asp Val Ser His Glu
    50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Gly Ala Pro Ile Glu
        115                 120                 125

Lys Thr Ile Ser Lys Ala Lys Gly Gln Pro Arg Glu Pro Gln Val Tyr
    130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Gly Gly Gly Gly Ser Gly Gly Gly Gly Ser Gly Gly Gly Gly Ser
                245                 250                 255
```

```
Gly Gly Gly Gly Ser Gln Asn Ser Lys Phe Gln Arg Asp Leu Val Thr
            260                 265                 270

Leu Arg Thr Asp Phe Ser Asn Phe Thr Ser Asn Thr Val Ala Glu Ile
        275                 280                 285

Gln Ala Leu Thr Ser Gln Gly Ser Ser Leu Glu Glu Thr Ile Ala Ser
    290                 295                 300

Leu Lys Ala Glu Val Glu Gly Phe Lys Gln Glu Arg Gln Ala Val His
305                 310                 315                 320

Ser Glu Met Leu Leu Arg Val Gln Gln Leu Val Gln Asp Leu Lys Lys
                325                 330                 335

Leu Thr Cys Gln Val Ala Thr Leu Asn Asn Asn Gly Glu Glu Ala Ser
            340                 345                 350

Thr Glu Gly Thr Cys Cys Pro Val Asn Trp Val Glu His Gln Asp Ser
        355                 360                 365

Cys Tyr Trp Phe Ser His Ser Gly Met Ser Trp Ala Glu Ala Glu Lys
    370                 375                 380

Tyr Cys Gln Leu Lys Asn Ala His Leu Val Val Ile Asn Ser Arg Glu
385                 390                 395                 400

Glu Gln Asn Phe Val Gln Lys Tyr Leu Gly Ser Ala Tyr Thr Trp Met
                405                 410                 415

Gly Leu Ser Asp Pro Glu Gly Ala Trp Lys Trp Val Asp Gly Thr Asp
            420                 425                 430

Tyr Ala Thr Gly Phe Gln Asn Trp Lys Pro Gly Gln Pro Asp Asp Trp
        435                 440                 445

Gln Gly His Gly Leu Gly Gly Gly Glu Asp Cys Ala His Phe His Pro
    450                 455                 460

Asp Gly Arg Trp Asn Asp Asp Val Cys Gln Arg Pro Tyr His Trp Val
465                 470                 475                 480

Cys Glu Ala Gly Leu Gly Gln Thr Ser Gln Glu Ser His
                485                 490


<210> SEQ ID NO 135
<211> LENGTH: 19
<212> TYPE: PRT
<213> ORGANISM: Artificial Sequence
<220> FEATURE:
<223> OTHER INFORMATION: leader 1-Synthetic peptide

<400> SEQUENCE: 135

Met Asp Trp Thr Trp Arg Ile Leu Phe Leu Val Ala Ala Ala Thr Gly
1               5                   10                  15

Ala His Ser


<210> SEQ ID NO 136
<211> LENGTH: 22
<212> TYPE: PRT
<213> ORGANISM: Artificial Sequence
<220> FEATURE:
<223> OTHER INFORMATION: leader 2-Synthetic peptide

<400> SEQUENCE: 136

Met Asp Met Arg Val Pro Ala Gln Leu Leu Gly Leu Leu Leu Leu Trp
1               5                   10                  15

Phe Pro Gly Ala Arg Cys
            20


<210> SEQ ID NO 137
```

<211> LENGTH: 19
<212> TYPE: PRT
<213> ORGANISM: Artificial Sequence
<220> FEATURE:
<223> OTHER INFORMATION: leader 3-Synthetic peptide

<400> SEQUENCE: 137

```
Met Gly Trp Ser Cys Ile Ile Leu Phe Leu Val Ala Thr Ala Thr Gly
1               5                   10                  15

Val His Ser
```

<210> SEQ ID NO 138
<211> LENGTH: 165
<212> TYPE: PRT
<213> ORGANISM: Homo sapiens

<400> SEQUENCE: 138

```
Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 139
<211> LENGTH: 165
<212> TYPE: PRT
<213> ORGANISM: Artificial Sequence
<220> FEATURE:
<223> OTHER INFORMATION: IFNa2a-Synthetic peptide

<400> SEQUENCE: 139

```
Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80
```

```
Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 140
<211> LENGTH: 82
<212> TYPE: DNA
<213> ORGANISM: Artificial Sequence
<220> FEATURE:
<223> OTHER INFORMATION: DP47-v4-4: pos. Synthetic oligonucleotide
<220> FEATURE:
<221> NAME/KEY: misc_feature
<222> LOCATION: (29)..(31)
<223> OTHER INFORMATION: (mrn): K=70, R=30%
<220> FEATURE:
<221> NAME/KEY: misc_feature
<222> LOCATION: (31)..(41)
<223> OTHER INFORMATION: n is a, c, g, or t
<220> FEATURE:
<221> NAME/KEY: misc_feature
<222> LOCATION: (32)..(34)
<223> OTHER INFORMATION: (nnn): G/D=20, E/V/S=10, A/P/R/L/T/Y=5%
<220> FEATURE:
<221> NAME/KEY: misc_feature
<222> LOCATION: (35)..(40)
<223> OTHER INFORMATION: (2x nnn), each: G/Y/S=15, A/D/T/R/P/L/V/N/W/F/
      I/E =4,6%
<220> FEATURE:
<221> NAME/KEY: misc_feature
<222> LOCATION: (41)..(43)
<223> OTHER INFORMATION: (nvn): G/A/Y=20, P/W/S/D/T=8%
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (44)..(46)
<223> OTHER INFORMATION: (ndn): F=46, L/M=15, G/I/Y=8%
<220> FEATURE:
<221> NAME/KEY: misc_feature
<222> LOCATION: (46)..(46)
<223> OTHER INFORMATION: n is a, c, g, or t

<400> SEQUENCE: 140
cgaggacacg gccgtatatt actgtgcgmr nnnnnnnnnn nvnndngact actggggcca     60
aggaaccctg gtcaccgtct cg                                              82

<210> SEQ ID NO 141
<211> LENGTH: 88
<212> TYPE: DNA
<213> ORGANISM: Artificial Sequence
<220> FEATURE:
<223> OTHER INFORMATION: DP47-v4-6: Synthetic oligonucleotide
<220> FEATURE:
<221> NAME/KEY: misc_feature
<222> LOCATION: (29)..(31)
<223> OTHER INFORMATION: (mrn): K=70, R=30%
<220> FEATURE:
<221> NAME/KEY: misc_feature
<222> LOCATION: (31)..(47)

<223> OTHER INFORMATION: n is a, c, g, or t
<220> FEATURE:
<221> NAME/KEY: misc_feature
<222> LOCATION: (32)..(34)
<223> OTHER INFORMATION: (nnn): G/D=20, E/V/S=10, A/P/R/L/T/Y=5%
<220> FEATURE:
<221> NAME/KEY: misc_feature
<222> LOCATION: (35)..(46)
<223> OTHER INFORMATION: (4x nnn), each: G/Y/S=15, A/D/T/R/P/L/V/N/W/F/
I/E =4,6%
<220> FEATURE:
<221> NAME/KEY: misc_feature
<222> LOCATION: (47)..(49)
<223> OTHER INFORMATION: (nvn): G/A/Y=20, P/W/S/D/T=8%
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (50)..(52)
<223> OTHER INFORMATION: (nvn): G/A/Y=20, P/W/S/D/T=8%
<220> FEATURE:
<221> NAME/KEY: misc_feature
<222> LOCATION: (52)..(52)
<223> OTHER INFORMATION: n is a, c, g, or t

<400> SEQUENCE: 141
cgaggacacg gccgtatatt actgtgcgmr nnnnnnnnnn nnnnnnnvnn dngactactg 60
gggccaagga accctggtca ccgtctcg 88

<210> SEQ ID NO 142
<211> LENGTH: 94
<212> TYPE: DNA
<213> ORGANISM: Artificial Sequence
<220> FEATURE:
<223> OTHER INFORMATION: DP47-v4-8: Synthetic oligonucleotide
<220> FEATURE:
<221> NAME/KEY: misc_feature
<222> LOCATION: (29)..(31)
<223> OTHER INFORMATION: K=70, R=30%
<220> FEATURE:
<221> NAME/KEY: misc_feature
<222> LOCATION: (31)..(53)
<223> OTHER INFORMATION: n is a, c, g, or t
<220> FEATURE:
<221> NAME/KEY: misc_feature
<222> LOCATION: (32)..(34)
<223> OTHER INFORMATION: (nnn): G/D=20, E/V/S=10, A/P/R/L/T/Y=5%
<220> FEATURE:
<221> NAME/KEY: misc_feature
<222> LOCATION: (35)..(52)
<223> OTHER INFORMATION: (6x nnn), each: G/Y/S=15, A/D/T/R/P/L/V/N/W/F/
I/E =4,6%
<220> FEATURE:
<221> NAME/KEY: misc_feature
<222> LOCATION: (53)..(55)
<223> OTHER INFORMATION: (nvn): G/A/Y=20, P/W/S/D/T=8%
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (56)..(58)
<223> OTHER INFORMATION: (ndn): F=46, L/M=15, G/I/Y=8%
<220> FEATURE:
<221> NAME/KEY: misc_feature
<222> LOCATION: (58)..(58)
<223> OTHER INFORMATION: n is a, c, g, or t

<400> SEQUENCE: 142
cgaggacacg gccgtatatt actgtgcgmr nnnnnnnnnn nnnnnnnnnn nnnvnndnga 60
ctactggggc caaggaaccc tggtcaccgt ctcg 94

<210> SEQ ID NO 143
<211> LENGTH: 85
<212> TYPE: DNA
<213> ORGANISM: Artificial Sequence
<220> FEATURE:
<223> OTHER INFORMATION: Vl_3_19_L3r_V: Synthetic oligonucleotide
<220> FEATURE:
<221> NAME/KEY: misc_feature
<222> LOCATION: (32)..(32)
<223> OTHER INFORMATION: original base and 40% randomization as M
<220> FEATURE:
<221> NAME/KEY: misc_feature
<222> LOCATION: (33)..(34)
<223> OTHER INFORMATION: 60% original base and 40% randomization as N
<220> FEATURE:
<221> NAME/KEY: misc_feature
<222> LOCATION: (35)..(35)
<223> OTHER INFORMATION: original base and 40% randomization as M
<220> FEATURE:
<221> NAME/KEY: misc_feature
<222> LOCATION: (36)..(37)
<223> OTHER INFORMATION: 60% original base and 40% randomization as N
<220> FEATURE:
<221> NAME/KEY: misc_feature
<222> LOCATION: (38)..(38)
<223> OTHER INFORMATION: original base and 40% randomization as M
<220> FEATURE:
<221> NAME/KEY: misc_feature
<222> LOCATION: (39)..(40)
<223> OTHER INFORMATION: 60% original base and 40% randomization as N
<220> FEATURE:
<221> NAME/KEY: misc_feature
<222> LOCATION: (41)..(41)
<223> OTHER INFORMATION: original base and 40% randomization as M
<220> FEATURE:
<221> NAME/KEY: misc_feature
<222> LOCATION: (42)..(43)
<223> OTHER INFORMATION: 60% original base and 40% randomization as N
<220> FEATURE:
<221> NAME/KEY: misc_feature
<222> LOCATION: (44)..(44)
<223> OTHER INFORMATION: original base and 40% randomization as M
<220> FEATURE:
<221> NAME/KEY: misc_feature
<222> LOCATION: (45)..(46)
<223> OTHER INFORMATION: 60% original base and 40% randomization as N
<220> FEATURE:
<221> NAME/KEY: misc_feature
<222> LOCATION: (47)..(47)
<223> OTHER INFORMATION: original base and 40% randomization as M
<220> FEATURE:
<221> NAME/KEY: misc_feature
<222> LOCATION: (48)..(49)
<223> OTHER INFORMATION: 60% original base and 40% randomization as N
<220> FEATURE:
<221> NAME/KEY: misc_feature
<222> LOCATION: (50)..(50)
<223> OTHER INFORMATION: 60% original base and 40% randomization as M
<220> FEATURE:
<221> NAME/KEY: misc_feature
<222> LOCATION: (51)..(52)
<223> OTHER INFORMATION: 60% original base and 40% randomization as N

<400> SEQUENCE: 143
ggacggtcag cttggtccct ccgccgaata cvhvattacc gctactatca cgggagttac 60
agtaatagtc agcctcatct tccgc 85

<210> SEQ ID NO 144
<211> LENGTH: 88
<212> TYPE: DNA
<213> ORGANISM: Artificial Sequence
<220> FEATURE:
<223> OTHER INFORMATION: Vl_3_19_L3r_HV: Synthetic oligonucleotide
<220> FEATURE:

<221> NAME/KEY: misc_feature
<222> LOCATION: (32)..(32)
<223> OTHER INFORMATION: 60% original base and 40% randomization as M
<220> FEATURE:
<221> NAME/KEY: misc_feature
<222> LOCATION: (33)..(34)
<223> OTHER INFORMATION: 60% original base and 40% randomization as N
<220> FEATURE:
<221> NAME/KEY: misc_feature
<222> LOCATION: (35)..(35)
<223> OTHER INFORMATION: 60% original base and 40% randomization as M
<220> FEATURE:
<221> NAME/KEY: misc_feature
<222> LOCATION: (36)..(37)
<223> OTHER INFORMATION: 60% original base and 40% randomization as N
<220> FEATURE:
<221> NAME/KEY: misc_feature
<222> LOCATION: (38)..(38)
<223> OTHER INFORMATION: 60% original base and 40% randomization as M
<220> FEATURE:
<221> NAME/KEY: misc_feature
<222> LOCATION: (39)..(40)
<223> OTHER INFORMATION: 60% original base and 40% randomization as N
<220> FEATURE:
<221> NAME/KEY: misc_feature
<222> LOCATION: (41)..(41)
<223> OTHER INFORMATION: 60% original base and 40% randomization as M
<220> FEATURE:
<221> NAME/KEY: misc_feature
<222> LOCATION: (42)..(43)
<223> OTHER INFORMATION: 60% original base and 40% randomization as N
<220> FEATURE:
<221> NAME/KEY: misc_feature
<222> LOCATION: (44)..(44)
<223> OTHER INFORMATION: 60% original base and 40% randomization as M
<220> FEATURE:
<221> NAME/KEY: misc_feature
<222> LOCATION: (45)..(46)
<223> OTHER INFORMATION: 60% original base and 40% randomization as N
<220> FEATURE:
<221> NAME/KEY: misc_feature
<222> LOCATION: (47)..(47)
<223> OTHER INFORMATION: 60% original base and 40% randomization as M
<220> FEATURE:
<221> NAME/KEY: misc_feature
<222> LOCATION: (48)..(49)
<223> OTHER INFORMATION: 60% original base and 40% randomization as N
<220> FEATURE:
<221> NAME/KEY: misc_feature
<222> LOCATION: (50)..(50)
<223> OTHER INFORMATION: 60% original base and 40% randomization as M
<220> FEATURE:
<221> NAME/KEY: misc_feature
<222> LOCATION: (51)..(52)
<223> OTHER INFORMATION: 60% original base and 40% randomization as N
<220> FEATURE:
<221> NAME/KEY: misc_feature
<222> LOCATION: (53)..(53)
<223> OTHER INFORMATION: 60% original base and 40% randomization as M
<220> FEATURE:
<221> NAME/KEY: misc_feature
<222> LOCATION: (54)..(55)
<223> OTHER INFORMATION: 60% original base and 40% randomization as N

<400> SEQUENCE: 144
ggacggtcag cttggtccct ccgccgaata ccmmatgatt accgctacta tcacgggagt 60
tacagtaata gtcagcctca tcttccgc 88

<210> SEQ ID NO 145
<211> LENGTH: 91
<212> TYPE: DNA
<213> ORGANISM: Artificial Sequence
<220> FEATURE:
<223> OTHER INFORMATION: Vl_3_19_L3r_HLV: Synthetic oligonucleotide
<220> FEATURE:
<221> NAME/KEY: misc_feature
<222> LOCATION: (32)..(32)
<223> OTHER INFORMATION: 60% original base and 40% randomization as M
<220> FEATURE:
<221> NAME/KEY: misc_feature
<222> LOCATION: (33)..(34)
<223> OTHER INFORMATION: 60% original base and 40% randomization as N
<220> FEATURE:
<221> NAME/KEY: misc_feature
<222> LOCATION: (35)..(35)
<223> OTHER INFORMATION: 60% original base and 40% randomization as M
<220> FEATURE:
<221> NAME/KEY: misc_feature
<222> LOCATION: (36)..(37)
<223> OTHER INFORMATION: 60% original base and 40% randomization as N
<220> FEATURE:
<221> NAME/KEY: misc_feature
<222> LOCATION: (38)..(38)
<223> OTHER INFORMATION: 60% original base and 40% randomization as M
<220> FEATURE:
<221> NAME/KEY: misc_feature
<222> LOCATION: (39)..(40)
<223> OTHER INFORMATION: 60% original base and 40% randomization as N
<220> FEATURE:
<221> NAME/KEY: misc_feature
<222> LOCATION: (41)..(41)
<223> OTHER INFORMATION: 60% original base and 40% randomization as M
<220> FEATURE:
<221> NAME/KEY: misc_feature
<222> LOCATION: (42)..(43)
<223> OTHER INFORMATION: 60% original base and 40% randomization as N
<220> FEATURE:
<221> NAME/KEY: misc_feature
<222> LOCATION: (44)..(44)
<223> OTHER INFORMATION: 60% original base and 40% randomization as M
<220> FEATURE:
<221> NAME/KEY: misc_feature
<222> LOCATION: (45)..(46)
<223> OTHER INFORMATION: 60% original base and 40% randomization as N
<220> FEATURE:
<221> NAME/KEY: misc_feature
<222> LOCATION: (47)..(47)
<223> OTHER INFORMATION: 60% original base and 40% randomization as M
<220> FEATURE:
<221> NAME/KEY: misc_feature
<222> LOCATION: (48)..(49)
<223> OTHER INFORMATION: 60% original base and 40% randomization as N
<220> FEATURE:
<221> NAME/KEY: misc_feature
<222> LOCATION: (50)..(50)
<223> OTHER INFORMATION: 60% original base and 40% randomization as M
<220> FEATURE:
<221> NAME/KEY: misc_feature
<222> LOCATION: (51)..(52)
<223> OTHER INFORMATION: 60% original base and 40% randomization as N
<220> FEATURE:
<221> NAME/KEY: misc_feature
<222> LOCATION: (53)..(53)
<223> OTHER INFORMATION: 60% original base and 40% randomization as M
<220> FEATURE:
<221> NAME/KEY: misc_feature
<222> LOCATION: (54)..(55)
<223> OTHER INFORMATION: 60% original base and 40% randomization as N
<220> FEATURE:
<221> NAME/KEY: misc_feature
<222> LOCATION: (56)..(56)
<223> OTHER INFORMATION: 60% original base and 40% randomization as M
<220> FEATURE:
<221> NAME/KEY: misc_feature
<222> LOCATION: (57)..(58)
<223> OTHER INFORMATION: 60% original base and 40% randomization as N

<400> SEQUENCE: 145
ggacggtcag cttggtccct ccgccgaata crhmvwgatg attaccgcta ctatcacggg 60
agttacagta atagtcagcc tcatcttccg c 91

<210> SEQ ID NO 146

<211> LENGTH: 26
<212> TYPE: DNA
<213> ORGANISM: Artificial Sequence
<220> FEATURE:
<223> OTHER INFORMATION: LMB3-Synthetic oligonucleotide

<400> SEQUENCE: 146
caggaaacag ctatgaccat gattac 26

<210> SEQ ID NO 147
<211> LENGTH: 30
<212> TYPE: DNA
<213> ORGANISM: Artificial Sequence
<220> FEATURE:
<223> OTHER INFORMATION: fdseqlong-Synthetic oligonucleotide

<400> SEQUENCE: 147
gacgttagta aatgaatttt ctgtatgagg 30

<210> SEQ ID NO 148
<211> LENGTH: 28
<212> TYPE: DNA
<213> ORGANISM: Artificial Sequence
<220> FEATURE:
<223> OTHER INFORMATION: RJH80-Synthetic oligonucleotide

<400> SEQUENCE: 148
ttcggcggag ggaccaagct gaccgtcc 28

<210> SEQ ID NO 149
<211> LENGTH: 25
<212> TYPE: DNA
<213> ORGANISM: Artificial Sequence
<220> FEATURE:
<223> OTHER INFORMATION: DP47CDR3_ba (mod)-Synthetic oligonucleotide

<400> SEQUENCE: 149
cgcacagtaa tatacggccg tgtcc 25

<210> SEQ ID NO 150
<211> LENGTH: 24
<212> TYPE: DNA
<213> ORGANISM: Artificial Sequence
<220> FEATURE:
<223> OTHER INFORMATION: LCDR3rev-Synthetic oligonucleotide

<400> SEQUENCE: 150
ggagttacag taatagtcag cctc 24

<210> SEQ ID NO 151
<211> LENGTH: 84
<212> TYPE: DNA
<213> ORGANISM: Artificial Sequence
<220> FEATURE:
<223> OTHER INFORMATION: LCDR3 rand: Synthetic oligonucleotide
<220> FEATURE:
<221> NAME/KEY: misc_feature
<222> LOCATION: (25)..(57)
<223> OTHER INFORMATION: n is a, c, g, or t
<220> FEATURE:
<221> NAME/KEY: misc_feature
<222> LOCATION: (25)..(27)
<223> OTHER INFORMATION: 50% R, Z
<220> FEATURE:
<221> NAME/KEY: misc_feature
<222> LOCATION: (28)..(30)
<223> OTHER INFORMATION: 50% D, X
<220> FEATURE:
<221> NAME/KEY: misc_feature -continued

```
<222> LOCATION: (31)..(33)
<223> OTHER INFORMATION: 50% I, X
<220> FEATURE:
<221> NAME/KEY: misc_feature
<222> LOCATION: (34)..(36)
<223> OTHER INFORMATION: 50% S, X
<220> FEATURE:
<221> NAME/KEY: misc_feature
<222> LOCATION: (37)..(39)
<223> OTHER INFORMATION: 50% S; X;
<220> FEATURE:
<221> NAME/KEY: misc_feature
<222> LOCATION: (40)..(42)
<223> OTHER INFORMATION: 50% N, X;
<220> FEATURE:
<221> NAME/KEY: misc_feature
<222> LOCATION: (43)..(45)
<223> OTHER INFORMATION: 50% R, X;
<220> FEATURE:
<221> NAME/KEY: misc_feature
<222> LOCATION: (46)..(48)
<223> OTHER INFORMATION: 50% A, Z;
<220> FEATURE:
<221> NAME/KEY: misc_feature
<222> LOCATION: (49)..(51)
<223> OTHER INFORMATION: 50% V, X;
<220> FEATURE:
<221> NAME/KEY: misc_feature
<222> LOCATION: (52)..(54)
<223> OTHER INFORMATION: 50% R, X;
<220> FEATURE:
<221> NAME/KEY: misc_feature
<222> LOCATION: (55)..(57)
<223> OTHER INFORMATION: 50% N, X. X=2.8% rest (no C); Z=3.1% rest (no
      S, T, C).

<400> SEQUENCE: 151

gaggctgact attactgtaa ctccnnnnnn nnnnnnnnnn nnnnnnnnnn nnnnnnnttc     60

ggcggaggga ccaagctgac cgtc                                            84
```

ASPGR ANTIBODIES AND USES THEREOF

CROSS-REFERENCE TO RELATED APPLICATIONS

This application is a divisional of U.S. patent application Ser. No. 14/419,824 filed Feb. 5, 2015, which is a 371 National phase of PCT International Application No. PCT/EP2013/066432, filed Aug. 6, 2013, which claims the benefit of U.S. provisional application No. 61/681,239 filed Aug. 9, 2012, the contents of which are herein incorporated by reference in their entirety.

FIELD OF THE INVENTION

The present invention generally relates to antibodies specific for asialoglycoprotein receptor (ASGPR) and their use for selectively delivering effector moieties that influence cellular activity. In addition, the present invention relates to polynucleotides encoding such antibodies, and vectors and host cells comprising such polynucleotides. The invention further relates to methods for producing the antibodies of the invention, and to methods of using them in the treatment of disease.

BACKGROUND

Asialoglycoprotein receptor (ASGPR) is a transmembrane receptor composed of two subunits, H1 and H2. The subunits are believed to oligomerize through their extracellular stalk regions. ASGPR is a member of the C-type lectin family (calcium-ion dependent lectin) and mediates the endocytosis and degradation of a wide variety of desialylated glycoproteins. ASGPR is selectively expressed on liver parenchymal cells (hepatocytes), which makes it an attractive target for liver-specific therapies. Many liver diseases, e.g. hepatitis, liver cirrhosis or hepatocellular carcinoma (HCC), can be caused directly or indirectly by viral infection, such as hepatitis virus B (HBV) or C (HCV) infection. Chronic infection with HCV is one of the major causes of cirrhosis and HCC. Similarly, chronic HBV infection accounts for 5-10% of chronic liver disease and cirrhosis in the US. Approved therapies for HBV and HCV infection include interferons (IFN), such as interferon alpha. However, side effects have hampered development and widespread use of these therapies in many cases. Such IFN-associated side effects are thought to be due in part to induction of interferon-stimulated genes (ISGs) in peripheral blood cells following systemic exposure to IFN. Hence, to minimize side effects associated with IFN therapy for liver diseases, and also to augment the antiviral effect of conventional interferons, it is desirable to selectively deliver IFN to the liver. ASGPR has been recognized as potential target molecule on hepatocytes for such selective delivery. For example, WO 92/22310 describes an approach for targeting interferon to the liver by conjugation of recombinant IFN to an asialoglycoprotein. In a similar approach, an interferon molecule itself has been modified to produce asialo-interferon for binding to ASGPR (Eto and Takahashi, Nat Med 5, 577-581 (1999)) More recently, an approach based on anti-ASGPR single variable domain (dAb) antibodies has been described (WO 2011/086143).

However, none of these approaches has been shown to be clinically successful so far, and there remains a need for improved targeting molecules for selective delivery of therapeutic molecules, e.g. interferon, to the liver. The antibodies of the present invention combine several advantageous properties, which make them particularly suitable for targeting effector moieties such as interferons to ASGPR-expressing cells, e.g. for the treatment of liver diseases.

SUMMARY OF THE INVENTION

In one aspect, the invention provides an antibody capable of specific binding to asialoglycoprotein receptor (ASGPR), wherein the antibody comprises a) the heavy chain variable region sequence of SEQ ID NO: 16 and the light chain variable region sequence of SEQ ID NO: 14; b) the heavy chain variable region sequence of SEQ ID NO: 4 and the light chain variable region sequence of SEQ ID NO: 2; c) the heavy chain variable region sequence of SEQ ID NO: 8 and the light chain variable region sequence of SEQ ID NO: 6; d) the heavy chain variable region sequence of SEQ ID NO: 12 and the light chain variable region sequence of SEQ ID NO: 10; e) the heavy chain variable region sequence of SEQ ID NO: 20 and the light chain variable region sequence of SEQ ID NO: 18; f) the heavy chain variable region sequence of SEQ ID NO: 24 and the light chain variable region sequence of SEQ ID NO: 22; g) the heavy chain variable region sequence of SEQ ID NO: 28 and the light chain variable region sequence of SEQ ID NO: 26; h) the heavy chain variable region sequence of SEQ ID NO: 4 and the light chain variable region sequence of SEQ ID NO: 30; i) the heavy chain variable region sequence of SEQ ID NO: 4 and the light chain variable region sequence of SEQ ID NO: 32; j) the heavy chain variable region sequence of SEQ ID NO: 4 and the light chain variable region sequence of SEQ ID NO: 34; or k) the heavy chain variable region sequence of SEQ ID NO: 24 and the light chain variable region sequence of SEQ ID NO: 22.

In a particular embodiment, the antibody comprises the heavy chain variable region sequence of SEQ ID NO: 16 and the light chain variable region sequence of SEQ ID NO: 14. In another particular embodiment, the antibody comprises the heavy chain variable region sequence of SEQ ID NO: 4 and the light chain variable region sequence of SEQ ID NO: 2.

In a further aspect, the invention provides an antibody capable of specific binding to ASGPR, wherein the antibody competes for binding to an epitope of ASGPR with an antibody comprising the heavy chain variable region sequence of SEQ ID NO: 16 and the light chain variable region sequence of SEQ ID NO: 14. In one embodiment, said antibody recognizes an epitope in the stalk region of ASGPR. In one embodiment, said antibody is an affinity matured variant of the antibody comprising the heavy chain variable region sequence of SEQ ID NO: 16 and the light chain variable region sequence of SEQ ID NO: 14. In one embodiment, said antibody comprises a heavy chain variable region sequence that is at least about 96%, 97%, 98% or 99% identical to the sequence of SEQ ID NO: 16, and a light chain variable region sequence that is at least about 96%, 97%, 98% or 99% identical to the sequence of SEQ ID NO: 14. In one embodiment, said antibody comprises the light chain variable region sequence of SEQ ID NO: 14 with one, two, three, four, five, six or seven, particularly two, three, four or five, amino acid substitutions. In one embodiment, said antibody comprises the heavy chain variable region sequence of SEQ ID NO: 16 with one, two, three, four, five, six or seven, particularly two, three, four or five, amino acid substitutions.

In still a further aspect, the invention provides a an antibody capable of specific binding to ASGPR, wherein the antibody competes for binding to an epitope of ASGPR with an antibody comprising the heavy chain variable region sequence of SEQ ID NO: 4 and the light chain variable region sequence of SEQ ID NO: 2. In one embodiment, said antibody recognizes an epitope in the carbohydrate recognition domain (CRD) of ASGPR. In one embodiment, said antibody is an affinity matured variant of the antibody comprising the heavy chain variable region sequence of SEQ ID NO: 4 and the light chain variable region sequence of SEQ ID NO: 2. In one embodiment, said antibody comprises a heavy chain variable region sequence that is at least about 96%, 97%, 98% or 99% identical to the sequence of SEQ ID NO: 4, and a light chain variable region sequence that is at least about 96%, 97%, 98% or 99% identical to the sequence of SEQ ID NO: 2. In one embodiment, said antibody comprises the light chain variable region sequence of SEQ ID NO: 2 with one, two, three, four, five, six or seven, particularly two, three, four or five, amino acid substitutions. In one embodiment, said antibody comprises the heavy chain variable region sequence of SEQ ID NO: 4 with one, two, three, four, five, six or seven, particularly two, three, four or five, amino acid substitutions. In one embodiment, said antibody comprises a) the heavy chain variable region sequence of SEQ ID NO: 4 and the light chain variable region sequence of SEQ ID NO: 36; b) the heavy chain variable region sequence of SEQ ID NO: 4 and the light chain variable region sequence of SEQ ID NO: 38; c) the heavy chain variable region sequence of SEQ ID NO: 8 and the light chain variable region sequence of SEQ ID NO: 40; d) the heavy chain variable region sequence of SEQ ID NO: 12 and the light chain variable region sequence of SEQ ID NO: 42; e) the heavy chain variable region sequence of SEQ ID NO: 20 and the light chain variable region sequence of SEQ ID NO: 44; f) the heavy chain variable region sequence of SEQ ID NO: 24 and the light chain variable region sequence of SEQ ID NO: 46; or g) the heavy chain variable region sequence of SEQ ID NO: 28 and the light chain variable region sequence of SEQ ID NO: 48.

In one embodiment, the antibody of the invention is capable of specific binding to human and cynomolgus monkey ASGPR. In one embodiment, the antibody binds to human ASGPR with an dissociation constant ($K_D$) of smaller than 1 μM, particularly smaller than 100 nM, more particularly smaller than 1 nM, when measured as Fab fragment by Surface Plasmon Resonance (SPR). In one embodiment, the antibody binds to human ASGPR with a $K_D$ of smaller than 1 μM, particularly smaller than 500 nM, more particularly smaller than 100 nM or even smaller than 10 nM, when measured as $IgG_1$ by fluoresecence resonance energy transfer (FRET). In one embodiment, the antibody does not compete with a natural ligand of ASGPR for binding to ASGPR. In a specific embodiment, said natural ligand of ASGPR is asialofetuin. In one embodiment, the antibody does not detectably bind to CLEC10A, particularly human CLEC10A. In one embodiment, the antibody does not specifically bind to cells lacking ASGPR expression, particularly human cells, more particularly human blood cells. In one embodiment, the antibody is internalized into a cell expressing ASGPR upon binding of the antibody to ASGPR on the surface of said cell. In a specific embodiment, the antibody is recycled back to the surface of said cell at about the same rate as it is internalized into said cell. In one embodiment, the antibody does not significantly induce downregulation of ASGPR expression at the surface of a cell upon binding of the antibody to ASGPR on the surface of said cell.

In one embodiment, the antibody of the invention is a human antibody. In one embodiment, the antibody comprises a human Fc region, particularly an IgG Fc region, more particularly an $IgG_1$ Fc region. In one embodiment, the antibody is a full-length antibody. In one embodiment, the antibody is an IgG class antibody, particularly an $IgG_1$ subclass antibody. In one embodiment, the antibody comprises in the Fc region a modification reducing binding affinity of the antibody to an Fc receptor, particularly an Fcγ receptor. In a specific embodiment, said Fc receptor is an activating Fc receptor. In a further specific embodiment, said Fc receptor is selected from the group of FcγRIIIa (CD16a), FcγRI (CD64), FcγRIIa (CD32), and FcαRI (CD89). In a more specific embodiment, said Fc receptor is FcγRIIIa, particularly human FcγRIIIa. In one embodiment, the antibody comprises an amino acid substitution in the Fc region at a position selected from P329, L234 and L235 (EU numbering). In one embodiment, the antibody comprises the amino acid substitutions P329G, L234A and L235A in the Fc region (EU numbering). In a further embodiment, the antibody comprises in the Fc region a modification promoting heterodimerization of two non-identical antibody heavy chains. In a specific embodiment, said modification is a knob-into-hole modification, comprising a knob modification in one of the antibody heavy chains and a hole modification in the other one of the two antibody heavy chains. In one embodiment, the antibody comprises a modification within the interface between the two antibody heavy chains in the CH3 domain, wherein i) in the CH3 domain of one heavy chain, an amino acid residue is replaced with an amino acid residue having a larger side chain volume, thereby generating a protuberance ("knob") within the interface in the CH3 domain of one heavy chain which is positionable in a cavity ("hole") within the interface in the CH3 domain of the other heavy chain, and ii) in the CH3 domain of the other heavy chain, an amino acid residue is replaced with an amino acid residue having a smaller side chain volume, thereby generating a cavity ("hole") within the interface in the second CH3 domain within which a protuberance ("knob") within the interface in the first CH3 domain is positionable. In one embodiment, the antibody comprises the amino acid substitution T366W and optionally the amino acid substitution S354C in one of the antibody heavy chains, and the amino acid substitutions T366S, L368A, Y407V and optionally Y349C in the other one of the antibody heavy chains.

In one aspect, the invention provides an antibody capable of specific binding to ASGPR according to any of the above embodiments, wherein an effector moiety is attached to the antibody. In one embodiment, not more than one effector moiety is attached to the antibody. In one embodiment said effector moiety is a cytokine molecule. In one embodiment, said cytokine molecule is fused at its amino-terminal amino acid to the carboxy-terminal amino acid of one of the antibody heavy chains, optionally through a peptide linker. In one embodiment, said cytokine molecule is a human cytokine. In one embodiment, said cytokine molecule is an interferon molecule. In a specific embodiment, said interferon molecule is interferon alpha, particularly human interferon alpha, more particularly human interferon alpha 2 (see SEQ ID NO: 138) or human interferon alpha 2a (see SEQ ID NO: 139). In one embodiment, wherein the cytokine molecule is an interferon molecule, the antibody has anti-viral activity in cells expressing ASGPR on their surface. In a specific embodiment, the antibody has no anti-viral activity in cells not expressing significant levels of ASGPR on their surface. In a further specific embodiment, said anti-viral activity is selected from inhibition of viral infection, inhibition of virus replication, inhibition of cell killing and induction of interferon-stimulated genes.

The invention further provides a polynucleotide encoding the antibody of the invention. Further provided is a vector, particularly an expression vector, comprising the polynucleotide of the invention. In another aspect, the invention provides a host cell comprising the polynucleotide or the vector of the invention. The invention also provides a method for producing an antibody of the invention, comprising the steps of (i) culturing the host cell of the invention under conditions suitable for expression of said antibody, and (ii) recovering said antibody. Also provided is an antibody capable of specific binding to ASGPR, produced by said method.

In one aspect, the invention provides a pharmaceutical composition comprising the antibody of the invention and a pharmaceutically acceptable carrier. The antibody or the pharmaceutical composition of the invention is also provided for use as a medicament, and for use in the treatment or prophylaxis of a liver disease, specifically a viral infection, more specifically hepatitis virus infection, particularly hepatitis B virus (HBV) infection. The antibody or the pharmaceutical composition of the invention is also provided for use in the treatment or prophylaxis of cancer, specifically liver cancer, more specifically hepatocellular carcinoma (HCC). Further provided is the use of the antibody of the invention for the manufacture of a medicament for the treatment of a disease in an individual in need thereof, and a method of treating a disease in an individual, comprising administering to said individual a therapeutically effective amount of a composition comprising the antibody of the invention in a pharmaceutically acceptable form. In one embodiment, said disease is a liver disease. In a more specific embodiment, said liver disease is a viral infection. In an even more specific embodiment, said liver disease is hepatitis virus infection, particularly HBV infection. In another embodiment, said disease is cancer. In a more specific embodiment, said cancer is liver cancer. In an even more specific embodiment, said liver cancer is hepatocellular carcinoma (HCC). In one embodiment, said individual is a mammal, particularly a human. In a further aspect, the antibody of the invention is provided for targeting a cell expressing ASGPR in an individual. Also provided is a method for targeting a cell expressing ASGPR in an individual, comprising administering to said individual a composition comprising the antibody of the invention in a pharmaceutically acceptable form. In one embodiment, said cell is a liver cell, particularly a hepatocyte. In one embodiment, said individual is a mammal, particularly a human.

BRIEF DESCRIPTION OF THE DRAWINGS

FIG. 8. Randomization strategy of the LCDR3 region of clone 51A12. Shown are (A) the LCDR3 protein sequence of the parental clone 51A12, (B) the LCDR3 protein sequence of the plasmid serving as a template for the library without cysteines and glycosylation sequence, and (C) the randomized positions in LCDR3. During generation of the library, trinucleotide primers allow to exclude triplets encoding cysteines or amino acids contributing to the formation of a glycosylation site.

FIGS. 19A-19D. Purification and analytical characterization of monovalent 51A12 kih IgG-IFNα. The purification method involved an affinity step (protein A) 19(A) followed by size exclusion chromatography (Superdex 200, GE Healthcare) 19(B). The final product was analyzed and characterized by analytical size exclusion chromatography (Superdex 200 column) 19(C) and microfluidic protein analysis (Caliper) or SDS-PAGE 15(D).

DETAILED DESCRIPTION OF THE INVENTION

Definitions

Figure 1:
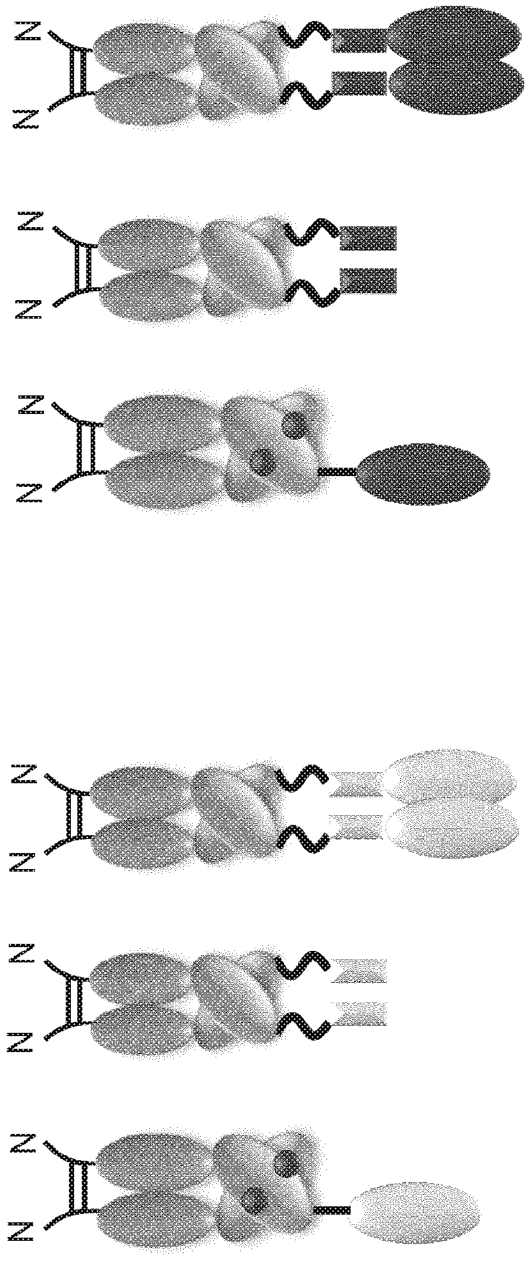
FIG. 1. Schematic diagram of the generated antigen constructs. The nucleotide sequences of all antigens were fused to the C-terminal end of a human-derived $IgG_1$ Fc sequence. The ASGPR1- and CLEC10A-derived CRDs were fused to a sequence encoding an Fc(hole) fragment and co-expressed with a sequence encoding an Fc(knob) fragment resulting in a monomeric display per Fc dimer. From left to right: Fc-CRD (ASGPR1), Fc-stalk (ASGPR1), Fc-stalk-CRD (ASGPR1), Fc-CRD (CLEC10A), Fc-stalk (CLEC10A), Fc-stalk-CRD (CLEC10A). Thick, curved line: $(G_4S)_3$ linker; thick, straight line: Xa and IgAse cleavage site.

Terms are used herein as generally used in the art, unless otherwise defined in the following. "Asialoglycoprotein receptor", abbreviated as ASGPR, refers to any native ASGPR from any vertebrate source, including mammals such as primates (e.g. humans), non-human primates (e.g. cynomolgus monkeys) and rodents (e.g. mice and rats), unless otherwise indicated. The term encompasses "full-length," unprocessed ASGPR as well as any form of ASGPR that results from processing in the cell. The term also encompasses naturally occurring variants of ASGPR, e.g., splice variants or allelic variants. In one embodiment, the antibody of the invention is capable of specific binding to human ASGPR, particularly human ASGPR H1, more particularly the extracellular domain of human ASGPR H1.

The amino acid sequence of human ASGPR H1 (also known as CLEC4H1) is shown in UniProt (www.uniprot.org) accession no. P07306 (version 131), or NCBI (www.ncbi.nlm nih.gov/) RefSeq NP_001662.1. The extracellular domain (ECD) of human ASGPR H1 extends from amino acid position 62 to 291. The nucleotide and amino acid sequences of a human ASGPR H1 ECD fused to a human Fc region is shown in SEQ ID NOs 129 and 130, respectively. The ASGPR H1 ECD comprises the stalk region, which extends from amino acid position 62 of the full sequence to around amino acid position 160 (SEQ ID NOs 123 and 124 show nucleotide and amino acid sequences of a human ASGPR H1 stalk region fused to a human Fc region), and the carbohydrate recognition domain (CRD), which extends from around amino acid position 161 of the full sequence to around amino acid position 278 (SEQ ID NOs 117 and 118 show nucleotide and amino acid sequences of a human ASGPR H1 CRD region fused to a human Fc region). In one embodiment, the antibody is also capable of binding to cynomolgus ASGPR, particularly cynomolgus ASGPR H1, more particularly the extracellular domain of cynomolgus ASGPR The sequence of cynomolgus ASGPR H1 is shown in NCBI GenBank accession no. EHH57654.1. SEQ ID NOs 131 and 132 show the nucleotide and amino acid sequences, respectively, of a cynomolgus ASGPR H1 ECD fused to a human Fc region.

By "human CLEC10A" is meant the protein described in UniProt accession no. Q8IUN9 (version 86), particularly the extracellular domain of said protein which extends from amino acid position 61 to amino acid position 316 of the full sequence. SEQ ID NOs 133 and 134 show the nucleotide and amino acid sequences, respectively, of a human CLEC10A ECD fused to a human Fc region.

As used herein, the term "conjugate" refers to a fusion polypeptide molecule that includes one effector moiety and a further peptide molecule, particularly an antibody. A fusion protein of an antibody and an effector moiety is referred to as an "immunoconjugate". An (immune)conjugate as referred to herein is a fusion protein, i.e. the components of the (immune)conjugate are linked to each other by peptide-bonds, either directly or through peptide linkers.

An "epitope" is a region of an antigen that is bound by an antibody. The term refers to a site (e.g. a contiguous stretch of amino acids or a conformational configuration made up of different regions of non-contiguous amino acids) on a polypeptide macromolecule to which an antibody binds, forming an antibody-antigen complex.

An "antibody that competes for binding to an epitope" with a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

By "specific binding" is meant that the binding is selective for the antigen and can be discriminated from unwanted or non-specific interactions. The ability of an antibody to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antibody to an unrelated protein is less than about 10% of the binding of the antibody to the antigen as measured, e.g. by SPR. In certain embodiments, an antibody that binds to the antigen has a dissociation constant ($K_D$) of ≤1 μM, ≤100 nM, ≤10 nM, ≤1 nM, ≤0.1 nM, ≤0.01 nM, or ≤0.001 nM (e.g. 10' M or less, e.g. from $10^{-8}$M to $10^{-13}$ M, e.g. from $10^{-9}$M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

"Reduced binding", for example reduced binding to an Fc receptor, refers to a decrease in affinity for the respective interaction, as measured for example by SPR. For clarity the term includes also reduction of the affinity to zero (or below the detection limit of the analytic method), i.e. complete abolishment of the interaction. Conversely, "increased binding" refers to an increase in binding affinity for the respective interaction.

By "internalization" is meant the removal of a molecule from the surface from a cell by uptake of said molecule into the intracellular space. A particular form of internalization is receptor-mediated endocytosis, which occurs upon binding of a ligand or antibody to a cell surface (membrane-spanning) receptor, by inward budding of plasma membrane vesicles containing the receptor and bound ligand or antibody. Internalization can be assessed using art-known techniques. A method based on determination of protein levels on the cell surface by FACS is described in the Examples hereinbelow.

The term "recycling" as used herein refers to the re-appearance of a molecule on the surface of a cell after previous internalization of said molecule into said cell. Recycling implies that the molecule is not degraded within the cell upon internalization. If recycling occurs at the same rate as internalization, a dynamic steady state is reached wherein the number of molecules on the cell surface stays essentially constant. Recycling can be detected by techniques well known in the art, e.g. by determination of protein levels on the cell surface by FACS or using (confocal) microscopy methods as described in the Examples hereinbelow.

By "downregulation" is meant the reduction of the copy number of a certain protein, e.g. a cell surface receptor, within or at the surface of a cell. Downregulation as used herein particularly refers to a reduction in the copy number of a cell surface protein present at the cell surface, e.g. by internalization and/or degradation, or reduced expression. Downregulation of protein levels can be detected by various methods established in the art, including e.g. Western blot (for overall protein levels) or FACS (for surface protein levels).

As used herein, the term "effector moiety" refers to a molecule, particularly a polypeptide molecule (e.g. a protein or glycoprotein), that influences cellular activity, for example, through signal transduction or other cellular pathways. Accordingly, the effector moiety can be associated with receptor-mediated signaling that transmits a signal from outside the cell membrane to modulate a response in a cell bearing one or more receptors for the effector moiety. In one embodiment, an effector moiety can elicit a cytotoxic response in cells bearing one or more receptors for the effector moiety. In another embodiment, an effector moiety can elicit a proliferative response in cells bearing one or more receptors for the effector moiety. In another embodiment, an effector moiety can elicit differentiation in cells bearing receptors for the effector moiety. In another embodiment, an effector moiety can alter expression (i.e. upregulate or downregulate) of an endogenous cellular protein in cells bearing receptors for the effector moiety. Non-limiting examples of effector moieties include small molecules, cytokines, growth factors, hormones, enzymes, substrates, and cofactors. The effector moiety can be associated with the antibody in a variety of configurations.

The term "attached" includes linkage by any kind of interaction, including chemical or peptide bonds.

"Fused" refers to components that are linked by peptide bonds, either directly or via one or more peptide linkers.

As used herein, the term "cytokine" refers to a molecule that mediates and/or regulates a biological or cellular function or process (e.g. immunity, inflammation, and hematopoiesis). The term "cytokine" as used herein includes lymphokines, chemokines, monokines, and interleukins. Examples of cytokines include, but are not limited to, GM-CSF, IL-1α, IL-1β, IL-2, IL-3, IL-4, IL-5, IL-6, IL-7, IL-8, IL-10, IL-12, IFN-α, IFN-β, IFN-γ, MIP-1α, MIP-1β, TGF-β, TNF-α, and TNF-β. Particular cytokines are interferons (IFN), particularly IFN-α. In particular embodiments the cytokine is a human cytokine. The sequences of particular cytokines, human IFNα2 and IFNα2a, are shown in SEQ ID NOs 138 and 139, respectively.

"Interferon-stimulated genes" (ISGs) refers to genes the expression of which in a cell can be stimulated by contacting said cell with an interferon molecule, particularly an IFNα molecule. Typically, ISGs comprise a recognition sequence (e.g. an interferon-stimulated response element (ISRE)) to which one or more interferon-activated signaling molecules (e.g. STATs) can bind, thereby leading to enhanced expression of the ISG. Examples of ISGs include MX1 (myxovirus restistance 1, also known as interferon-induced protein p78), RSAD2 (radical S-adenosyl methionine domain containing 2, also known as cytomegalovirus-induced gene 5), HRASLS2 (HRAS-like suppressor 2), IFIT1 (interferon-induced protein with tetratricopeptide repeats 1), and IFITM2 (interferone-induced transmembrane protein 2).

As used herein, the term "single-chain" refers to a molecule comprising amino acid monomers linearly linked by peptide bonds. In one embodiment, the effector moiety is a single-chain peptide molecule. Non-limiting examples of single-chain effector moieties include cytokines, growth factors, hormones, enzymes, substrates, and cofactors. When the effector moiety is a cytokine and the cytokine of interest is normally found as a multimer in nature, each subunit of the multimeric cytokine is sequentially encoded by the single-chain of the effector moiety. Accordingly, non-limiting examples of useful single-chain effector moieties include GM-CSF, IL-1α, IL-1β, IL-2, IL-3, IL-4, IL-5, IL-6, IL-7, IL-8, IL-10, IL-12, IL-15, IFN-α, IFN-β, IFN-γ, MIP-1α, MIP-1β, TGF-β, TNF-α, and TNF-β.

As used herein, the term "effector moiety receptor" refers to a polypeptide molecule capable of binding specifically to an effector moiety. Where an effector moiety specifically binds to more than one receptor, all receptors that specifically bind to the effector moiety are "effector moiety receptors" for that effector moiety. For example, where IFNα is the effector moiety, the effector moiety receptor that binds to an IFNα molecule (e.g. an antibody fused to IFNα) is the IFNα receptor 1 or 2 (see UniProt accession no. P17181 (version 121) and NCBI RefSeq NP_000620.2 for human IFNα receptor 1, and UniProt accession no. P48551 (version 131) and NCBI RefSeqs NP_997467.1 & NP_997468.1 for human IFNα receptor 2).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. *E. coli* or phage), as described herein.

The terms "full length antibody", "intact antibody", and "whole antibody" are used herein interchangeably to refer to an antibody having a structure substantially similar to a native antibody structure or having heavy chains that contain an Fc region as defined herein.

"Native antibodies" refer to naturally occurring immunoglobulin molecules with varying structures. For example, native IgG class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. $\gamma_1$ ($IgG_1$), $\gamma_2$ ($IgG_2$), $\gamma_3$ ($IgG_3$), $\gamma_4$ ($IgG_4$), $\alpha_1$ ($IgA_1$) and $\alpha_2$ ($IgA_2$). The light chain of an antibody may be assigned to one of two types, called kappa (κ) and lambda (λ), based on the amino acid sequence of its constant domain. An IgG class antibody essentially consists of two Fab fragments and an Fc domain, linked via the immunoglobulin hinge region.

As used herein, "Fab fragment" refers to an antibody fragment comprising a light chain fragment comprising a VL domain and a constant domain of a light chain (CL), and a VH domain and a first constant domain (CH1) of a heavy chain.

The "class" of an antibody or immunoglobulin refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g. Kindt et al., Kuby Immunology, $6^{th}$ ed., W.H. Freeman and Co., page 91 (2007). A single VH or VL domain may be sufficient to confer antigen-binding specificity.

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia and Lesk, J. Mol. Biol. 196, 901-917 (1987)). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat et al., Sequences of Proteins of Immunological Interest, 5th Ed. Public Health Service, National Institutes of Health, Bethesda, Md. (1991)). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (see Almagro and Fransson, Front. Biosci. 13, 1619-1633 (2008)). Unless otherwise indicated, HVR residues and other residues in the variable domain (e.g. FR residues) are numbered herein according to Kabat et al., supra (referred to as "Kabat numbering").

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "parent antibody" herein refers to an antibody that serves as a starting point or basis for the preparation of an antibody variant. In one embodiment, the parent antibody is a humanized or human antibody.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "Fc domain" or "Fc region" herein is used to define a C-terminal region of an antibody heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protroberance" ("knob") in one chain thereof and a corresponding introduced "cavity" ("hole") in the other chain thereof; see U.S. Pat. No. 5,821,333, expressly incorporated herein by reference). Such variant CH3 domains may be used to promote heterodimerization of two non-identical antibody heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637 (version 141)).

The term "peptide linker" refers to a peptide comprising one or more amino acids, typically about 2-20 amino acids. Peptide linkers are known in the art or are described herein. Suitable, non-immunogenic linker peptides include, for example, $(G_4S)_n$, $(SG_4)_n$ or $G_4(SG_4)_n$ peptide linkers. "n" is generally a number between 1 and 10, typically between 2 and 4.

A "modification promoting heterodimerization" is a manipulation of the peptide backbone or the post-translational modifications of a polypeptide, e.g. an antibody heavy chain, that reduces or prevents the association of the polypeptide with an identical polypeptide to form a homodimer. A modification promoting heterodimerization as used herein particularly includes separate modifications made to each of two polypeptides desired to form a dimer, wherein the modifications are complementary to each other so as to promote association of the two polypeptides. For example, a modification promoting heterodimerization may alter the structure or charge of one or both of the polypeptides desired to form a dimer so as to make their association sterically or electrostatically favorable, respectively. Heterodimerization occurs between two non-identical polypeptides, such as two antibody heavy chains wherein further components attached to each of the heavy chains (e.g. effector moiety) are not the same. In the antibodies according to the present invention, the modification promoting heterodimerization is in the Fc domain, particularly in the CH3 domain. In some embodiments the modification promoting heterodimerziation comprises an amino acid mutation, specifically an amino acid substitution. In a particular embodiment, the modification promoting heterodimerization comprises a separate amino acid mutation, specifically an amino acid substitution, in each of the two antibody heavy chains.

A "knob-into-hole modification" refers to a modification within the interface between two antibody heavy chains in the CH3 domain, wherein i) in the CH3 domain of one heavy chain, an amino acid residue is replaced with an amino acid residue having a larger side chain volume, thereby generating a protuberance ("knob") within the interface in the CH3 domain of one heavy chain which is positionable in a cavity ("hole") within the interface in the CH3 domain of the other heavy chain, and ii) in the CH3 domain of the other heavy chain, an amino acid residue is replaced with an amino acid residue having a smaller side chain volume, thereby generating a cavity ("hole") within the interface in the second CH3 domain within which a protuberance ("knob") within the interface in the first CH3 domain is positionable. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains.

An amino acid "substitution" refers to the replacement in a polypeptide of one amino acid with another amino acid. In one embodiment, an amino acid is replaced with another amino acid having similar structural and/or chemical properties, e.g., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Non-conservative substitutions will entail exchanging a member of one of these classes for another class. For example, amino acid substitutions can also result in replacing one amino acid with another amino acid having different structural and/or chemical properties, for example, replacing an amino acid from one group (e.g., polar) with another amino acid from a different group (e.g., basic) Amino acid substitutions can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid substitution. For example, a substitution from proline at position 329 of the Fc domain to glycine can be indicated as 329G, G329, $G_{329}$, P329G, or Pro329Gly.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program. "Polynucleotide" or "nucleic acid" as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. A sequence of nucleotides may be interrupted by non-nucleotide components. A polynucleotide may comprise modification(s) made after synthesis, such as conjugation to a label.

The term "vector" as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antibodies of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

Antibodies of the Invention

The invention provides novel antibodies, particularly monoclonal antibodies, that bind to the asialoglycoprotein receptor (ASGPR).

In a first aspect, the invention provides an antibody capable of specific binding to asialoglycoprotein receptor (ASGPR), wherein the antibody comprises a) the heavy chain variable region sequence of SEQ ID NO: 16 and the light chain variable region sequence of SEQ ID NO: 14; b) the heavy chain variable region sequence of SEQ ID NO: 4 and the light chain variable region sequence of SEQ ID NO: 2; c) the heavy chain variable region sequence of SEQ ID NO: 8 and the light chain variable region sequence of SEQ ID NO: 6; d) the heavy chain variable region sequence of SEQ ID NO: 12 and the light chain variable region sequence of SEQ ID NO: 10; e) the heavy chain variable region sequence of SEQ ID NO: 20 and the light chain variable region sequence of SEQ ID NO: 18; f) the heavy chain variable region sequence of SEQ ID NO: 24 and the light chain variable region sequence of SEQ ID NO: 22; g) the heavy chain variable region sequence of SEQ ID NO: 28 and the light chain variable region sequence of SEQ ID NO: 26; h) the heavy chain variable region sequence of SEQ ID NO: 4 and the light chain variable region sequence of SEQ ID NO: 30; i) the heavy chain variable region sequence of SEQ ID NO: 4 and the light chain variable region sequence of SEQ ID NO: 32; j) the heavy chain variable region sequence of SEQ ID NO: 4 and the light chain variable region sequence of SEQ ID NO: 34; or k) the heavy chain variable region sequence of SEQ ID NO: 24 and the light chain variable region sequence of SEQ ID NO: 22.

A particular antibody according to the invention comprises the heavy chain variable region sequence of SEQ ID NO: 16 and the light chain variable region sequence of SEQ ID NO: 14. This antibody clone is designated 4F3. Another particular antibody according to the invention comprises the heavy chain variable region sequence of SEQ ID NO: 4 and the light chain variable region sequence of SEQ ID NO: 2. This antibody is designated 51A12.

The invention provides antibodies which are capable of specific binding to ASGPR and compete for binding to an epitope of ASGPR with antibody 4F3. In one embodiment, such an antibody binds to the same epitope as 4F3. The 4F3 antibody recognizes an epitope in the stalk region of ASGPR. Accordingly, in one embodiment, such an antibody recognizes an epitope in the stalk region of ASGPR. Also contemplated by the invention are affinity matured variants of the 4F3 antibody. In one embodiment, such an antibody comprises a heavy chain variable region sequence that is at least about 96%, 97%, 98% or 99% identical to the sequence of SEQ ID NO: 16, and a light chain variable region sequence that is at least about 96%, 97%, 98% or 99% identical to the sequence of SEQ ID NO: 14. In one embodiment, such an antibody comprises the light chain variable region sequence of SEQ ID NO: 14 with one, two, three, four, five, six or seven, particularly two, three, four or five, amino acid substitutions. In one embodiment, such an antibody comprises the heavy chain variable region sequence of SEQ ID NO: 16 with one, two, three, four, five, six or seven, particularly two, three, four or five, amino acid substitutions. Variants of the 4F3 antibody may also comprise a heavy chain variable region which is identical to the heavy chain variable region of 4F3, together with a variant light chain variable region, or vice versa.

The invention further provides antibodies which are capable of specific binding to ASGPR and compete for binding to an epitope of ASGPR with antibody 51A12. In one embodiment, such and antibody binds to the same epitope as 51A12. The 51A12 antibody recognizes and epitope in the carbohydrate recognition domain (CRD) of ASGPR. Accordingly, in one embodiment, such an antibody recognizes an epitope in the CRD of ASGPR. Also contemplated by the invention are affinity matured variants of the 51A12 antibody, particularly variants obtained by randomization of the light chain CDR3 or 51A12. In one embodiment, such an antibody comprises a heavy chain variable region sequence that is at least about 96%, 97%, 98% or 99% identical to the sequence of SEQ ID NO: 4, and a light chain variable region sequence that is at least about 96%, 97%, 98% or 99% identical to the sequence of SEQ ID NO: 2. In one embodiment, such an antibody comprises the light chain variable region sequence of SEQ ID NO: 2 with one, two, three, four, five, six or seven, particularly two, three, four or five, amino acid substitutions. In one embodiment, such an antibody comprises the heavy chain variable region sequence of SEQ ID NO: 4 with one, two, three, four, five, six or seven, particularly two, three, four or five, amino acid substitutions. Variants of the 51A12 antibody may also comprise a heavy chain variable region which is identical to the heavy chain variable region of 51A12, together with a variant light chain variable region, or vice versa. In one embodiment, such an antibody comprises a) the heavy chain variable region sequence of SEQ ID NO: 4 and the light chain variable region sequence of SEQ ID NO: 36; b) the heavy chain variable region sequence of SEQ ID NO: 4 and the light chain variable region sequence of SEQ ID NO: 38; c) the heavy chain variable region sequence of SEQ ID NO: 8 and the light chain variable region sequence of SEQ ID NO: 40; d) the heavy chain variable region sequence of SEQ ID NO: 12 and the light chain variable region sequence of SEQ ID NO: 42; e) the heavy chain variable region sequence of SEQ ID NO: 20 and the light chain variable region sequence of SEQ ID NO: 44; f) the heavy chain variable region sequence of SEQ ID NO: 24 and the light chain variable region sequence of SEQ ID NO: 46; or g) the heavy chain variable region sequence of SEQ ID NO: 28 and the light chain variable region sequence of SEQ ID NO: 48.

Preferably, the antibodies of the invention are human antibodies, i.e. the antibodies comprise human variable and constant regions. In one embodiment, the antibodies comprise a human Fc region, particularly a human IgG Fc region, more particularly a human $IgG_1$ Fc region. Particular antibodies according to the invention are full-length antibodies, particularly full-length IgG class antibodies, more particularly full-length $IgG_1$ subclass antibodies. Alternatively, the antibodies may be antibody fragments. In one embodiment, the antibodies are Fab fragments or scFv fragments. In some embodiments, the antibodies comprise a Fab fragment and an Fc region, particularly a human IgG Fc region, more particularly a human $IgG_1$ Fc region, linked by an immunoglobulin hinge region, particularly a human IgG hinge region, more particularly a human $IgG_1$ hinge region. Specifically, the antibodies may comprise a Fab fragment and an Fc region, linked by an immunoglobulin hinge region, wherein no further Fab fragment is present. In such embodiments, the antibodies are essentially full-length antibodies, lacking one Fab fragment.

Fc regions comprised in the antibodies of the invention may comprise various modifications, as compared to a native Fc region.

While the Fc domain confers to the antibodies favorable pharmacokinetic properties, including a long serum half-life which contributes to good accumulation in the target tissue and a favorable tissue-blood distribution ratio, it may at the same time lead to undesirable targeting of the antibodies to cells expressing Fc receptors rather than to the preferred antigen-bearing cells. Moreover, the co-activation of Fc receptor signaling pathways may lead to cytokine release which, particularly in antibodies having an effector moiety (e.g. a cytokine) attached, results in excessive activation of cytokine receptors and severe side effects upon systemic administration.

Therefore, in some embodiments, the antibodies comprise in the Fc region a modification reducing binding affinity of the antibody to an Fc receptor, particularly an Fcγ receptor, as compared to a corresponding antibody comprising an unmodified Fc region. Binding to Fc receptors can be easily determined e.g. by ELISA, or by Surface Plasmon Resonance (SPR) using standard instrumentation such as a BIAcore instrument (GE Healthcare) and Fc receptors such as may be obtained by recombinant expression. A specific illustrative and exemplary embodiment for measuring binding affinity is described in the following. According to one embodiment, Binding affinity to an Fc receptor is measured by surface plasmon resonance using a BIACORE® T100 machine (GE Healthcare) at 25° C. with ligand (Fc receptor) immobilized on CMS chips. Briefly, carboxymethylated dextran biosensor chips (CMS, GE Healthcare) are activated with N-ethyl-N'-(3-dimethylaminopropyl)-carbodiimide hydrochloride (EDC) and N-hydroxysuccinimide (NHS) according to the supplier's instructions. Recombinant ligand is diluted with 10 mM sodium acetate, pH 5.5, to 0.5-30 μg/ml before injection at a flow rate of 10 μl/min to achieve approximately 100-5000 response units (RU) of coupled protein. Following the injection of the ligand, 1 M ethanolamine is injected to block unreacted groups. For kinetics measurements, three- to five-fold serial dilutions of antibody (range between ~0.01 nM to 300 nM) are injected in HBS-EP+ (GE Healthcare, 10 mM HEPES, 150 mM NaCl, 3 mM EDTA, 0.05% Surfactant P20, pH 7.4) at 25° C. at a flow rate of approximately 30-50 μl/min Association rates ($k_{on}$) and dissociation rates ($k_{off}$) are calculated using a simple one-to-one Langmuir binding model (BIACORE® T100 Evaluation Software version 1.1.1) by simultaneously fitting the association and dissociation sensorgrams. The equilibrium dissociation constant ($K_D$) is calculated as the ratio $k_{off}/k_{on}$. See, e.g., Chen et al., J Mol Biol 293, 865-881 (1999). Alternatively, binding affinity antibodies to Fc receptors may be evaluated using cell lines known to express particular Fc receptors, such as NK cells expressing FcγIIIa receptor.

In the modification comprises one or more amino acid mutation that reduces the binding affinity of the antibody to an Fc receptor. Typically, the same one or more amino acid mutation is present in each of the two antibody heavy chains in the Fc domain. In one embodiment said amino acid mutation reduces the binding affinity of the antibody to the Fc receptor by at least 2-fold, at least 5-fold, or at least 10-fold. In embodiments where there is more than one amino acid mutation that reduces the binding affinity of the antibody to the Fc receptor, the combination of these amino acid mutations may reduce the binding affinity of the antibody to the Fc receptor by at least 10-fold, at least 20-fold, or even at least 50-fold. In one embodiment the antibody exhibits less than 20%, particularly less than 10%, more particularly less than 5% of the binding affinity to an Fc receptor as compared to an antibody comprising an unmodified Fc domain.

In one embodiment the Fc receptor is an activating Fc receptor. In a specific embodiment the Fc receptor is an Fcγ receptor, more specifically an FcγRIIIa, FcγRI or FcγRIIa receptor. Preferably, binding to each of these receptors is reduced. In some embodiments binding affinity to a complement component, specifically binding affinity to C1q, is also reduced. In one embodiment binding affinity to neonatal Fc receptor (FcRn) is not reduced. Substantially similar binding to FcRn, i.e. preservation of the binding affinity of the antibody to said receptor, is achieved when the antibody exhibits greater than about 70% of the binding affinity of an unmodified form of the antibody to FcRn. Antibodies of the invention may exhibit greater than about 80% and even greater than about 90% of such affinity. In one embodiment the amino acid mutation is an amino acid substitution. In one embodiment the antibody comprises an amino acid substitution in the Fc region at position P329 (EU numbering). In a more specific embodiment the amino acid substitution is P329A or P329G, particularly P329G. In one embodiment the antibody comprises a further amino acid substitution in the Fc region at a position selected from S228, E233, L234, L235, N297 and P331. In a more specific embodiment the further amino acid substitution is S228P, E233P, L234A, L235A, L235E, N297A, N297D or P331S. In a particular embodiment the antibody comprises amino acid substitutions in the Fc region at positions P329, L234 and L235. In a more particular embodiment the antibody comprises the amino acid mutations L234A, L235A and P329G (LALA P329G). This combination of amino acid substitutions almost completely abolishes Fcγ receptor binding of a human IgG antibody, as described in PCT patent application no. PCT/EP2012/055393, incorporated herein by reference in its entirety. PCT patent application no. PCT/EP2012/055393 also describes methods of preparing such modified antibodies and methods for determining its properties such as Fc receptor binding or effector functions.

Antibodies comprising modifications in the Fc region can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Antibodies which comprise modifications reducing Fc receptor binding generally have reduced effector functions, particularly reduced ADCC, as compared to corresponding unmodified antibodies. In some embodiments the antibodies have reduced ADCC. In specific embodiments the reduced ADCC is less than 20% of the ADCC induced by a corresponding antibody comprising an unmodified Fc region. Effector function of an antibody can be measured by methods known in the art. Examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998). In some embodiments binding of the antibody to a complement component, specifically to C1q, is also reduced. Accordingly, complement-dependent cytotoxicity (CDC) may also be reduced. C1q binding assays may be carried out to determine whether the antibody is able to bind C1q and hence has CDC activity. See e.g. C1q and C3c binding ELISA in WO 2006/029879 and WO 2005/100402. To assess complement activation, a CDC assay may be performed (see, for example, Gazzano-Santoro et al., J Immunol Methods 202, 163 (1996); Cragg et al., Blood 101, 1045-1052 (2003); and Cragg and Glennie, Blood 103, 2738-2743 (2004)).

In addition to the antibodies described hereinabove and in PCT patent application no. PCT/EP2012/055393, antibodies with reduced Fc receptor binding and/or effector function also include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

$IgG_4$ antibodies exhibit reduced binding affinity to Fc receptors and reduced effector functions as compared to $IgG_1$ antibodies. Hence, in some embodiments, the antibodies of the invention are $IgG_4$ subclass antibodies, particularly human $IgG_4$ subclass antibodies. In one embodiment the $IgG_4$ antibody comprises amino acid substitutions in the Fc region at position S228, specifically the amino acid substitution S228P. To further reduce its binding affinity to an Fc receptor and/or its effector function, in one embodiment the $IgG_4$ antibody comprises an amino acid substitution at position L235, specifically the amino acid substitution L235E. In another embodiment, the $IgG_4$ antibody comprises an amino acid substitution at position P329, specifically the amino acid substitution P329G. In a particular embodiment, the $IgG_4$ antibody comprises amino acid substitutions at positions S228, L235 and P329, specifically amino acid substitutions S228P, L235E and P329G. Such modified $IgG_4$ antibodies and their Fcγ receptor binding properties are described in PCT patent application no. PCT/EP2012/055393, incorporated herein by reference in its entirety.

Antibodies according to the invention may have effector moieties such as cytokines attached. In particular embodiments, the antibodies comprise only one single effector moiety, fused to one of the two antibody heavy chains, thus these antibodies comprise two non-identical polypeptide chains. Similarly, the antibodies of the invention may be full-length antibodies, lacking one of the Fab fragments, hence comprising a full antibody heavy chain and an antibody heavy chain lacking the VH and CH1 domains. Recombinant co-expression of these polypeptides and subsequent dimerization leads to several possible combinations of the two polypeptides, out of which only heterodimers of the two non-identical polypeptides are useful. To improve the yield and purity of such antibodies in recombinant production, it can thus be advantageous to introduce in the Fc region of the antibody a modification which hinders the formation of homodimers of two identical polypeptides (e.g. two polypeptides comprising an effector moiety, or two polypeptides lacking an effector moiety) and/or promotes the formation of heterodimers of a polypeptide comprising an effector moiety and a polypeptide lacking an effector moiety. Accordingly, in some embodiments, the antibodies of the invention comprise in the Fc region a modification promoting heterodimerization of two non-identical antibody heavy chains. The site of most extensive protein-protein interaction between the two heavy chains of a human IgG antibody is in the CH3 domain of the Fc region. Thus, in one embodiment said modification is in the CH3 domain of the Fc region. In a specific embodiment, said modification is a knob-into-hole modification, comprising a knob modification in one of the antibody heavy chains and a hole modification in the other one of the two antibody heavy chains. The knob-into-hole technology is described e.g. in U.S. Pat. No. 5,731,168; U.S. Pat. No. 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). Hence, in one embodiment, the antibody comprises a modification within the interface between the two antibody heavy chains in the CH3 domain, wherein i) in the CH3 domain of one heavy chain, an amino acid residue is replaced with an amino acid residue having a larger side chain volume, thereby generating a protuberance ("knob") within the interface in the CH3 domain of one heavy chain which is positionable in a cavity ("hole") within the interface in the CH3 domain of the other heavy chain, and ii) in the CH3 domain of the other heavy chain, an amino acid residue is replaced with an amino acid residue having a smaller side chain volume, thereby generating a cavity ("hole") within the interface in the second CH3 domain within which a protuberance ("knob") within the interface in the first CH3 domain is positionable. The protuberance and cavity can be made by altering the nucleic acid encoding the polypeptides, e.g. by site-specific mutagenesis, or by peptide synthesis. In a specific embodiment a knob modification comprises the amino acid substitution T366W (EU numbering) in one of the two antibody heavy chains, and the hole modification comprises the amino acid substitutions T366S, L368A and Y407V (EU numbering) in the other one of the two antibody heavy chains. In a further specific embodiment, the antibody heavy chain comprising the knob modification additionally comprises the amino acid substitution S354C, and the antibody heavy chain comprising the hole modification additionally comprises the amino acid substitution Y349C. Introduction of these two cysteine residues results in formation of a disulfide bridge between the two antibody heavy chains in the Fc region, further stabilizing the dimer (Carter, J Immunol Methods 248, 7-15 (2001)). In an alternative embodiment a modification promoting heterodimerization of two non-identical antibody heavy chains comprises a modification mediating electrostatic steering effects, e.g. as described in PCT publication WO 2009/089004. Generally, this method involves replacement of one or more amino acid residues at the interface of the two antibody heavy chains by charged amino acid residues so that homodimer formation becomes electrostatically unfavorable but heterodimerization electrostatically favorable. In a particular embodiment wherein the antibody has an effector moiety attached to it, the effector moiety is fused to the amino- or carboxy-terminal amino acid of the antibody heavy chain comprising the knob modification. Without wishing to be bound by theory, fusion of the effector moiety to the knob-containing heavy chain will further minimize the generation of homodimeric antibodies comprising two effector moieties (steric clash of two knob-containing polypeptides). Similarly, in embodiments wherein the antibody comprises a only single Fab fragment fused to an Fc region, the Fab fragment is preferably fused to the heavy chain of the Fc region comprising the knob modification.

The antibodies of the invention combine a number of properties which are particularly advantageous, for example for therapeutic applications. For example, the antibodies are cross-reactive for human and cynomolgus monkey, which enables e.g. in vivo studies in cynomolgus monkeys prior to human use. Hence, in one embodiment, the antibody of the invention is capable of specific binding to human and cynomolgus monkey ASGPR. Furthermore, the antibodies of the invention bind ASGPR with particularly strong affinity and/or avidity. In one embodiment, the antibody binds to human ASGPR with an dissociation constant ($K_D$) of smaller than 1 μM, particularly smaller than 100 nM, more particularly smaller than 1 nM, when measured as Fab fragment by Surface Plasmon Resonance (SPR). A method for measuring binding affinity by SPR is described herein. Specifically, measurement is made at a temperature of 25° C. In one embodiment, affinity ($K_D$) of antibodies as Fab fragments is measured by SPR using a ProteOn XPR36 instrument (Biorad) at 25° C. with biotinylated mono-(avi-Fc-human ASGPR H1 CRD, SEQ ID NO: 118) or bivalent (avi-Fc-human ASGPR H1 stalk-CRD, SEQ ID NO: 130) ASGPR H1 antigens immobilized on NLC chips by neutravidin capture. In an exemplary method, antigens for immobilization are diluted with PBST (10 mM phosphate, 150 mM NaCl pH 7.4, 0.005% Tween-20) to 10 μg/ml, and injected at 30 μl/min at varying contact times, to achieve immobilization levels of 200, 400 or 800 response units (RU) in vertical orientation. Subsequently, analytes (antibodies) are injected. For one-shot kinetics measurements, injection direction is changed to horizontal orientation, and two-fold dilution series of purified Fab fragments (varying concentration ranges between 100 and 6.25 nM) are injected simultaneously at 50, 60 or 100 μl/min along separate channels 1-5, with association times of 150 or 200 s, and dissociation times of 240 or 600 s. Buffer (PBST) is injected along the sixth channel to provide an "in-line" blank for referencing. Association rate constants ($k_{on}$) and dissociation rate constants ($k_{off}$) are calculated using a simple one-to-one Langmuir binding model in ProteOn Manager v3.1 software by simultaneously fitting the association and dissociation sensorgrams. The equilibrium dissociation constant ($K_D$) is calculated as the ratio $k_{off}/k_{on}$. Regeneration is performed in horizontal orientation using 10 mM glycine, pH 1.5 at a flow rate of 100 μl/min for a contact time of 30 s. In another embodiment, the antibody binds to human ASGPR with a $K_D$ of smaller than 1 μM, particularly smaller than 500 nM, more particularly smaller than 100 nM or even smaller than 10 nM, when measured as $IgG_1$ by fluoresecence resonance energy transfer (FRET). A method for measuring binding affinity (or avidity) by FRET is described herein. In one embodiment, the measurement is performed by contacting cells expressing full-length ASGPR protein labeled with a FRET donor molecule with the antibodies, and detection of bound antibodies by a secondary antibody labeled with a suitable FRET acceptor molecule. In an exemplary method, the DNA sequence encoding for the SNAP Tag (plasmid purchased from Cisbio) is amplified by PCR and ligated into an expression vector, containing the full length human ASGPR H1 sequence (Origene). The resulting fusion protein is comprised of full-length ASGPR H1 with a C-terminal SNAP tag. HEK293 cells are transfected with 10 μg DNA using Lipofectamine 2000 as transfection reagent. After an incubation time of 20 h, cells are washed with PBS and incubated for 1 h at 37° C. in LabMed buffer (Cisbio) containing 100 nM SNAP-Lumi4Tb (Cisbio), leading to specific labeling of the SNAP Tag. Subsequently, cells are washed 4 times with LabMed buffer to remove unbound dye. The labeling efficiency is determined by measuring the emission of terbium at 615 nm compared to buffer. Cells can then be stored frozen at −80° C. for up to 6 months. Avidity is measured by adding ASGPR-specific antibodies at a concentration ranging from 50-0.39 nM to labeled cells (100 cells per well) followed by addition of anti-human Fc-d2 (Cisbio, final 200 nM per well) as acceptor molecule for the FRET. After an incubation time of 3 h at RT the emission of the acceptor dye (665 nm) as well as of the donor dye (615 nm) is determined using a fluorescence Reader (Victor 3, Perkin Elmer). The ratio of acceptor to donor emission is calculated and the ratio of the background control (cells with anti-human Fc-d2) subtracted. Curves can be analysed in GraphPad Prism5 software and $K_D$ values calculated. A further advantage of the antibodies of the invention is that they do not compete for binding to ASGPR with natural ligands of the receptor (asialoglycoproteins such as e.g. asialofetuin), i.e. antibody binding is not affected by the presence of ASGPR ligand and does not interfere with the natural function of ASGPR. In one embodiment, the antibody does not compete with a natural ligand of ASGPR for binding to ASGPR. In a specific embodiment, said natural ligand of ASGPR is asialofetuin. Competition can be measured by methods well known in the art. In one embodiment, competition with a natural ligand of ASGPR is measured by FACS, for example using an ASGPR-expressing cell line, fluorescently labeled ligand, and detection of bound antibodies with a secondary antibody having a different fluorescent label. In an exemplary method, the hepatocellular carcinoma cell line HepG2 is used. 0.2 mio cells per well in a 96 well round bottom plate are incubated with 40 μl of Alexa488 labeled asialofetuin (from fetal calf serum, Sigma Aldrich #A4781, final concentration 100 μg/ml) at 4° C. for 30 min The binding is performed in the presence of calcium, as ligand binding to ASGPR is calcium dependent. Unbound protein is removed by washing the cells once with HBSS containing 0.1% BSA. Then 40 μl of the anti-ASGPR antibodies (30, 6, and 1.25 μg/ml final concentration) are added to the cells in the presence of 100 μg/ml asialofetuin. Cells are incubated for 30 min at 4° C. and unbound protein is removed by washing the cells once. An APC-conjugated AffiniPure goat anti-human IgG Fc gamma fragment-specific secondary F(ab')2 fragment (Jackson ImmunoResearch #109-136-170; working solution 1:50 in HBSS containing 0.1% BSA) is used as an secondary antibody. After 30 min incubation at 4° C. unbound secondary antibody is removed by washing. Cells are fixed using 1% PFA and binding of ligand as well as antibodies is analyzed using BD FACS CantoII (Software BD DIVA). A major advantage of the antibodies of the invention is their high specificity for ASGPR. For example, despite their strong binding to human ASGPR H1, the antibodies do not detectably bind to CLEC10A, which was identified as the closest homologue of human ASGPR H1. In one embodiment, the antibody does not detectably bind to CLEC10A, particularly human CLEC10A. Specifically, the antibody does not detectably bind to CLEC10A wherein binding is measured by SPR (as described herein). Moreover, the antibodies bind to cells which do not express ASGPR only to a similar extent as a corresponding untargeted antibody (isotype control). Hence, in one embodiment, the antibody does not specifically bind to cells lacking ASGPR expression, particularly human cells, more particularly human blood cells. Exemplary cells lacking ASGPR expression include Hela cells (a human cell line derived from cervical cancer), A459 human non-small cell lung cancer cells, human embryonic kidney (HEK) cells, and (human) PBMCs. Binding, or lack of binding, to specific cells can easily be determined for example by FACS. Such methods are well established in the art and also described in the Examples hereinbelow. An important feature of anti-ASGPR antibodies are their internalization characteristics. For example, if the antibody is to be used to target an effector moiety to ASGPR-expressing cells, it is desirable for the antibody to be present on the cell surface for a sufficiently long time for activation of effector moiety receptors. The antibodies of the present invention, upon binding to ASGPR, are internalized into the ASGPR-expressing cell, however, they are recycled back to the cell surface without being degraded inside the cell. Hence, in one embodiment, the antibody is internalized into a cell expressing ASGPR upon binding of the antibody to ASGPR on the surface of said cell. In a specific embodiment, the antibody is recycled back to the surface of said cell at about the same rate as it is internalized into said cell. Internalization and recycling of cell surface proteins or antibodies bound thereto can easily be measured by established methods, such as FACS or (confocal) microscopy techniques. In one embodiment, internalization and/or recycling are measured by FACS. For an antibody to have sustained effects, it is important that its target antigen is present at essentially constant levels. Frequently, antibody binding to target antigens induces downregulation of the latter, leading to reduced efficacy of antibodies. However, the antibodies of the present invention do not have such effect. In one embodiment, the antibody does not significantly induce downregulation of ASGPR expression at the surface of a cell upon binding of the antibody to ASGPR on the surface of said cell. The level of antigen expression at the surface of a cell can easily be determined by established methods such as FACS.

Antibodies with Attached Effector Moieties

Particularly useful antibodies according to the present invention are antibodies having an effector moiety, e.g. a cytokine, attached. Antibodies fused to an effector moiety such as a cytokine are also referred to as immunoconjugates herein. The antibodies with attached effector moieties can incorporate, singly or in combination, any of the features described hereinabove in relation to the antibodies of the invention.

Accordingly, in one aspect, the invention provides an antibody capable of specific binding to ASGPR according to any of the above embodiments, wherein an effector moiety is attached to the antibody. In one embodiment, not more than one effector moiety is attached to the antibody. The absence of further effector moieties may reduce targeting of the antibody to sites where the respective effector moiety receptor is presented, thereby improving targeting to and accumulation at sites where the actual target antigen of the antibody, ASGPR, is presented. Furthermore, the absence of an avidity effect for the respective effector moiety receptor can reduce activation of effector moiety receptor-positive cells in peripheral blood upon intravenous administration of the antibody. The effector moieties for use in the invention are generally polypeptides that influence cellular activity, for example, through signal transduction pathways. Accordingly, an effector moiety useful in the invention can be associated with receptor-mediated signaling that transmits a signal from outside the cell membrane to modulate a response within the cell. For example, an effector moiety can be a cytokine. In particular embodiments the effector moiety is human. In particular embodiments, the effector moiety is a peptide molecule and is fused to the antibody through peptide bonds (i.e. the antibody and effector moiety form a fusion protein). In one embodiment, the effector moiety is single-chain peptide molecule. In a further embodiment, the effector moiety is fused at its amino-terminal amino acid to the carboxy-terminal amino acid of one of the heavy chains of the antibody, optionally through a peptide linker. Suitable, non-immunogenic peptide linkers include, for example, $(G_4S)_n$, $(SG_4)_n$ or $G_4(SG_4)_n$ peptide linkers. "n" is generally a number between 1 and 10, typically between 2 and 4. In embodiments wherein the antibody comprises a knob-into-hole modification in the Fc region as described above, it is preferable to fuse the effector moiety to the antibody heavy chain comprising the knob modification.

In one embodiment said effector moiety is a cytokine molecule. Examples of useful cytokines include, but are not limited to, GM-CSF, IL-1α, IL-1β, IL-2, IL-3, IL-4, IL-5, IL-6, IL-7, IL-8, IL-10, IL-12, IL-21, IFN-α, IFN-β, IFN-γ, MIP-1α, MIP-1β, TGF-β, TNF-α, and TNF-β. In one embodiment, said cytokine molecule is fused at its amino-terminal amino acid to the carboxy-terminal amino acid of one of the antibody heavy chains, optionally through a peptide linker. In one embodiment, said cytokine molecule is a human cytokine. In one embodiment, said cytokine molecule is an interferon molecule. In a specific embodiment, said interferon molecule is interferon alpha, particularly human interferon alpha, more particularly human interferon alpha 2 (see SEQ ID NO: 138) or human interferon alpha 2a (see SEQ ID NO: 139). Interferon alpha is known to have anti-viral activities. Hence, attaching an interferon molecule to an antibody of the invention is particularly useful for targeting virus-infected ASGPR-expressing cells. In one embodiment, wherein the cytokine molecule is an interferon molecule, the antibody has anti-viral activity in cells expressing ASGPR on their surface. In one embodiment, said cells are liver cells, particularly hepatocytes, more particularly human hepatocytes. In one embodiment, said anti-viral activity is selective. In a specific embodiment, the antibody has no anti-viral activity in cells not expressing significant levels of ASGPR on their surface. In one embodiment, said cells are blood cells, particularly human blood cells. In one embodiment, said anti-viral activity This selectivity of interferon molecules attached to anti-ASGPR antibodies according to the invention is in contrast to untargeted interferon molecules, which do not distinguish between any intended target cells (e.g. hepatocytes) and cells which should not be affected (e.g. blood cells), and is crucial for possible therapeutic use without major toxicity issues. In a further specific embodiment, said anti-viral activity is selected from inhibition of viral infection, inhibition of virus replication, inhibition of cell killing and induction of one or more interferon-stimulated gene. In a specific embodiment, the one or more interferon-stimulated gene is selected from the group of MX1 (myxovirus resistance 1, also known as interferon-induced protein p78), RSAD2 (radical S-adenosyl methionine domain containing 2, also known as cytomegalovirus-induced gene 5), HRASLS2 (HRAS-like suppressor 2), IFIT1 (interferon-induced protein with tetratricopeptide repeats 1), and IFITM2 (interferone-induced transmembrane protein 2). In one embodiment, the induction of one or more interferon-stimulated gene is at least a 1.5-fold, particularly at least a 2-fold, more particularly at least a 5-fold induction on mRNA level, as compared to induction by a corresponding antibody without interferon molecule attached. Gene induction on mRNA level can be measured by methods well established in the art, including quantitative reverse-transcription (RT) PCR or microarray analysis, as described herein. Inhibition of cell killing can be determined for example by a virus protection assay, wherein cells are preincubated with the test compound, followed by addition of virus and quantification of living cells after incubation. An exemplary such assay is described in the Examples. Madin-Darby bovine kidney (MDBK) cells are pre-incubated with the antibodies and controls for 1-4 h. Vesicular stomatitis virus is then added for additional 16-24 h. At the end of this incubation step, living cells are stained with crystal violet staining solution (0.5%) and quantification of living cells is performed using a microplate reader at 550-600 nm with a reference wavelength of 690 nm. An exemplary assay for assessment of virus replication is also provided in the Examples. This assay uses a Huh 7-derived hepatocarcinoma cell line stably transfected with bicistronic hepatitis C virus (HCV) replicon of which the first open reading frame, driven by the HCV IRES, contains the *renilla* luciferase gene in fusion with the neomycin phosphotransferase gene (NPTII) and the second open reading frame, driven by EMCV IRES, contains the HCV non-structural genes NS3, NS4a, NS4b, NSSA and NSSB derived from the NK5.1 replicon backbone. Cells are cultured at 37° C. in a humidified atmosphere with 5% $CO_2$ in DMEM supplemented with Glutamax™ and 100 mg/ml sodium pyruvate. The medium was further supplemented with 10% (v/v) FBS (v/v) penicillin/streptomycin and 1% (v/v) geneticin. The cells in DMEM containing 5% (v/v) FBS are plated in 96-well plates at 5000 cells/well in 90 μl volume. 24 hours after plating, antibodies (or medium as a control) are added to the cells in 3-fold dilutions over 12 wells (0.01-2000 pM), in a volume of 10 μl, so that the final volume after addition of antibody is 100 *Renilla* luciferase reporter signal is read 72 hours after adding antibodies, using the *Renilla* Luciferase Assay system (Promega, #E2820). The $EC_{50}$ values are calculated as the compound concentration at which a 50% reduction in the level of *renilla* luciferase reporter is observed as compared to control samples (in the absence of antibody). Dose-response curves and $EC_{50}$ values are obtained by using the XLfit4 program (ID Business Solutions Ltd., Surrey, UK). In a particular embodiment, the antibody according to the invention is a full-length human $IgG_1$ antibody comprising the heavy chain variable region sequence of SEQ ID NO: 16 and the light chain variable region sequence of SEQ ID NO: 14, said antibody comprising in the Fc region a modification reducing binding affinity of the antibody to FcγRIIIa and a knob-into-hole modification, said knob-into-hole modification comprising a knob modification in one of the antibody heavy chains and a hole modification in the other one of the antibody heavy chains, and said antibody having an IFNα2 molecule fused at the N-terminal amino acid to the C-terminal amino acid of one of the antibody heavy chains through a peptide linker. In a specific embodiment, said modification reducing binding affinity of the antibody to FcγRIIIa comprises the amino acid substitutions L234A, L235A and P329G (EU numbering) in each of the antibody heavy chains. In a further specific embodiment, said knob modification comprises the amino acid substitution T366W and the hole modification comprises the amino acid substitutions T366S, L368A and Y407V. In still a further specific embodiment, said IFNα2 molecule is fused to the antibody heavy chain comprising the knob modification. In an even more specific embodiment, said antibody comprises the polypeptide sequences of SEQ ID NO: 68, SEQ ID NO: 70 and SEQ ID NO: 72, or variants thereof that retain functionality.

In another particular embodiment, the antibody according to the invention is a full-length human $IgG_1$ antibody comprising the heavy chain variable region sequence of SEQ ID NO: 4 and the light chain variable region sequence of SEQ ID NO: 2, said antibody comprising in the Fc region a modification reducing binding affinity of the antibody to FcγRIIIa and a knob-into-hole modification, said knob-into-hole modification comprising a knob modification in one of the antibody heavy chains and a hole modification in the other one of the antibody heavy chains, and said antibody having an IFNα2 molecule fused at the N-terminal amino acid to the C-terminal amino acid of one of the antibody heavy chains through a peptide linker. In a specific embodiment, said modification reducing binding affinity of the antibody to FcγRIIIa comprises the amino acid substitutions L234A, L235A and P329G (EU numbering) in each of the antibody heavy chains. In a further specific embodiment, said knob modification comprises the amino acid substitution T366W and the hole modification comprises the amino acid substitutions T366S, L368A and Y407V. In still a further specific embodiment, said IFNα2 molecule is fused to the antibody heavy chain comprising the knob modification. In an even more specific embodiment, said antibody comprises the polypeptide sequences of SEQ ID NO: 50, SEQ ID NO: 52 and SEQ ID NO: 54, or variants thereof that retain functionality.

In still another particular embodiment, the antibody according to the invention is a full-length human $IgG_1$ antibody comprising the heavy chain variable region sequence of SEQ ID NO: 4 and a light chain variable region sequence selected from the group of SEQ ID NO: 36, SEQ ID NO: 38, SEQ ID NO: 40, SEQ ID NO: 42, SEQ ID NO: 44, SEQ ID NO: 46 and SEQ ID NO: 48, said antibody comprising in the Fc region a modification reducing binding affinity of the antibody to FcγRIIIa and a knob-into-hole modification, said knob-into-hole modification comprising a knob modification in one of the antibody heavy chains and a hole modification in the other one of the antibody heavy chains, and said antibody having an IFNα2 molecule fused at the N-terminal amino acid to the C-terminal amino acid of one of the antibody heavy chains through a peptide linker. In a specific embodiment, said modification reducing binding affinity of the antibody to FcγRIIIa comprises the amino acid substitutions L234A, L235A and P329G (EU numbering) in each of the antibody heavy chains. In a further specific embodiment, said knob modification comprises the amino acid substitution T366W and the hole modification comprises the amino acid substitutions T366S, L368A and Y407V. In still a further specific embodiment, said IFNα2 molecule is fused to the antibody heavy chain comprising the knob modification. In an even more specific embodiment, said antibody comprises the polypeptide sequences of SEQ ID NO: 52, SEQ ID NO: 54 and a polypeptide sequence selected from the group of SEQ ID NO: 96, SEQ ID NO: 98, SEQ ID NO: 100, SEQ ID NO: 102, SEQ ID NO: 104, SEQ ID NO: 106 and SEQ ID NO: 108, or variants thereof that retain functionality.

In a further embodiment, the antibody of the invention comprises the polypeptide sequences of SEQ ID NO: 92, SEQ ID NO: 52 and SEQ ID NO: 54, or variants thereof that retain functionality. In another embodiment, the antibody according to the invention comprises the polypeptide sequences of SEQ ID NO: 94, SEQ ID NO: 52 and SEQ ID NO: 54, or variants thereof that retain functionality. In still a further embodiment, the antibody according to the invention comprises the polypeptide sequences of SEQ ID NO: 56, SEQ ID NO: 58 and SEQ ID NO: 60, or variants thereof that retain functionality. In a further embodiment, the antibody according to the invention comprises the polypeptide sequences of SEQ ID NO: 62, SEQ ID NO: 64 and SEQ ID NO: 66, or variants thereof that retain functionality. In a further embodiment, the antibody according to the invention comprises the polypeptide sequences of SEQ ID NO: 74, SEQ ID NO: 76 and SEQ ID NO: 78, or variants thereof that retain functionality. In a further embodiment, the antibody according to the invention comprises the polypeptide sequences of SEQ ID NO: 80, SEQ ID NO: 82 and SEQ ID NO: 84, or variants thereof that retain functionality. In a further embodiment, the antibody according to the invention comprises the polypeptide sequences of SEQ ID NO: 86, SEQ ID NO: 88 and SEQ ID NO: 90, or variants thereof that retain functionality.

In an alternative embodiment, the antibody according to the invention is a full-length human $IgG_1$ antibody lacking one of the two Fab fragments and comprising the heavy chain variable region sequence of SEQ ID NO: 16 and the light chain variable region sequence of SEQ ID NO: 14, said antibody comprising in the Fc region a modification reducing binding affinity of the antibody to FcγRIIIa and a knob-into-hole modification, said knob-into-hole modification comprising a knob modification in one of the antibody heavy chains and a hole modification in the other one of the antibody heavy chains, and said antibody having an IFNα2 molecule fused at the N-terminal amino acid to the C-terminal amino acid of one of the antibody heavy chains through a peptide linker. In a specific embodiment, said modification reducing binding affinity of the antibody to FcγRIIIa comprises the amino acid substitutions L234A, L235A and P329G (EU numbering) in each of the antibody heavy chains. In a further specific embodiment, said knob modification comprises the amino acid substitution T366W and the hole modification comprises the amino acid substitutions T366S, L368A and Y407V. In still a further specific embodiment, said IFNα2 molecule is fused to the antibody heavy chain comprising the knob modification. In an even more specific embodiment, said antibody comprises the polypeptide sequences of SEQ ID NO: 68, SEQ ID NO: 70 and SEQ ID NO: 116, or variants thereof that retain functionality.

In another alternative embodiment, the antibody according to the invention is a full-length human $IgG_1$ antibody lacking one of the two Fab fragments and comprising the heavy chain variable region sequence of SEQ ID NO: 4 and the light chain variable region sequence of SEQ ID NO: 2, said antibody comprising in the Fc region a modification reducing binding affinity of the antibody to FcγRIIIa and a knob-into-hole modification, said knob-into-hole modification comprising a knob modification in one of the antibody heavy chains and a hole modification in the other one of the antibody heavy chains, and said antibody having an IFNα2 molecule fused at the N-terminal amino acid to the C-terminal amino acid of one of the antibody heavy chains through a peptide linker. In a specific embodiment, said modification reducing binding affinity of the antibody to FcγRIIIa comprises the amino acid substitutions L234A, L235A and P329G (EU numbering) in each of the antibody heavy chains. In a further specific embodiment, said knob modification comprises the amino acid substitution T366W and the hole modification comprises the amino acid substitutions T366S, L368A and Y407V. In still a further specific embodiment, said IFNα2 molecule is fused to the antibody heavy chain comprising the knob modification. In an even more specific embodiment, said antibody comprises the polypeptide sequences of SEQ ID NO: 50, SEQ ID NO: 52 and SEQ ID NO: 116, or variants thereof that retain functionality.

In still another alternative embodiment, the antibody according to the invention is a full-length human $IgG_1$ antibody lacking one of the two Fab fragments and comprising the heavy chain variable region sequence of SEQ ID NO: 4 and a light chain variable region sequence selected from the group of SEQ ID NO: 36, SEQ ID NO: 38, SEQ ID NO: 40, SEQ ID NO: 42, SEQ ID NO: 44, SEQ ID NO: 46 and SEQ ID NO: 48, said antibody comprising in the Fc region a modification reducing binding affinity of the antibody to FcγRIIIa and a knob-into-hole modification, said knob-into-hole modification comprising a knob modification in one of the antibody heavy chains and a hole modification in the other one of the antibody heavy chains, and said antibody having an IFNα2 molecule fused at the N-terminal amino acid to the C-terminal amino acid of one of the antibody heavy chains through a peptide linker. In a specific embodiment, said modification reducing binding affinity of the antibody to FcγRIIIa comprises the amino acid substitutions L234A, L235A and P329G (EU numbering) in each of the antibody heavy chains. In a further specific embodiment, said knob modification comprises the amino acid substitution T366W and the hole modification comprises the amino acid substitutions T366S, L368A and Y407V. In still a further specific embodiment, said IFNα2 molecule is fused to the antibody heavy chain comprising the knob modification. In an even more specific embodiment, said antibody comprises the polypeptide sequences of SEQ ID NO: 52, SEQ ID NO: 116 and a polypeptide sequence selected from the group of SEQ ID NO: 96, SEQ ID NO: 98, SEQ ID NO: 100, SEQ ID NO: 102, SEQ ID NO: 104, SEQ ID NO: 106 and SEQ ID NO: 108, or variants thereof that retain functionality.

In a further embodiment, the antibody of the invention comprises the polypeptide sequences of SEQ ID NO: 92, SEQ ID NO: 52 and SEQ ID NO: 116, or variants thereof that retain functionality. In another embodiment, the antibody according to the invention comprises the polypeptide sequences of SEQ ID NO: 94, SEQ ID NO: 52 and SEQ ID NO: 116, or variants thereof that retain functionality. In still a further embodiment, the antibody according to the invention comprises the polypeptide sequences of SEQ ID NO: 56, SEQ ID NO: 58 and SEQ ID NO: 116, or variants thereof that retain functionality. In a further embodiment, the antibody according to the invention comprises the polypeptide sequences of SEQ ID NO: 62, SEQ ID NO: 64 and SEQ ID NO: 116, or variants thereof that retain functionality. In a further embodiment, the antibody according to the invention comprises the polypeptide sequences of SEQ ID NO: 74, SEQ ID NO: 76 and SEQ ID NO: 116, or variants thereof that retain functionality. In a further embodiment, the antibody according to the invention comprises the polypeptide sequences of SEQ ID NO: 80, SEQ ID NO: 82 and SEQ ID NO: 116, or variants thereof that retain functionality. In a further embodiment, the antibody according to the invention comprises the polypeptide sequences of SEQ ID NO: 86, SEQ ID NO: 88 and SEQ ID NO: 116, or variants thereof that retain functionality.

Antibodies of the invention include those that have sequences that are at least about 80%, 85%, 90%, 95%, 96%, 97%, 98%, 99%, or 100% identical to the sequences set forth in SEQ ID NOs 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108 and 116, including functional fragments or variants thereof. The invention also encompasses antibodies comprising these sequences with conservative amino acid substitutions.

Polynucleotides

The invention further provides polynucleotides encoding an antibody as described herein or an antigen binding portion thereof.

Polynucleotides of the invention include those that are at least about 80%, 85%, 90%, 95%, 96%, 97%, 98%, 99%, or 100% identical to the sequences set forth in SEQ ID NOs 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109 and 117, including functional fragments or variants thereof.

The polynucleotides encoding antibodies of the invention may be expressed as a single polynucleotide that encodes the entire antibody or as multiple (e.g., two or more) polynucleotides that are co-expressed. Polypeptides encoded by polynucleotides that are co-expressed may associate through, e.g., disulfide bonds or other means to form a functional antibody. For example, the light chain portion of an antibody may be encoded by a separate polynucleotide from the heavy chain portion of the antibody. When co-expressed, the heavy chain polypeptides will associate with the light chain polypeptides to form the antibody. In another example, the heavy chain portion of the antibody comprising an effector moiety could be encoded by a separate polynucleotide from the other heavy chain portion of the antibody. When co-expressed, the heavy chain polypeptides will associate to form a functional antibody (together with the light chain polypeptide(s)).

In one embodiment, the present invention is directed to a polynucleotide encoding an antibody or an antigen binding portion thereof, wherein the polynucleotide comprises a sequence that encodes a variable region sequence as shown in SEQ ID NO 2, 4, 6, 8, 10, 12, 14, 16, 18, 20, 22, 24, 26, 28, 30, 32, 34, 36, 38, 40, 42, 44, 46 or 48. In another embodiment, the present invention is directed to a polynucleotide encoding an antibody or an antigen binding portion thereof, wherein the polynucleotide comprises a sequence that encodes a polypeptide sequence as shown in SEQ ID NO 50, 52, 54, 56, 58, 60, 62, 64, 66, 68, 70, 72, 74, 76, 78, 80, 82, 84, 86, 88, 90, 92, 94, 96, 98, 100, 102, 104, 106, 108 or 116. In another embodiment, the invention is further directed to a polynucleotide encoding an antibody or an antigen binding portion thereof, wherein the polynucleotide comprises a sequence that is at least about 80%, 85%, 90%, 95%, 96%, 97%, 98%, or 99% identical to a nucleic acid sequence shown SEQ ID NO 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109 or 117. In another embodiment, the invention is directed to a polynucleotide encoding an antibody or an antigen binding portion thereof, wherein the polynucleotide comprises a nucleic acid sequence shown in SEQ ID NO 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109 or 117. In another embodiment, the invention is directed to a polynucleotide encoding an antibody or antigen binding portion thereof, wherein the polynucleotide comprises a sequence that encodes a variable region sequence that is at least about 80%, 85%, 90%, 95%, 96%, 97%, 98%, or 99% identical to an amino acid sequence of SEQ ID NO 2, 4, 6, 8, 10, 12, 14, 16, 18, 20, 22, 24, 26, 28, 30, 32, 34, 36, 38, 40, 42, 44, 46 or 48. In another embodiment, the invention is directed to a polynucleotide encoding an antibody or an antigen binding portion thereof, wherein the polynucleotide comprises a sequence that encodes a polypeptide sequence that is at least 80%, 85%, 90%, 95%, 96%, 97%, 98%, or 99% identical to an amino acid sequence of SEQ ID NO 50, 52, 54, 56, 58, 60, 62, 64, 66, 68, 70, 72, 74, 76, 78, 80, 82, 84, 86, 88, 90, 92, 94, 96, 98, 100, 102, 104, 106, 108 or 116. The invention encompasses a polynucleotide encoding an antibody or an antigen binding portion thereof, wherein the polynucleotide comprises a sequence that encodes the variable region sequences of SEQ ID NO 2, 4, 6, 8, 10, 12, 14, 16, 18, 20, 22, 24, 26, 28, 30, 32, 34, 36, 38, 40, 42, 44, 46 or 48 with conservative amino acid substitutions. The invention also encompasses a polynucleotide encoding an antibody of the invention or an antigen binding portion thereof, wherein the polynucleotide comprises a sequence that encodes the polypeptide sequences of SEQ ID NO 50, 52, 54, 56, 58, 60, 62, 64, 66, 68, 70, 72, 74, 76, 78, 80, 82, 84, 86, 88, 90, 92, 94, 96, 98, 100, 102, 104, 106, 108 or 116 with conservative amino acid substitutions.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

Recombinant Methods

Antibodies of the invention may be obtained, for example, by solid-state peptide synthesis (e.g. Merrifield solid phase synthesis) or recombinant production. For recombinant production one or more polynucleotide encoding the antibody (fragment), e.g., as described above, is isolated and inserted into one or more vectors for further cloning and/or expression in a host cell. Such polynucleotide may be readily isolated and sequenced using conventional procedures. In one embodiment a vector, preferably an expression vector, comprising one or more of the polynucleotides of the invention is provided. Methods which are well known to those skilled in the art can be used to construct expression vectors containing the coding sequence of an antibody (fragment) along with appropriate transcriptional/translational control signals. These methods include in vitro recombinant DNA techniques, synthetic techniques and in vivo recombination/genetic recombination. See, for example, the techniques described in Maniatis et al., Molecular Cloning: a Laboratory Manual, Cold Spring Harbor Laboratory, N.Y. (1989); and Ausubel et al., Current Protocols in Molecular Biology, Greene Publishing Associates and Wiley Interscience, N.Y (1989). The expression vector can be part of a plasmid, virus, or may be a nucleic acid fragment. The expression vector includes an expression cassette into which the polynucleotide encoding the antibody (fragment) (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the antibody (fragment) of the invention, or variant or derivative thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit â-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the antibody is desired, DNA encoding a signal sequence may be placed upstream of the nucleic acid encoding an antibody of the invention or an antigen binding portion thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase. Exemplary amino acid sequences of secretory signal peptides are shown in SEQ ID NOs 135-137.

DNA encoding a short protein sequence that could be used to facilitate later purification (e.g. a histidine tag) or assist in labeling the antibody may be included within or at the ends of the antibody (fragment) encoding polynucleotide.

In a further embodiment, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one such embodiment a host cell comprises (e.g. has been transformed or transfected with) a vector comprising a polynucleotide that encodes (part of) an antibody of the invention. As used herein, the term "host cell" refers to any kind of cellular system which can be engineered to generate the antibodies of the invention or fragments thereof. Host cells suitable for replicating and for supporting expression of antibodies are well known in the art. Such cells may be transfected or transduced as appropriate with the particular expression vector and large quantities of vector containing cells can be grown for seeding large scale fermenters to obtain sufficient quantities of the antibody for clinical applications. Suitable host cells include prokaryotic microorganisms, such as *E. coli*, or various eukaryotic cells, such as Chinese hamster ovary cells (CHO), insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006). Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., YO, NS0, Sp20 cell). Standard technologies are known in the art to express foreign genes in these systems. Cells expressing a polypeptide comprising either the heavy or the light chain of an antibody, may be engineered so as to also express the other of the antibody chains such that the expressed product is an antibody that has both a heavy and a light chain.

In one embodiment, a method of producing an antibody according to the invention is provided, wherein the method comprises culturing a host cell comprising a polynucleotide encoding the antibody, as provided herein, under conditions suitable for expression of the antibody, and recovering the antibody from the host cell (or host cell culture medium).

Where an antibody is fused to an effector moiety, these components are genetically fused to each other. Antibodies can be designed such that its components are fused directly to each other or indirectly through a linker sequence. The composition and length of the linker may be determined in accordance with methods well known in the art and may be tested for efficacy. Additional sequences may also be included to incorporate a cleavage site to separate the individual components of the fusion if desired, for example an endopeptidase recognition sequence.

In certain embodiments the antibodies of the invention comprise at least an antibody variable region capable of binding to ASGPR. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of antibody can be used in the invention. Non-limiting antibodies useful in the present invention can be of murine, primate, or human origin. If the antibody is intended for human use, a chimeric form of antibody may be used wherein the constant regions of the antibody are from a human. A humanized or fully human form of the antibody can also be prepared in accordance with methods well known in the art (see e. g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Particular antibodies according to the invention are human antibodies. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments. A detailed description of the preparation of antibodies by phage display can be found in the Examples.

In certain embodiments, the antibodies of the present invention are engineered to have enhanced binding affinity according to, for example, the methods disclosed in PCT publication WO 2011/020783 (see Examples relating to affinity maturation) or U.S. Pat. Appl. Publ. No. 2004/0132066, the entire contents of which are hereby incorporated by reference. The ability of the antibody of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antibody that competes with a reference antibody for binding to a particular antigen, e.g. an antibody that competes with the 51A12 antibody for binding to ASGPR. In certain embodiments, such a competing antibody binds to the same epitope (e.g. a linear or a conformational epitope) that is bound by the reference antibody. Detailed exemplary methods for mapping an epitope to which an antibody binds are provided in Morris (1996) "Epitope Mapping Protocols", in Methods in Molecular Biology vol. 66 (Humana Press, Totowa, N.J.). In an exemplary competition assay, immobilized antigen (e.g. ASGPR) is incubated in a solution comprising a first labeled antibody that binds to the antigen (e.g. 51A12 antibody) and a second unlabeled antibody that is being tested for its ability to compete with the first antibody for binding to the antigen. The second antibody may be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to the antigen. See Harlow and Lane (1988) Antibodies: A Laboratory Manual ch. 14 (Cold Spring Harbor Laboratory, Cold Spring Harbor, N.Y.).

Antibodies prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the antibody binds. For example, for affinity chromatography purification of antibodies of the invention, a matrix with protein A or protein G may be used. Sequential Protein A or G affinity chromatography and size exclusion chromatography can be used to isolate an antibody essentially as described in the Examples. The purity of the antibody can be determined by any of a variety of well known analytical methods including gel electrophoresis, high pressure liquid chromatography, and the like. For example, the heavy chain fusion proteins expressed as described in the Examples were shown to be intact and properly assembled as demonstrated by reducing SDS-PAGE (see e.g. FIG. 13-19).

Compositions, Formulations, and Routes of Administration

In a further aspect, the invention provides pharmaceutical compositions comprising any of the antibodies provided herein, e.g., for use in any of the below therapeutic methods. In one embodiment, a pharmaceutical composition comprises any of the antibodies provided herein and a pharmaceutically acceptable carrier. In another embodiment, a pharmaceutical composition comprises any of the antibodies provided herein and at least one additional therapeutic agent, e.g., as described below.

Further provided is a method of producing an antibody of the invention in a form suitable for administration in vivo, the method comprising (a) obtaining an antibody according to the invention, and (b) formulating the antibody with at least one pharmaceutically acceptable carrier, whereby a preparation of antibody is formulated for administration in vivo.

Pharmaceutical compositions of the present invention comprise a therapeutically effective amount of one or more antibody dissolved or dispersed in a pharmaceutically acceptable carrier. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one antibody and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countries. Preferred compositions are lyophilized formulations or aqueous solutions. As used herein, "pharmaceutically acceptable carrier" includes any and all solvents, buffers, dispersion media, coatings, surfactants, antioxidants, preservatives (e.g. antibacterial agents, antifungal agents), isotonic agents, absorption delaying agents, salts, preservatives, antioxidants, proteins, drugs, drug stabilizers, polymers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The composition may comprise different types of carriers depending on whether it is to be administered in solid, liquid or aerosol form, and whether it need to be sterile for such routes of administration as injection. Antibodies of the present invention (and any additional therapeutic agent) can be administered intravenously, intradermally, intraarterially, intraperitoneally, intralesionally, intracranially, intraarticularly, intraprostatically, intrasplenically, intrarenally, intrapleurally, intratracheally, intranasally, intravitreally, intravaginally, intrarectally, intratumorally, intramuscularly, intraperitoneally, subcutaneously, subconj unctivally, intravesicularlly, mucosally, intrapericardially, intraumbilically, intraocularally, orally, topically, locally, by inhalation (e.g. aerosol inhalation), injection, infusion, continuous infusion, localized perfusion bathing target cells directly, via a catheter, via a lavage, in cremes, in lipid compositions (e.g. liposomes), or by other method or any combination of the forgoing as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the antibodies of the invention.

Parenteral compositions include those designed for administration by injection, e.g. subcutaneous, intradermal, intralesional, intravenous, intraarterial intramuscular, intrathecal or intraperitoneal injection. For injection, the antibodies of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the antibodies may be in powder form for constitution with a suitable vehicle, e.g., sterile pyrogen-free water, before use. Sterile injectable solutions are prepared by incorporating the antibodies of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

In addition to the compositions described previously, the antibodies may also be formulated as a depot preparation. Such long acting formulations may be administered by implantation (for example subcutaneously or intramuscularly) or by intramuscular injection. Thus, for example, the antibodies may be formulated with suitable polymeric or hydrophobic materials (for example as an emulsion in an acceptable oil) or ion exchange resins, or as sparingly soluble derivatives, for example, as a sparingly soluble salt.

Pharmaceutical compositions comprising the antibodies of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The antibodies may be formulated into a composition in a free acid or base, neutral or salt form. Pharmaceutically acceptable salts are salts that substantially retain the biological activity of the free acid or base. These include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

Therapeutic Methods and Compositions

Any of the antibodies provided herein may be used in therapeutic methods.

For use in therapeutic methods, antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, antibodies of the invention for use as a medicament are provided. In further aspects, antibodies of the invention for use in treating a disease are provided. In certain embodiments, antibodies of the invention for use in a method of treatment are provided. In one embodiment, the invention provides an antibody as described herein for use in the treatment of a disease in an individual in need thereof. In certain embodiments, the invention provides an antibody for use in a method of treating an individual having a disease comprising administering to the individual a therapeutically effective amount of the antibody. In certain embodiments the disease to be treated is a liver disease. Exemplary liver diseases include hepatits, cirrhosis, or liver cancer such as hepatocellular carcinoma. In a particular embodiment the disease is a viral infection, particularly a hepatitis virus infection, more particularly HBV infection. In another particular embodiment the disease is cancer, particularly liver cancer, more particularly hepatocellular carcinoma (HCC). In certain embodiments the method further comprises administering to the individual a therapeutically effective amount of at least one additional therapeutic agent, e.g., an anti-viral agent if the disease to be treated is a viral infection or an anti-cancer agent if the disease to be treated is cancer. An "individual" according to any of the above embodiments is a mammal, preferably a human.

In a further aspect, the invention provides for the use of an antibody of the invention in the manufacture or preparation of a medicament for the treatment of a disease in an individual in need thereof. In one embodiment, the medicament is for use in a method of treating a disease comprising administering to an individual having the disease a therapeutically effective amount of the medicament. In certain embodiments the disease to be treated is a liver disease. In a particular embodiment the disease is a viral infection, particularly a hepatitis virus infection, more particularly HBV infection. In other embodiments the disease to be treated is cancer. In a particular embodiment the disease is liver cancer, particularly hepatocellular carcinoma (HCC). In one embodiment, the method further comprises administering to the individual a therapeutically effective amount of at least one additional therapeutic agent, e.g., an anti-viral agent if the disease to be treated is a viral infection or an anti-cancer agent if the disease to be treated is cancer. An "individual" according to any of the above embodiments may be a mammal, preferably a human.

In a further aspect, the invention provides a method for treating a disease in an individual, comprising administering to said individual a therapeutically effective amount of an antibody of the invention. In one embodiment a composition is administered to said individual, comprising antibody of the invention in a pharmaceutically acceptable form. In certain embodiments the disease to be treated is a liver disease. In a particular embodiment the disease is a viral infection, particularly a hepatitis virus infection, more particularly HBV infection. In other embodiments the disease to be treated is cancer. In a particular embodiment, the disease is liver cancer, particularly hepatocellular carcinoma (HCC). In certain embodiments the method further comprises administering to the individual a therapeutically effective amount of at least one additional therapeutic agent, e.g., an anti-viral agent if the disease to be treated is a viral infection or an anti-cancer agent if the disease to be treated is cancer. An "individual" according to any of the above embodiments may be a mammal, preferably a human.

The antibodies of the invention are also useful as diagnostic reagents. The binding of an antibody to an antigenic determinant can be readily detected by a label attached to the antibody or by using a labeled secondary antibody specific for the antibody of the invention.

In some embodiments, an effective amount of an antibody of the invention is administered to a cell. In other embodiments, a therapeutically effective amount of an antibody of the invention is administered to an individual for the treatment of disease.

For the prevention or treatment of disease, the appropriate dosage of an antibody of the invention (when used alone or in combination with one or more other additional therapeutic agents) will depend on the type of disease to be treated, the route of administration, the body weight of the patient, the type of antibody, the severity and course of the disease, whether the antibody is administered for preventive or therapeutic purposes, previous or concurrent therapeutic interventions, the patient's clinical history and response to the antibody, and the discretion of the attending physician.

The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The antibody is suitably administered to the patient at one time or over a series of treatments. Depending on the type and severity of the disease, about 1 μg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.005 mg/kg to about 10 mg/kg. In other non-limiting examples, a dose may also comprise from about 1 μg/kg body weight, about 5 μg/kg body weight, about 10 μg/kg body weight, about 50 μg/kg body weight, about 100 μg/kg body weight, about 200 μg/kg body weight, about 350 μg/kg body weight, about 500 μg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In non-limiting examples of a derivable range from the numbers listed herein, a range of about 5 mg/kg body weight to about 100 mg/kg body weight, about 5 μg/kg body weight to about 500 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

The antibodies of the invention will generally be used in an amount effective to achieve the intended purpose. For use to treat or prevent a disease condition, the antibodies of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the antibodies which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the antibodies may not be related to plasma concentration. One having skill in the art will be able to optimize therapeutically effective local dosages without undue experimentation.

A therapeutically effective dose of the antibodies described herein will generally provide therapeutic benefit without causing substantial toxicity. Toxicity and therapeutic efficacy of an antibodies can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Antibodies that exhibit large therapeutic indices are preferred. In one embodiment, the antibody according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with antibodies of the invention would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The antibodies of the invention may be administered in combination with one or more other agents in therapy. For instance, an antibody of the invention may be co-administered with at least one additional therapeutic agent. The term "therapeutic agent" encompasses any agent administered to treat a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is an anti-viral agent. In other embodiments, an additional therapeutic agent is an anti-cancer agent.

Such other agents are suitably present in combination in amounts that are effective for the purpose intended. The effective amount of such other agents depends on the amount of antibody used, the type of disorder or treatment, and other factors discussed above. The antibodies are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the antibody of the invention can occur prior to, simultaneously, and/or following, administration of the additional therapeutic agent and/or adjuvant.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided above.

Recombinant DNA Techniques

Standard methods were used to manipulate DNA as described in Sambrook, J. et al, Molecular cloning: A laboratory manual; Cold Spring Harbor Laboratory press, Cold spring Harbor, N.Y., 1989. The molecular biological reagents were used according to the manufacturer's instructions.

General information regarding the nucleotide sequences of human immunoglobulin light and heavy chains is given in: Kabat, E. A. et al. (1991) Sequences of Proteins of Immunological Interest, Fifth Ed., NIH Publication No 91-3242.

DNA Sequencing

DNA sequences were determined by double strand sequencing

Gene Synthesis

Desired gene segments, where required, were either generated by PCR using appropriate templates or were synthesized at Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow subcloning into the respective expression vectors. All constructs were designed with a 5'-end DNA sequence coding for a leader peptide which targets proteins for secretion in eukaryotic cells. SEQ ID NOs 135-137 give exemplary leader peptides.

Cloning of Antigen Expression Vectors

The amplified DNA fragments encoding the antigen of interest were inserted in frame into a mammalian recipient vector downstream of a human $IgG_1$ Fc coding fragment serving as solubility- and purification tag (FIG. 1). Expression of antigen-Fc fusions with a wild type Fc sequence (SEQ ID NOs 123, 125, 127, 129, 131, 133) resulted in homodimeric molecules (avi-Fc-human ASGPR H1 stalk: SEQ ID NO: 124, avi-Fc-cynomolgus ASGPR H1 stalk: SEQ ID NO: 126, avi-Fc-human ASGPR H1 stalk CRD: SEQ ID NO: 130, avi-Fc-cynomolgus ASGPR H1 stalk CRD: SEQ ID NO: 132). Protein CLEC10A was identified as the closest homologue to ASGPR H1 and the constructs avi-Fc-human CLEC10A stalk (SEQ ID NO: 128) and avi-Fc-human CLEC10A stalk CRD (SEQ ID NO: 134) were expressed for testing the specificity of the selected binders. In order to express the antigen in a monomeric state, the DNA fragment was fused to an Fc part containing the "hole" mutations (SEQ ID NOs 117, 119) and was co-expressed with an Fc-"knob" (SEQ ID NO: 121) counterpart (Fc-human ASGPR H1 CRD: SEQ ID NOs 118 and 122, avi-Fc-human CLEC10A CRD: SEQ ID NOs 120 and 122). The antigen expression was generally driven by an MPSV promoter and transcription was terminated by a synthetic polyA signal sequence located downstream of the CDS. In addition, all constructs contained an N-terminal Avi tag allowing specific biotinylation during co-expression with Bir A biotin ligase. In addition to the expression cassette, each vector contained an EBV oriP sequence for autonomous replication in EBV-EBNA expressing cell lines.

Production and Purification of Antigens and Antibodies

Both antigens and antibodies were transiently transfected into HEK 293 cells, stably expressing the EBV-derived protein EBNA. A simultaneously co-transfected plasmid encoding biotin ligase Bir A allowed Avi tag-specific biotinylation in vivo. The proteins were then purified using a protein A column followed by gel filtration.

Generation of a Generic Lambda Fab-Library

Figure 2:
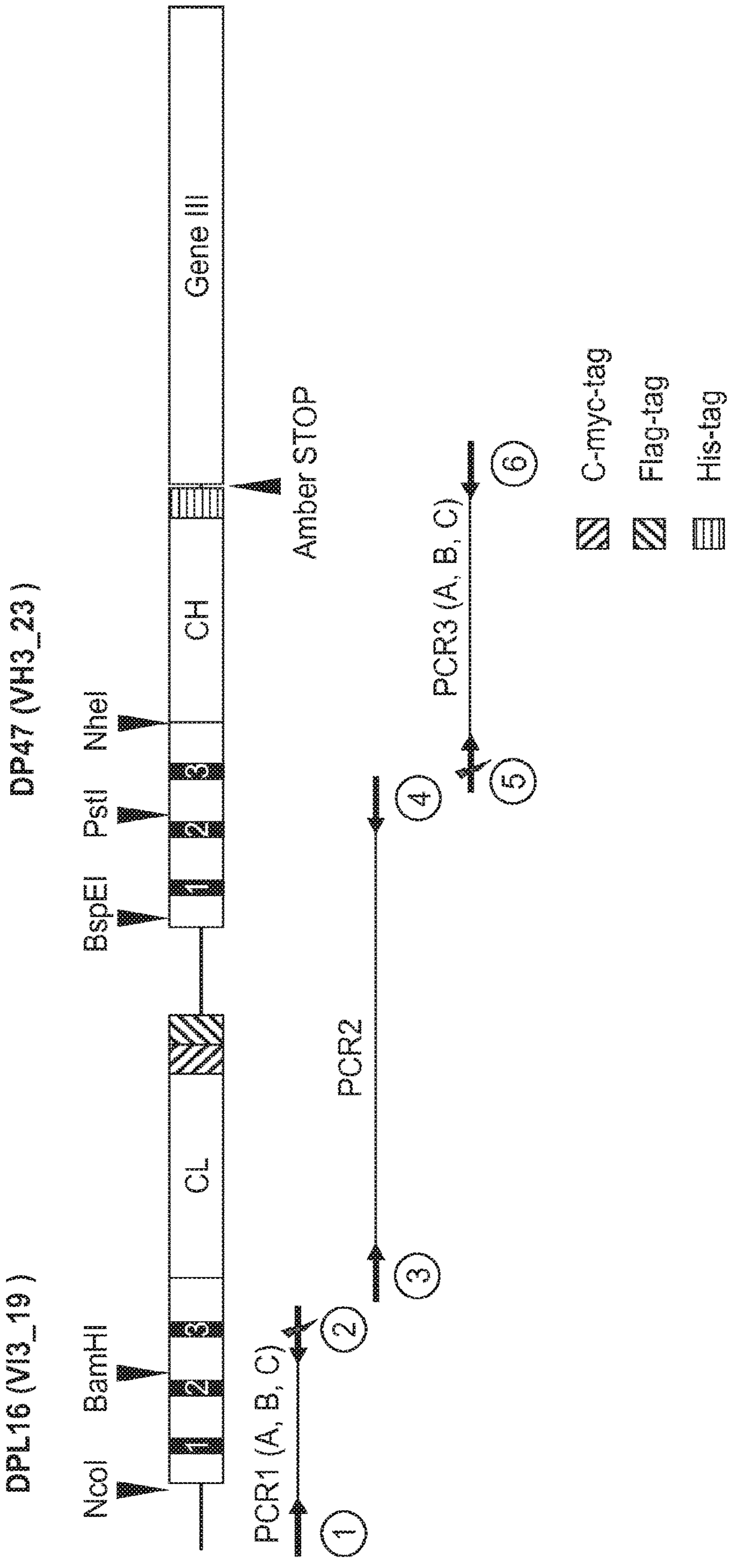
FIG. 2. Schematic overview of the generation of the generic Fab library randomized in the CDR3 regions of the heavy and the light chain. In a first step, three PCR fragments were generated which were then fused by (splicing by overlapping extension; SOE) PCR. The final fragment was gel-purified, digested with NcoI/NheI alongside with similarly treated acceptor phagemid, ligated and transformed into bacteria. PCR1 (A, B, C): (1) LMB3; (2) (A) VI_3_19_L3r_V/(B) VI_3_19_L3r_HV/(C) VI_3_19_L3r_HLV. PCR2: (3) RJH80; (4) DP47CDR3_ba (mod). PCR3 (A, B, C): (5) (A) DP47 v4 4/(B) DP47 v4 6/(C) DP47 v4 8; (6) fdseqlong.

A generic lambda antibody library in the Fab-format was generated on the basis of human germline genes using the following V-domain pairings: V13_19 lambda light chain with VH3_23 heavy chain resulting in a DP47-lambda library. The library was randomized in CDR3 of the light chain (L3) and CDR3 of the heavy chain (H3) and was assembled from three fragments by "splicing by overlapping extension" (SOE) PCR. Fragment 1 comprises the 5' end of the antibody gene including randomized L3, fragment 2 is a central constant fragment spanning from the end of L3 to the beginning of H3, whereas fragment 3 comprises randomized H3 and the 3' portion of the Fab fragment. The following primer combinations were used to generate library fragments for library: fragment 1 (LMB3 (SEQ ID NO: 146)—V1_3_19_L3r primers (SEQ ID NOs 143-145)), fragment 2 (RJH80 (SEQ ID NO: 148)—DP47CDR3_ba (mod) (SEQ ID NO: 149)), fragment 3 (DP47-v4 primers (SEQ ID NO: 140-142)—fdseqlong (SEQ ID NO: 147) (Table 1). PCR parameters for production of library fragments were 5 min initial denaturation at 94° C., 25 cycles of 60 sec 94° C., 60 sec 55° C., 60 sec 72° C. and terminal elongation for 10 min at 72° C. For assembly PCR, using equimolar ratios of the 3 fragments as template, parameters were 3 min initial denaturation at 94° C. and 5 cycles of 60 s 94° C., 60 sec 55° C., 120 sec 72° C. At this stage, outer primers were added and additional 20 cycles were performed prior to a terminal elongation for 10 min at 72° C. (FIG. 2). After assembly of sufficient amounts of full length randomized Fab fragments, they were digested with NcoI/NheI alongside with similarly treated acceptor phagemid vector. 15 μg of Fab library insert were ligated with 13.3 μg of phagemid vector. Purified ligations were used for 60 transformations resulting in $1.5\times10^9$ transformants. Phagemid particles displaying the Fab library were rescued and purified by PEG/NaCl purification to be used for selections.

TABLE 1

Sequences of primers used for the generation of the generic lambda library.

| SEQ ID NO | NAME | SEQUENCE |
|---|---|---|
| 140 | DP47-v4-4 | CGAGGACACGGCCGTATATTACTGTGCG-5-1-2-2-3-4-GAC-TAC-TGGGGCCAAGGAACCCTGGTCACCGTCTCG<br>1: G/D = 20, E/V/S = 10, A/P/R/L/T/Y = 5%; 2: G/Y/S = 15, A/D/T/R/P/L/V/N/W/F/I/E = 4,6%; 3: G/A/Y = 20, P/W/S/D/T = 8%; 4: F = 46, L/M = 15, G/I/Y = 8%; 5: K = 70, R = 30% |
| 141 | DP47-v4-6 | CGAGGACACGGCCGTATATTACTGTGCG-5-1-2-2-2-2-3-4-GAC-TAC-TGGGGCCAAGGAACCCTGGTCACCGTCTCG<br>1: G/D = 20, E/V/S = 10, A/P/R/L/T/Y = 5%; 2: G/Y/S = 15, A/D/T/R/P/L/V/N/W/F/I/E = 4,6%; 3: G/A/Y = 20, P/W/S/D/T = 8%; 4: F = 46, L/M = 15, G/I/Y = 8%; 5: K = 70, R = 30% |
| 142 | DP47-v4-8 | CGAGGACACGGCCGTATATTACTGTGCG-5-1-2-2-2-2-2-2-3-4-GAC-TAC-TGGGGCCAAGGAACCCTGGTCACCGTCTCG<br>1: G/D = 20, E/V/S = 10, A/P/R/L/T/Y = 5%; 2: G/Y/S = 15, A/D/T/R/P/L/V/N/W/F/I/E = 4,6%; 2: G/A/Y = 20, P/W/S/D/T = 8%; 4: F = 46, L/M = 15, G/I/Y = 8%; 5: K = 70, R = 30% |
| 143 | V1_3_19_ L3r_V | GGACGGTCAGCTTGGTCCCTCCGCCGAATAC V***HV*** A***TT*** A***CC*** G***CT*** A***CT*** A***TC*** A***CG*** GGAGTTACAGTAATAGTCAGCCTCATCTTCCGC<br>underlined: 60% original base and 40% randomization as M<br>bolded and italic: 60% original base and 40% randomization as N |
| 144 | V1_3_19_ L3r_HV | GGACGGTCAGCTTGGTCCCTCCGCCGAATAC C***MM*** A***TG*** A***TT*** A***CC*** G***CT*** A***CT*** A***TC*** A***CG*** GGAGTTACAGTAATAGTCAGCCTCATCTTCCGC<br>underlined: 60% original base and 40% randomization as M<br>bolded and italic: 60% original base and 40% randomization as N |
| 145 | V1_3_19 _L3r_HLV | GGACGGTCAGCTTGGTCCCTCCGCCGAATAC R***HM*** V***WG*** A***TG*** A***TT*** A***CC*** G***CT*** A***CT*** A***TC*** A***CG*** GGAGTTACAGTAATAGTCAGCCTCATCTTC CGC<br>underlined: 60% original base and 40% randomization as M<br>bolded and italic: 60% original base and 40% randomization as N |
| 146 | LMB3 | CAGGAAACAGCTATGACCATGATTAC |
| 147 | fdseqlong | GACGTTAGTAAATGAATTTTCTGTATGAGG |
| 148 | RJH80 | TTCGGCGGAGGGACCAAGCTGACCGTCC |
| 149 | DP47CDR3_ ba (mod) | CGCACAGTAATATACGGCCGTGTCC |

Selection of Anti-Human ASGPR H1 Binders from a Generic Lambda Fab Library

Selections against the complete or fragments of the extracellular domain (ECD) of human ASGPR H1 were carried out using HEK293-expressed monomeric or dimeric human ASGPR protein fragments fused to the Fc-portion of a human IgG1 antibody (SEQ ID NO: 118, 120, 124, 126, 128, 130, 132, 134). While ASGPR H1 CRD and CLEC10A CRD were expressed as monomeric Fc fusions using the Fc "knob-into-hole" format (only one Fc carrying a C-terminally fused CRD), all stalk fragments and total ECDs were expressed as homodimeric Fc fusion proteins (FIG. 1). The antigens were enzymatically biotinylated by co-expression of the biotin ligase Bir A via an N-terminal avi-tag. Panning rounds were performed in solution according to the following pattern: (1) Preclearing of $\sim10^{12}$ phagemid particles using human $IgG_1$ coated at 10 μg/ml onto NUNC maxisorp plates to avoid Fc-binders, (2) binding of non-Fc binding phagemid particles from the supernatant of the pre-clearing reaction to 100 nM biotinylated antigen protein for 0.5 h in a total volume of 1 ml, (3) capture of biotinylated antigen and attached specifically binding phage by addition of $5.4\times10^7$ streptavidin-coated magnetic beads for 10 min, (4) washing of beads using 5×1 ml PBS/Tween-20 and 5×1 ml PBS, (5) elution of phage particles by addition of 1 ml 100 mM triethylamine (TEA) for 10 min and neutralization by addition of 500 μl 1M Tris/HCl pH 7.4, (6) Re-infection of log-phase *E. coli* TG1 cells with the phage particles in the supernatant, infection with helperphage VCSM13 and subsequent PEG/NaCl precipitation of phagemid particles to be used in subsequent selection rounds. Selections were carried out over 3-5 rounds using either constant or decreasing (from $10^{-7}$ M to $2\times10^{-9}$ M) antigen concentrations. In round 2, capture of antigen-phage complexes was performed using neutravidin plates instead of streptavidin beads. Specific binders were identified by ELISA as follows: 100 μl of 50 nM biotinylated human Fc-stalk-CRD, Fc-CRD, or Fc-stalk per well were coated on neutravidin plates. Fab-containing bacterial supernatants were added and binding Fabs were detected via their Flag-tags by using an anti-Flag/HRP secondary antibody. Clones exhibiting significant signals over background were short-listed for sequencing (SEQ ID NOs 1, 3, 5, 7, 9, 11, 13, 15, 17, 19, 21, 23, 25 and 27) and further analyses.

Purification of Fabs

Fabs from bacterial cultures (protein sequence of variable domains listed as SEQ ID NOs 2, 4, 6, 8, 10, 12, 14, 16, 18, 20, 22, 24, 26 and 28) were purified for the exact analysis of the kinetic parameters. For each clone, a 500 ml culture was inoculated with bacteria harboring the corresponding phagemid and induced with 1 mM IPTG at an $OD_{600}$ 0.9. Afterwards, the cultures were incubated at 25° C. overnight and harvested by centrifugation. After the incubation of the resuspended pellet for 20 min in 25 ml PPB buffer (30 mM Tris-HCl pH 8, 1 mM EDTA, 20% sucrose), bacteria were centrifuged again and the supernatant was harvested. This incubation step was repeated once with 25 ml of a 5 mM $MgSO_4$ solution. The supernatants of both incubation steps were pooled, filtered and loaded on an IMAC column (His gravitrap, GE Healthcare). Subsequently, the column was washed with 40 ml washing buffer (500 mM NaCl, 20 mM imidazole, 20 mM $NaH_2PO_4$ pH 7.4). After the elution (500 mM NaCl, 500 mM imidazole, 20 mM $NaH_2PO_4$ pH 7.4) the eluate was re-buffered using PD10 columns (GE Healthcare). The kinetic parameters of the purified Fabs were then studied by SPR-analysis (Proteon XPR36, Biorad) in a dilution row that ranged from 200 nM to 6.25 nM.

Affinity-Determination by SPR

Affinity ($K_D$) of selected Fab clones was measured by surface plasmon resonance using a ProteOn XPR36 instrument (Biorad) at 25° C. with biotinylated mono-(avi-Fc-human ASGPR H1 CRD, SEQ ID NO: 118) or bivalent (avi-Fc-human ASGPR H1 stalk-CRD, SEQ ID NO: 130) ASGPR H1 antigens immobilized on NLC chips by neutravidin capture Immobilization of recombinant antigens (ligand): Antigens were diluted with PBST (10 mM phosphate, 150 mM NaCl pH 7.4, 0.005% Tween-20) to 10 μg/ml, then injected at 30 μl/min at varying contact times, to achieve immobilization levels of 200, 400 or 800 response units (RU) in vertical orientation. Injection of analytes: For one-shot kinetics measurements, injection direction was changed to horizontal orientation, two-fold dilution series of purified Fab (varying concentration ranges between 100 and 6.25 nM) were injected simultaneously at 50, 60 or 100 μl/min along separate channels 1-5, with association times of 150 or 200 s, and dissociation times of 240 or 600 s. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Regeneration was performed in horizontal orientation using 10 mM glycine, pH 1.5 at a flow rate of 100 μl/min for a contact time of 30 s. Two clones, 51A12 (SEQ ID NO: 002 and 004) and 52C4 (SEQ ID NO: 006 and 008), were found to be specific to the ASGPR H1 CRD. Remarkably, clone 51A12 revealed an affinity in the subnanomolar range. Clones 5A4 (SEQ ID NO: 010 and 012), 4F3 (SEQ ID NO: 014 and 016), R5C2 (SEQ ID NO: 018 and 020), R9E10 (SEQ ID NO: 022 and 024), and R9E10 (SEQ ID NO: 026 and 028) were raised either against the stalk region of ASGPR H1 or the interface between the stalk and CRD. The affinity to their corresponding human and cynomolgus epitopes was similar. In contrast, no binding to avi-Fc-human CLEC10A stalk CRD (SEQ ID NO: 134) was detected, demonstrating the high specificity of these binders. Interestingly, clone 5A4 demonstrated strong binding to the stalk antigen but not to stalk-CRD. The kinetic and thermodynamic data of all measurements are summarized in Table 2.

TABLE 2

Kinetic and thermodynamic parameters of anti-ASGPR H1 Fabs.

| Antibody clone | huASGPR H1 stalk ka (1/Ms) kd (1/s) KD (M) | cyASGPR H1 stalk ka (1/Ms) kd (1/s) KD (M) | huASGPR H1 stalk CRD ka (1/Ms) kd (1/s) KD (M) | cyASGPR H1 stalk CRD ka (1/Ms) kd (1/s) KD (M) | hu/cyASGPR H1 CRD ka (1/Ms) kd (1/s) KD (M) | huCLEC10A stalk CRD ka (1/Ms) kd (1/s) KD (M) |
|---|---|---|---|---|---|---|
| 52C4 | | | | | $1.39\times10^5$<br>$3.96\times10^{-3}$<br>$2.86\times10^{-8}$ | no binding |
| 51A12 | | | | | $1.10\times10^5$<br>$6.28\times10^{-5}$<br>$5.70\times10^{-10}$ | no binding |
| 5A4 | $2.44\times10^5$<br>$1.05\times10^{-3}$<br>$4.30\times10^{-9}$ | $3.72\times10^5$<br>$1.40\times10^{-3}$<br>$3.76\times10^{-9}$ | | | | no binding |

TABLE 2-continued

Kinetic and thermodynamic parameters of anti-ASGPR H1 Fabs.

| Antibody clone | huASGPR H1 stalk ka (1/Ms) kd (1/s) KD (M) | cyASGPR H1 stalk ka (1/Ms) kd (1/s) KD (M) | huASGPR H1 stalk CRD ka (1/Ms) kd (1/s) KD (M) | cyASGPR H1 stalk CRD ka (1/Ms) kd (1/s) KD (M) | hu/cyASGPR H1 CRD ka (1/Ms) kd (1/s) KD (M) | huCLEC10A stalk CRD ka (1/Ms) kd (1/s) KD (M) |
|---|---|---|---|---|---|---|
| 4F3 | $1.51 \times 10^{5}$ | $1.43 \times 10^{5}$ | $2.24 \times 10^{5}$ | $1.69 \times 10^{5}$ | | no binding |
| | $4.45 \times 10^{-3}$ | $4.80 \times 10^{-3}$ | $4.08 \times 10^{-3}$ | $3.65 \times 10^{-3}$ | | |
| | $2.95 \times 10^{-8}$ | $3.36 \times 10^{-8}$ | $1.82 \times 10^{-8}$ | $2.16 \times 10^{-8}$ | | |
| R9E10 | | | $5.86 \times 10^{5}$ | $4.60 \times 10^{5}$ | | no binding |
| | | | $2.11 \times 10^{-3}$ | $1.99 \times 10^{-3}$ | | |
| | | | $3.60 \times 10^{-9}$ | $4.34 \times 10^{-9}$ | | |
| R7E12 | | | $2.94 \times 10^{5}$ | $2.47 \times 10^{5}$ | | no binding |
| | | | $2.68 \times 10^{-3}$ | $2.36 \times 10^{-3}$ | | |
| | | | $9.12 \times 10^{-9}$ | $9.55 \times 10^{-9}$ | | |
| R5C2 | | | $4.23 \times 10^{5}$ | $3.34 \times 10^{5}$ | | no binding |
| | | | $1.12 \times 10^{-3}$ | $1.14 \times 10^{-3}$ | | |
| | | | $2.65 \times 10^{-9}$ | $3.41 \times 10^{-9}$ | | |

Cloning of Variable Antibody Domains into Expression Vectors

All Fabs demonstrating specific binding to their corresponding antigen by SPR were converted into an $IgG_1$/lambda antibody. Therefor, the PCR-amplified DNA fragments of heavy and light chain v-domains were inserted in frame into either the human $IgG_1$ constant heavy chain or the human constant lambda light chain containing respective recipient mammalian expression vector. The antibody expression was driven by an MPSV promoter and transcription was terminated by a synthetic polyA signal sequence located downstream of the CDS. In addition to the expression cassette each vector contained an EBV oriP sequence for autonomous replication in EBV-EBNA expressing cell lines.

Binding Analysis of the Antibodies to HepG2 Cells

Figure 3:
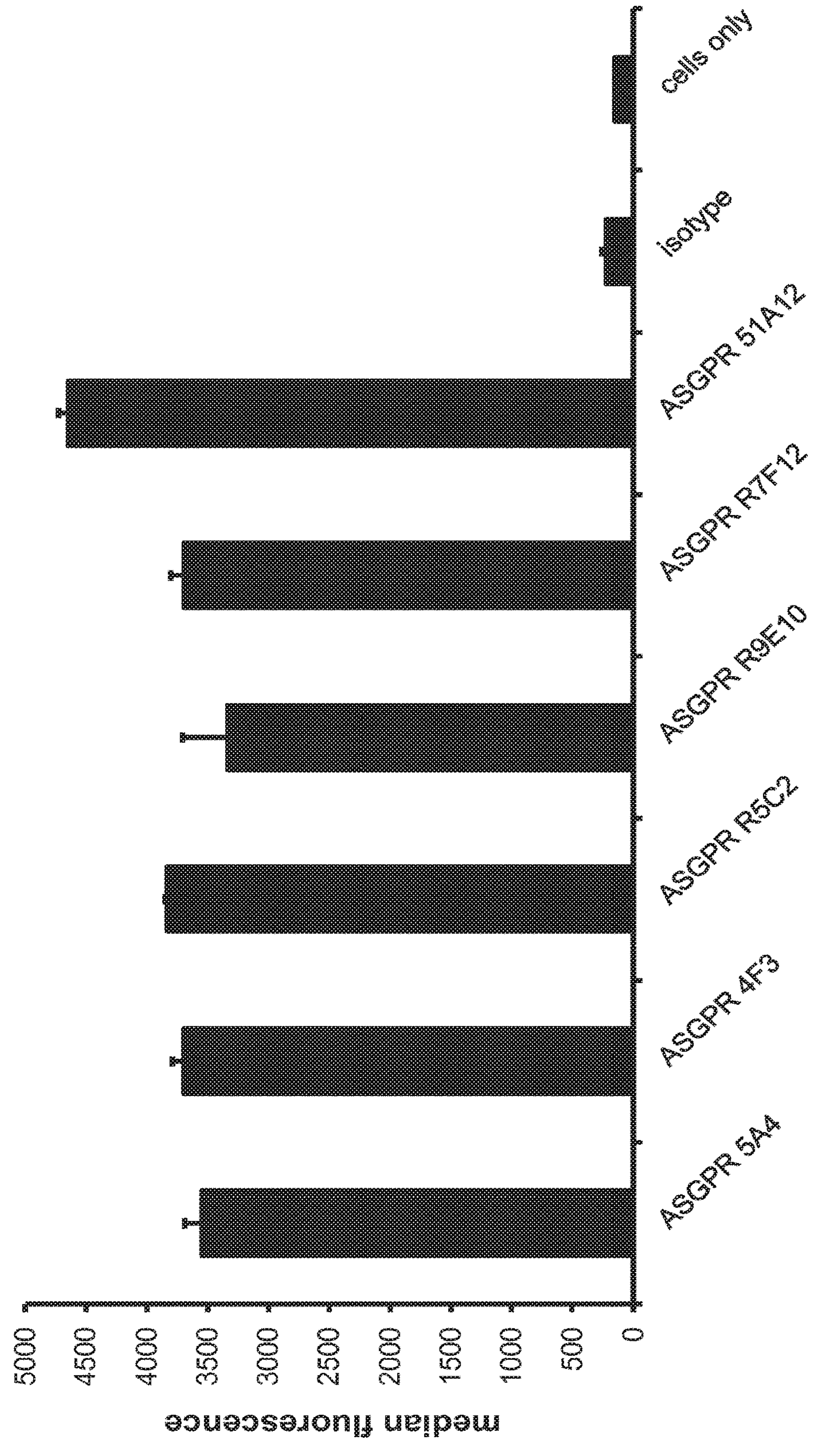
FIG. 3. Binding analysis of selected anti-human ASGPR H1-specific clones to HepG2 cells as human $IgG_1$ antibodies. Antibody concentration was 30 μg/ml. An isotype control antibody served as a negative control.

Binding of human $IgG_1$ anti-ASGPR antibodies to the hepatocellular carcinoma cell line HepG2 was measured by FACS. Briefly, 0.2 mio cells per well in a 96 well round bottom plate were incubated in 300 μl with the anti-ASGPR antibodies at a concentration of 30 μg/ml for 30 min at 4° C. Unbound antibody was removed by washing the cells with PBS containing 0.1% BSA. Bound antibodies were detected with FITC-conjugated AffiniPure goat anti-human IgG Fc gamma fragment-specific secondary F(ab')2 fragment (Jackson ImmunoResearch #109-096-098; working solution 1:20 in PBS, 0.1% BSA). After 30 min incubation at 4° C. unbound antibody was removed by washing and cells were fixed using 1% PFA. Cells were analyzed using BD FACS Cantoll (Software BD DIVA) (FIG. 3). All antibodies showed strong binding to the HepG2 cells.

Fluorescence Resonance Energy Transfer Assay

Figure 4:
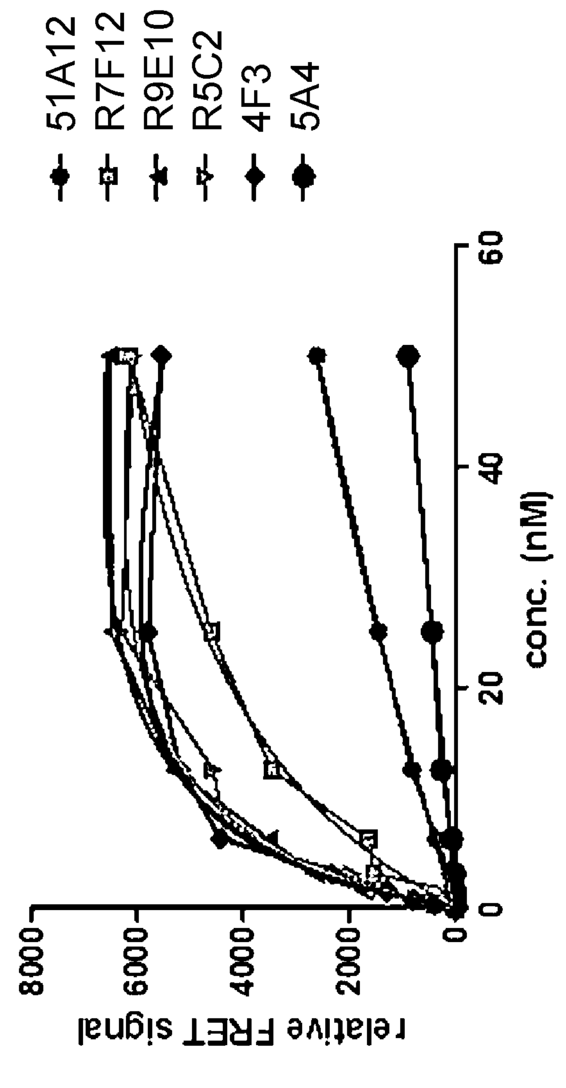
FIG. 4. FRET analysis on transiently transfected cells expressing a transmembrane ASGPR H1-SNAP tag fusion protein labeled with terbium. Analysis was done by adding antibodies at a concentration ranging from 50-0.39 nM followed by addition of an anti-humanFc-d2 (final 200 nM per well) as acceptor molecule. Specific FRET signal was measured after 3 h and KD values were calculated ($KD_{51A12}$=200 nM, $KDR_{7F12}$=22 nM, $KD_{R9E10}$=6.2 nM, $KD_{R5C2}$=5.9 nM, $KD_{4F3}$=4.5 nM).

The avidity of the IgGs to their epitope on ASGPR-expressing cells was determined by Fluorescence Resonance Energy Transfer (FRET) analysis. For this analysis, the DNA sequence encoding for the SNAP Tag (plasmid purchased from Cisbio) was amplified by PCR and ligated into an expression vector, containing the full length human ASGPR H1 sequence (Origene). The resulting fusion protein was comprised of full-length ASGPR H1 with a C-terminal SNAP tag. HEK293 cells were transfected with 10 μg DNA using Lipofectamine 2000 as transfection reagent. After an incubation time of 20 h, cells were washed with PBS and incubated for 1 h at 37° C. in LabMed buffer (Cisbio) containing 100 nM SNAP-Lumi4Tb (Cibsio), leading to specific labeling of the SNAP Tag. Subsequently, cells were washed 4 times with LabMed buffer to remove unbound dye. The labeling efficiency was determined by measuring the emission of terbium at 615 nm compared to buffer. Cells were then stored frozen at −80° C. for up to 6 months. Avidity was measured by adding ASGPR-specific antibodies at a concentration ranging from 50-0.39 nM to labeled cells (100 cells per well) followed by addition of anti-humanFc-d2 (final 200 nM per well) as acceptor molecule for the FRET. After an incubation time of 3 h at RT the emission of the acceptor dye (665 nm) as well as of the donor dye (615 nm) was determined using a fluorescence Reader (Victor 3, Perkin Elmer). The ratio of acceptor to donor emission was calculated and the ratio of the background control (cells with anti-huFc-d2) subtracted. Curves were analysed in GraphPad Prism5 and $K_D$ values calculated (FIG. 4). While clone 4F3 shows the lowest affinity to ASGPR H1 stalk-CRD measured by SPR (Table 2), binding intensity as an IgG to the cell surface is driven by strong avidity making 4F3 to the clone with the strongest binding intensity at low concentrations. In contrast, clone 51A12 which binds to the CRD shows a significantly weaker binding intensity at low antibody concentrations to cells than to the purified antigen in SPR studies.

Binding Competition with a Natural ASGPR Ligand

Competition of the ASGPR antibodies with a desialylated glycoprotein such as asialofetuin as a natural ligand for ASGPR was analyzed using the hepatocellular carcinoma cell line HepG2. 0.2 mio cells per well in a 96 well round bottom plate were incubated with 40 μl of Alexa488 labeled asialofetuin (from fetal calf serum, Sigma Aldrich #A4781, final concentration 100 μg/ml) at 4° C. for 30 min The binding was performed in the presence of calcium, as ligand binding to ASGPR is calcium dependent. Unbound protein was removed by washing the cells once with HBSS containing 0.1% BSA. Then 40 μl of the anti-ASGPR antibodies (30, 6, and 1.25 μg/ml final concentration) were added to the cells in the presence of 100 μg/ml asialofetuin. Cells were incubated for 30 min at 4° C. and unbound protein was removed by washing the cells once. An APC-conjugated AffiniPure goat anti-human IgG Fc gamma fragment-specific secondary F(ab')2 fragment (Jackson ImmunoResearch #109-136-170; working solution 1:50 in HBSS containing 0.1% BSA) was used as an secondary antibody. After 30 min incubation at 4° C. unbound secondary antibody was removed by washing. Cells were fixed using 1% PFA and analyzed using BD FACS Cantoll (Software BD DIVA).

Figures 5A, 5B:
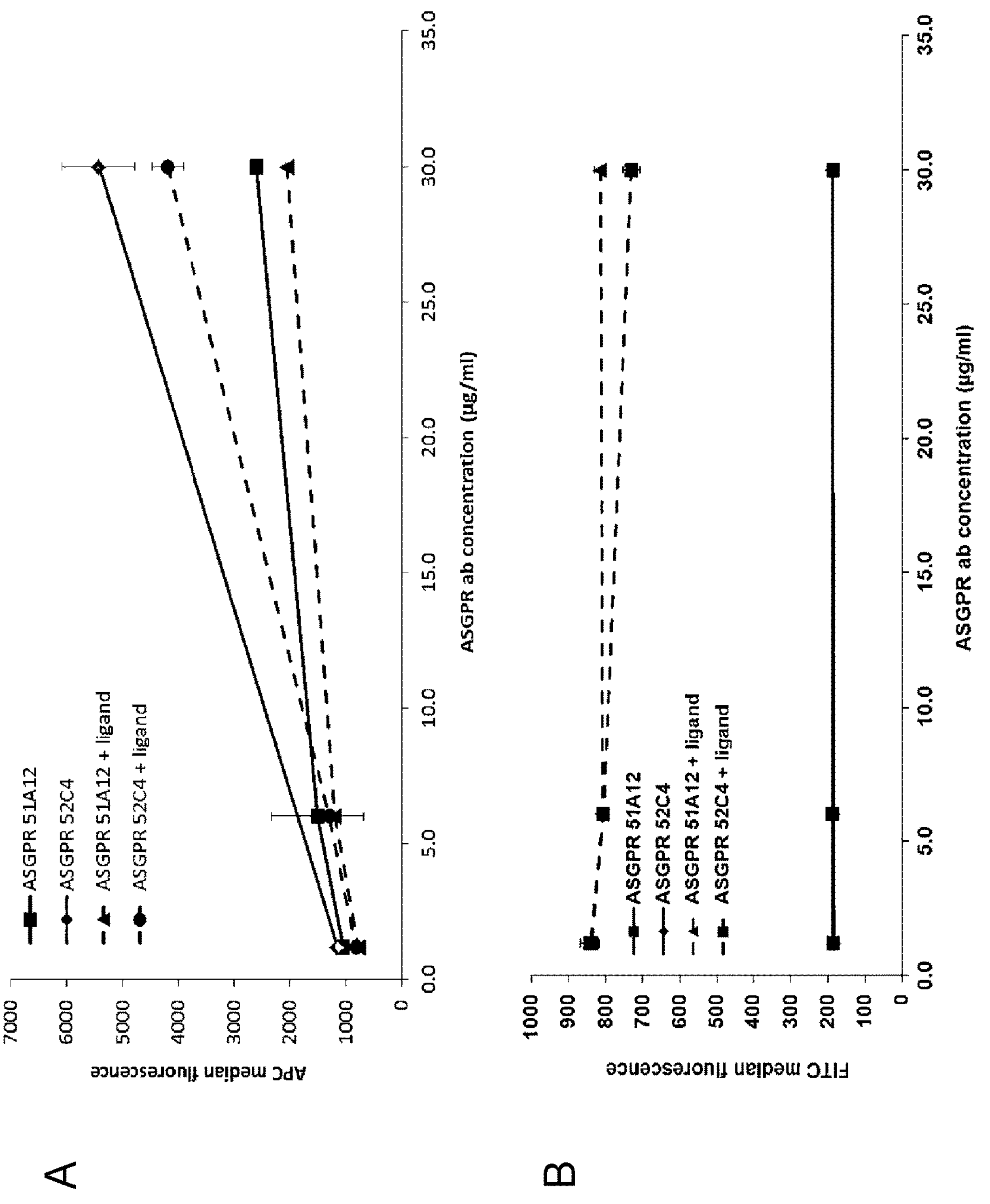
FIGS. 5A-5B. Competition of asialofetuin, a natural ligand for ASGPR, and anti-ASGPR H1 antibodies. HepG2 cells were pre-incubated with labeled asialofetuin before indicated antibodies were added in a dilution row to the cells. Binding of both components to the cells was analyzed by FACS analysis. 5(A) antibody detection; 5(B) asialofetuin detection.
Figures 6A, 6B:
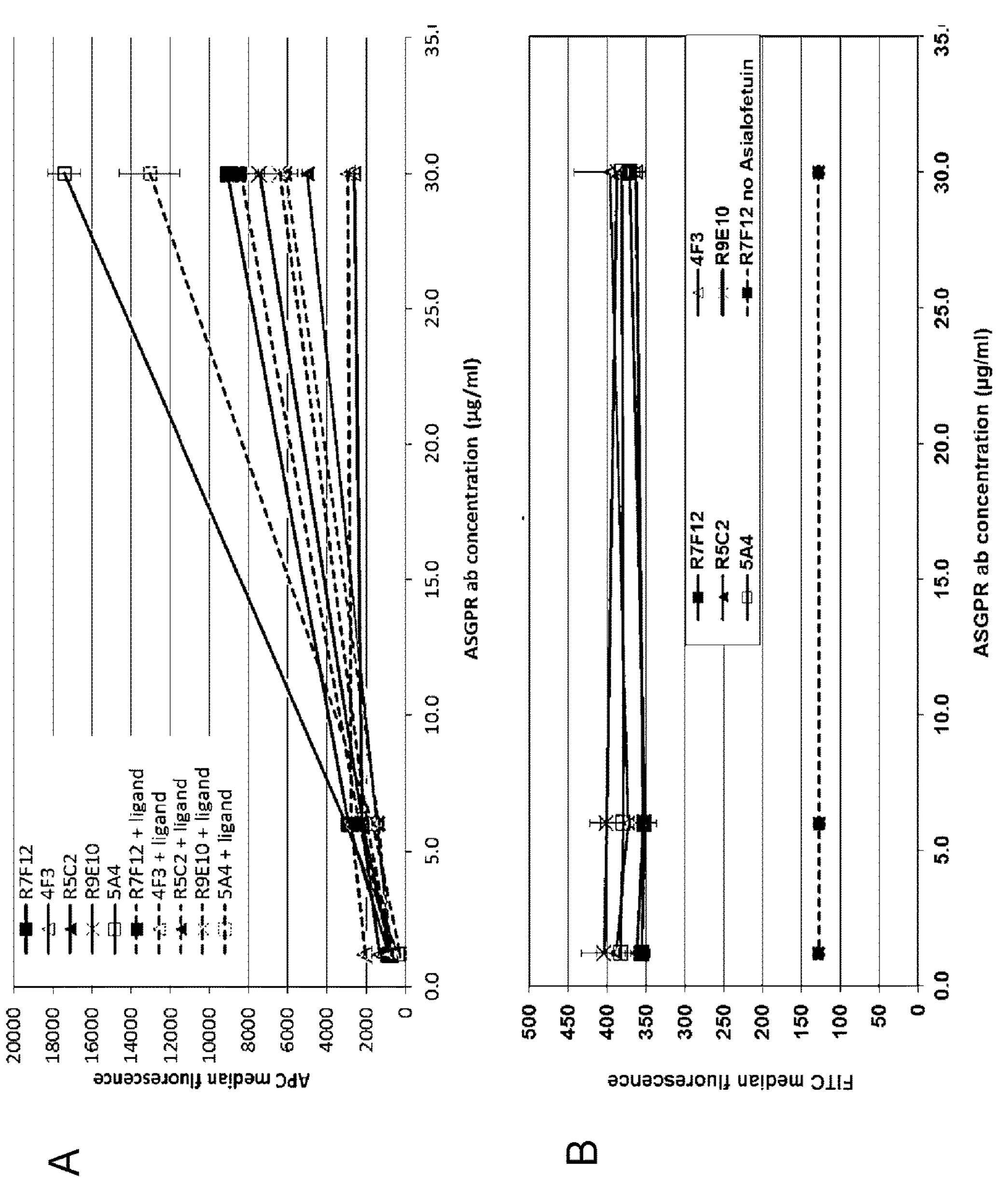
FIGS. 6A-6B. Competition of asialofetuin, a natural ligand for ASGPR, and anti-ASGPR H1 antibodies. HepG2 cells were pre-incubated with labeled asialofetuin before indicated antibodies were added in a dilution row to the cells. Binding of both components to the cells was analyzed by FACS analysis. 6(A) antibody detection; 6(B) asialofetuin detection.

Analysis of both the CRD-specific and the stalk-CRD-specific antibodies revealed that antibodies bind to ASGPR H1 independently of the presence of the asialofetuin and vice versa, and no binding competition takes place. (FIGS. 5 and 6).

Internalization Study

Figures 7A, 7B:
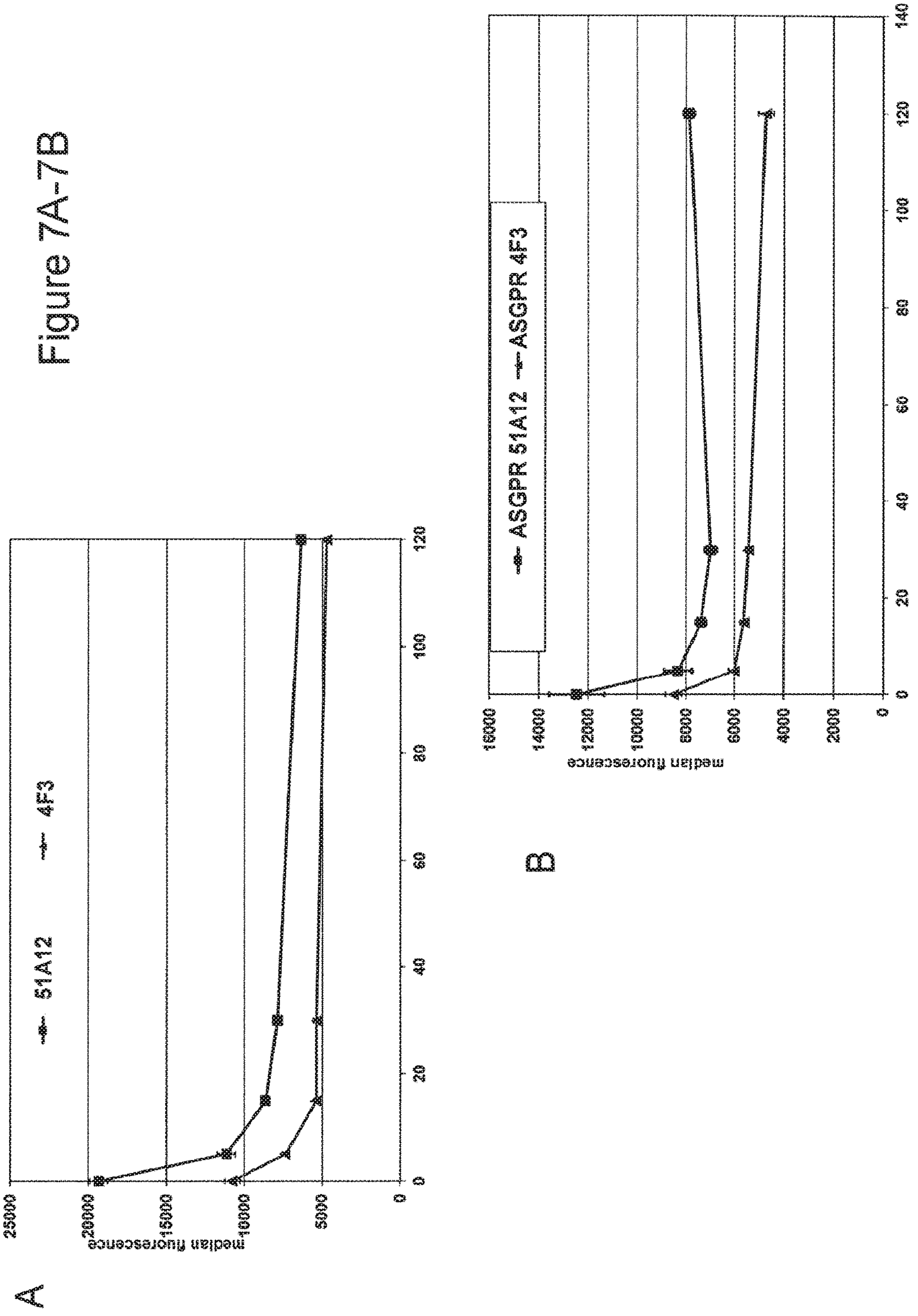
FIGS. 7A-7D. Internalization analysis of the two anti-human ASGPR H1 antibody clones 51A12 and 4F3 as IgGs. 7(A) antibodies were incubated with HepG2 cells at 4° C. to prevent internalization, and washed at 4° C. before the cells were cultured in pre-warmed medium and incubated at 37° C. for up to 120 min. Samples were taken at indicated time points, labeled with the secondary antibody on ice and fixed using PFA. 7(B) Same steps were performed as described under 7(A) but antibodies were incubated with the cells at 37° C. allowing ASGPR to internalize. 7(C) Same steps were performed as described under 7(A), but using directly FITC-labeled antibodies. Cell surface-bound antibodies were detected using PE-conjugated anti-Fc antibody. 7(D) Same experiment as under 7(C) but showing FITC signal, representing both surface-exposed and internalized antibodies.
Figures 7C, 7D:
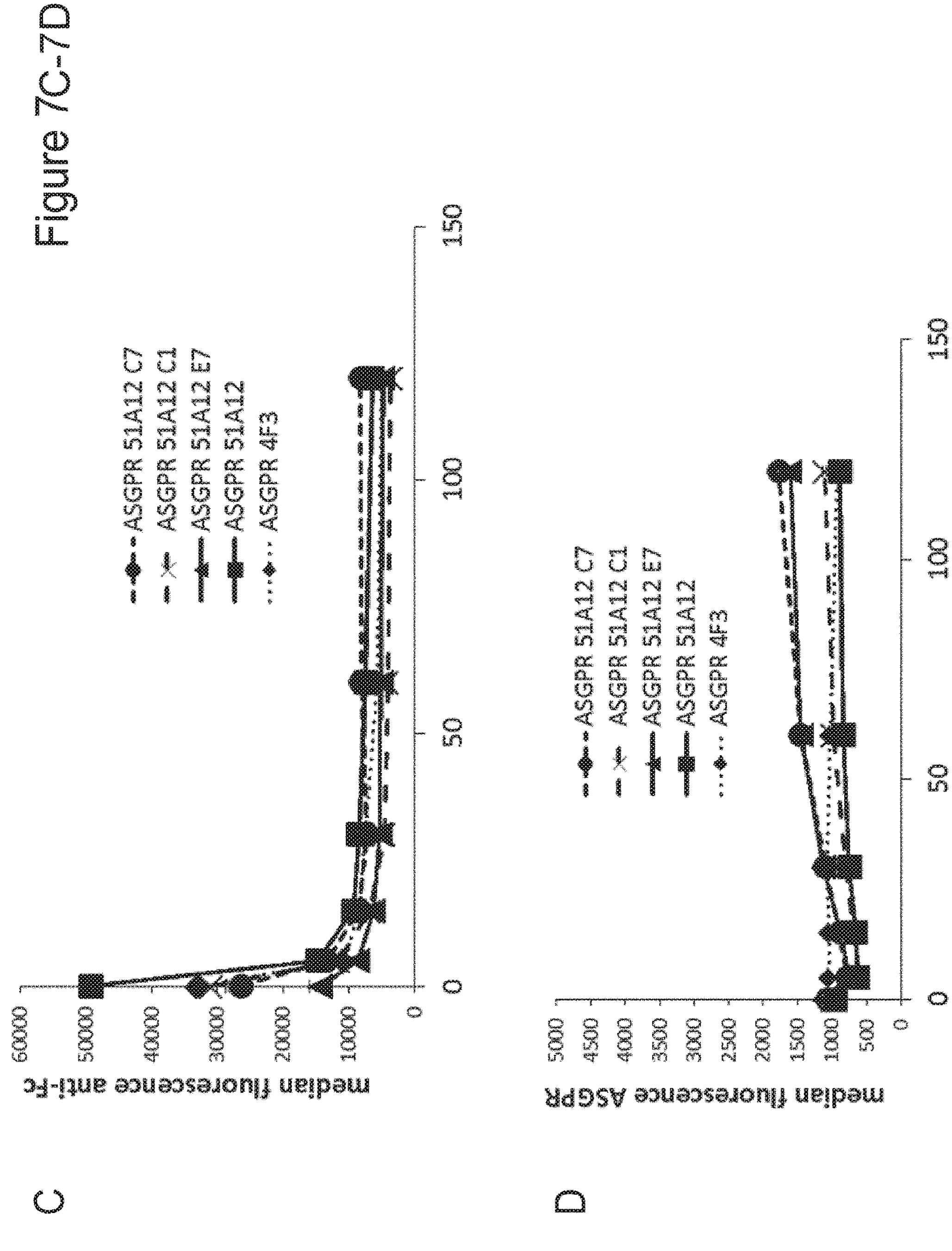

Uptake of desialylated glycoproteins into liver cells after binding to ASGPR is known to occur very rapidly. During this receptor-mediated endocytosis, the lumen of the endosome becomes acidic allowing the receptor-ligand complexes to dissociate. While the ligand is targeted for degradation in lysosomes, ASGPR was shown to recycle back to the cell surface. In order to analyze the retention time of the antibodies on the cell surface, internalization of the ASGPR-antibody complex was analyzed using the hepatocellular carcinoma cell line HepG2. ASGPR-positive HepG2 cells were shifted in cell culture medium to 4° C. in order to inhibit internalization. After 45 min incubation with the antibodies (30 μg/ml) on a shaker at 4° C., unbound antibodies were removed by washing twice with cold PBS and cells were re-suspended and cultured in pre-warmed medium at 37° C. to re-activate the cellular metabolism including receptor-mediated endocytosis. One aliquot was taken immediately and stored on ice which represents time point zero. Remaining cells were incubated at 37° C. and after 5, 15, 30 and 120 min additional samples were taken and washed with cold PBS to stop further internalization. Cell surface-bound antibodies were detected using PE-conjugated AffiniPure goat anti-human IgG Fc gamma-specific secondary F(ab')2 antibody Fragment (Jackson ImmunoResearch #109-116-170, working solution 1:50). After 30 min incubation at 4° C. unbound antibody was removed by washing with PBS containing 0.1% BSA. Cells were fixed using 1% PFA and analyzed using BD FACS CantoII (Software BD DIVA). FIG. 7A shows exemplary cell surface exposed antibody levels of clones 4F3 and 51A12. Interestingly, extracellular antibody signal decreased significantly (up to 60% signal decrease) during the first 30 min but then decrease delayed for the rest of the time course. This result indicates that antibodies are internalized very efficiently but then eventually recycle back to the cell surface leading to a dynamic steady state condition of constant internalization and recycling. In order to support this hypothesis, the same experiment was performed, but incubation of the cells with the antibodies was performed in cell culture medium for 45 min at 37° C. These conditions allow receptor-antibody complexes to be formed and be internalized during the entire incubation time, eventually leading to a steady state of constant endocytosis and recycling. Afterwards, unbound antibody was removed by washing twice with warm PBS and cells were re-suspended in warm medium. One sample was taken immediately and stored on ice which represents time point zero. Remaining cells were incubated at 37° C. and after 5, 15, 30 and 120 min additional samples were taken and washed with cold PBS to stop further internalization. Detection of surface-exposed antibodies was performed as described above. FACS analysis revealed that the decrease of the signal intensity was less pronounced during the time course of the experiment after antibody incubation at 37° C. than 4° C. suggesting that incubation of the antibodies at 37° C. yields in an equilibrium of internalization and recycling of the antibody-receptor complex (FIG. 7B). In order to further endorse the hypothesis of constant internalization and recycling, internalization of ASGPR H1-specific antibodies was further analyzed using a set of directly FITC-labeled antibodies. As before, labeled antibodies were incubated with HepG2 cells at 4° C. allowing the antibodies to bind to ASGPR H1 but not to internalize. After 45 min incubation with the antibodies (30 μg/ml) on a shaker at 4° C., unbound antibodies were removed by washing twice with cold PBS and cells were re-suspended and cultured in pre-warmed medium at 37° C. to re-activate the cellular metabolism including receptor-mediated endocytosis. A cell aliquot was taken after 0, 5, 15, 30 and 120 min and washed with cold PBS to stop further internalization. Cell surface-bound antibodies were detected using PE-conjugated AffiniPure goat anti-human IgG Fc gamma-specific secondary F(ab')2 antibody Fragment (Jackson ImmunoResearch #109-116-170, working solution 1:50). As seen before, the detection level of surface-exposed decreased significantly during the first 30 min before it stabilized (FIG. 7C). However, detection of the IgGs by FITC signal, representing both surface-exposed and internalized antibodies, revealed that the total amount of antibody stayed constant over time (FIG. 7D). This result strongly supports the finding that antibodies are in a dynamic steady state condition of constant internalization and recycling.

Generation of a Clone 51A12-Based L3 Affinity Library

Figure 9:
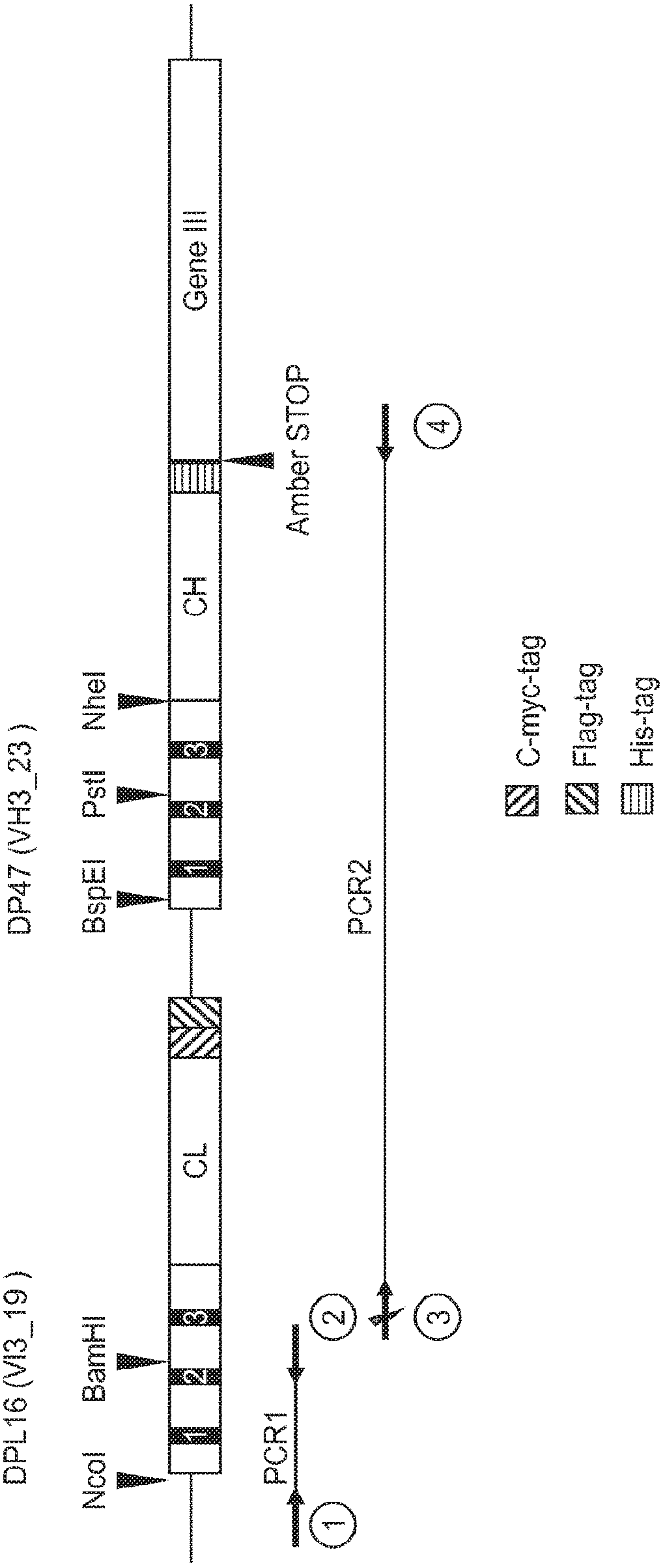
FIG. 9. Schematic overview of the generation of the affinity maturation library randomized in LCDR3 of the template 51A12 (A82G, C112S, C113S, S116A) (SEQ ID NO: 33). In a first step, two PCR fragments were generated which were then fused by (SOE) PCR. The final fragment was gel-purified, digested with NcoI/PstI alongside with similarly treated acceptor phagemid, ligated and transformed into bacteria. PCR1: (1) LMB3, (2) LCDR3rev. PCR2: (3) LCDR3rand, (4) fdseqlong.

Analysis of the antibody sequences revealed two hot spots in the CDR3 region of the 51A12 light chain, namely two adjacent cysteines and a glycosylation site (FIG. 8). For the generation of 51A12-derived clones without cysteines and glycosylation, a maturation library randomized in LCDR3 was generated. The sequence of clone 51A12 (A82G, C112S, C113S, S116A) (SEQ ID NO: 33) was used as a template for the randomization. Triplets encoding positions "RDISSNRAVRN" were randomized throughout the segment. For the generation of the library, a DNA portion resulting from a two-fragment overlap PCR product was cloned into the phage vector. For the generation of fragment 1, the primer combination LCDR3 rand (SEQ ID NO: 151) and fdseqlong (SEQ ID NO: 147) (Table 1 and 3) were used, using clone 51A12 (A82G, C112S, C113S, S116A) as a template. Amplification conditions included an initial 5 min 94° C. incubation step followed by 25 cycles, each consisting of a 30 sec 94° C. denaturation, a 30 sec 60° C. annealing, and a 90 sec 72° C. elongation step, followed by a final 10 min 72° C. elongation step. The resulting fragment was purified on an agarose gel. Fragment 2 was generated with the primer combination LCDR3rev (SEQ ID NO: 150) and LMB3 (SEQ ID NO: 146) (Table 1 and 3). Amplification conditions included an initial 5 min 94° C. incubation step followed by 25 cycles, each consisting of a 30 sec 94° C. denaturation, a 30 sec 60° C. annealing, and a 30 sec 72° C. elongation step, followed by a final 10 min 72° C. elongation step. For the assembly of both fragments, equimolar amounts of fragment 1 and 2 were used Amplification conditions included an initial 5 min 94° C. incubation step followed by 5 cycles without primers, each cycle consisting of a 1 min 94° C. denaturation, a 1 min 60° C. annealing, and a 120 sec 72° C. elongation step. After the addition of the outer primers LMB3 and fdseqlong, 20 additional cycles were performed using the same parameters. At the end, a final 10 min 72° C. incubation step was performed. Both, the resulting gel-purified DNA fragment and clone 51A12 (A82G, C112S, C113S, S116A) (SEQ ID NO: 33) were digested with NcoI/PstI (FIG. 9). For generation of the library, ligation was performed with 10 μg insert and 30 μg vector. Purified ligation was transformed into TG1 bacteria by electroporation resulting in $3\times10^9$ transformants Phagemid particles displaying the Fab library were rescued and purified by PEG/NaCl purification to be used for selections.

TABLE 3

Sequences of primers used for the generation of the L3 affinity maturation library.

| SEQ ID | NAME | SEQUENCE |
|---|---|---|
| 150 | LCDR3rev | GGAGTTACAGTAATAGTCAGCCTC |
| 151 | LCDR3 rand | GAGGCTGACTATTACTGTAACTCC 1-2-3-4-5-6-7-8-9-10-11 TTCGGCGGAGGGACCAAGCTGACCGTC 1: 50% R, 3.1% Rest (no S, T, C); 2: 50% D, 2.8% Rest (no C); 3: 50% I, 2.8% Rest (no C); 4: 50% S, 2.8% Rest (no C); 5: 50% S, 2.8% Rest (no C); 6: 50% N, 2.8% Rest (no C); 7: 50% R, 2.8% Rest (no C); 8: 50% A, 3.1% Rest (no S, T, C); 9: 50% V, 2.8% Rest (no C); 10: 50% R, 2.8% Rest (no C); 11: 50% N, 2.8% Rest (no C) |

Selection of Affinity Matured 51A12-Derived Clones without Cysteines and Glycosylation Site Generation of affinity-matured 51A12-derived Fabs without cysteines and glycosylation site within LCDR3 was carried out by phage display using standard protocols (Silacci et al. (2005), Proteomics 5, 2340-50). In the first panning round, selection was carried out in solution according to the following procedure: (1) binding of ~$10^{12}$ phagemid particles to 10 nM biotinylated Fc-CRD for 0.5 h in a total volume of 1 ml, (2) capture of biotinylated Fc-CRD and specifically bound phage particles by addition of 5.4×$10^7$ streptavidin-coated magnetic beads for 10 min, (3) washing of beads using 5×1 ml PBS/Tween-20 and 5×1 ml PBS, (4) elution of phage particles by addition of 1 ml 100 mM TEA for 10 min and neutralization by adding 500 μl 1M Tris/HCl pH 7.4, (5) re-infection of exponentially growing *E. coli* TG1 bacteria, and (6) infection with helperphage VCSM13 and subsequent PEG/NaCl precipitation of phagemid particles to be used in subsequent selection rounds. Selections were carried out over three rounds using decreasing (from $10\times10^{-9}$ M to $0.5\times10^{-9}$ M) antigen concentrations. In round 2 and 3, capture of antigen-phage complexes was performed using neutravidin plates instead of streptavidin beads. In addition, neutravidin plates were washed for 3 h in 2 l PBS. Specific binders were identified by ELISA as follows: 100 μl of 50 nM biotinylated Fc-CRD per well were coated on neutravidin plates. Fab-containing bacterial supernatants were added and binding Fabs were detected via their Flag-tags by using an anti-Flag/HRP secondary antibody. ELISA-positive clones were bacterially expressed as soluble Fab fragments in 96-well format and supernatants were subjected to a kinetic screening experiment by SPR-analysis using Proteon XPR36. Clones expressing Fabs with the highest affinity constants were identified and the light chains of the corresponding phagemids were sequenced (51A12_C1, SEQ ID NO: 35; 51A12_C7, SEQ ID NO: 37; 51A12_E7, SEQ ID NO: 39; 51A12_H3, SEQ ID NO: 41; 51A12_A6, SEQ ID NO: 43; 51A12_D1, SEQ ID NO: 45; 51A12_H6, SEQ ID NO: 47). All clones were devoid of any critical amino acids in the CDR3 region of the light chain.

Affinity Determination of the 51A12-Based Affinity Matured Clones by SPR

Affinity ($K_D$) of purified 51A12-derived Fab fragments consisting of the parental heavy chain (SEQ ID NO: 4) and the affinity-matured light chains (51A12_C1, SEQ ID NO: 36; 51A12_C7, SEQ ID NO: 38; 51A12_E7, SEQ ID NO: 40; 51A12_H3, SEQ ID NO: 42; 51A12_A6, SEQ ID NO: 44; 51A12_D1, SEQ ID NO: 46; 51A12_H6, SEQ ID NO: 48) was measured by surface plasmon resonance using a ProteOn XPR36 instrument (Biorad) at 25° C. with biotinylated mono-(avi-Fc-human ASGPR H1 CRD, SEQ ID NO: 118) or bivalent (avi-Fc-human ASGPR H1 stalk-CRD, SEQ ID NO: 130) ASGPR H1 antigens immobilized on NLC chips by neutravidin capture. Immobilization of recombinant antigens (ligand): Antigens were diluted with PBST (10 mM phosphate, 150 mM NaCl pH 7.4, 0.005% Tween-20) to 10 μg/ml, then injected at 30 μl/min at varying contact times, to achieve immobilization levels of 200, 400 or 800 response units (RU) in vertical orientation. Injection of analytes: For one-shot kinetics measurements, injection direction was changed to horizontal orientation, two-fold dilution series of purified Fab (varying concentration ranges between 12.5 and 0.78 nM) were injected simultaneously at 100 μl/min along separate channels 1-5, with association times of 150 or 200 s, and dissociation times of 3600 s. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Regeneration was performed in horizontal orientation using 10 mM glycine, pH 1.5 at a flow rate of 100 μl/min for a contact time of 30 s. While most of the selected clones showed similar affinities like the parental clone, clone 51A12_A6 (SEQ ID NO: 44) showed a significantly improved affinity (Table 4).

TABLE 4

Kinetic and thermodynamic parameters of affinity-matured anti-ASGPR1 Fabs.

| ASGPR CRD-specific | human/cyno ASGPR1 CRD | | |
|---|---|---|---|
| binders | ka (1/Ms) | kd (1/s) | KD (M) |
| 51A12 | 1.10E+05 | 6.28E−05 | 5.70E−10 |
| 51A12 A82G S116A | 1.27E+05 | 1.60E−04 | 1.25E−09 |
| 51A12 S116A | 1.31E+05 | 1.78E−4 | 1.43E−09 |
| 51A12_C1 | 1.74E+05 | 4.19E−05 | 2.41E−10 |
| 51A12_E7 | 2.15E+05 | 9.64E−05 | 4.48E−10 |
| 51A12_H3 | 1.63E+05 | 8.30E−05 | 5.10E−10 |
| 51A12_A6 | 3.26E+05 | 2.61E−05 | 8.01E−11 |
| 51A12_C7 | 1.99E+05 | 4.67E−05 | 2.35E−10 |
| 51A12_D1 | 4.00E+05 | 8.85E−05 | 2.21E−10 |
| 51A12_H6 | 0.86E+05 | 2.79E−05 | 3.25E−10 |

Binding Analysis of the Affinity Matured 51A12 Derivatives to HepG2 Cells

Figure 10:
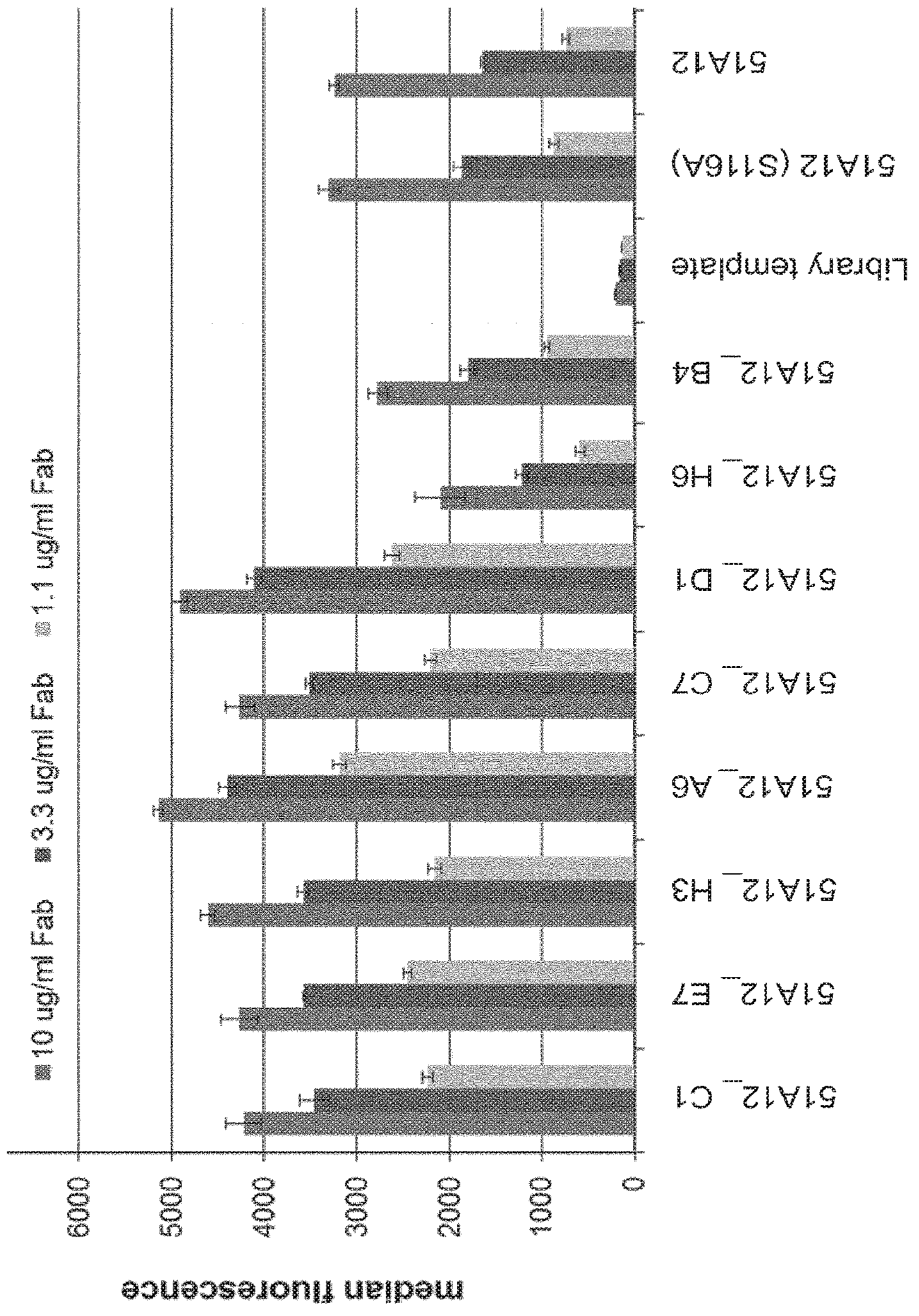
FIG. 10. Binding analysis of affinity-matured 51A12-derived clones to HepG2 cells as human Fab fragments. Fab concentrations of 10, 3.3, and 1.1 μg/ml were used. The parental clone 51A12 (SEQ ID NOs 2 and 4), 51A12 (S116A) (SEQ ID NOs 4 and 30), a clone devoid of the glycosylation sequence, and 51A12 (A82G, C112S, C113S, S116A) (SEQ ID NOs 4 and 34), the template clone for the affinity maturation library, served as controls.
Figures 11A, 11B:
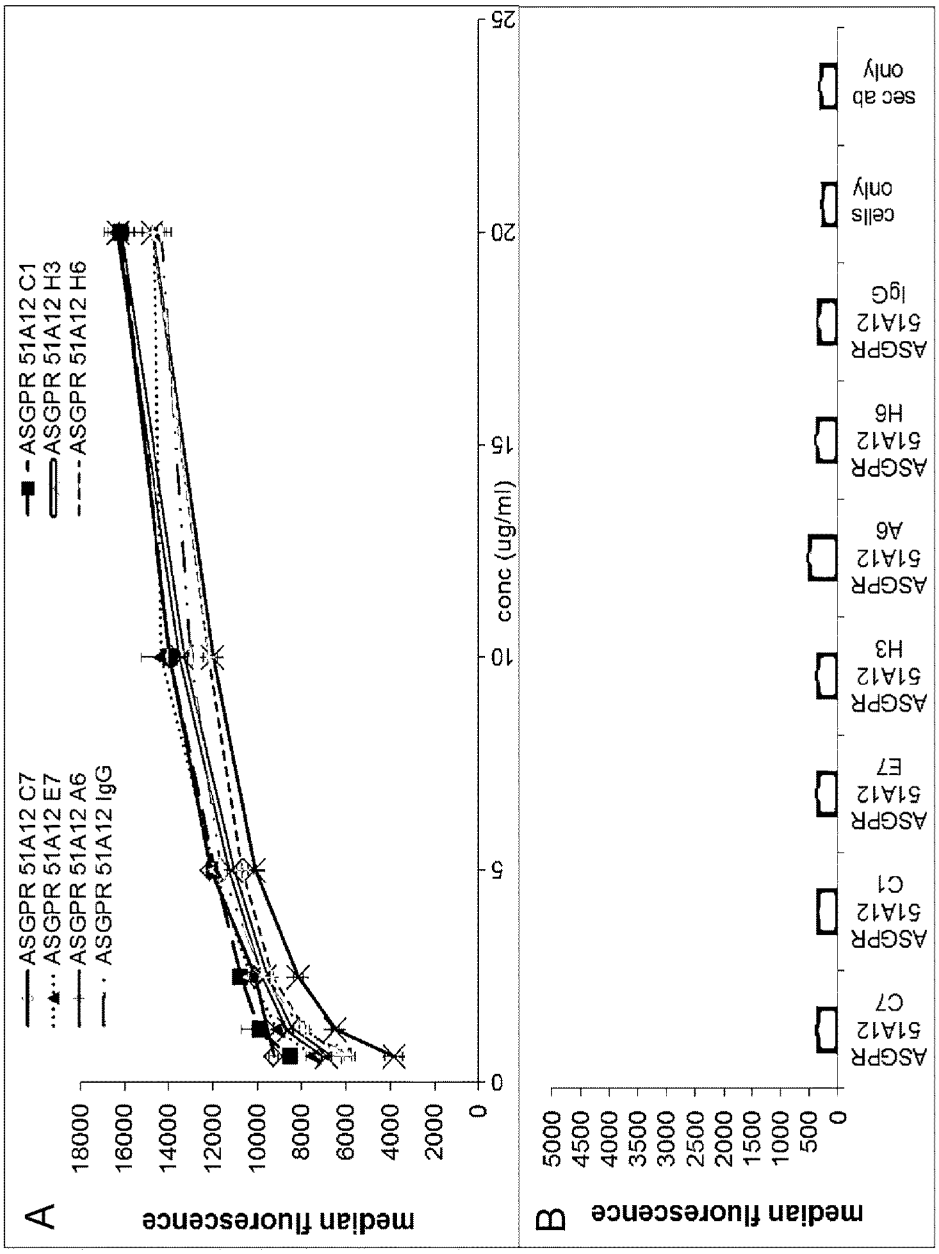
FIGS. 11A-11B. Binding analysis of affinity-matured 51A12-derived clones to HepG2 cells as human $IgG_1$ antibodies. Concentrations in a dilution row ranging from 0.01 to 20 μg/ml were used. The parental clone 51A12 (SEQ ID NOs 2 and 4) served as a control 11(A). Binding analysis to Hela cells at a concentration of 10 μg/ml was used as a negative control 11(B).

Binding of the selected affinity matured 51A12 derivatives to the ASGPR-positive hepatocellular carcinoma cell line HepG2 was measured by FACS. As a negative control, the ASGPR-negative cell line Hela was used. 0.2 mio cells per well in a 96 well round bottom plate were incubated in 300 μl with either purified Fab fragments (1.1, 3.3 and 10 μg/ml) or human $IgG_1$-converted antibodies (0.01, 0.04, 0.1, 0.4, 1.1, 3.3 and 10 μg/ml) for 30 min at 4° C. Unbound molecules were removed by washing the cells with PBS containing 0.1% BSA. Bound molecules were detected with either a FITC-conjugated AffiniPure goat anti-human F(ab')2 fragment-specific secondary F(ab')2 fragment (Jackson Immuno Research Lab #109-096-097) or a FITC-conjugated AffiniPure goat anti-human IgG Fc gamma fragment-specific secondary F(ab')2 fragment (Jackson ImmunoResearch #109-096-098; working solution 1:20 in PBS, 0.1% BSA). After 30 min incubation at 4° C. unbound antibody was removed by washing and cells were fixed using 1% PFA. Cells were analyzed using BD FACS CantoII (Software BD DIVA). Analysis of the Fab binding to HepG2 cells revealed strong binding of all clones (FIG. 10). Variant 51A12_A6 (SEQ ID NO: 44) was the strongest binder in both SPR analysis and the cell binding study. Binding analysis of the clone variants as $IgG_1$-converted antibodies to HepG2 cells resulted in a similarly strong binding pattern for all clones (FIG. 11A) while binding to Hela cells at the highest antibody concentration was very weak or not detectable (FIG. 11B), underlining the specificity of these clone variants.

Generation of IgG-IFNα DNA Constructs

Figures 12A, 12B:
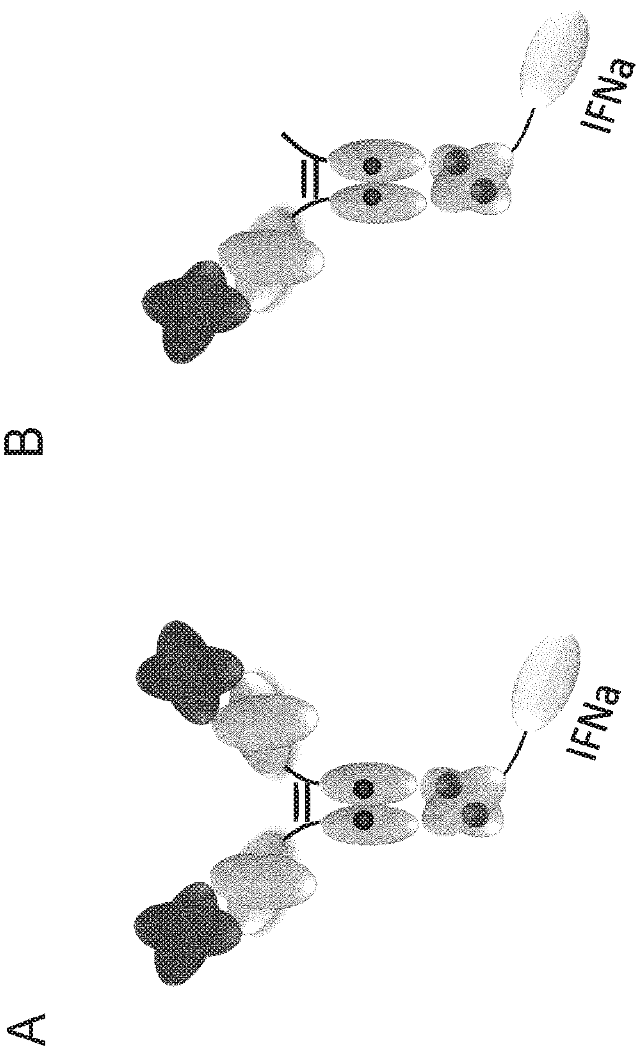
FIGS. 12A-12B. Schematic diagram of the generated antibody-cytokine conjugates. The gene encoding interferon-α2a was fused to the C terminal end of an ASGPR H1-specific antibody heavy chain comprising a knob modification. While bivalent ASGPR binding of the antibody-cytokine protein was achieved by co-expression of the corresponding ASGPR H1-specific heavy chain comprising a hole modification and the light chain (12(A), 2:1 valency), expression of a Fc(hole) fragment sequence resulted in a monomeric antibody-cytokine conjugate with only one ASGPR H1-specific binding site per molecule (12(B), 1:1 valency). Small black dots: modification preventing FcγR binding (for example L234A L235A P329G). Large black dots: modification promoting heterodimerization (for example knob-into-hole).
Figures 13A, 13B, 13C, 13D:
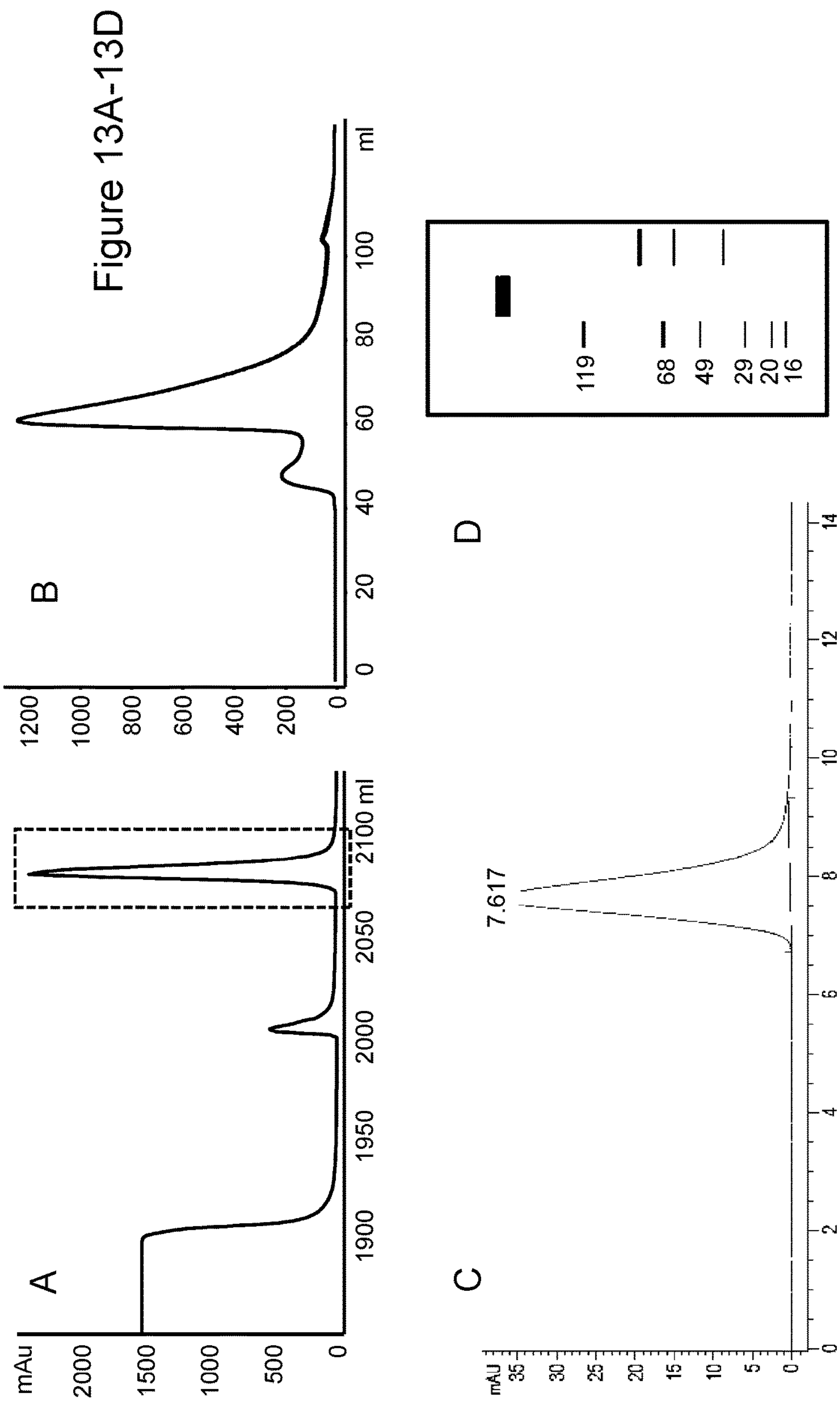
FIGS. 13A-13D. Purification and analytical characterization of selected antibody-IFNα immunoconjugates (FIG. 13: 51A12 kih IgG-IFNα). 13(A) followed by size exclusion chromatography (Superdex 200, GE Healthcare) 13(B). The final product was analyzed and characterized by analytical size exclusion chromatography (Superdex 200 column) 13(C) and microfluidic protein analysis (Caliper) or SDS-PAGE 13(D).
Figures 14A, 14B, 14C, 14D:
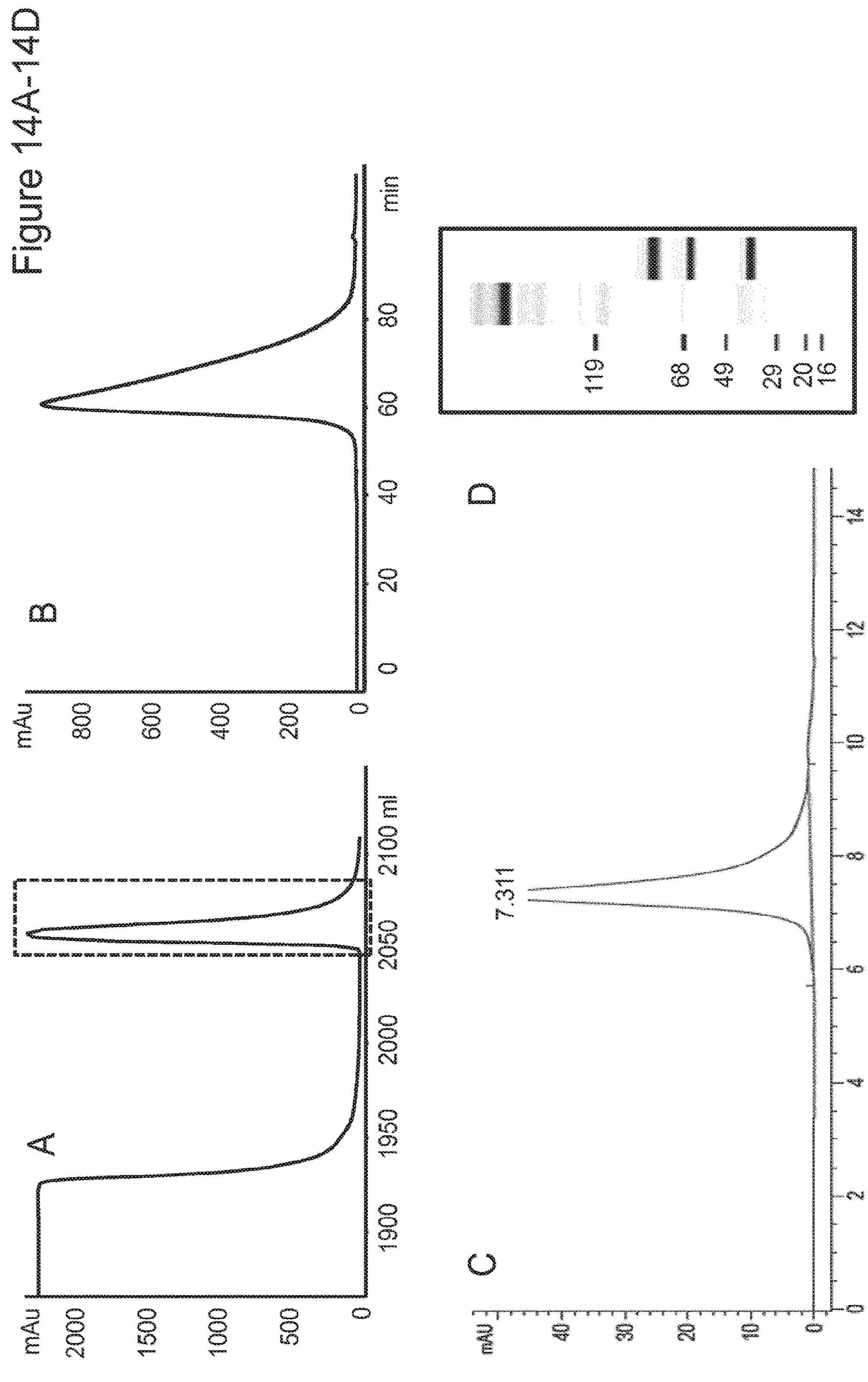
FIGS. 14A-14D. Purification and analytical characterization of 4F3 kih IgG-IFNα. The purification method involved an affinity step (protein A) 14(A) followed by size exclusion chromatography (Superdex 200, GE Healthcare) 14(B). The final product was analyzed and characterized by analytical size exclusion chromatography (Superdex 200 column) 14(C) and microfluidic protein analysis (Caliper) or SDS-PAGE 14(D).
Figures 15A, 15B, 15C, 15D:
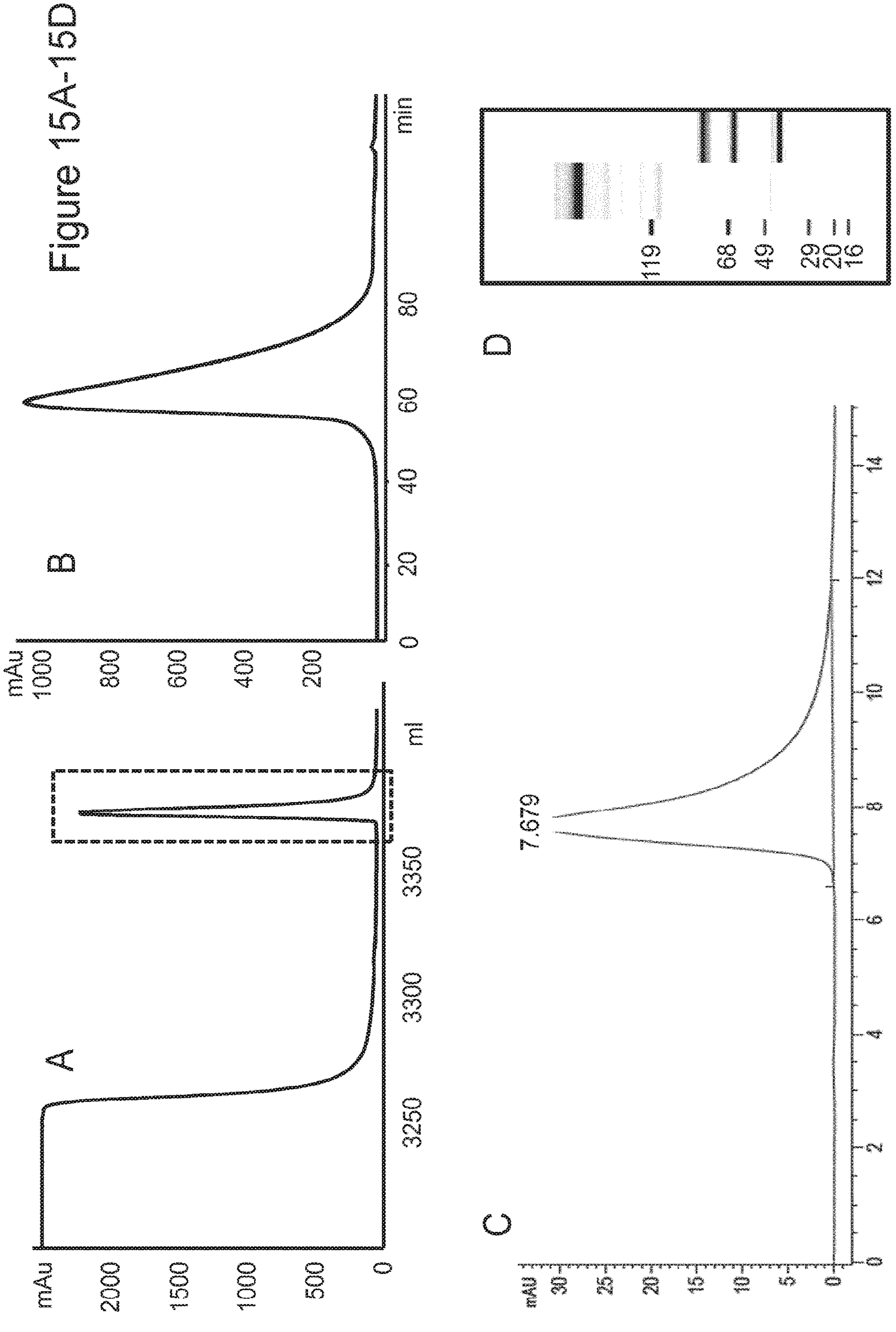
FIGS. 15A-15D. Purification and analytical characterization of 51A12 (C7) kih IgG-IFNα. The purification method involved an affinity step (protein A) 15(A) followed by size exclusion chromatography (Superdex 200, GE Healthcare) 15(B). The final product was analyzed and characterized by analytical size exclusion chromatography (Superdex 200 column) 15(C) and microfluidic protein analysis (Caliper) or SDS-PAGE 15(D).
Figures 16A, 16B, 16C, 16D:
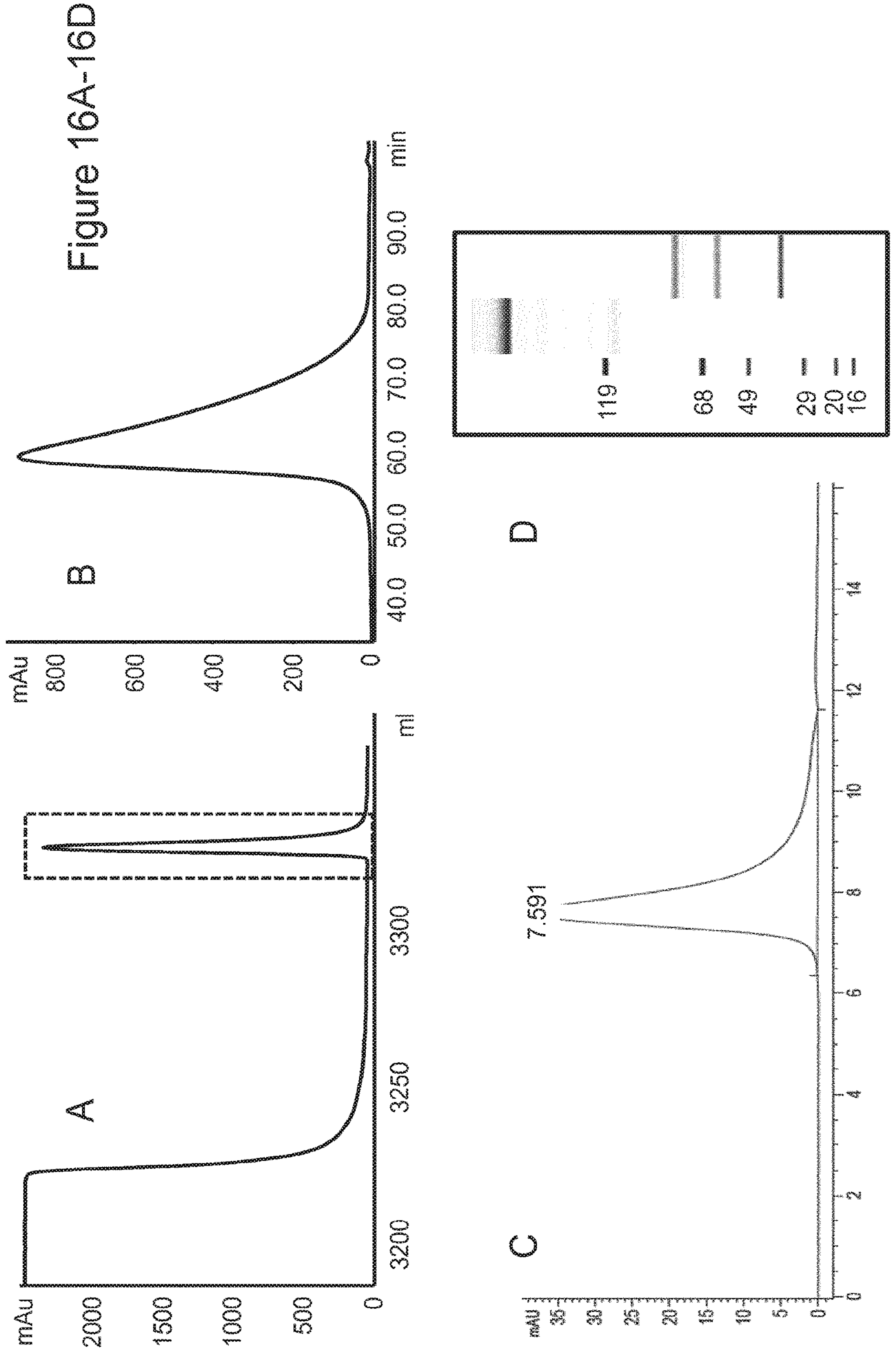
FIGS. 16A-16D. Purification and analytical characterization of 51A12 (C1) kih IgG-IFNα. The purification method involved an affinity step (protein A) 16(A) followed by size exclusion chromatography (Superdex 200, GE Healthcare) 16(B). The final product was analyzed and characterized by analytical size exclusion chromatography (Superdex 200 column) 16(C) and microfluidic protein analysis (Caliper) or SDS-PAGE 16(D).
Figures 17A, 17B, 17C, 17D:
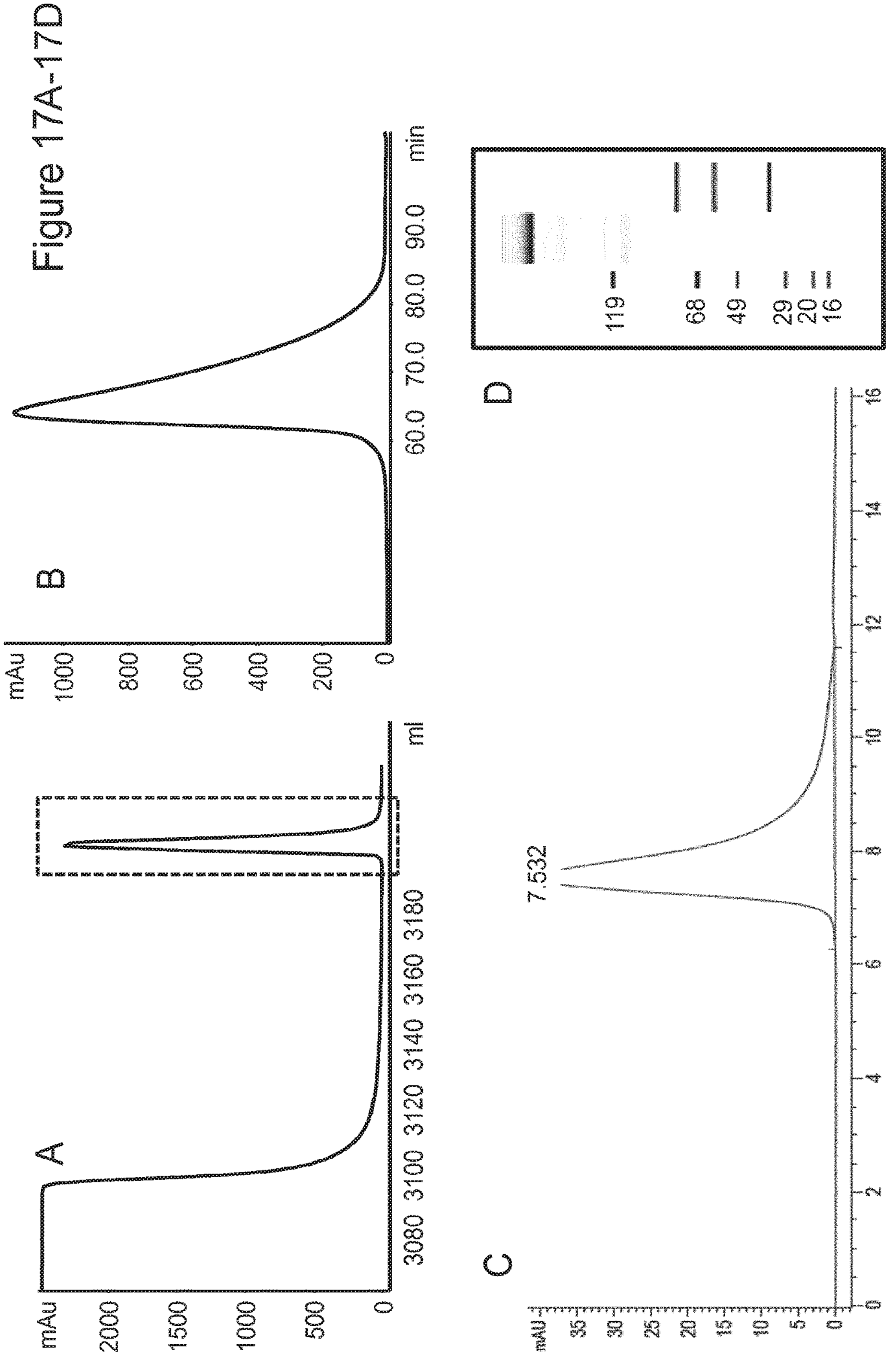
FIGS. 17A-17D. Purification and analytical characterization of 51A12 (E7) kih IgG-IFNα. The purification method involved an affinity step (protein A) 17(A) followed by size exclusion chromatography (Superdex 200, GE Healthcare) 17(B). The final product was analyzed and characterized by analytical size exclusion chromatography (Superdex 200 column) 17(C) and microfluidic protein analysis (Caliper) or SDS-PAGE 17(D).
Figures 18A, 18B, 18C, 18D:
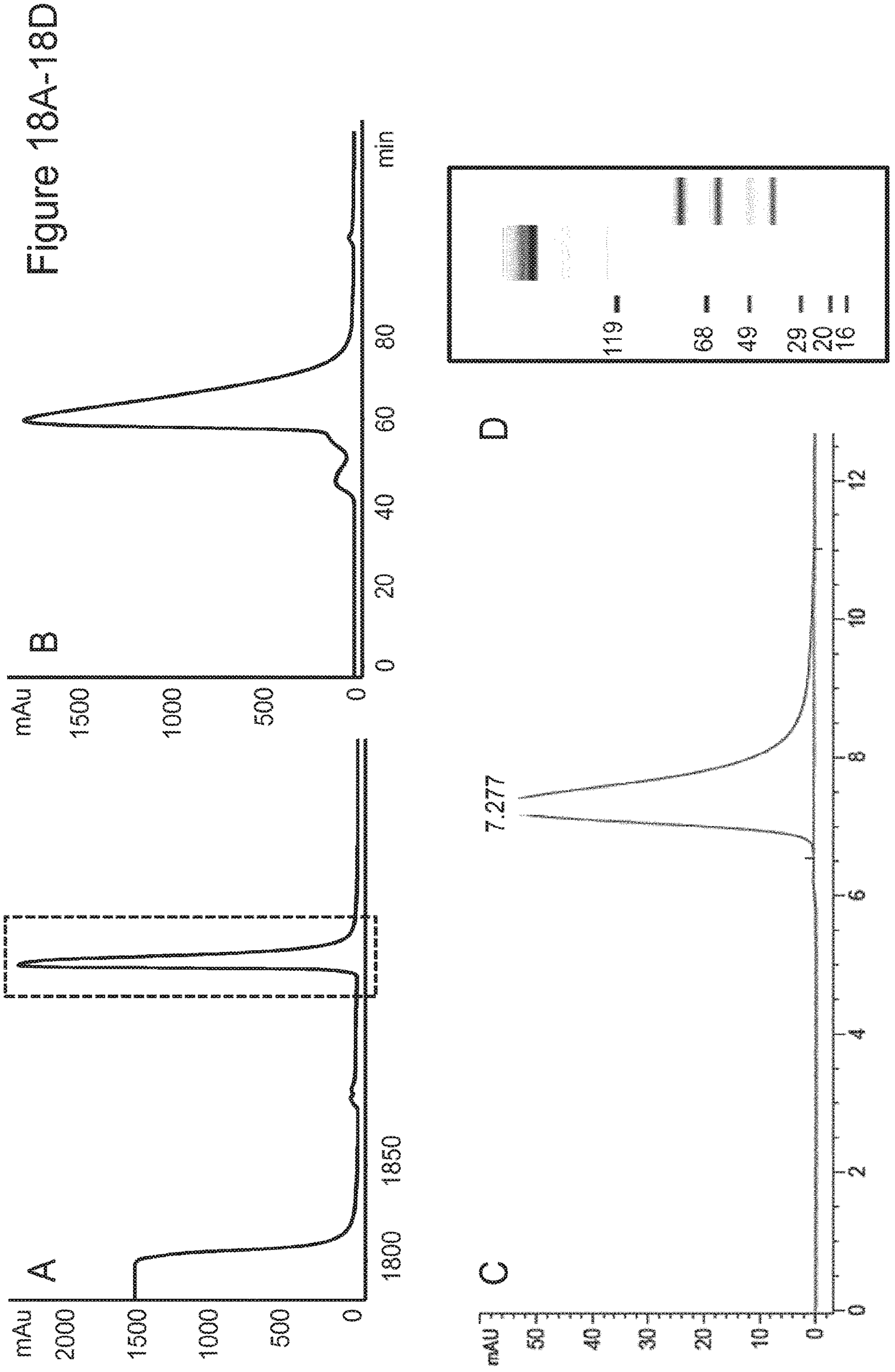
FIGS. 18A-18D. Purification and analytical characterization of isotype control kih IgG-IFNα. The purification method involved an affinity step (protein A) 18(A) followed by size exclusion chromatography (Superdex 200, GE Healthcare) 18(B). The final product was analyzed and characterized by analytical size exclusion chromatography (Superdex 200 column) 18(C) and microfluidic protein analysis (Caliper) or SDS-PAGE 18(D).
Figures 19A, 19B, 19C:
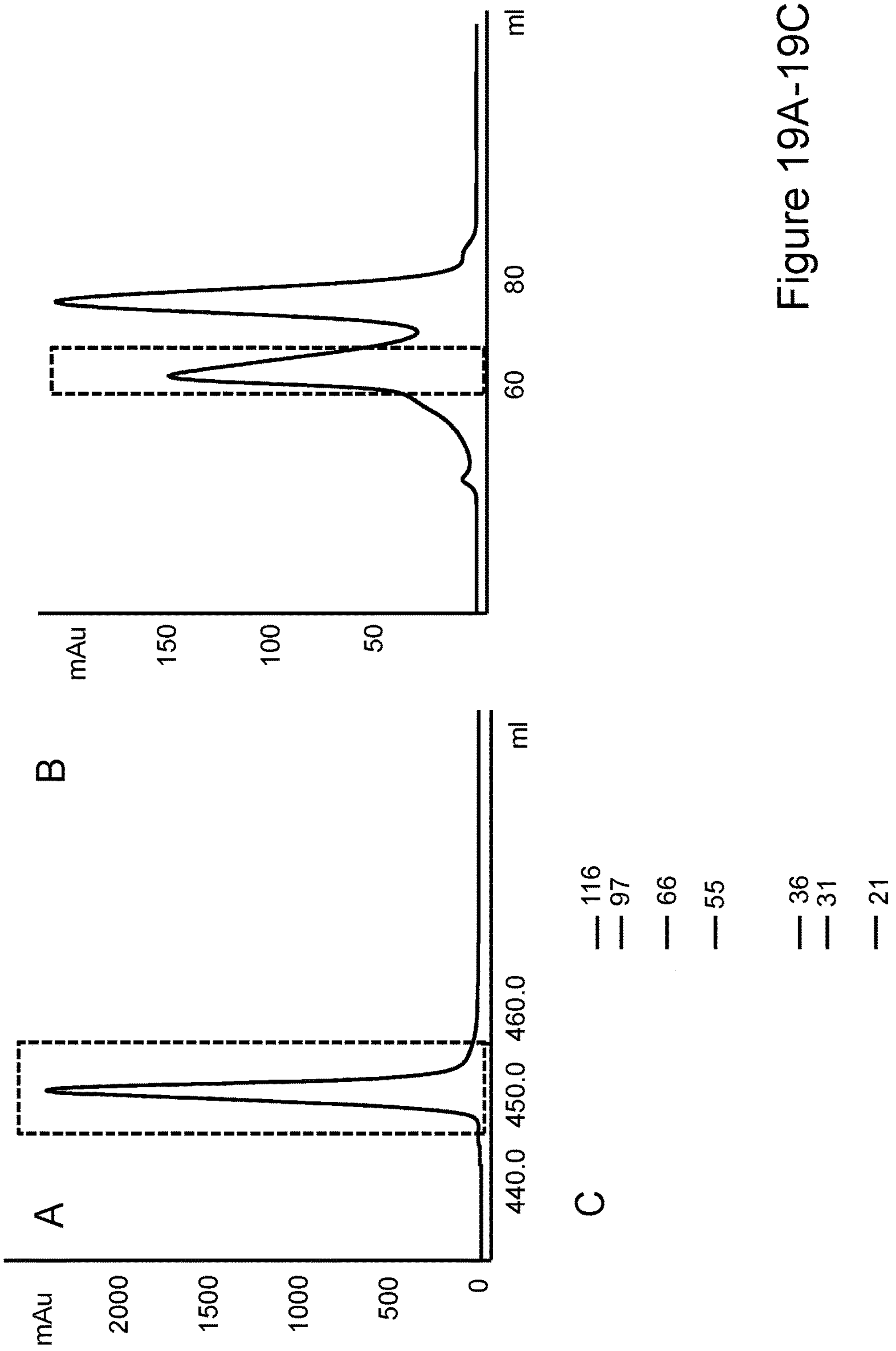

DNA sequences encoding ASGPR H1-targeted IgG-IFNα fusion proteins were generated based on the ASGPR H1-antibodies 51A12, 51A12 (S116A), 51A12 (A82G, S116A), 52C4, 5A4, 4F3, R5C2, R9E10, R7E12, 51A12_C1, 51A12_C7, 51A12_E7, 51A12_H3, 51A12_A6, 51A12_D1 and 51A12_H6 wherein one Interferon-α2a (IFNα) was fused to the C-terminus of one heterodimeric heavy chain as shown in FIG. 12A. Targeting to the liver hepatocytes where ASGPR H1 is selectively expressed is achieved via the bivalent antibody Fab region (avidity effect). Heterodimerization resulting in the presence of a single IFNα is achieved by application of the knob-into-hole (kih) technology. In order to minimize the generation of homodimeric IgG-cytokine fusions, the cytokine was fused to the C-terminus (with deletion of the C-terminal Lys residue) of the knob-containing IgG heavy chain via a $(G_4S)_3$ linker. The antibody-cytokine fusion has IgG-like properties. To reduce FcγR binding/effector function and prevent FcR co-activation, P329G L234A L235A (LALA) mutations were introduced in the Fc domain. However, FcRn binding is not impaired. The DNA sequences encoding these immunoconjugates are given in SEQ ID NOs 49, 51 and 53 (51A12), SEQ ID NOs 55, 57 and 59 (52C4), SEQ ID NOs 93, 51 and 53 (51A12 A82G, S116A), SEQ ID NOs 91, 51 and 53 (51A12, S116A), SEQ ID NOs 61, 63 and 65 (5A4), SEQ ID NOs 67, 69 and 71 (4F3), SEQ ID NOs 73, 75 and 77 (R5C2), SEQ ID NOs 79, 81 and 83 (R9E19), SEQ ID NOs 85, 87 and 89 (R7E12), SEQ ID NOs 95, 51 and 53 (51A12_C1), SEQ ID NOs 97, 51 and 53 (51A12_C7), SEQ ID NOs 99, 51 and 53 (51A12_E7), SEQ ID NOs 101, 51 and 53 (51A12_H3), SEQ ID NOs 103, 51 and 53 (51A12_A6), SEQ ID NOs 105, 51 and 53 (51A12_D1), SEQ ID NOs 107, 51 and 53 (51A12_H6). In addition, an alternative hole-heavy chain was created where both VH and CH1 domains were deleted (SEQ ID NO: 115). The resulting Fc fragment was able to hetero-dimerize with the full-length knob heavy chain leading to a monovalent antibody with a single cytokine fusion (FIG. 12B). As a negative control for functional assays, corresponding DNA constructs encoding a control DP47GS/DPL16 non-targeted IgG-IFNα protein wherein the IgG does not bind to a specified target was generated. The DNA sequence of this isotype immunoconjugate is given in SEQ ID NOs 109, 111 and 113.

Expression and Purification of the Antibody-Cytokine Constructs

Immunoconjugates were produced by co-transfecting exponentially growing HEK293-EBNA cells with the mammalian expression vectors using calcium phosphate-transfection. Alternatively, HEK293-EBNA cells growing in suspension were transfected by polyethylenimine (PEI) with the respective expression vectors. Subsequently, the IgG-cytokine fusion proteins were purified from the supernatant by a method composed of one affinity step (protein A) followed by size exclusion chromatography (Superdex 200, GE Healthcare). The protein A column (HiTrap ProtA, GE Healthcare) was equilibrated in 20 mM sodium phosphate, 20 mM sodium citrate pH 7.5. After loading of the supernatant, the column was first washed with 20 mM sodium phosphate, 20 mM sodium citrate, pH 7.5 and subsequently washed with 13.3 mM sodium phosphate, 20 mM sodium citrate, 500 mM sodium chloride, pH 5.45. The IgG-cytokine fusion protein was eluted with 20 mM sodium citrate, 100 mM sodium chloride, 100 mM glycine, pH 3. Fractions were neutralized, pooled, and purified by size exclusion chromatography (HiLoad 16/60 Superdex 200, GE Healthcare) in final formulation buffer (25 mM potassium phosphate, 125 mM sodium chloride, 100 mM glycine pH 6.7 or 20 mM histidine, 140 mM NaCl, pH 6.0). The protein concentration of purified protein samples was determined by measuring the optical density (OD) at 280 nm, using the molar extinction coefficient calculated on the basis of the amino acid sequence. Purity and molecular weight of immunoconjugates were analyzed by SDS-PAGE or Caliper in the presence and absence of a reducing agent (5 mM 1,4-dithiotreitol). The NuPAGE® Pre-Cast gel system (Invitrogen) was used according to the manufacturer's instructions (4-20% Tris-glycine gels or 3-12% Bis-Tris). The aggregate content of immunoconjugate samples was analyzed using a Superdex 200 10/300GL analytical size-exclusion column (GE Healthcare) in 2 mM MOPS, 150 mM NaCl, 0.02% $NaN_3$, pH 7.3 running buffer at 25° C. A summary of the analytical data is shown for selected clones in FIG. 13 (51A12 kih IgG IFNα, SEQ ID NOs 50, 52, 54), FIG. 14 (4F3 kih IgG IFNα, SEQ ID NOs 68, 70, 72), FIG. 15 (51A12_C1 kih IgG IFNα, SEQ ID NO: 96, 52, 54), FIG. 16 (51A12_E7 kih IgG IFNα, SEQ ID NO: 100, 52, 54), FIG. 17 (51A12_C7 kih IgG IFNα, SEQ ID NO: 98, 52, 54), FIG. 18 (untargeted kih IgG IFNα, SEQ ID NO: 110, 112, 114) and FIG. 19 (monovalent 51A12 kih IgG IFNα, SEQ ID NO: 50, 52, 116).

Affinity-Determination of IgG-IFNα Immunoconjugates to ASGPR H1 by SPR

The ASGPR H1 binding activity of clones 51A12 and 52C4 used as exemplary IgG-IFNα immunoconjugates was determined and compared to the corresponding unmodified IgG antibodies by surface plasmon resonance (SPR) on a ProteOn XPR36 instrument (Biorad). Biotinylated avi-Fc human ASGPR H1 CRD antigen was immobilized on NLC chips by neutravidin capture. Immobilization of recombinant antigens (ligand): Antigens were diluted with PBST (10 mM phosphate, 150 mM sodium chloride pH 7.4, 0.005% Tween-20) to 10 μg/ml, then injected at 30 μl/min at varying contact times, to achieve immobilization levels of 400 response units (RU) in vertical orientation. Injection of analytes: For one-shot kinetics measurements, injection direction was changed to horizontal orientation, two-fold dilution series of purified IgGs, mono- and bivalent antibody-cytokine fusions (varying concentration ranges between 50 and 3.25 nM) were injected simultaneously at 50 µl/min along separate channels 1-5, with association times of 120 or 200 s, and dissociation times of 300 s. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Regeneration was performed in horizontal orientation using 10 mM glycine, pH 1.5 at a flow rate of 100 µl/min for a contact time of 30 s. The data show that—within the error of the method—the affinity (monovalent display) and avidity (dimeric display) for human ASGPR H1 is retained for both clone 51A12-based (SEQ ID NOs 50, 52, 54) and clone 52C4-based (SEQ ID NOs 56, 58, 60) immunoconjugate (Table 5).

TABLE 5

Kinetic and thermodynamic parameters of the monovalent and bivalent binding formats of clone 51A12 and 52C4 to ASGPR H1.

| | # of binding | human/cyno ASGPR1 CRD | | |
|---|---|---|---|---|
| Name of the binder | arms | $k_{on}$ (1/Ms) | $k_{off}$ (1/s) | $K_D$ (M) |
| 51A12 IgG | 2 | $3.5 \times 10^{5}$ | $7.34 \times 10^{-5}$ | $2.1 \times 10^{-10}$ |
| 51A12 kih IgG-IFNα | 2 | $6.74 \times 10^{5}$ | $15.7 \times 10^{-5}$ | $2.33 \times 10^{-10}$ |
| 51A12 Fab | 1 | $1.10 \times 10^{5}$ | $6.28 \times 10^{-5}$ | $5.71 \times 10^{-10}$ |
| monovalent 51A12 kih IgG-IFNα | 1 | $2.45 \times 10^{5}$ | $13.9 \times 10^{-5}$ | $5.68 \times 10^{-10}$ |
| 52C4 IgG | 2 | $5.57 \times 10^{5}$ | $49.9 \times 10^{-5}$ | $0.89 \times 10^{-9}$ |
| 52C4 kih IgG-IFNα | 2 | $4.26 \times 10^{5}$ | $49E \times 10^{-5}$ | $1.15 \times 10^{-9}$ |
| 52C4 Fab | 1 | $1.39 \times 10^{5}$ | $396 \times 10^{-5}$ | $28.6 \times 10^{-9}$ |
| monovalent 52C4 kih IgG-IFNα | 1 | $1.14 \times 10^{5}$ | $302 \times 10^{-5}$ | $26.5 \times 10^{-9}$ |

Binding of IgG-IFNα Immunoconjugates to ASGPR-Positive and -Negative Cells

Figures 20A, 20B:
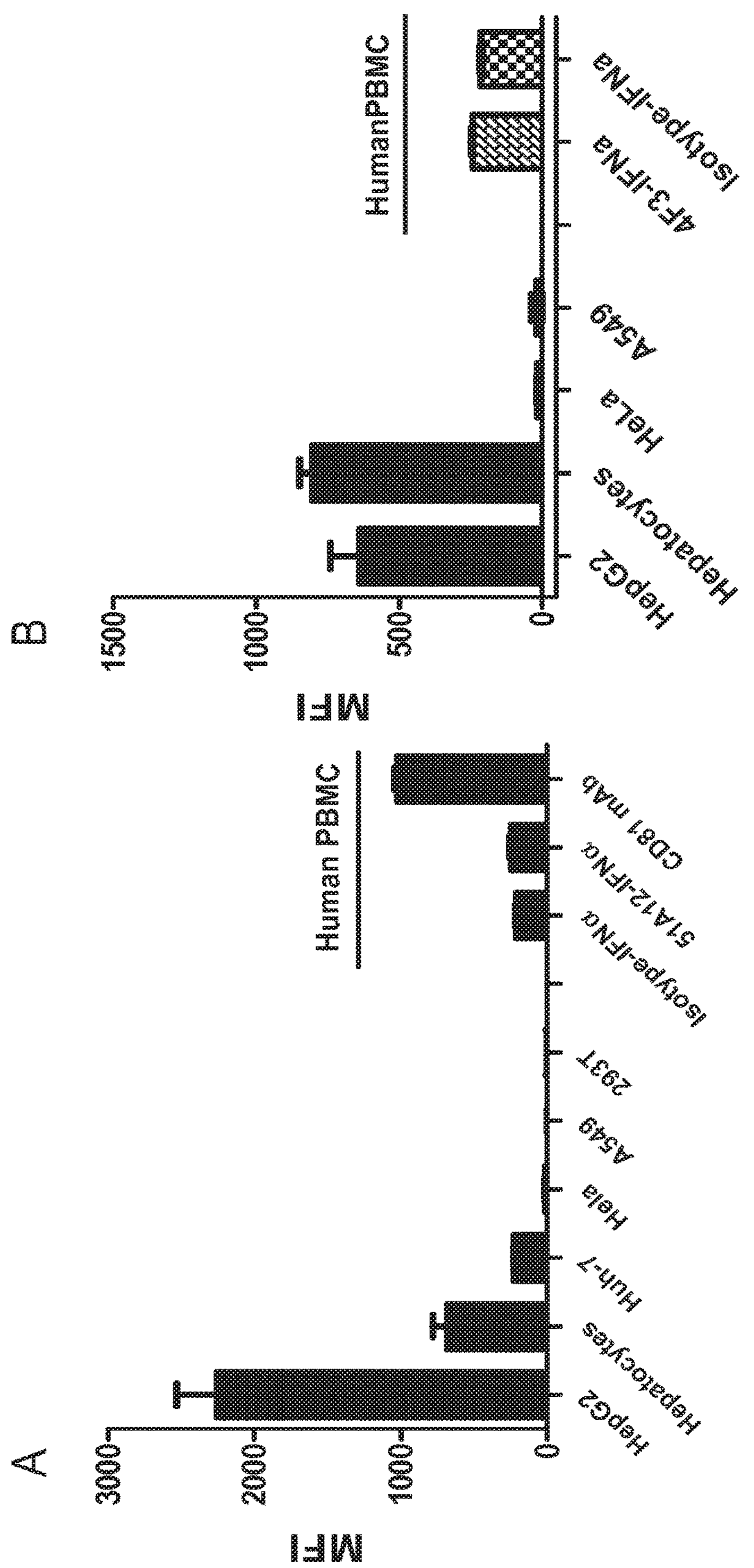
FIGS. 20A-20B. Binding selectivity of ASGPR-specific IgG kih IFNα fusion constructs 51A12 20(A) and 4F3 20(B). HepG2, primary human hepatocytes, Huh-7 cells, A549 cells, Hela cells, and 293T cells were incubated with 1 μg/ml 51A12-IFNα 20(A) or 4F3-IFNα 20(B) for 45 min on ice. After three washes, cells were stained with secondary goat anti-human IgG antibody on ice for 30 min, and the cells were washed three times before being analyzed using a Calibur flow cytometer. Binding to human PBMC was performed by using 1 μg/ml of directly labeled 51A12 IgG kih IFNα 20(A) and 4F3 IgG kih IFNα 20(B) using the Zenon® R-Phycoerythrin Human IgG Labeling Kit according to manufacturer's instructions, isotype IgG kih IFNα and a CD81 mAb were used as negative and positive controls, respectively.
Figures 21A, 21B, 21C, 21D:
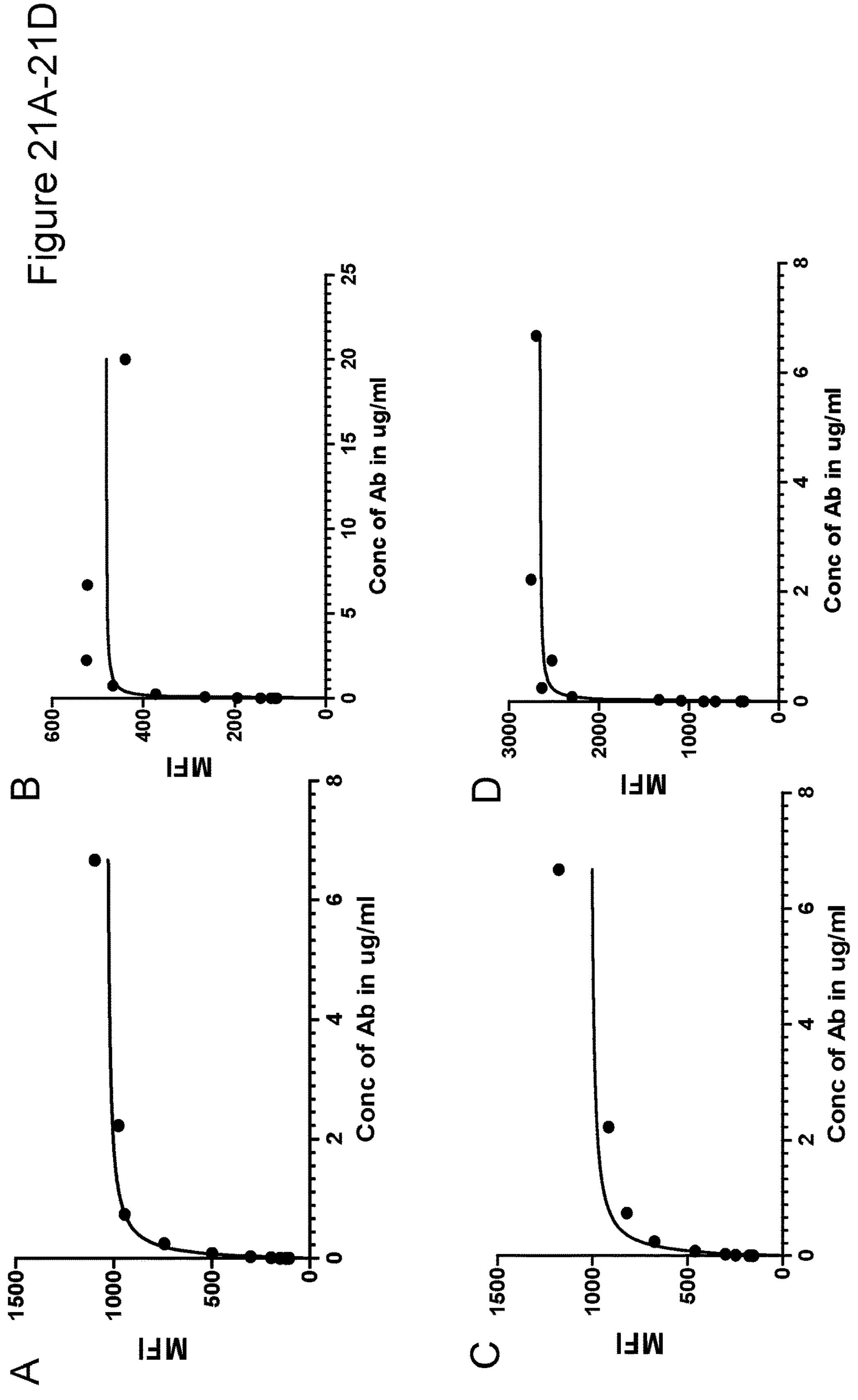
FIGS. 21A-21D. Binding saturation curves of ASGPR mAb 4F3-IFNα on primary human hepatocytes and HepG2 cells. Binding saturation of ASGPR mAb 4F3-IFNα on human hepatocytes derived from three different donors 21(A-C) and HepG2 cells 21(D). Cells were incubated with serially diluted 4F3 IgG kih IFNα for 45 min on ice. After three washes, cells were stained with secondary goat anti-human IgG antibody on ice for 30 min, and washed again three times before being analyzed using a Calibur flow cytometer.

In order to characterize the specificity of the antibody conjugates, antibody-cytokine conjugates were incubated with both ASGPR-positive and negative cells and specific binding was measured by FACS analysis. For this, primary human hepatocytes (from 3 donors; purchased from Celsis In Vitro Technologies (Baltimore, Md.)), Huh-7 cells, HepG2 cells, A549 cells, Hela cells, and 293T cells (each $1 \times 10^{5}$) were incubated with 1 µg of ASGPR H1-specific IgG kih IFNα samples for 45 min on ice. After washing, the cells were incubated with a labeled goat anti-human IgG secondary antibody (BD Biosciences, San Diego, Calif.) for 30 min on ice. After three washes, the stained cells were analyzed by FACS analysis using a Calibur flow cytometer. In all FACS assays, an isotype control conjugate (untargeted kih IgG IFNα, SEQ ID NOs 110, 112, 114) was used to determine the background, which was subtracted from the MFI values for the tested antibodies. Binding analysis to human peripheral blood mononuclear cells (PBMC) was performed by using directly labeled antibody conjugates (Zenon® R-Phycoerythrin Human IgG Labeling Kit, Life Technologies) according to manufacturer's instructions. Binding analysis revealed that clone 51A12 IgG kih IFNα (SEQ ID NOs 50, 52, 54) and 4F3 IgG kih IFNα (SEQ ID NOs 68, 70, 72) showed highly specific binding to ASGPR-positive cells while the signal on ASGPR-negative cells was comparable to the isotype control conjugate (FIG. 20). In addition, binding saturation curves of clone 4F3 IgG kih IFNα were analyzed. For this, the antibody-IFNα conjugate was incubated with primary human hepatocytes (from 3 donors) in a dilution row ranging from 0.0001 to 6.7 µg/ml and binding intensity was recorded by FACS analysis. As shown in FIG. 21 binding saturation on primary human hepatocytes as well as on the control cell line HepG2 was reached at 0.25-0.74 µg/ml antibody concentrations, and higher antibody concentration did not significantly increase the binding signal further.

Analysis of the Surface-Exposed ASGPR Level on HepG2 Cells Over Time

Figures 22A, 22B:
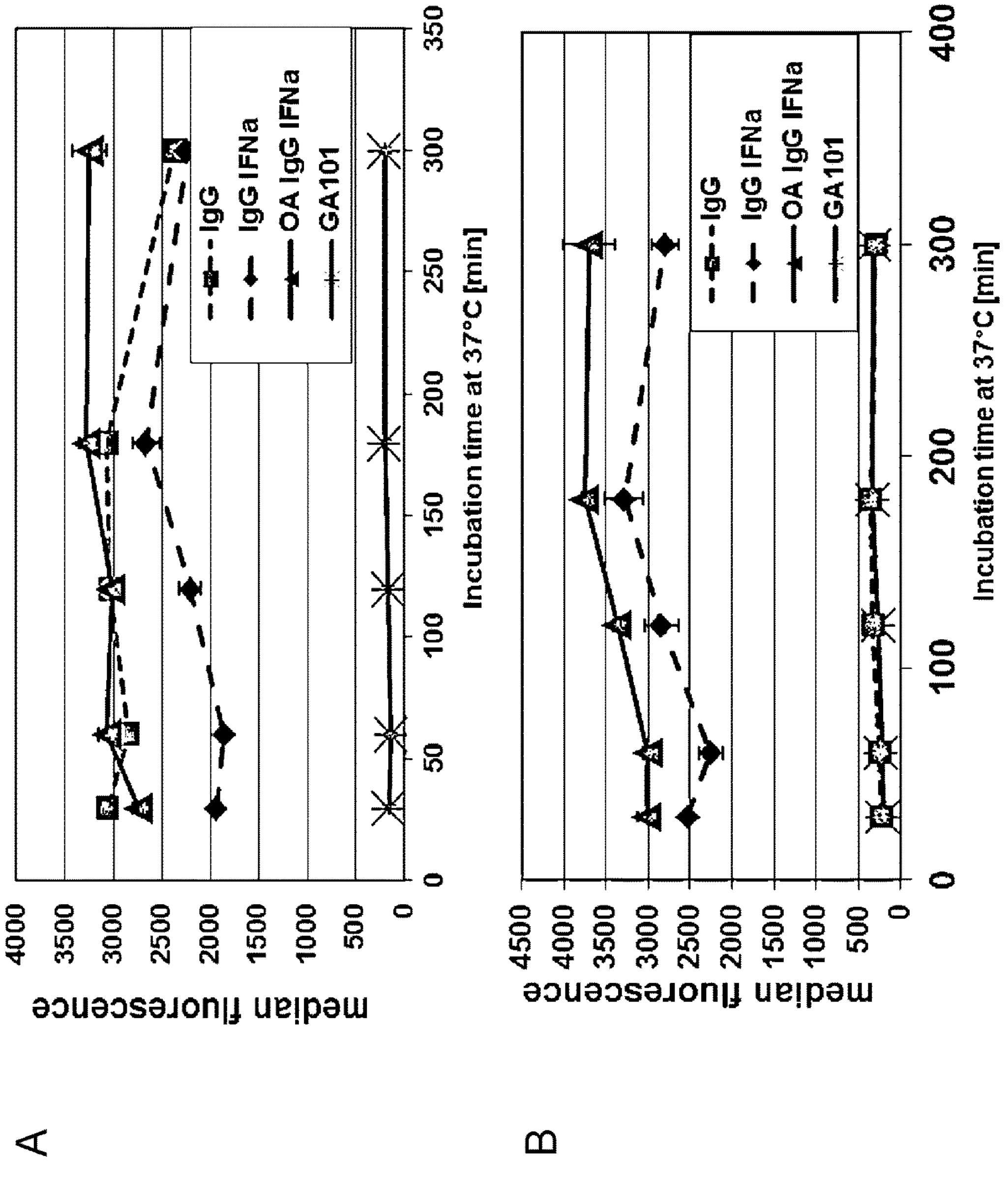
FIGS. 22A-22B. Analysis of the surface-exposed levels of ASGPR over time in presence of specific antibodies. HepG2 cells were incubated with either ASGPR-specific clone 51A12 IgG or the corresponding monovalent or bivalent antibody-cytokine conjugate. Cell samples were taken after up to 5 hrs and binding of the IgG constructs to ASGPR was measured by detection of either the antibody 22(A) or the cytokine 22(B). An anti-CD20 antibody (GA101) was used as a negative control.

Uptake of desialylated glycoproteins into liver cells after binding to ASGPR is known to occur very rapidly. During this receptor-mediated endocytosis, the lumen of the endosome becomes acidic allowing the receptor-ligand complexes to dissociate. While the ligand is targeted for degradation in lysosomes, ASGPR was shown to recycle back to the cell surface. Since receptor binding followed by internalization was shown for several receptors to trigger down-regulation of receptor expression, the levels of surface-exposed ASGPR in the presence of anti ASGPR H1 antibodies was measured over time. For this experiment, HepG2 cells were incubated for up to 5 h with clone 51A12-derived antibodies, either as IgG or as mono- or bivalent antibody-IFNα fusion proteins. As a negative control, an unrelated antibody without binding specificity to HepG2 cells was used (GA101) (all antibodies at 30 µg/ml). During incubation at 37° C., samples were taken after 30, 60, 120, 180, and 300 min and washed with cold PBS. Cell surface bound antibodies were detected using an APC-conjugated goat anti-human IgG Fcg fragment specific F(ab')2 fragment (Jackson Immuno Research Lab, working solution 1:50). After 30 min incubation at 4° C. unbound antibody was removed by washing with PBS containing 0.1% BSA. Cells were fixed using 1% PFA and analyzed using BD FACS CantoII (Software BD DIVA). In order to verify the integrity of the antibody-cytokine fusion, the presence of IFNα was also detected. Cells were incubated with a mouse monoclonal antibody against human interferon alpha (MMHA-1, #21105-1, R&D Systems, 5 µg/ml) for 30 min at 4° C. Unbound antibody was removed by washing with PBS containing 0.1% BSA and a FITC-conjugated anti-mouse F(ab')2 Fragment (Serotec, STAR105F; working solution 1:50) was used as secondary antibody. Cells were fixed using 1% PFA and analyzed using BD FACS CantoII (Software BD DIVA). The results shown in FIG. 22 demonstrate the constant level of surface-exposed antibody bound to ASGPR without any binding-induced down-regulation of the receptor over the measured time period. Of note, the monomeric IgG-IFNα construct gave the strongest signal, most likely due to the fact that twice the number of monomeric IgG-IFNα molecules can bind per ASGPR complex (FIG. 22A).

Confocal Microscopy

Figures 23A, 23B:
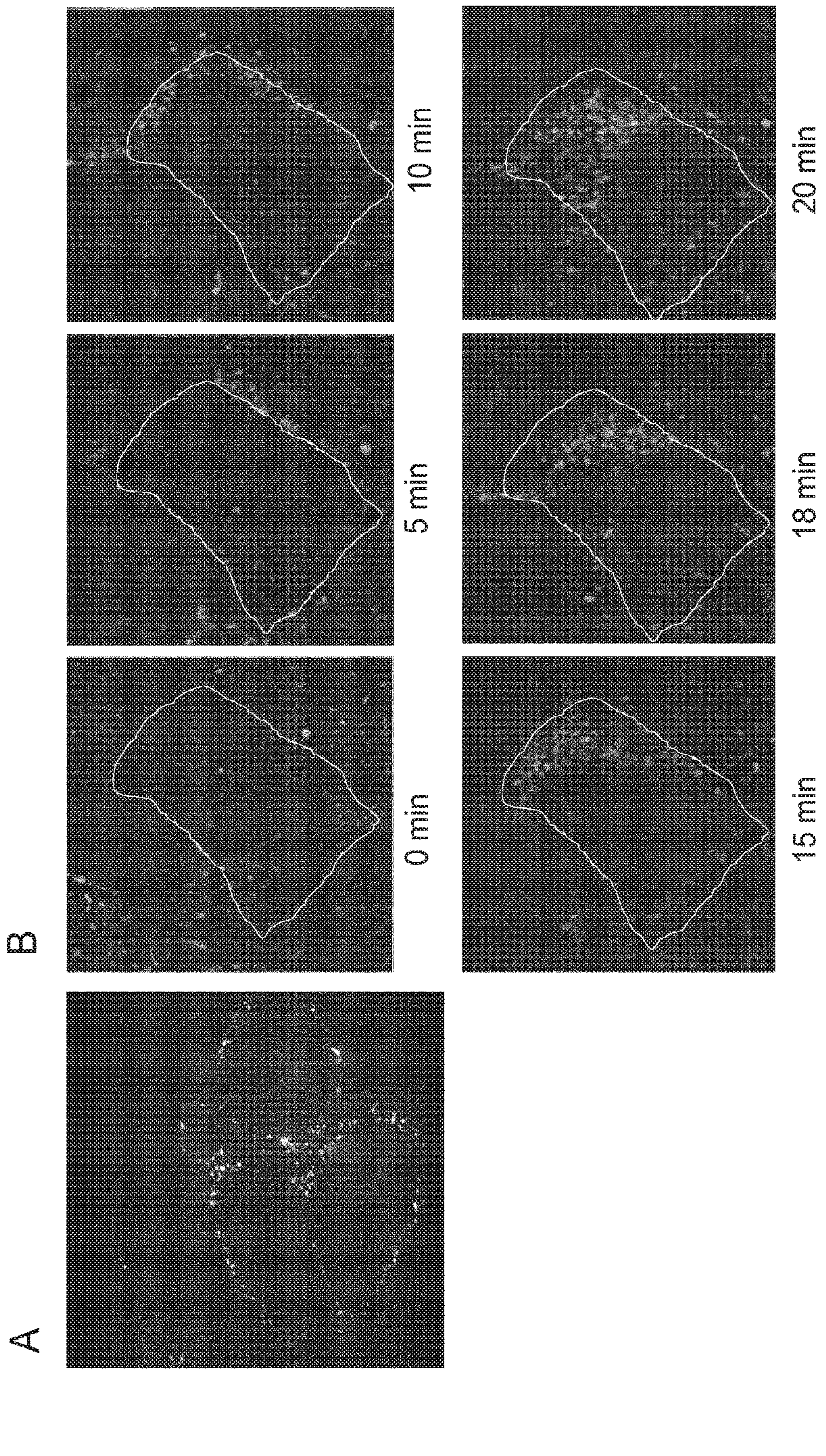
FIGS. 23A-23B. Rapid internalization of clone 51A12 antibody-cytokine conjugate. Alexa488-labeled 51A12 IgG kih IFNα construct was incubated with HepG2 cells and ASGPR-mediated internalization of the construct was recorded by confocal microscopy for 1 h over 10 stacks (z-level). Binding of the antibody-cytokine conjugate on the cell surface occurs in clusters rather than homogenous distribution 23(A). Once bound to the cell surface, the conjugate internalizes very rapidly in vesicles which are transported into the cell body (23B, single cell surrounded). Vesicles are then recycled back to the apical side of the cell (not shown).

Three-dimensional and time-resolved analysis of the ASGPR-mediated internalization of the antibody-cytokine fusion constructs was performed by confocal microscopy. For this analysis, HepG2 cells were grown to 50-60% confluency on glass-bottom dishes (Nunc) in a cell incubator. The dishes were then rinsed twice with pre-warmed PBS (37° C.) to replace the medium with PBS and quickly placed on the microscope stage (at 37° C., 5% $CO_2$). For this experiment, clone 51A12 kih IgG IFNα was directly labeled with Alexa488. The labeled construct (20 µg/ml) was added to HepG2 cells directly at the microscope stage. Acquisitions started 5 min after antibody addition using a spinningdisk confocal microscope. Data acquisitions occurred every 3 sec for 1 h (100× magnification) on 10 stacks (z-level) that covered the entire cell thickness. Binding of the antibody-cytokine construct to surface-exposed ASGPR was not equally distributed but found to be clustered (FIG. 23A). Clusters were spread over the whole surface. Time-resolved analysis of this experiment clearly revealed the immediate internalization of the antibody-cytokine fusion construct within minutes (FIG. 23B). After internalization of the IgG-cytokine constructs in vesicles, the proteins are then transported back to the surface on the apical side of the cell (data not shown).

Affinity-Determination of IgG-IFNα Immune Conjugates to Interferon-Alpha Receptor 2 by SPR The binding activity of IgG-IFNα immune conjugates to the high affinity Interferon-alpha receptor 2 (IFNAR2) was determined and compared to Roferon by surface plasmon resonance (SPR) on a ProteOn XPR36 instrument (Biorad). Commercially available IFNAR2-Fc fusion proteins (R&D Systems) were immobilized in vertical orientation on the sensorchip surface by standard amine coupling. For one-shot kinetics measurements, injection direction was changed to horizontal orientation, two-fold dilution series of purified antibody-cytokine fusions (varying concentration ranges between 50 and 3.25 nM) were injected simultaneously at 50 μl/min along separate channels 1-5, with association times of 120 or 200 s, and dissociation times of 300 s. Buffer (PBST) was injected along the sixth channel to provide an "in-line" blank for referencing. Association rate constants ($k_{on}$) and dissociation rate constants ($k_{off}$) were calculated using a simple one-to-one Langmuir binding model in ProteOn Manager v3.1 software by simultaneously fitting the association and dissociation sensorgrams. The equilibrium dissociation constant ($K_D$) was calculated as the ratio $k_{off}/k_{on}$. Regeneration was performed in horizontal orientation using 10 mM glycine, pH 1.5 at a flow rate of 100 μl/min for a contact time of 30 s. The measured affinity of antibody-cytokine fusion protein was around ($k_{on}$ $1.57\times10^{6}$ 1/Ms; $k_{off}$ $6.15\times10^{-3}$ 1/s; $K_D$ 4 nM) and thus comparable to the published affinity of recombinantly produced protein Roferon, indicating that the fusion of IFNα to the C-terminal end of an IgG has no impact on the binding affinity to IFNAR2.

Determination of the Antiviral Activity of ASGPR mAb-IFNα

In order to analyze the functional activity of IFNα as part of the IgG-cytokine fusion, and to compare it with Roferon, biological activity of the IFNα fusion constructs was tested in a virus protection assay. For this study, MDBK cells were pre-incubated with either Roferon or the antibody-cytokine fusions for 1-4 h. Vesicular stomatitis virus was then added for additional 16-24 h. At the end of this incubation step, living cells were stained with crystal violet staining solution (0.5%) and quantification of living cells was performed using a microplate reader at 550-600 nm with a reference wavelength of 690 nm. Biological activity of all IgG-cytokine constructs was determined in a full dose-response curve analysis against a standardized Roferon solution with a 4 Parameter-Logistics fitting function. As shown in Table 6, the antibody-IFNα fusion constructs show an activity that corresponds to about 5% of Roferon's activity, independent of the antibody's binding valency. Since the fusion of IFNα to the C-terminal end of an IgG has no impact on the binding affinity to IFNAR2 (shown above) it is likely that the interaction to the low affinity interferon-alpha receptor 1 (IFNAR1) is sterically impaired, ultimately leading to a reduced signaling of the IFNAR holocomplex.

Antiviral Activity of the ASGPR-Specific IgG-IFNα Conjugates in HCV Replicon and EMCV CPE Assays In order to characterize and compare the functional activity of the IgG-IFNα fusion proteins with commercially available Roferon and Pegasys (peginterferon-α2a), antiviral activity was studied using ASGPR-positive (Huh7-2209-3) and ASGPR-negative cells (Hela).

In order to analyze the antiviral activity of the compounds on ASGPR-negative cells, HeLa cells were seeded at 15,000/well in 96-well opaque-walled plate. After overnight culture, the wells were evacuated and 50 μl antibody-cytokine conjugate diluted in EMEM (with 10% FBS) was added. The HeLa cells were pre-treated with the IgG-IFNα constructs for 3 h at 37° C., before the 50 μl EMCV (VR-1762, ATCC) were added into each well (2,000 TCID50/well in EMEM). The viable cells were measured 24 h post infection using the CellTiter-Glo kit (G7572, Promega). 100 μl CellTiter-Glo reagent was added to each well and incubated at room temperature for 10 min with gentle shaking. Then the luminescence signal was recorded by using a Berthold Mithras Luminometer (Berthold Technologies). The results represent percentage of survival cells (FIG. 24A) and all $EC_{50}$ values as well as the number of experimental reiterations are summarized in Table 7. On ASGPR-negative Hela cells, the $EC_{50}$ values for Roferon are up to 75-fold smaller than for other compounds such as 4F3 IgG kih IFNα, indicating that the functional activity of this compound is much higher than of the other compounds tested. In contrast, the activity of Pegasys was comparable to those of the ASGPR-specific IgG kih IFNα conjugates.

The ASGPR-positive Huh 7-derived hepatocarcinoma cell line 2209-23 was developed by stable transfection of a bicistronic HCV replicon of which the first open reading frame, driven by the HCV IRES, contains the *renilla* luciferase gene in fusion with the neomycin phosphotransferase gene (NPTII) and the second open reading frame, driven by EMCV IRES, contains the HCV non-structural genes NS3, NS4a, NS4b, NSSA and NSSB derived from the NK5.1 replicon backbone. Cells were cultured at 37° C. in a humidified atmosphere with 5% $CO_2$ in DMEM supplemented with Glutamax™ and 100 mg/ml sodium pyruvate (#10569-010). The medium was further supplemented with 10% (v/v) FBS (#10082-139), 1% (v/v) penicillin/streptomycin (#15140-122) and 1% (v/v) geneticin. All reagents were obtained from Invitrogen.

Figures 24A, 24B:
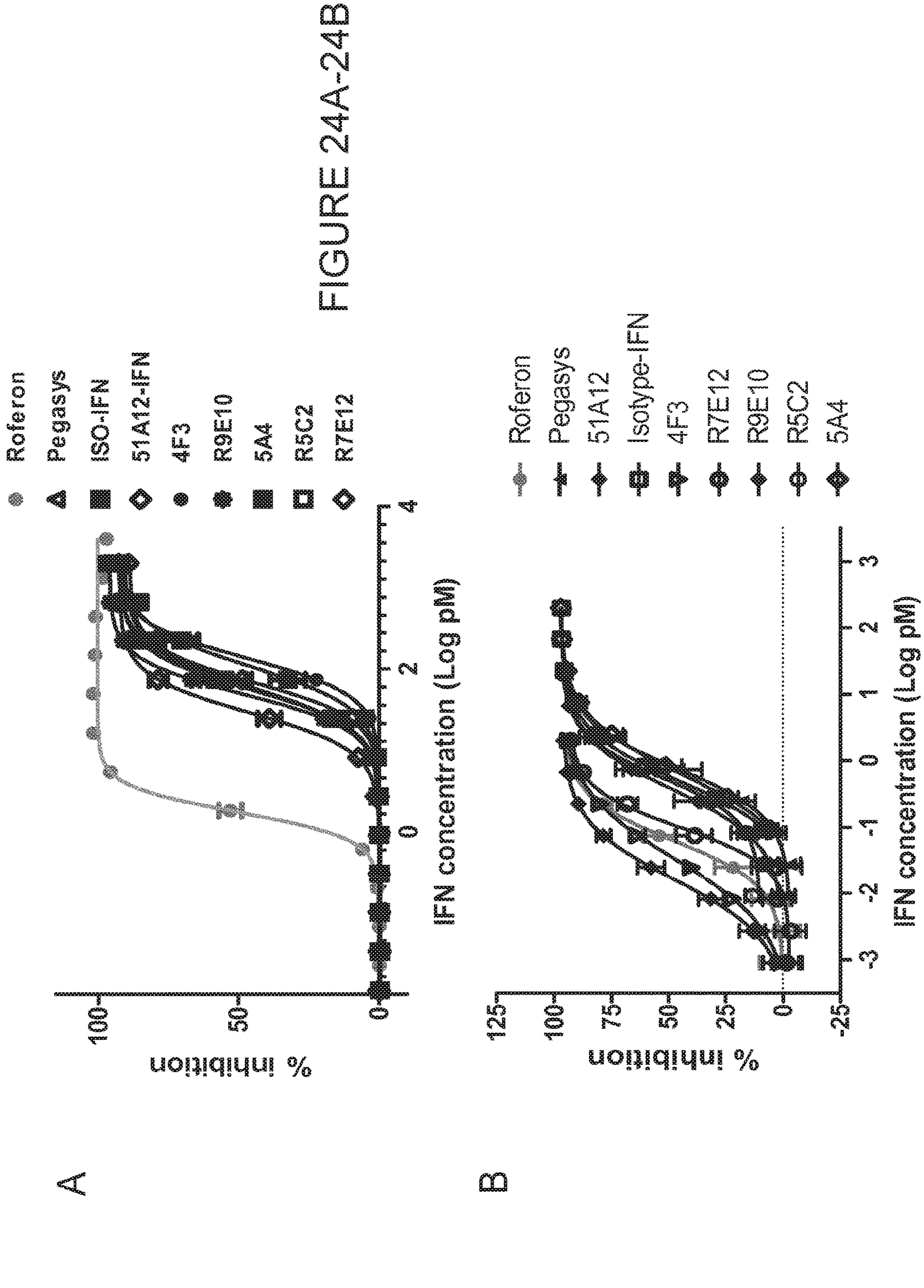
FIGS. 24A-24B. Antiviral activity of ASGPR mAb-IFNα molecules and other control IFN molecules in EMCV CPE 24(A) and HCV replicon 24(B) assays. 24(A) Hela cells were pretreated with serially diluted IFN molecules for 3 h before adding EMCV virus. Cells were cultured for 24 h, and cell viability was measured by adding CellTiter Glo. 24(B) Huh-7 2209 replicon cells were treated with serially diluted IFN molecules and luciferase activity was measured after 3 days.

Huh 7 2209-23 cells in DMEM containing 5% (v/v) Fetal Bovine Serum were plated in 96-well plates at 5000 cells/well in 90 μl volume. 24 hours after plating, antibody-cytokine conjugates (or medium as a control) were added to the cells in 3-fold dilutions over 12 wells (0.01-2000 pM), in a volume of 10 μl. Final volume after addition of compound was 100 *Renilla* luciferase reporter signal was read 72 hours after adding compounds, using the *Renilla* Luciferase Assay system (Promega, # E2820). The $EC_{50}$ values were calculated as the compound concentration at which a 50% reduction in the level of *renilla* luciferase reporter was observed as compared to control samples (in the absence of compound). Dose-response curves and $EC_{50}$ values were obtained by using the XLfit4 program (ID Business Solutions Ltd., Surrey, UK). Despite the reduced antiviral activity of the antibody-cytokine constructs when exposed to ASGPR-negative cells (Table 6 and FIG. 24A), clones 51A12 IgG kih IFNα and 4F3 IgG kih IFNα were more potent in protecting cells from viral infection and multiplication than Roferon when incubated with the ASGPR-positive cell line Huh7 2209-23 (FIG. 24B and Table 7). In contrast, the potency of the isotype control (untargeted IgG kih IFNα) was significantly lower, underlining the positive consequence of targeting the IgG kih IFNα conjugates to ASGPR H1.

TABLE 7

Summary of antiviral activity of various ASGPR H1-specific antibody-IFNα conjugates.

| | HCV Replicon (Huh-7) | | | EMCV assay (Hela) | | |
|---|---|---|---|---|---|---|
| IFNa Molecule | Mean EC50 (pM) | STDEV | n = | Mean EC50 (pM) | STDEV | n = |
| Roferon | 0.07 | 0.03 | 4 | 1.8 | 0.4 | 6 |
| Pegasys | 0.96 | 0.46 | 5 | 61.2 | 9.4 | 9 |
| Isotype-IFN | 0.59 | 0.12 | 3 | 108.3 | 5.0 | 6 |
| 51A12-IFN | 0.02 | 0.01 | 4 | 68.2 | 14.4 | 6 |
| 4F3-IFNα | 0.04 | 0.01 | 4 | 135.6 | 20.1 | 6 |
| R7E12-IFN | 0.11 | 0.04 | 3 | 29.2 | 2.3 | 6 |
| R9E10-IFN | 0.43 | 0.21 | 3 | 49.0 | 5.6 | 6 |
| R5C2-IFN | 0.54 | 0.23 | 3 | 56.3 | 4.9 | 6 |
| 5A4-IFN | 0.86 | 0.4 | 3 | 58.7 | 5.8 | 6 |

IFNα Activity of the ASGPR-Specific IgG-IFNα Conjugates in Hepatic and Non-Hepatic Cells IFNα exerts its antiviral activities through induction of hundreds of IFN-stimulated genes (ISG). To verify the antiviral activities, and further confirm the ASGPR-targeting mediated enhanced IFNα activity, we determined the ISG expression in hepatic and non-hepatic cells. Hepatic cells (primary hepatocytes and HepG2) and non-hepatic cells (human PBMC and Hela) were treated with various serially diluted IFNα molecules for 6 h and total RNA was extracted from cells using 5PRIME RNA extraction kit (#FP2302530, 5PRIME, Gaithersburg, Md.).

TaqMan (real-time PCR) assays for ISG genes MX1 and RSAD2 were custom designed. Assays were selected to lie within the Affymetrix probe sequence of interest or within the 3' coding sequence of the reference mRNAs of interest.

All gene expression assays were performed on an ABI PRISM® 7900HT Sequence Detection System (Applied Biosystems). PCR mix consisted of 10 μl PerfeCTa® qPCR FastMix, ROX™ (Quanta), 1 μl TaqMan or 0.06 μl IDT assay, and 2 μl DEPC-treated water (Ambion, Applied Biosystems) for each reaction. cDNA samples were diluted to 10 ng/μl in RNase-free water (Ambion, Applied Biosystems), and 7 μl added to a 384-well optical plate (Applied Biosystems) containing 13 μl pre-distributed assay PCR mix. All samples were queried with one assay for a target gene or one for the endogenous control gene assays, 18S, GAPDH (Rhesus), ACTB (Rhesus) and GUSB (Rhesus) (TaqMan Gene Expression Assays, Applied Biosystems). Each measurement was performed in triplicate. The following PCR conditions were used: 45° C. for 2 min, then 95° C. for 3 min, followed by 40 cycles at 95° C. for 15 s and 60° C. for 45 s.

Figures 25A, 25B, 25C, 25D:
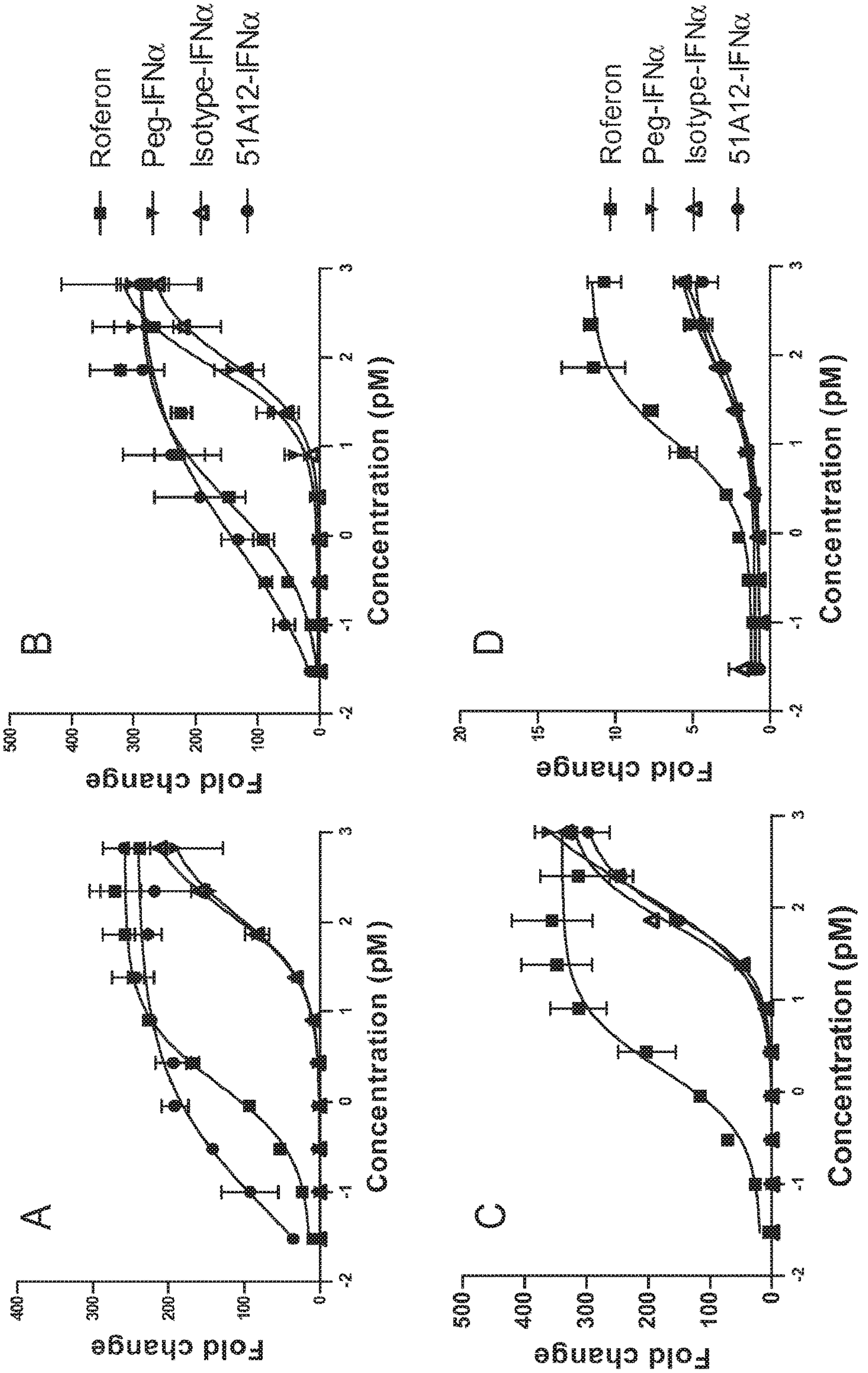
FIGS. 25A-25D. ISG induction by 51A12-IFNα in various hepatic and non-hepatic cells. Hepatic cells (primary hepatocytes 25(B) and HepG2 25(A)) and non-hepatic cells (human PBMC 25(D) and Hela 25(C)) were treated with various serially diluted IFNα molecules for 6 h, total RNA was extracted and TaqMan RT-PCR was used to quantify ISG MX1 25(A, C) and Rsad2 25(B, D) gene expression. Data shown are from three or more experiments.

The expression levels of target genes were normalized to the geometric mean of 18S, ACTB, GAPDH and GUSB and represented as relative expression (E), $E=2^{(\Delta Ct)}$, where ΔCt is the difference between reference and target gene cycles at which the amplification exceeds an arbitrary threshold. As shown in FIG. 25, isotype IgG kih IFNα control showed reduced ISG induction compared to Roferon, with similar activity to Pegasys (PEG-IFNα) in all cells. In the ASGPR-negative Hela and PBMC cells, clone 51A12 IgG kih IFNα also showed reduced activity, similar to the isotype control. However, in the ASGPR-positive hepatic cells HepG2 and primary human hepatocytes, clone 51A12 IgG kih IFNα showed enhanced IFNα activity compared to the isotype control, to a similar level of Roferon. This result confirms the above-described enhanced antiviral activity of the 51A12 antibody-IFNα conjugate.

Figures 26A, 26B:
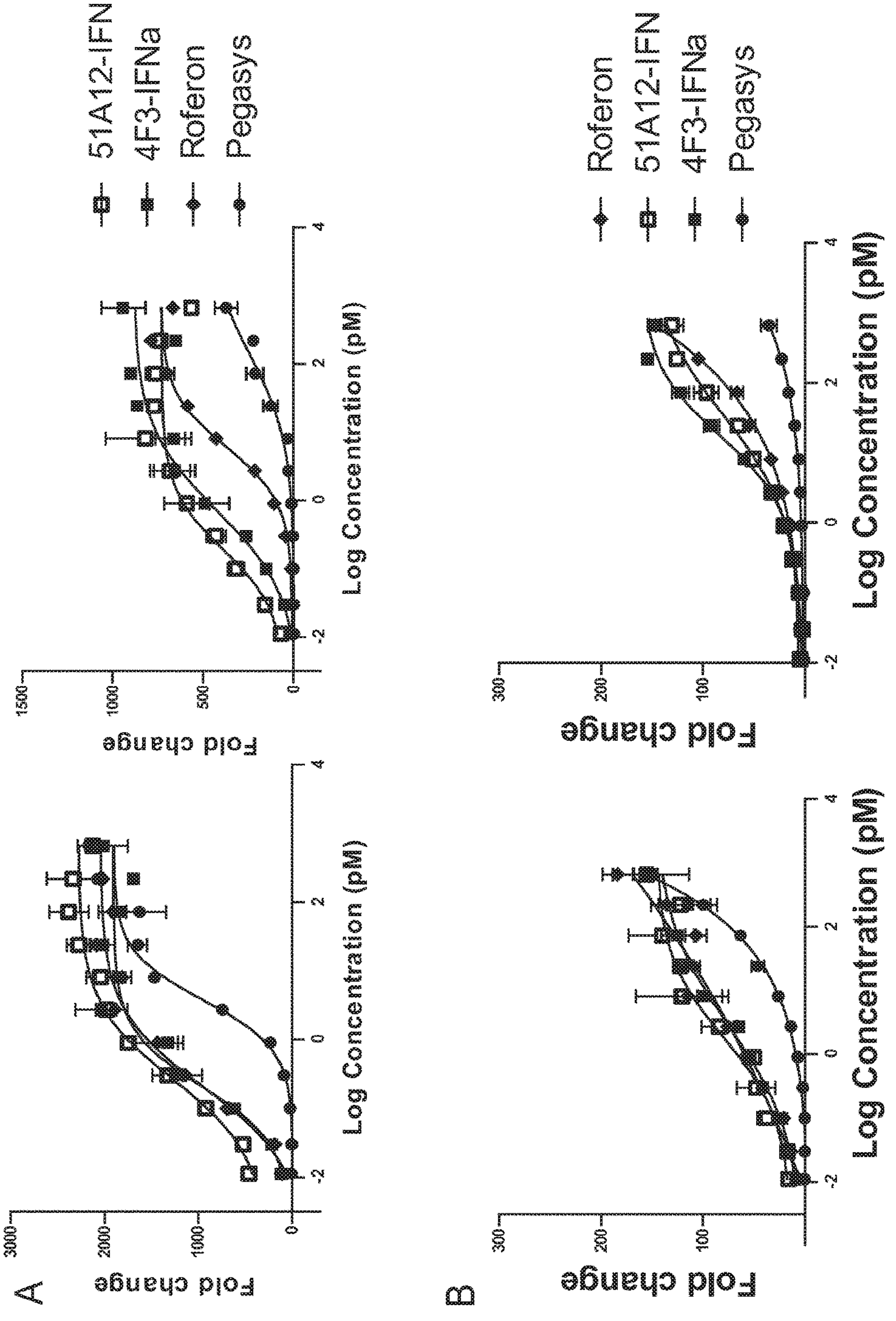
FIGS. 26A-26B. Sustained ISG induction by 51A12-IFNα and 4F3-IFNα in primary human hepatocytes (PHH) 26(B) and Huh7 26(A) cells. Primary human hepatocytes (PHH) and Huh7 cells were treated with serially diluted IFNα molecules for 6 h (left) and 72 h (right), total RNA was extracted and TaqMan RT-PCR was used to quantify ISG MX1 26(A) and Rsad2 26(B) gene expression.

In order to understand whether these ASGPR-targeted IFNα molecules have sustained IFNα activity, we monitored ISG expression in Huh-7 and primary hepatocytes for up to 72 h. As shown in FIG. 26, both ASGPR-targeting IFNα molecules 51A12 IgG kih IFNα and 4F3 IgG kih IFNα showed sustained ISG induction at 72 h after treatment, while Pegasys and Roferon showed significantly reduced ISG induction at 72 h.

Cynomolgus Monkey Single Dose PK/PD Study

Encouraged by in vitro results that ASGPR antibody-based targeted IFNα molecules showed reduced IFNα activity in non-hepatic cells and enhanced IFNα activity in hepatic cells (liver-targeted IFNα effects), a cynomolgus monkey study was designed to confirm the liver-targeted IFNα effects in vivo. Because the ASGPR-specific clone 51A12 binds to human and monkey ASGPR with identical affinity and human IFNα has similar activity in the monkeys, monkeys can be used as PK/PD models for liver-targeted IFNα proof-of-concept studies. In the monkey study we directly compared 51A12 IgG kih IFNα and isotype IgG kih IFNα control. Both molecules were injected subcutaneously at dosage levels of either 1 or 10 μg/kg, monkey blood and liver biopsy samples were collected before and after dosing, and their PK (pharmacokinetics) and PD (pharmacodynamics) were monitored. The dose groups are listed in Table 8.

TABLE 8

Twelve cynomolgus monkeys were divided into four groups as shown below.

| Group | Dose (μg/kg), compound | No of Animals | Formulation Strength (μg/ml) |
|---|---|---|---|
| 1 | 10 μg/kg, 51A12, SC, Single Dose | 3 | 20 |
| 2 | 1 μg/kg, 51A12, SC, Single Dose | 3 | 2 |
| 3 | 10 μg/kg, iso-control, SC, Single Dose | 3 | 20 |
| 4 | 1 μg/kg, iso-control, SC, Single Dose | 3 | 2 |

Sample Collection, Transfer and Storage

Blood (approximately 1 ml) was collected from each animal 5 days before dosage and at 2, 6, 12, 24, 48, 72, 96, 168, and 336 hours after injection. Samples for pharmacokinetics were collected into tubes without anticoagulant. Blood for pharmacokinetics was collected prior to the pharmacodynamic blood collections.

For the gene expression study, blood (approximately 2.5 ml) was collected from each animal 5 days before dosage and at 2, 6, 12, 24, 48, 72, 96, 168, and 336 hours after injection. Samples were collected into PAXgene™ blood RNA collection tubes and the tubes were mixed by inverting 8-10 times. The PAXgene™ blood RNA collection tube was the last tube drawn in the phlebotomy sequence (i.e. after the clinical pathology and pharmacokinetic collections).

Liver tissue was collected from two separate locations (at least 25 mg/sample) in the liver via laparoscopic procedure from each animal on day −5, and on day 2, day 4 and day 8. Each tissue sample was excised and immediately placed into separate pre-weighed and labeled cryo-vial tubes and flash-frozen in liquid nitrogen. Because of the need for immediate freezing, the sample vials were not weighed after collection of the liver samples. For day −5 and day 2, the first liver tissue aliquot for each animal was taken from the left lateral lobe of the liver, and the second liver tissue aliquot for each animal was taken from the right lateral lobe of the liver. For day 4 and day 8, the first liver tissue aliquot for each animal was taken from the left medial lobe of the liver, and the second liver tissue aliquot for each animal was taken from the right medial lobe of the liver. Liver biopsy samples were snap-frozen in 2 ml tubes. RNAlater-ICE (P/N 7031, Ambion), pre-chilled on dry ice, was added to frozen tissues and stored at −80° C. Blood samples were received in PAXgene tubes according to the protocol and stored at −80° C. prior to processing.

Measurement of Clone 51A12 IgG Kih IFNα and Isotype IgG Kih IFNα Control in Monkey Serum Samples Aliquots of cynomolgus monkey serum were analyzed for the dosed compound using a sandwich ELISA assay that uses an anti-IFNα antibody (Lot no. 34495-28, Roche Nutley, N.J., USA) as the capture reagent and HRP-labeled anti-human Fc antibody (Lot no. Wbr72_MM_090602, Roche Diagnostics, Penzberg, Germany) as the detection reagent. After coating of plates with anti-IFNα antibody at room temperature for 1 h, the plates were treated with 2% BSA blocking buffer for 1 h. After washing, HRP-labeled anti-human Fc antibody was added to each well and incubated for 1 h with gentle shaking. After washing, 100 μl/well TMB substrate solution (#11 484 281 001, Roche Diagnostics, Penzberg, Germany) was added for about 20 min The reaction was then stopped by adding 50 μl/well 2N HCl. The plates were read within 2 min at 450 nm with reference wavelength of 650 nm. The lower limit of quantitation (LLOQ) of this method was 10 ng/ml. The precision (% CV) and accuracy (% relative error) of the assay met the acceptance criteria. Assay performance, as monitored by the analysis of QC samples analyzed along with the samples, was as shown in Table 9. The serum concentrations are shown in Table 10-13. A single injection of isotype IgG kih IFNα at 10 μg/kg yielded significant exposure in the blood that peaked at around 100 ng/ml for one week. In contrast, at the same dose level, 51A12 IgG kih IFNα was below quantification level at any time point. Both molecules were undetectable in the blood at 1 μg/kg dose level. The PK parameters are summarized in Table 14.

TABLE 9

Analytical performance of clone 51A12 IgG kih IFNα quality control samples in cynomolgus monkey serum.

| Run Date | Curve Number | QC1 30.0 ng/mL | QC2 90.0 ng/mL | QC3 270 ng/mL |
|---|---|---|---|---|
| 13-Dec-2011 | 1 | 24.3 | 78.8 | 252 |
| | | 29.1 | 95.2 | 236 |
| 13-Dec-2011 | 2 | * | 76.4 | 251 |
| | | 26.3 | 94.7 | 24 |
| 28-Dec-2011 | 3 | 21.7 | 74.7 | 245 |
| | | 28.6 | 84.3 | 264 |
| | 4 | 25.4 | 82.5 | 288 |
| | | 28.2 | 91.2 | 279 |
| Mean | | 26.3 | 84.7 | 258 |
| % CV | | 10.2 | 9.6 | 6.9 |
| % Rel. Error | | −12.3 | −5.9 | −4.4 |

* Deactivated

TABLE 10

Serum concentration (ng/ml) of 1 μg/kg isotype IgG kih IFNα.

| Time [h] | Subject 1 | Subject 2 | Subject 3 | Mean | S.D. | % CV | n |
|---|---|---|---|---|---|---|---|
| 0 | BLQ < 10.0 | BLQ < 10.0 | BLQ < 10.0 | | | | |
| 2 | BLQ < 10.0 | BLQ < 10.0 | BLQ < 10.0 | | | | |
| 6 | BLQ < 10.0 | BLQ < 10.0 | BLQ < 10.0 | | | | |
| 12 | BLQ < 10.0 | BLQ < 10.0 | BLQ < 10.0 | | | | |
| 24 | BLQ < 10.0 | BLQ < 10.0 | BLQ < 10.0 | | | | |
| 48 | BLQ < 10.0 | BLQ < 10.0 | BLQ < 10.0 | | | | |
| 72 | BLQ < 10.0 | BLQ < 10.0 | BLQ < 10.0 | | | | |
| 96 | BLQ < 10.0 | BLQ < 10.0 | BLQ < 10.0 | | | | |
| 168 | BLQ < 10.0 | BLQ < 10.0 | BLQ < 10.0 | | | | |
| 336 | BLQ < 10.0 | BLQ < 10.0 | BLQ < 10.0 | | | | |

TABLE 11

Serum concentration (ng/ml) of 1 μg/kg 51A12 IgG kih IFNα.

| Time [h] | Subject 1 | Subject 2 | Subject 3 | Mean | S.D. | % CV | n |
|---|---|---|---|---|---|---|---|
| 0 | BLQ < 10.0 | BLQ < 10.0 | BLQ < 10.0 | | | | |
| 2 | BLQ < 10.0 | BLQ < 10.0 | BLQ < 10.0 | | | | |
| 6 | BLQ < 10.0 | BLQ < 10.0 | BLQ < 10.0 | | | | |
| 12 | BLQ < 10.0 | BLQ < 10.0 | BLQ < 10.0 | | | | |
| 24 | BLQ < 10.0 | BLQ < 10.0 | BLQ < 10.0 | | | | |
| 48 | BLQ < 10.0 | BLQ < 10.0 | BLQ < 10.0 | | | | |
| 72 | BLQ < 10.0 | BLQ < 10.0 | BLQ < 10.0 | | | | |
| 96 | BLQ < 10.0 | BLQ < 10.0 | BLQ < 10.0 | | | | |
| 168 | BLQ < 10.0 | BLQ < 10.0 | BLQ < 10.0 | | | | |
| 336 | BLQ < 10.0 | BLQ < 10.0 | BLQ < 10.0 | | | | |

TABLE 12

| Serum concentration (ng/ml) of 10 μg/kg 51A12 IgG kih IFNα. | | | | | | | |
|---|---|---|---|---|---|---|---|
| Time [h] | Subject 1 | Subject 2 | Subject 3 | Mean | S.D. | % CV | n |
| 0 | BLQ < 10.0 | BLQ < 10.0 | BLQ < 10.0 | | | | |
| 2 | BLQ < 10.0 | BLQ < 10.0 | BLQ < 10.0 | | | | |
| 6 | BLQ < 10.0 | BLQ < 10.0 | BLQ < 10.0 | | | | |
| 12 | BLQ < 10.0 | BLQ < 10.0 | BLQ < 10.0 | | | | |
| 24 | BLQ < 10.0 | BLQ < 10.0 | BLQ < 10.0 | | | | |
| 48 | BLQ < 10.0 | BLQ < 10.0 | BLQ < 10.0 | | | | |
| 72 | BLQ < 10.0 | BLQ < 10.0 | BLQ < 10.0 | | | | |
| 96 | BLQ < 10.0 | BLQ < 10.0 | BLQ < 10.0 | | | | |
| 168 | BLQ < 10.0 | BLQ < 10.0 | BLQ < 10.0 | | | | |
| 336 | BLQ < 10.0 | BLQ < 10.0 | BLQ < 10.0 | | | | |

TABLE 13

| Serum concentration (ng/ml) at 10 μg/kg isotype IgG kih IFNα. | | | | | | | |
|---|---|---|---|---|---|---|---|
| Time [h] | Subject 1 | Subject 2 | Subject 3 | Mean | S.D. | % CV | n |
| 0 | BLQ < 10.0 | BLQ < 10.0 | BLQ < 10.0 | | | | |
| 2 | BLQ < 10.0 | 33.7 | 12.4 | 23.1 | | | 2 |
| 6 | 49.8 | 40.9 | 61.5 | 50.7 | 10.3 | 20.3 | 3 |
| 12 | 66.4 | 44.3 | 67.9 | 59.5 | 13.2 | 22.2 | 3 |
| 24 | 109 | 63.1 | 71.1 | 81.1 | 24.5 | 30.2 | 3 |
| 48 | 119 | 99.3 | 88.3 | 102 | 15.6 | 15.3 | 3 |
| 72 | 105 | 88.2 | 94.0 | 95.7 | 8.53 | 8.9 | 3 |
| 96 | 124 | 85.0 | 95.2 | 101 | 20.2 | 20.0 | 3 |
| 168 | 78.9 | 56.5 | 58.3 | 64.6 | 12.4 | 19.2 | 3 |
| 336 | 19.6 | 11.0 | BLQ < 10.0 | 15.3 | | | 2 |

TABLE 14

| Cynomolgus monkey serum PK parameters of 10 μg/kg isotype-IFNα. | | | | | | | | |
|---|---|---|---|---|---|---|---|---|
| Parameter | Units | Subject 1 | Subject 2 | Subject 3 | Mean | S.D. | % CV | n |
| original dose | μg/kg | 10 | 10 | 10 | | | | |
| $C_{max}$ | ng/ml | 124 | 99 | 95 | 106 | 16 | 14.8 | 3 |
| $T_{max}$ | hours | 96 | 48 | 96 | 80 | 28 | 34.6 | 3 |
| AUC | ng * hours/ml | 25251 | 18124 | 13279 | 18885 | 6022 | 31.9 | 3 |
| AUC interval | hours | (0-336) | (0-336) | (0-168) | | | | |
| AUC/dose | ng * hours/ml/μg/kg | 2525 | 1812 | 1328 | 1888 | 602 | 31.9 | 3 |
| AUC extrap | ng * hours/ml | 27615 | 19253 | 21839 | 22903 | 4281 | 18.7 | 3 |
| % AUC extrap | % | 8.6 | 5.9 | 39 | 17.9 | 18.5 | 104 | 3 |
| AUC extrap/ dose | ng * hours/ml/μg/kg | 2762 | 1925 | 2184 | 2290 | 428 | 18.7 | 3 |
| $T_{1/2}$ | hours | 83.6 | 71.1 | 102 | 85.5 | 15.4 | 18.0 | 3 |

RNA Extraction

Total RNA was extracted from 96 liver biopsy samples (48 animals×2 biopsies per sampling) using the Qiagen RNeasy Mini Kit (P/N 74104) and quantitated on the Nanodrop 8000. Total RNA quality of the liver samples was assessed on the Caliper LabChip GX. RNA from all samples was of sufficient quantity and quality to perform qPCR and microarray-based gene expression measurements.

Total RNA isolation and quantitation from 120 blood samples was performed at Expression Analysis (Raleigh, N.C.). Total RNA quality of the blood samples was assessed on the Agilent Bioanalyzer 2100. RNA from all samples was of sufficient quantity and quality to perform qPCR and microarray-based gene expression measurements.

Microarray Analysis

Two separate protocols were used to convert total RNA into cDNA: Affymetrix GeneChip HT 3' IVT Express (P/N 901225) and NuGEN Ovation RNA Amplification System V2 (P/N 3100-60).

Blood 100 ng total RNA from liver biopsy samples was converted into double-stranded cDNA and amplified RNA (aRNA) using the GeneChip HT 3' IVT Express Kit according to the manufacturer's protocols. The hybridization mix contained 12.5 μg aRNA, 2× Hybridization Mix (P/N 900720), DMSO, 20× Hybridization Controls, and Oligo B2 Controls.

Liver 50 ng total RNA from blood samples was converted to single-stranded cDNA using the NuGEN Ovation RNA Amplification System V2 kit following the manufacturer's protocol. The hybridization mix contained 3 μg SPIA-amplified cDNA, 2× Hybridization Mix (P/N 900720), DMSO, 20× Hybridization Controls, and Oligo B2 Controls.

The hybridization mixes for liver and blood samples were hybridized to Affymetrix GeneChip Human Genome U133 Plus 2.0 Arrays. Staining and washing steps were performed as suggested by the manufacturer (Affymetrix). Each hybridized Affymetrix GeneChip array was scanned with a GeneChip Scanner 3000 7G (Agilent/Affymetrix). Image analysis was performed with the Affymetrix GCOS software. The resulting .cel files were assessed using standardized quality control metrics. Data were normalized and expression value calculation/differential expression was determined using standard data analysis packages.

Figure 27:
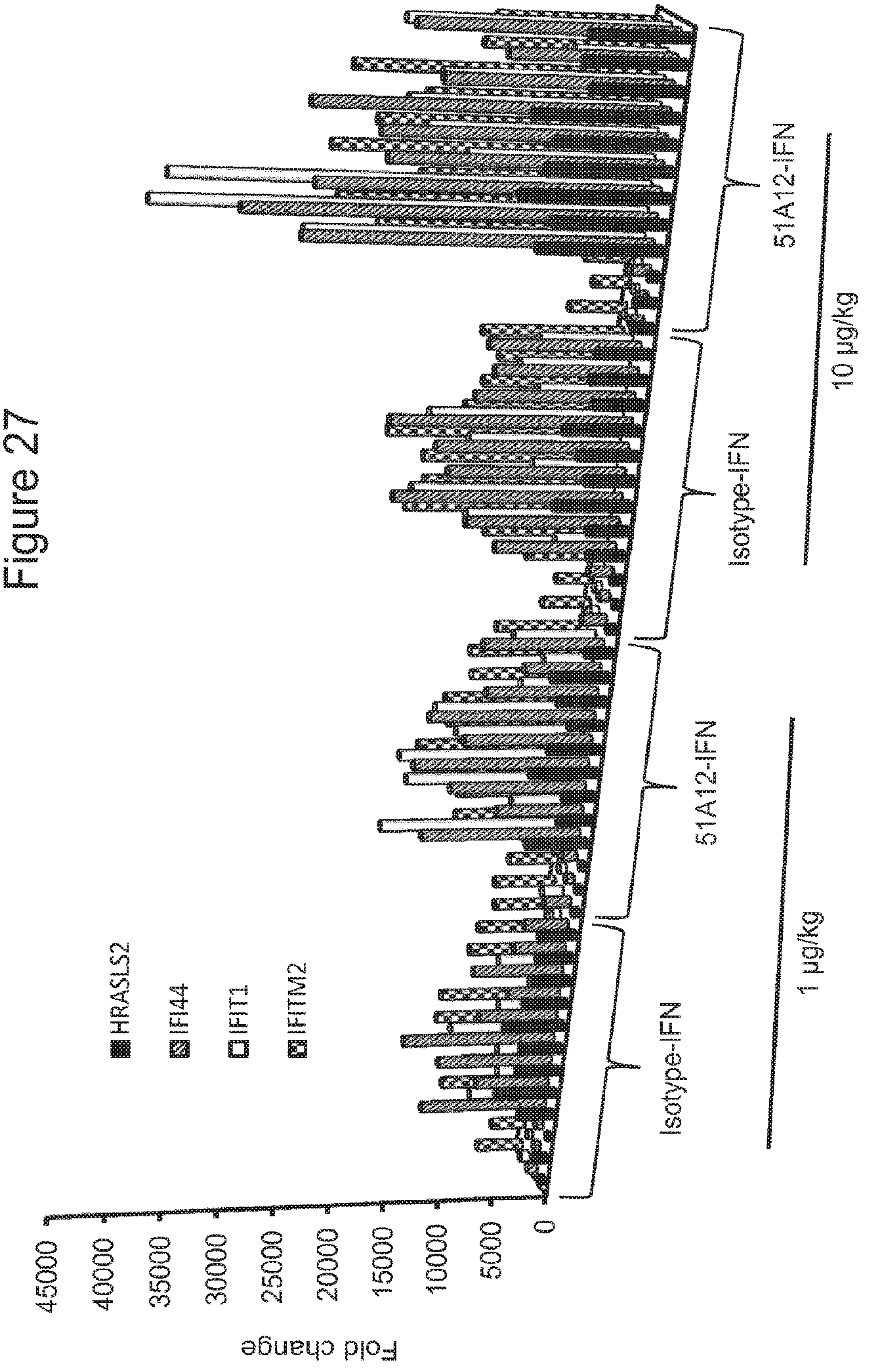
FIG. 27. Representative ISG expression in monkey liver samples. Monkey liver samples from the four dose groups collected at different time points were analyzed by microarray. Expression of four representative ISG genes is shown in a 3D graph. The four dose groups are indicated. For each dose group, from left to right, bars represent ISG fold induction at day −5, day 2, day 4, and day 8 of the 3 monkeys.

In FIG. 27 the expression of four representative ISGs HRASLS2, ITI44, IFIT1, and IFITM2 in monkey liver samples is graphed. More robust induction of the expression of these four ISGs was found in 51A12 IgG kih IFNα dosed monkeys, in comparison to the isotype IgG kih IFNα dosed monkeys.

IFN Gene Expression Analysis (M3.1 Heatmap)

Figure 28A:
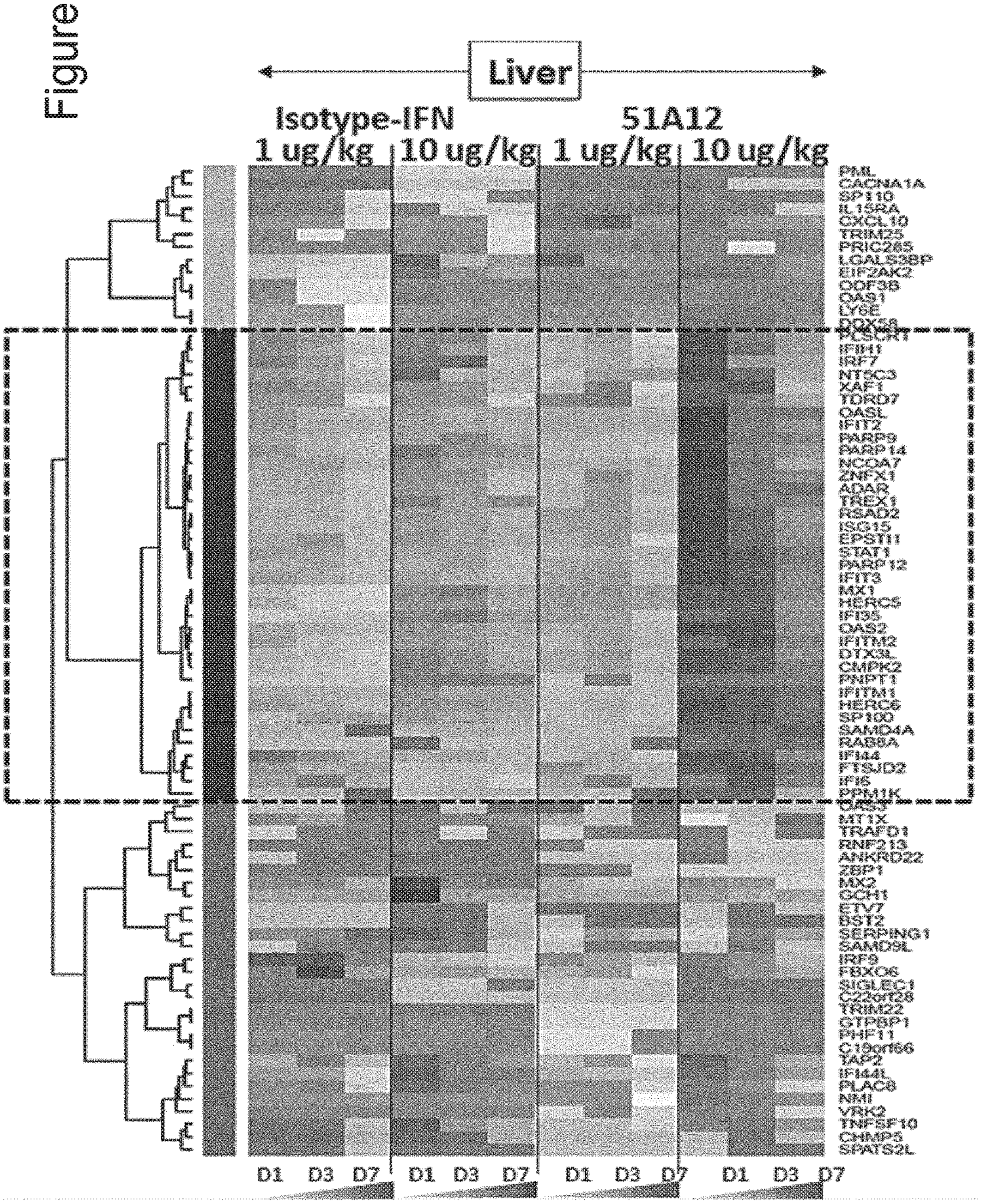
FIGS. 28A-28B. Blood and liver gene expression heatmaps (IFN module M3.1). mRNA microarray analysis was performed on blood PBMC and liver biopsy samples, and their IFNα response was analyzed with gene modules determined from blood transcriptomics studies (Chaussabel et al. (2008), Immunity 29, 150-64). In panel 28(A), the fold-change expression values from baseline (see inset) for the genes of the interferon module M3.1 were plotted in heatmap form for both blood and liver samples using the R statistics package (www.r-project.org). Non-supervised hierarchical clustering of the liver interferon-induced genes reveals a highly induced subset (dashed rectangle) in the 10 μg/kg dose of 51A12 but not the isotype-IFNα compound at days 1 and 3. 28(B) This subset of genes was plotted for both liver and blood. Non-supervised hierarchical clustering this subset reveals a differential pattern of expression between blood and liver where the upper half of the heatmap shows induction in liver for 51A12 but not isotype-IFNα at the 10 μg/kg dose and in the lower half, induction in blood only for isotype-IFNα at the high dose.
Figure 28B:
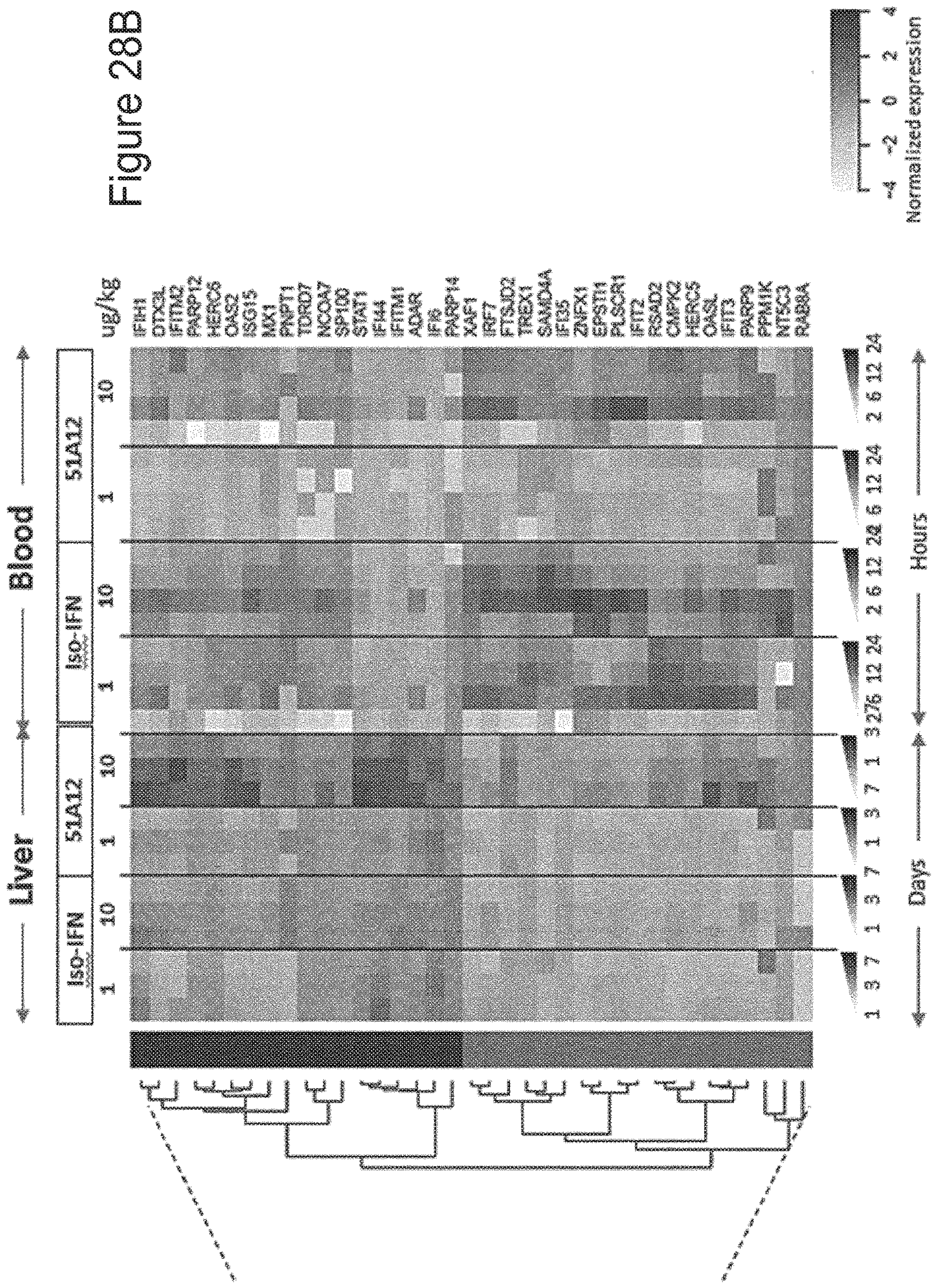
Figure 29:
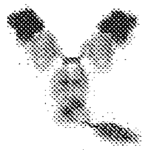
FIG. 29. Functional IFNα activity of the antibody-cytokine conjugate in comparison to Roferon.
Figure 29:
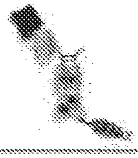
Figure 29:
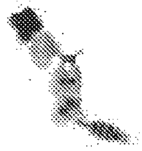

In order to more comprehensively analyze the IFNα stimulated gene expression by IFNα molecules, IFNα response was analyzed with IFN gene modules determined from blood transcriptomics studies (Chaussabel et al. (2008), Immunity 29, 150-64). As shown in FIG. 28A, the fold-change expression values from baseline for the genes of the interferon module M3.1 were plotted in heatmap form for both blood and liver samples using the R statistics package (www.r-project.org). Non-supervised hierarchical clustering of the liver interferon-induced genes reveals a highly induced subset (dashed rectangle) in the 10 μg/kg dose of 51A12 but not the isotype IFNα compound at days 1 and 3. Non-supervised hierarchical clustering this subset reveals a differential pattern of expression between blood and liver where some of the genes were more significantly induced in liver by 51A12 but not isotype-IFNα at the 10 μg/kg dose and other genes were more significantly induced in blood by isotype IFNα at the high dose (FIG. 28B).

In summary, ASGPR-targeting IFNα molecule 51A12 IgG kih IFNα showed undetectable exposure in the blood, and lower IFNα activity (ISG expression stimulation) in the blood but higher IFNα activity in monkey liver, as compared to isotype IFNα control.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating a hepatitis virus infection in an individual in need thereof comprising administering to said individual a therapeutically effective amount of a composition comprising an antibody in a pharmaceutically acceptable form, wherein the antibody specifically binds to asialoglycoprotein receptor (ASGPR) and comprises:

a) heavy chain variable region sequence of SEQ ID NO: 4 and a light chain variable region sequence of SEQ ID NO: 2;

b) a heavy chain variable region sequence of SEQ ID NO: 4 and a light chain variable region sequence of SEQ ID NO: 30;

c) a heavy chain variable region sequence of SEQ ID NO: 4 and a light chain variable region sequence of SEQ ID NO: 32;

d) a heavy chain variable region sequence of SEQ ID NO: 4 and a light chain variable region sequence of SEQ ID NO: 34;

e) a heavy chain variable region sequence of SEQ ID NO: 4 and a light chain variable region sequence of SEQ ID NO: 38;

f) a heavy chain variable region sequence of SEQ ID NO: 4 and a light chain variable region sequence of SEQ ID NO: 40;

g) a heavy chain variable region sequence of SEQ ID NO: 4 and a light chain variable region sequence of SEQ ID NO: 42;

h) a heavy chain variable region sequence of SEQ ID NO: 4 and a light chain variable region sequence of SEQ ID NO: 44;

i) a heavy chain variable region sequence of SEQ ID NO: 4 and a light chain variable region sequence of SEQ ID NO: 46;

j) a heavy chain variable region sequence of SEQ ID NO: 4 and a light chain variable region sequence of SEQ ID NO: 48.

2. The method of claim 1, wherein the antibody comprises:

a) a heavy chain variable region sequence of SEQ ID NO: 4 and a light chain variable region sequence of SEQ ID NO: 2;

b) a heavy chain variable region sequence of SEQ ID NO: 4 and a light chain variable region sequence of SEQ ID NO: 30;

c) a heavy chain variable region sequence of SEQ ID NO: 4 and a light chain variable region sequence of SEQ ID NO: 32; or d) a heavy chain variable region sequence of SEQ ID NO: 4 and a light chain variable region sequence of SEQ ID NO: 34.

3. The method of claim 1, wherein the antibody comprises a heavy chain variable region sequence of SEQ ID NO: 4 and a light chain variable region sequence of SEQ ID NO: 2.

4. The method of claim 1, wherein the antibody is specific to human and cynomolgus monkey ASGPR.

5. The method of claim 1, wherein said infection is HBV infection.

* * * * *